(12) United States Patent
Colosi et al.

(10) Patent No.: US 12,239,692 B2
(45) Date of Patent: *Mar. 4, 2025

(54) ADENO-ASSOCIATED VIRUS FACTOR VIII VECTORS

(71) Applicants: BIOMARIN PHARMACEUTICAL INC., Novato, CA (US); UCL BUSINESS LTD, London (GB); ST. JUDE CHILDREN'S RESEARCH HOSPITAL, Memphis, TN (US)

(72) Inventors: Peter Cameron Colosi, Novato, CA (US); Amit Nathwani, London (GB); Jenny McIntosh, London (GB); Edward Tuddenham, London (GB); Andrew Davidoff, Memphis, TN (US)

(73) Assignees: BIOMARIN PHARMACEUTICAL INC., Novato, CA (US); UCL BUSINESS LTD, London (GB); ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,286

(22) Filed: Jun. 30, 2022

(65) Prior Publication Data

US 2022/0339262 A1   Oct. 27, 2022

Related U.S. Application Data

(63) Continuation of application No. 16/588,130, filed on Sep. 30, 2019, now Pat. No. 11,406,690, which is a continuation of application No. 15/294,310, filed on Oct. 14, 2016, now Pat. No. 10,463,718, which is a continuation of application No. 14/482,648, filed on Sep. 10, 2014, now Pat. No. 9,504,762.

(60) Provisional application No. 61/877,042, filed on Sep. 12, 2013.

(51) Int. Cl.

| | | |
|---|---|---|
| A01N 63/00 | (2020.01) | |
| A61K 38/37 | (2006.01) | |
| A61K 48/00 | (2006.01) | |
| C07K 14/755 | (2006.01) | |
| C12N 7/00 | (2006.01) | |
| C12N 15/86 | (2006.01) | |

(52) U.S. Cl.
CPC .......... *A61K 38/37* (2013.01); *A61K 48/0058* (2013.01); *A61K 48/0066* (2013.01); *C07K 14/755* (2013.01); *C12N 7/00* (2013.01); *C12N 15/86* (2013.01); *C12N 2750/14132* (2013.01); *C12N 2750/14142* (2013.01); *C12N 2750/14143* (2013.01); *C12N 2750/14151* (2013.01); *C12N 2800/22* (2013.01); *C12N 2830/008* (2013.01)

(58) Field of Classification Search
USPC ......................................................... 424/93.1
See application file for complete search history.

(56) References Cited

U.S. PATENT DOCUMENTS

| | | | |
|---|---|---|---|
| 6,200,560 B1 | 3/2001 | Couto et al. | |
| 6,221,349 B1 | 4/2001 | Couto et al. | |
| 6,383,794 B1 * | 5/2002 | Mountz | C12N 15/86 435/235.1 |
| 6,521,225 B1 * | 2/2003 | Srivastava | A61P 1/16 424/93.1 |
| 7,351,577 B2 | 4/2008 | Couto et al. | |
| 8,030,065 B2 | 10/2011 | Gray | |
| 9,393,323 B2 | 7/2016 | Nathwani et al. | |
| 2003/0096787 A1 | 5/2003 | Perricaudet et al. | |
| 2007/0042462 A1 | 2/2007 | Hildinger | |
| 2008/0131403 A1 * | 6/2008 | Wang | C12N 15/1137 435/235.1 |
| 2013/0024960 A1 | 1/2013 | Nathwani et al. | |
| 2015/0023946 A1 * | 1/2015 | Zollner | A61K 38/37 530/383 |

FOREIGN PATENT DOCUMENTS

| | | | |
|---|---|---|---|
| CN | 105636981 B | 11/2020 | |
| RU | 2001125671 A | 8/2003 | |
| RU | 2219241 C2 | 12/2003 | |
| WO | WO-2007/003582 A2 | 1/2007 | |
| WO | WO-2011005968 A1 * | 1/2011 | ............. A61K 38/37 |

OTHER PUBLICATIONS

Edelstein (Journal Gene Med., 2004, vol. 6, p. 597-602).*
Wu (Mol. Therapy, 2008, vol. 16, No. 2, p. 280-289).*
Lu (Human Gene Therapy, Jun. 2008, vol. 19, No. 6, p. 648-654).*
Ishiwata (J. Gene Med., 2009, vol. 11, p. 1020-1029).*
McIntosh (Blood Apr. 2013, vol. 121, No. 17, p. 3335-3344).*
Rogers (Front Biosci., 2015, vol. 20, p. 556-603).*
Wang (J. Virol., 1996, vol. 70, p. 1668-1677).*
Wang (J. Virol., 1997, vol. 71, p. 3077-3082).*
Nissen (BMC Hematology, 2018, vol. 18, No. 17, p. 1-4) (Year: 2018).*
Burton et al., Coexpression of factor VIII heavy and light chain adeno-associated viral vectors produces biologically active protein, Proc. Natl. Acad. Sci. USA, 96(22):12725-30 (Oct. 1999).
Chao et al., Sustained expression of human factor VIII in mice using a parvovirus-based vector, Blood, 95(5):1594-9 (Mar. 2000).
De Simone et al., Cis- and trans-acting elements responsible for the cell-specific expression of the human alpha 1-antitrypsin gene, EMBO J., 6(9):2759-66 (1987).
Edelstein et al., Gene therapy clinical trials worldwide 1989-2004—an overview, J. Gene Med., 6(6):597-602 (2004).

(Continued)

*Primary Examiner* — Michael C Wilson
(74) *Attorney, Agent, or Firm* — MARSHALL, GERSTEIN & BORUN LLP

(57) ABSTRACT

The invention provides improved adeno-associated virus (AAV) Factor VIII (FVIII) vectors, including AAV FVIII vectors that produce a functional Factor VIII polypeptide and AAV FVIII vectors with high expression activity.

5 Claims, 21 Drawing Sheets

Specification includes a Sequence Listing.

(56) References Cited

OTHER PUBLICATIONS

European Patent Application No. 14771729.2, Third Party Observations Communication Pursuant to Rule 114(2) EPC, dated Feb. 18, 2019.
Fijnvandraat et al., Recombinant, B-domain deleted factor VIII (r-VIII SQ): pharmacokinetics and initial safety aspects in hemophilia A patients, Thromb. Haemost., 77(2):298-302 (1997).
Ghosh et al., Expanding adeno-associated viral vector capacity: a tale of two vectors, Biotechnol. Genet. Eng. Rev., 24:165-77 (2007).
Gnatenko et al., Human factor VIII can be packaged and functionally expressed in an adeno-associated virus background: applicability to haemophilia A gene therapy, Br. J. Haematol., 104(1):27-36 (Jan. 1999).
Hirsch et al., Little vector, big gene transduction: fragmented genome reassembly of adeno-associated virus, Mol. Ther., 18(1):6-8 (2010).
International Preliminary Report on Patentability, International Application No. PCT/US2014/054960, dated Mar. 15, 2016.
International Search Report and Written Opinion, International Application No. PCT/US2014/054960, mailed Dec. 22, 2014.
Ishiwata et al., Liver-restricted expression of the canine factor VIII gene facilitates prevention of inhibitor formation in factor VIII-deficient mice, J. Gene Med., 11(11):1020-9 (2009).
Japanese Patent Application No. 2016-542067, Notice of Reasons for Rejection, mailed Feb. 14, 2019.
Japanese Patent Application No. 2016-542067, Notice of Reasons for Rejection, mailed Jul. 4, 2018.
Lijun, Research progress of helper adenoviral vector and its mediated gene therapy, International Journal of Virology, 13(5): 151-155 (Oct. 2006).
Lu et al., Complete correction of hemophilia A with adeno-associated viral vectors containing a full-size expression cassette, Hum. Gene Ther., 19(6):648-54 (2008).
McIntosh et al., Therapeutic levels of FVIII following a single peripheral vein administration of rAAV vector encoding a novel human factor VIII variant, Blood, 121(17):3335-44 (2013).
Miao et al., Bioengineering of coagulation factor VIII for improved secretion, Blood, 103(9):3412-9 (2004).
Nathwani et al., Adenovirus-associated virus vector-mediated gene transfer in hemophilia B, N. Engl. J. Med., 365(25):2357-65 (2011).
Rogers et al., Gene therapy for hemophilia, Front Biosci (Landmark Ed.), 20:556-603 (2015).
Sandberg et al., Structural and functional characteristics of the B-domain-deleted recombinant factor VIII protein, r-VIII SQ, Thomb. Haemost., 85(1):93-100 (2001).
Sarkar et al., A single adeno-associated virus (AAV)-murine factor VIII vector partially corrects the hemophilia A phenotype, J. Thromb. Haemost., 1(2):220-6 (2003).
Ward et al., Codon optimization of human factor VIII cDNAs leads to high-level expression, Blood, 117(3):798-807 (2011).
Wu et al., Optimization of self-complementary AAV vectors for liver-directed expression results in sustained correction of hemophilia B at low vector dose, Mol. Ther., 16(2):280-9 (2008).
Yan et al., Inverted terminal repeat sequences are important for intermolecular recombination and circularization of adeno-associated virus genomes, J. Virol., 79(1):364-79 (2005).
Youjin et al., The treatment of hemophilia A: from protein replacement to AAV-mediated gene therapy, Biotechnol. Lett., 31(3):321-8 (Mar. 2009).

\* cited by examiner

Schematic of Proto 6

Insert ApoE/C1 enhancer (forward orientation) into FVIII intron

Schematic of Proto 7

Insert ApoE/C1 enhancer (reverse orientation) into FVIII intron

SEQUENCE LISTING

<160> NUMBER OF SEQ ID NOS: 45

<210> SEQ ID NO 1

<211> LENGTH: 4970
<212> TYPE: DNA
<213> ORGANISM: Adeno-Associated Virus

<400> SEQUENCE: 1

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240
gcccctgttt gctcctccga taactgtggt gaccttggtt aatattcacc agcagcctcc     300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgaggttc tgcttctctg ccaccaggag atactacctg     480
ggggctgtgg agctgagctg ggactacatg cagtctgacc tggggagct gcctgtggat     540 gccaggttcc cccccagagt gcccaagagc ttccccttca acacctctgt ggtgtacaag     600 aagacccctgt ttgtggagtt cactgaccac ctgttcaaca ttgccaagcc caggcccccc     660
tggatgggcc tgctgggccc caccatccag gctgaggtgt atgacactgt ggtgatcacc     720
ctgaagaaca tggccagcca cccttgtgagc ctgcatgctg tgggggtgag ctactggaag     780
gcctctgagg gggctgagta tgatgaccag accagccaga gggagaagga ggatgacaag     840
gtgttccctg ggggcagcca cacctatgtg tggcaggtgc tgaaggagaa tggcccccatg     900 gcctctgacc cctgtgcct gacctacagc tacctgagcc atgtggacct ggtgaaggac     960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga agtctgtgta ctggcatgtg attggcatgg gcaccaccccc tgaggtgcac    1260 agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggatg aagaacaatg aggaggctga ggactatgat    1500
gatgacctga ctgactctga gatggatgtg gtgaggtttg atgatgacaa cagccccagc    1560
ttcatccaga tcaggtctgt ggccaagaag cacccccaaga cctgggtgca ctacattgct    1620
gctgaggagg aggactggga ctatgccccc ctggtgctgg ccccctgatga caggagctac    1680 aagagccagt acctgaacaa tggccccag aggattggca ggaagtacaa gaaggtcagg    1740
ttcatggcct acactgatga aaccttcaag accaggagg ccatccagca tgagtctggc    1800
atcctgggcc cctgctgta tggggagtg ggggacaccc tgctgatcat cttcaagaac    1860
caggccagca ggccctacaa catctacccc catggcatca ctgatgtgag gcccctgtac    1920
agcaggaggc tgcccaaggg ggtgaagcac ctgaaggact ccccatcct gcctggggag    1980 atcttcaagt acaagtggac tgtgactgtg gaggatggcc ccaccaagtc tgaccccagg    2040
tgcctgacca gatactacag cagctttgtg aacatggaga gggacctggc ctctggcctg    2100
attggccccc tgctgatctg ctacaaggag tctgtggacc agagggggcaa ccagatcatg    2160 tctgacaaga ggaatgtgat cctgttctct gtgtttgatg agaacaggag ctggtacctg    2220
```

| | |
|---|---|
| actgagaaca tccagaggtt cctgcccaac cctgctgggg tgcagctgga ggaccctgag | 2280 |
| ttccaggcca gcaacatcat gcacagcatc aatggctatg tgtttgacag cctgcagctg | 2340 |
| tctgtgtgcc tgcatgaggt ggcctactgg tacatcctga gcattggggc ccagactgac | 2400 |
| ttcctgtctg tgttcttctc tggctacacc ttcaagcaca gatggtgta tgaggacacc | 2460 |
| ctgaccctgt tccccttctc tggggagact gtgttcatga gcatggagaa ccctggcctg | 2520 |
| tggattctgg gctgccacaa ctctgacttc aggaacaggg gcatgactgc cctgctgaaa | 2580 |
| gtctccagct gtgacaagaa cactggggac tactatgagg acagctatga ggacatctct | 2640 |
| gcctacctgc tgagcaagaa caatgccatt gagcccagga gcttcagcca gaacccccca | 2700 |
| gtgctgaaga ggcaccagag ggagatcacc aggaccaccc tgcagtctga ccaggaggag | 2760 |
| attgactatg atgacaccat ctctgtggag atgaagaagg aggactttga catctacgac | 2820 |
| gaggacgaga accagagccc caggagcttc agaagaaga ccaggcacta cttcattgct | 2880 |
| gctgtgagag ggctgtggga ctatggcatg agcagcagcc ccatgtgct gaggaacagg | 2940 |
| gcccagtctg gctctgtgcc ccagttcaag aaggtggtgt tccaggagtt cactgatggc | 3000 |
| agcttcaccc agcccctgta cagagggag ctgaatgagc acctgggcct gctgggcccc | 3060 |
| tacatcaggg ctgaggtgga ggacaacatc atggtgacct tcaggaacca ggccagcagg | 3120 |
| ccctacagct tctacagcag cctgatcagc tatgaggagg accagaggca ggggctgag | 3180 |
| cccaggaaga actttgtgaa gcccaatgaa accaagacct acttctggaa ggtgcagcac | 3240 |
| cacatggccc ccaccaagga tgagtttgac tgcaaggcct gggcctactt ctctgatgtg | 3300 |
| gacctggaga aggatgtgca ctctggcctg attggccccc tgctggtgtg ccacaccaac | 3360 |
| accctgaacc ctgcccatgg caggcaggtg actgtgcagg agtttgccct gttcttcacc | 3420 |
| atctttgatg aaaccaagag ctggtacttc actgagaaca tggagaggaa ctgcagggcc | 3480 |
| ccctgcaaca tccagatgga ggaccccacc ttcaaggaga actacaggtt ccatgccatc | 3540 |
| aatggctaca tcatggacac cctgcctggc ctggtgatgg cccaggacca gaggatcagg | 3600 |
| tggtacctgc tgagcatggg cagcaatgag aacatccaca gcatccactt ctctggccat | 3660 |
| gtgttcactg tgaggaagaa ggaggagtac aagatggccc tgtacaacct gtaccctggg | 3720 |
| gtgtttgaga ctgtggagat gctgcccagc aaggctggca tctggagggt ggagtgcctg | 3780 |
| attggggagc acctgcatgc tggcatgagc accctgttcc tggtgtacag caacaagtgc | 3840 |
| cagaccccc tgggcatggc ctctggccac atcagggact tccagatcac tgcctctggc | 3900 |
| cagtatggcc agtgggcccc caagctggcc aggctgcact actctggcag catcaatgcc | 3960 |
| tggagcacca aggagccctt cagctggatc aaggtggacc tgctggcccc catgatcatc | 4020 |
| catggcatca gacccagggg gccaggcag aagttcagca gcctgtacat cagccagttc | 4080 |
| atcatcatgt acagcctgga tggcaagaag tggcagacct cagggcaa cagcactggc | 4140 |
| accctgatgt tgttctttgg caatgtggac agctctggca tcaagcacaa catcttcaac | 4200 |
| ccccccatca ttgccagata catcaggctg cacccacc actacagcat caggagcacc | 4260 |
| ctgaggatgg agctgatggg ctgtgacctg aacagctgca gcatgccct gggcatggag | 4320 |
| agcaaggcca tctctgatgc ccagatcact gccagcagct acttccaccaa catgtttgcc | 4380 |
| acctggagcc ccagcaaggc caggctgcac ctgcagggca ggagcaatgc ctggaggccc | 4440 |
| caggtcaaca ccccaaggga gtggctgcag gtggacttcc agaagaccat gaaggtgact | 4500 |
| ggggtgacca cccagggggt gaagagcctg ctgaccagca tgtatgtgaa ggagttcctg | 4560 |

-continued

| | |
|---|---|
| atcagcagca gccaggatgg ccaccagtgg accctgttct tccagaatgg caaggtgaag | 4620 |
| gtgttccagg gcaaccagga cagcttcacc cctgtggtga acagcctgga ccccccctg | 4680 |
| ctgaccagat acctgaggat tcaccccag agctgggtgc accagattgc cctgaggatg | 4740 |
| gaggtgctgg gctgtgaggc ccaggacctg tactgaaata aaagatcttt attttcatta | 4800 |
| gatctgtgtg ttggtttttt gtgtgaggaa ccctagtga tggagttggc cactccctct | 4860 |
| ctgcgcgctc gctcgctcac tgaggccggg cgaccaaagg tcgcccgacg cccgggcttt | 4920 |
| gcccgggcgg cctcagtgag cgagcgagcg cgcagagagg gagtggccaa | 4970 |

<210> SEQ ID NO 2
<211> LENGTH: 4950
<212> TYPE: DNA
<213> ORGANISM: Adeno-Associated Virus

<400> SEQUENCE: 2

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactgtttg ctgcttgcaa tgtttgccca ttttagggtg gacacaggac | 180 |
| gctgtggttt ctgagccagg gggcgactca gatcccagcc agtggactta gcccctgttt | 240 |
| gctcctccga taactggggt gaccttggtt aatattcacc agcagcctcc cccgttgccc | 300 |
| ctctggatcc actgcttaaa tacgacgag gacagggccc tgtctcctca gcttcaggca | 360 |
| ccaccactga cctgggacag tgaatcgcca ccatgcagat tgagctgagc acctgcttct | 420 |
| tcctgtgcct gctgaggttc tgcttctctg ccaccaggag atactacctg ggggctgtgg | 480 |
| agctgagctg ggactacatg cagtctgacc tggggagct gcctgtggat gccaggttcc | 540 |
| cccccagagt gcccaagagc ttccccttca cacctctgt ggtgtacaag aagaccctgt | 600 |
| tgtggagtt cactgaccac ctgttcaaca ttgccaagcc caggcccccc tggatgggcc | 660 |
| tgctgggccc caccatccag gctgaggtgt atgacactgt ggtgatcacc ctgaagaaca | 720 |
| tggccagcca ccctgtgagc ctgcatgctg tgggggtgag ctactggaag gcctctgagg | 780 |
| gggctgagta tgatgaccag accagccaga gggagaagga ggatgacaag gtgttccctg | 840 |
| ggggcagcca cacctatgtg tggcaggtgc tgaaggagaa tggccccatg gcctctgacc | 900 |
| ccctgtgcct gacctacagc tacctgagcc atgtggacct ggtgaaggac tgaactctg | 960 |
| gcctgattgg ggccctgctg gtgtgcaggg agggcagcct ggccaaggag aagacccaga | 1020 |
| ccctgcacaa gttcatcctg ctgtttgctg tgtttgatga gggcaagagc tggcactctg | 1080 |
| aaaccaagaa cagcctgatg caggacaggg atgctgcctc tgccagggcc tggcccaaga | 1140 |
| tgcacactgt gaatggctat gtgaacagga gcctgcctgg cctgattggc tgccacagga | 1200 |
| agtctgtgta ctggcatgtg attggcatgg gcaccacccc tgaggtgcac agcatcttcc | 1260 |
| tggagggcca caccttcctg gtcaggaacc acaggcaggc cagcctggag atcagcccca | 1320 |
| tcaccttcct gactgcccag accctgctga tggacctggg ccagttcctg ctgttctgcc | 1380 |
| acatcagcag ccaccagcat gatggcatgg aggcctatgt gaaggtggac agctgccctg | 1440 |
| aggagcccca gctgaggatg aagaacaatg aggaggctga ggactatgat gatgacctga | 1500 |
| ctgactctga gatggatgtg gtgaggtttg atgatgacaa cagccccagc ttcatccaga | 1560 |
| tcaggtctgt ggccaagaag caccccaaga cctgggtgca ctacattgct gctgaggagg | 1620 |
| aggactggga ctatgccccc ctggtgctgg cccctgatga caggagctac aagagccagt | 1680 |
| acctgaacaa tggcccccag aggattggca ggaagtacaa gaaggtcagg ttcatggcct | 1740 |

```
acactgatga aaccttcaag accagggagg ccatccagca tgagtctggc atcctgggcc    1800
ccctgctgta tggggaggtg ggggacaccc tgctgatcat cttcaagaac caggccagca    1860
ggccctacaa catctacccc catggcatca ctgatgtgag gcccctgtac agcaggaggc    1920
tgcccaaggg ggtgaagcac ctgaaggact tccccatcct gcctgggag atcttcaagt     1980
acaagtggac tgtgactgtg gaggatggcc ccaccaagtc tgaccccagg tgcctgacca    2040
gatactacag cagctttgtg aacatggaga gggacctggc ctctggcctg attgcccccc    2100
tgctgatctg ctacaaggag tctgtggacc agaggggcaa ccagatcatg tctgacaaga    2160
ggaatgtgat cctgttctct gtgtttgatg agaacaggg ctggtacctg actgagaaca     2220
tccagaggtt cctgcccaac cctgctgggg tgcagctgga ggaccctgag ttccaggcca    2280
gcaacatcat gcacagcatc aatggctatg tgtttgacag cctgcagctg tctgtgtgcc    2340
tgcatgaggt ggcctactgg tacatcctga gcattgggc ccagactgac ttcctgtctg     2400
tgttcttctc tggctacacc ttcaagcaca agatggtgta tgaggacacc ctgaccctgt    2460
tccccttctc tggggagact gtgttcatga gcatggagaa ccctggcctg tggattctgg    2520
gctgccacaa ctctgacttc aggaacaggg gcatgactgc cctgctgaaa gtctccagct    2580
gtgacaagaa cactggggac tactatgagg acagctatga ggacatctct gcctacctgc    2640
tgagcaagaa caatgccatt gagcccagga gcttcagcca gaaccccca gtgctgaaga     2700
ggcaccagag ggagatcacc aggaccaccc tgcagtctga ccaggaggag attgactatg    2760
atgacaccat ctctgtggag atgaagaagg aggactttga catctacgac gaggacgaga    2820
accagagccc caggagcttc cagaagaaga ccaggcacta cttcattgct gctgtggaga    2880
ggctgtggga ctatgcatg agcagcagcc cccatgtgct gaggaacagg gcccagtctg     2940
gctctgtgcc ccagttcaag aaggtggtgt tccaggagtt cactgatggc agcttcaccc    3000
agccctgta cagaggggag ctgaatgagc acctgggcct gctgggcccc tacatcaggg     3060
ctgaggtgga ggacaacatc atggtgacct tcaggaacca ggccagcagg ccctacagct    3120
tctacagcag cctgatcagc tatgaggagg accagaggca gggggctgag cccaggaaga    3180
actttgtgaa gcccaatgaa accaagacct acttctggaa ggtgcagcac cacatggccc    3240
ccaccaagga tgagttttgac tgcaaggcct gggcctactt ctctgatgtg acctggagga    3300
aggatgtgca ctctggcctg attggccccc tgctggtgtg ccacaccaac accctgaacc    3360
ctgcccatgg caggcaggtg actgtgcagg agtttgccct gttcttcacc atctttgatg    3420
aaaccaagag ctggtacttc actgagaaca tggagaggac ctgcagggcc ccctgcaaca    3480
tccagatgga ggaccccacc ttcaaggaga actacaggtt ccatgccatc aatggctaca    3540
tcatggacac cctgcctggc ctggtgatgg cccaggacca gaggatcagg tggtacctgc    3600
tgagcatggg cagcaatgag aacatccaca gcatccactt ctctggccat gtgttcactg    3660
tgaggaagaa ggaggagtac aagatggccc tgtacaacct gtaccctggg gtgttgaga    3720
ctgtggagat gctgcccagc aaggctggca tctggagggt ggagtgcctg attggggagc    3780
acctgcatgc tggcatgagc accctgttcc tggtgtacag caacaagtgc cagaccccc    3840
tgggcatggc ctctggccac atcagggact tccagatcac tgcctctggc cagtatggcc    3900
agtgggcccc caagctggcc aggctgcact actctggcag catcaatgcc tggagcacca    3960
aggagccctt cagctggatc aaggtggacc tgctggcccc catgatcatc catggcatca    4020
agacccaggg ggccaggcag aagttcagca gcctgtacat cagccagttc atcatcatgt    4080
```

```
acagcctgga tggcaagaag tggcagacct acaggggcaa cagcactggc accctgatgg    4140
tgttctttgg caatgtggac agctctggca tcaagcacaa catcttcaac cccccccatca   4200 ttgccagata catcaggctg caccccaccc actacagcat caggagcacc ctgaggatgg    4260
agctgatggg ctgtgacctg aacagctgca gcatgcccct gggcatggag agcaaggcca    4320
tctctgatgc ccagatcact gccagcagct acttcaccaa catgtttgcc acctggagcc    4380
ccagcaaggc caggctgcac ctgcagggca ggagcaatgc ctggaggccc caggtcaaca    4440
accccaagga gtggctgcag gtggacttcc agaagaccat gaaggtgact ggggtgacca    4500 cccaggggt gaagagcctg ctgaccagca tgtatgtgaa ggagttcctg atcagcagca    4560
gccaggatgg ccaccagtgg accctgttct tccagaatgg caaggtgaag gtgttccagg    4620
gcaaccagga cagcttcacc cctgtggtga cagcctgga ccccccccctg ctgaccagat    4680 acctgaggat tcaccccag agctgggtgc accagattgc cctgaggatg gaggtgctgg    4740
gctgtgaggc ccaggacctg tactgaaata aagatctttt attttcatta gatctgtgtg    4800
ttggtttttt gtgtgagtga tggagttggc cactccctct ctgcgcgctc gctcgctcac    4860
tgaggccggg cgaccaaagg tcgcccgacg cccgggcttt gcccgggcgg cctcagtgag    4920
cgagcgagcg cgcagagagg gagtggccaa                                    4950

<210> SEQ ID NO 3
<211> LENGTH: 4983
<212> TYPE: DNA
<213> ORGANISM: Adeno-Associated Virus

<400> SEQUENCE: 3
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactgggcg actcagatcc cagccagtgg acttagcccc tgtttgctcc    180
tccgataact ggggtgacct tggttaatat tcaccagcag cctcccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac aacctggctc agaaaccaca gcgtcctgtg    540
tccattctaa ttttttcctttt cttcacgcag atttcctcct agagtgccaa atcttttcc    600 attcaacacc tcagtcgtgt acaaaaagac tctgtttgta gaattcacgg atcacctttt    660
caacatcgct aagcccaggc cccctggat gggcctgctg ggcccaccga tccaggctga    720
ggtgtatgac actgtggtga tcaccctgaa gaacatggcc agccaccctg tgagcctgca    780
tgctgtgggg gtgagctact ggaaggcctc tgaggggcct gagtatgatg accagaccag    840 ccagaggga aaggaggatg acaaggtgtt ccctgggggc agccacacct atgtgtggca    900
ggtgctgaag gagaatggcc ccatggcctc tgaccccctg tgcctgacct acagctacct    960
gagccatgtg gacctggtga aggacctgaa ctctggcctg attggggccc tgctggtgtg    1020
cagggagggc agcctggcca aggagaagac ccagaccctg cacaagttca tcctgctgtt    1080
tgctgtgttt gatgagggca agagctggca ctctgaaacc aagaacagcc tgatgcagga    1140
cagggatgct gcctctgcca gggcctgcc caagatgcac actgtgaatg ctatgtgaa    1200 caggagcctg cctggcctga ttggctgcca caggaagtct gtgtactggc atgtgattgg    1260
```

```
catgggcacc acccctgagg tgcacagcat cttcctggag ggccacacct tcctggtcag    1320
gaaccacagg caggccagcc tggagatcag ccccatcacc ttcctgactg cccagaccct    1380
gctgatggac ctgggccagt tcctgctgtt ctgccacatc agcagccacc agcatgatgg    1440
catggaggcc tatgtgaagg tggacagctg ccctgaggag ccccagctga ggatgaagaa    1500
caatgaggag gctgaggact atgatgatga cctgactgac tctgagatgg atgtggtgag    1560
gtttgatgat gacaacagcc ccagcttcat ccagatcagg tctgtggcca agaagcaccc    1620
caagacctgg gtgcactaca ttgctgctga ggaggaggac tgggactatg ccccctggt     1680 gctgcccct gatgacagga gctacaagag ccagtacctg aacaatggcc cccagaggat     1740
tggcaggaag tacaagaagg tcaggttcat ggcctacact gatgaaacct tcaagaccag    1800
ggaggccatc cagcatgagt ctggcatcct gggcccccctg ctgtatgggg aggtggggga   1860
caccctgctg atcatcttca agaaccaggc cagcaggccc tacaacatct accccatgg     1920 catcactgat gtgaggcccc tgtacagcag gaggctgccc aagggggtga agcacctgaa    1980
ggacttcccc atcctgcctg ggagatcttc aagtacaag tggactgtga ctgtggagga    2040
tggccccacc aagtctgacc ccaggtgcct gaccagatac tacagcagct tgtgaacat    2100 ggagagggac ctggcctctg gcctgattgg cccctgctg atctgctaca aggagtctgt    2160
ggaccagagg ggcaaccaga tcatgtctga aagaggaat gtgatcctgt tctctgtgtt    2220
tgatgagaac aggagctggt acctgactga aacatccag aggttcctgc caaccctgc     2280 tggggtgcag ctggaggacc ctgagttcca ggccagcaac atcatgcaca gcatcaatgg    2340
ctatgtgttt gacagcctgc agctgtctgt gtgcctgcat gaggtggcct actggtacat    2400
cctgagcatt ggggcccaga ctgacttcct gtctgtgttc ttctctggct acaccttcaa    2460
gcacaagatg gtgtatgagg acaccctgac cctgttcccc ttctctgggg agactgtgtt    2520
catgagcatg gagaaccctg gcctgtggat tctgggctgc cacaactctg acttcaggaa    2580
caggggcatg actgccctgc tgaaagtctc cagctgtgac aagaacactg gggactacta    2640
tgaggacagc tatgaggaca tctctgccta cctgctgagc aagaacaatg ccattgagcc    2700
caggagcttc agccagaacc ccccagtgct gaagaggcac cagagggaga tcaccaggac    2760
caccctgcag tctgaccagg aggagattga ctatgatgac accatctctg tggagatgaa    2820
gaaggaggac tttgacatct acgacgagga cgagaaccag agcccagga gcttccagaa    2880 gaagaccagg cactacttca ttgctgctgt ggagaggctg tgggactatg catgagcag    2940 cagccccat gtgctgagga acagggccca gtctggctct gtgccccagt tcaagaaggt    3000
ggtgttccag gagttcactg atggcagctt cacccagccc ctgtacagag gggagctgaa    3060
tgagcacctg ggcctgctgg gccctacat cagggctgag gtgaggaca acatcatggt    3120 gaccttcagg aaccaggcca gcaggcccta cagcttctac agcagcctga tcagctatga    3180
ggaggaccag aggcaggggg ctgagcccag gaagaacttt gtgaagccca atgaaaccaa    3240
gacctacttc tggaaggtgc agcaccacat ggcccccacc aaggatgagt tgactgcaa     3300 ggcctgggcc tacttctctg atgtggacct ggagaaggat gtgcactctg gcctgattgg    3360 cccccctgctg gtgtgccaca ccaacaccct gaaccctgcc catggcaggc aggtgactgt    3420
gcaggagttt gccctgttct tcaccatctt tgatgaaacc aagagctggt acttcactga    3480
gaacatggag aggaactgca gggcccctg caacatccag atggaggacc ccaccttcaa    3540
ggagaactac aggttccatg ccatcaatgg ctacatcatg gacaccctgc ctggcctggt    3600
```

```
gatggcccag gaccagagga tcaggtggta cctgctgagc atgggcagca atgagaacat    3660
ccacagcatc cacttctctg gccatgtgtt cactgtgagg aagaaggagg agtacaagat    3720
ggccctgtac aacctgtacc ctggggtgtt tgagactgtg gagatgctgc ccagcaaggc    3780
tggcatctgg agggtggagt gcctgattgg ggagcacctg catgctggca tgagcaccct    3840
gttcctggtg tacagcaaca agtgccagac cccctgggc atggcctctg ccacatcag    3900
ggacttccag atcactgcct ctggccagta tggccagtgg gccccaagc tggccaggct    3960
gcactactct ggcagcatca tgcctggag caccaaggag cccttcagct ggatcaaggt    4020
ggacctgctg gcccccatga tcatccatgg catcaagacc caggggggcca ggcagaagtt    4080
cagcagcctg tacatcagcc agttcatcat catgtacagc ctggatggca agaagtggca    4140
gacctacagg ggcaacagca ctggcaccct gatggtgttc tttggcaatg tggacagctc    4200
tggcatcaag cacaacatct tcaaccccc catcattgcc agatacatca ggctgcaccc    4260
cacccactac agcatcagga gcaccctgag gatggagctg atgggctgtg acctgaacag    4320
ctgcagcatg cccctgggca tggagagcaa ggccatctct gatgcccaga tcactgccag    4380
cagctacttc accaacatgt tgccacctg gagcccagc aaggccaggc tgcacctgca    4440
gggcaggagc aatgcctgga ggccccaggt caacaaccc aaggagtggc tgcaggtgga    4500
cttccagaag accatgaagg tgactggggt gaccacccag ggggtgaaga gcctgctgac    4560
cagcatgtat gtgaaggagt tcctgatcag cagcagccag gatggccacc agtgaccct    4620
gttcttccag aatggcaagg tgaaggtgtt ccagggcaac caggacagct caccctgt    4680
ggtgaacagc ctggaccccc ccctgctgac cagatacctg aggattcacc ccagagctg    4740
ggtgcaccag attgccctga ggatggaggt gctgggctgt gaggcccagg acctgtacta    4800
ataaaagatc tttattttca ttagatctgt gtgttggttt tttgtgtgag tgatggagtt    4860
ggccactccc tctctgcgcg ctcgctcgct cactgaggcc gggcgaccaa aggtcgcccg    4920
acgcccgggc tttgcccggg cggcctcagt gagcgagcga gcgcgcagag agggagtggc    4980
caa                                                                  4983

<210> SEQ ID NO 4
<211> LENGTH: 4984
<212> TYPE: DNA
<213> ORGANISM: Adeno-Associated Virus

<400> SEQUENCE: 4
ttggccactc cctctctgcg cgctcgctcg ctcactgagg ccgccgggc aaagcccggg      60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac accctaaaat gggcaaacat tgcaagcagc    540
aaacattcta attttttcctt tcttcacgca gatttcctcc tagagtgcca aaatcttttc    600
cattcaacac ctcagtcgtg tacaaaaaga ctctgttttgt agaattcacg atcacctttt    660
tcaacatcgc taagcccagg ccccctgga tgggcctgct gggccccacc atccaggctg    720
```

```
aggtgtatga cactgtggtg atcaccctga agaacatggc cagccaccct gtgagcctgc    780
atgctgtggg ggtgagctac tggaaggcct ctgaggggga tgagtatgat gaccagacca    840
gccagaggga aaggaggat  gacaaggtgt tccctggggg cagccacacc tatgtgtggc    900
aggtgctgaa ggagaatggc cccatggcct ctgacccct  gtgcctgacc tacagctacc    960
tgagccatgt ggacctggtg aaggacctga actctggcct gattgggggcc tgctggtgt   1020 gcagggaggg cagcctggcc aaggagaaga cccagaccct gcacaagttc atcctgctgt   1080
ttgctgtgtt tgatgagggc aagagctggc actctgaaac caagaacagc ctgatgcagg   1140
acagggatgc tgcctctgcc agggcctggc ccaagatgca cactgtgaat ggctatgtga   1200
acaggagcct gcctggcctg attggctgcc acaggaagtc tgtgtactgg catgtgattg   1260
gcatgggcac caccctgag  gtgcacagca tcttcctgga gggccacacc ttcctggtca   1320
ggaaccacag gcaggccagc ctggagatca gccccatcac cttcctgact gcccagaccc   1380
tgctgatgga cctgggccag ttcctgctgt tctgccacat cagcagccac cagcatgatg   1440
gcatggaggc ctatgtgaag gtggacagct gccctgagga gccccagctg aggatgaaga   1500
acaatgagga ggctgaggac tatgatgatg acctgactga ctctgagatg gatgtggtga   1560
ggtttgatga tgacaacagc cccagcttca tccagatcag gtctgtggcc aagaagcacc   1620
ccaagacctg ggtgcactac attgctgctg aggaggagga ctgggactat gccccctgg   1680 tgctggcccc tgatgacagg agctacaaga gccagtacct gaacaatggc ccccagagga   1740
ttggcaggaa gtacaagaag gtcaggttca tggcctacac tgatgaaacc ttcaagacca   1800
gggaggccat ccagcatgag tctggcatcc tgggcccct  gctgtatggg gaggtgggg   1860 acaccctgct gatcatcttc aagaaccagg ccagcaggcc ctacaacatc tacccccatg   1920
gcatcactga tgtgaggccc ctgtacagca ggaggctgcc caagggggtg aagcacctga   1980
aggacttccc catcctgcct ggggagatct tcaagtacaa gtggactgtg actgtggagg   2040
atggccccac caagtctgac cccaggtgcc tgaccagata ctacagcagc tttgtgaaca   2100
tggagaggga cctggcctct ggcctgattg gcccctgct  gatctgctac aaggagtctg   2160
tggaccagag gggcaaccag atcatgtctg acaagaggaa tgtgatcctg ttctctgtgt   2220
ttgatgagaa caggagctgg tacctgactg agaacatcca gaggttcctg cccaaccctg   2280
ctggggtgca gctggaggac cctgagttcc aggccagcaa catcatgcac agcatcaatg   2340
gctatgtgtt tgacagcctg cagctgtctg tgtgcctgca tgaggtggcc tactggtaca   2400
tcctgagcat tggggcccag actgacttcc tgtctgtgtt cttctctggc tacaccttca   2460
agcacaagat ggtgtatgag gacaccctga ccctgttccc cttctctggg gagactgtgt   2520
tcatgagcat ggagaaccct ggcctgtgga ttctgggctg ccacaactct gacttcagga   2580
acaggggcat gactgccctg ctgaaagtct ccagctgtga caagaacact ggggactact   2640
atgaggacag ctatgaggac atctctgcct acctgctgag caagaacaat gccattgagc   2700
ccaggagctt cagccagaac ccccagtgc  tgaagaggca ccagagggag atcaccagga   2760
ccaccctgca gtctgaccag gaggagattg actatgatga ccatctct  gtggagatga   2820 agaaggagga ctttgacatc tacgacgagg acgagaacca gagccccagg gcttccaga   2880 agaagaccag gcactacttc attgctgctg tggagaggct gtgggactat gcatgagca   2940 gcagccccca tgtgctgagg aacagggccc agtctggctc tgtgccccag ttcaagaagg   3000
tggtgttcca ggagttcact gatggcagct tcacccagcc cctgtacaga ggggagctga   3060
```

| | |
|---|---:|
| atgagcacct gggcctgctg ggcccctaca tcagggctga ggtggaggac aacatcatgg | 3120 |
| tgaccttcag gaaccaggcc agcaggccct acagcttcta cagcagcctg atcagctatg | 3180 |
| aggaggacca gaggcagggg gctgagccca ggaagaactt tgtgaagccc aatgaaacca | 3240 |
| agacctactt ctggaaggtg cagcaccaca tggcccccac caaggatgag tttgactgca | 3300 |
| aggcctgggc ctacttctct gatgtggacc tggagaagga tgtgcactct ggcctgattg | 3360 |
| gcccctgct ggtgtgccac accaacaccc tgaaccctgc ccatggcagg caggtgactg | 3420 |
| tgcaggagtt tgccctgttc ttcaccatct ttgatgaaac caagagctgg tacttcactg | 3480 |
| agaacatgga gaggaactgc agggcccct gcaacatcca gatggaggac cccaccttca | 3540 |
| aggagaacta caggttccat gccatcaatg ctacatcat ggacaccctg cctggcctgg | 3600 |
| tgatggccca ggaccagagg atcaggtggt acctgctgag catgggcagc aatgagaaca | 3660 |
| tccacagcat ccacttctct ggccatgtgt tcactgtgag gaagaaggag gagtacaaga | 3720 |
| tggccctgta caacctgtac cctggggtgt tgagactgt ggagatgctg cccagcaagg | 3780 |
| ctggcatctg gagggtggag tgcctgattg gggagcacct gcatgctggc atgagcaccc | 3840 |
| tgttcctggt gtacagcaac aagtgccaga ccccctggg catggcctct ggccacatca | 3900 |
| gggacttcca gatcactgcc tctggccagt atggccagtg ggccccaag ctggccaggc | 3960 |
| tgcactactc tggcagcatc aatgcctgga gcaccaagga gcccttcagc tggatcaagg | 4020 |
| tggacctgct ggcccccatg atcatccatg gcatcaagac ccaggggcc aggcagaagt | 4080 |
| tcagcagcct gtacatcagc cagttcatca tcatgtacag cctggatggc aagaagtggc | 4140 |
| agacctacag gggcaacagc actggcaccc tgatggtgtt cttggcaat gtggacagct | 4200 |
| ctggcatcaa gcacaacatc ttcaaccccc ccatcattgc cagatacatc aggctgcacc | 4260 |
| ccacccacta cagcatcagg agcacccga ggatggagct gatgggctgt gacctgaaca | 4320 |
| gctgcagcat gccctgggc atggagagca aggccatctc tgatgcccag atcactgcca | 4380 |
| gcagctactt caccaacatg tttgccacct ggagccccag caaggccagg ctgcacctgc | 4440 |
| agggcaggag caatgcctgg aggcccagg tcaacaaccc caaggagtgg ctgcaggtgg | 4500 |
| acttccagaa gaccatgaag gtgactgggg tgaccccca ggggtgaag agcctgctga | 4560 |
| ccagcatgta tgtgaaggag ttcctgatca gcagcagcca ggatggccac cagtggaccc | 4620 |
| tgttcttcca gaatggcaag gtgaaggtgt tccaggcaa ccaggacagc ttcacccctg | 4680 |
| tggtgaacag cctggaccc ccctgctga ccagataCct gaggattcac ccccagagct | 4740 |
| gggtgcacca gattgccctg aggatggagg tgctgggctg tgaggcccag gacctgtact | 4800 |
| aataaaagat ctttattttc attagatctg tgtgttggtt ttttgtgtga gtgatggagt | 4860 |
| tggccactcc ctctctgcgc gctcgctcgc tcactgaggc cgggcgacca aaggtcgccc | 4920 |
| gacgcccggg ctttgcccgg gcggcctcag tgagcgagcg agcgcgcaga gagggagtgg | 4980 |
| ccaa | 4984 |

```
<210> SEQ ID NO 5
<211> LENGTH: 4805
<212> TYPE: DNA
<213> ORGANISM: Adeno-Associated Virus

<400> SEQUENCE: 5
```

| | |
|---|---:|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgtttg ctgcttgcaa tgtttgccca ttttagggtg | 180 |

```
gacacaggac gctgtggttt ctgagccagg gggcgactca gatcccagcc agtggactta    240
gccctgtttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgaggttc tgcttctctg ccaccaggag atactacctg    480
ggggctgtgg agctgagctg ggactacatg cagtctgacc tggggagct gcctgtggat    540 gccaggttcc cccccagagt gcccaagagc ttccccttca cacctctgt ggtgtacaag    600 aagaccctgt tgtggagtt cactgaccac ctgttcaaca ttgccaagcc caggcccccc    660
tggatgggcc tgctgggccc caccatccag gctgaggtgt atgacactgt ggtgatcacc    720
ctgaagaaca tggccagcca ccctgtgagc ctgcatgctg tgggggtgag ctactggaag    780
gcctctgagg gggctgagta tgatgaccag accagccaga gggagaagga ggatgacaag    840
gtgttccctg gggcagcca cacctatgtg tggcaggtgc tgaaggagaa tggccccatg    900
gcctctgacc ccctgtgcct gacctacagc tacctgagcc atgtggacct ggtgaaggac    960
ctgaactctg gcctgattgg ggccctgctg gtgtgcaggg agggcagcct ggccaaggag   1020
aagacccaga ccctgcacaa gttcatcctg ctgtttgctg tgtttgatga gggcaagagc   1080
tggcactctg aaaccaagaa cagcctgatg caggacaggg atgctgcctc tgccagggcc   1140
tggcccaaga tgcacactgt gaatggctat gtgaacagga gcctgcctgg cctgattggc   1200
tgccacagga agtctgtgta ctggcatgtg attggcatgg gcaccacccc tgaggtgcac   1260
agcatcttcc tggagggcca caccttcctg gtcaggaacc acaggcaggc cagcctggag   1320
atcagcccca tcaccttcct gactgcccag accctgctga tggacctggg ccagttcctg   1380
ctgttctgcc acatcagcag ccaccagcat gatggcatgg aggcctatgt gaaggtggac   1440
agctgccctg aggagcccca gctgaggatg aagaacaatg aggaggctga ggactatgat   1500
gatgacctga ctgactctga gatggatgtg gtgaggtttg atgatgacaa cagccccagc   1560
ttcatccaga tcaggtctgt ggccaagaag cacccccaaga cctgggtgca ctacattgct   1620
gctgaggagg aggactggga ctatgccccc ctggtgctgg cccctgatga caggagctac   1680
aagagccagt acctgaacaa tggccccag aggattggca ggaagtacaa gaaggtcagg   1740
ttcatggcct acactgatga aaccttcaag accaggagg ccatccagca tgagtctggc   1800
atcctgggcc cctgctgta tggggaggtg ggggacaccc tgctgatcat cttcaagaac   1860
caggccagca ggccctacaa catctacccc catggcatca ctgatgtgag gcccctgtac   1920
agcaggaggc tgcccaaggg ggtgaagcac ctgaaggact ccccatcct gcctggggag   1980 atcttcaagt acaagtggac tgtgactgtg gaggatggcc ccaccaagtc tgaccccagg   2040
tgcctgacca gatactacag cagctttgtg aacatggaga gggacctggc ctctggcctg   2100 attgccccc tgctgatctg ctacaaggag tctgtggacc agaggggcaa ccagatcatg   2160
tctgacaaga ggaatgtgat cctgttctct gtgtttgatg agaacaggag ctggtacctg   2220
actgagaaca tccagaggtt cctgcccaac cctgctgggg tgcagctgga ggaccctgag   2280
ttccaggcca gcaacatcat gcacagcatc aatggctatg tgtttgacag cctgcagctg   2340
tctgtgtgcc tgcatgaggt ggcctactgg tacatcctga gcattggggc ccagactgac   2400
ttcctgtctg tgttcttctc tggctacacc ttcaagcaca gatggtgta tgaggacacc   2460 ctgacccctgt tccccttctc tggggagact gtgttcatga gcatggagaa ccctggcctg   2520
```

```
tggattctgg gctgccacaa ctctgacttc aggaacaggg gcatgactgc cctgctgaaa      2580
gtctccagct gtgacaagaa cactggggac tactatgagg acagctatga ggacatctct      2640
gcctacctgc tgagcaagaa caatgccatt gagcccagga gcttccagaa gaagaccagg      2700
cactacttca ttgctgctgt ggagaggctg tgggactatg gcatgagcag cagcccccat      2760
gtgctgagga cagggccca gtctggctct gtgccccagt tcaagaaggt ggtgttccag       2820
gagttcactg atggcagctt cacccagccc ctgtacagag gggagctgaa tgagcacctg      2880
ggcctgctgg gcccctacat cagggctgag gtggaggaca acatcatggt gaccttcagg      2940
aaccaggcca gcaggcccta cagcttctac agcagcctga tcagctatga ggaggaccag      3000
aggcaggggg ctgagcccag gaagaacttt gtgaagccca atgaaaccaa gacctacttc      3060
tggaaggtgc agcaccacat ggccccacc aaggatgagt ttgactgcaa ggcctgggcc       3120
tacttctctg atgtggacct ggagaaggat gtgcactctg gcctgattgg cccctgctg       3180 gtgtgccaca ccaacaccct gaaccctgcc catggcaggc aggtgactgt gcaggagttt      3240
gccctgttct tcaccatctt tgatgaaacc aagagctgga cttcactga gaacatggag       3300 aggaactgca gggccccctg caacatccag atggaggacc ccaccttcaa ggagaactac      3360
aggttccatg ccatcaatgg ctacatcatg gacaccctgc ctggcctggt gatggcccag      3420
gaccagagga tcaggtggta cctgctgagc atgggcagca atgagaacat ccacagcatc      3480
cacttctctg gccatgtgtt cactgtgagg aagaaggagg agtacaagat ggccctgtac      3540
aacctgtacc ctgggggtgtt tgagactgtg gagatgctgc ccagcaaggc tggcatctgg      3600
agggtggagt gcctgattgg ggagcacctg catgctggca tgagcaccct gttcctggtg      3660
tacagcaaca agtgccagac cccctgggc atggcctctg ccacatcag ggacttccag         3720 atcactgcct ctggccagta tggccagtgg gcccccaagc tggccaggct gcactactct      3780
ggcagcatca atgcctggag caccaaggag cccttcagct ggatcaaggt ggacctgctg      3840
gcccccatga tcatccatgg catcaagacc cagggggcca ggcagaagtt cagcagcctg      3900
tacatcagcc agttcatcat catgtacagc ctggatggca agaagtggca gacctacagg      3960
ggcaacagca ctggcacct gatggtgttc tttggcaatg tggacagctc tggcatcaag       4020
cacaacatct tcaaccccc catcattgcc agatacatca ggctgcaccc cacccactac      4080
agcatcagga gcaccctgag gatggagctg atgggctgtg acctgaacag ctgcagcatg      4140
cccctgggca tggagagcaa ggccatctct gatgcccaga tcactgccag cagctacttc      4200
accaacatgt ttgccacctg gagccccagc aaggccaggc tgcacctgca gggcaggagc      4260
aatgcctgga ggccccaggt caacaacccc aaggagtggc tgcaggtgga cttccagaag      4320
accatgaagg tgactggggt gaccacccag ggggtgaaga gcctgctgac cagcatgtat      4380
gtgaaggagt tcctgatcag cagcagccag gatggccacc agtggaccct gttcttccag      4440
aatggcaagg tgaaggtgtt ccagggcaac caggacagct tcacccctgt ggtgaacagc      4500 ctggacccc cctgctgac cagataccctg aggattcacc cccagagctg ggtgcaccag       4560
attgccctga ggatggaggt gctgggctgt gaggcccagg acctgtactg aaataaaaga      4620 tcttttatttt cattagatct gtgtgttggt tttttgtgtg aggaaccct agtgatggag      4680 ttggccactc cctctctgcg cgctcgctcg ctcactgagg ccgggcgacc aaaggtcgcc      4740
cgacgcccgg gctttgcccg ggcggcctca gtgagcgagc gagcgcgcag agagggagtg      4800
gccaa                                                                  4805
```

```
<210> SEQ ID NO 6
<211> LENGTH: 4934
<212> TYPE: DNA
<213> ORGANISM: Adeno-Associated Virus

<400> SEQUENCE: 6
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggcatgtcct gtagggtctg atcggggcca ggattgtggg gatgtaagtc    600
tgcttggagg aaggtgcaga catcgggtta ggatggttgt gatgctattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg   1080
gtgaaggacc tgaactctgg cctgattggg gccctgctgg tgtgcaggga gggcagcctg   1140
gccaaggaga gacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccaccct   1380 gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagcccag ctgaggatga agaacaatga ggaggctgag   1620
gactatgatg atgacctgac tgactctgag atggatgtga tgagggttga tgatgacaac   1680
agccccagct tcatccagat caggtctgtg gccaagaagc accccaagac ctgggtgcac   1740
tacattgctg ctgaggagga ggactggac tatgcccccc tggtgctggc ccctgatgac   1800
aggagctaca agagccagta cctgaacaat ggccccccaga ggattggcag aagtacaag   1860 aaggtcaggt tcatggccta cactgatgaa accttcaaga ccagggaggc catccagcat   1920
gagtctggca tcctgggccc cctgctgtat gggaggtgg gggacaccct gctgatcatc   1980
ttcaagaacc aggccagcag gccctacaac atctaccccc atggcatcac tgatgtgagg   2040 ccctgtaca gcaggaggct gcccaagggg tgaagcacc tgaaggactt ccccatcctg   2100 cctgggaga tcttcaagta caagtggact gtgactgtgg aggatggccc caccaagtct   2160
```

```
gaccccaggt gcctgaccag atactacagc agctttgtga acatggagag ggacctggcc    2220
tctggcctga ttggcccect gctgatctgc tacaaggagt ctgtggacca gaggggcaac    2280
cagatcatgt ctgacaagag gaatgtgatc ctgttctctg tgtttgatga aacaggagc     2340 tggtacctga ctgagaacat ccagaggttc ctgcccaacc ctgctggggt gcagctggag    2400
gaccctgagt tccaggccag caacatcatg cacagcatca atggctatgt gtttgacagc    2460
ctgcagctgc tgtgtgcct gcatgaggtg gcctactggt acatcctgag cattggggcc     2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg gagaggctgt gggactatgg catgagcagc    2880
agcccccatg tgctgaggaa cagggcccag tctggctctg tgcccagtt caagaaggtg     2940 gtgttccagg agttcactga tggcagcttc acccagcccc tgtacagagg ggagctgaat    3000
gagcacctgg gcctgctggg ccctacatc agggctgagg tggaggacaa catcatggtg     3060
accttcagga accaggccag caggccctac agcttctaca gcagcctgat cagctatgag    3120
gaggaccaga ggcaggggc tgagcccagg aagaactttg tgaagcccaa tgaaaccaag     3180
acctacttct ggaaggtgca gcaccacatg gcccccacca aggatgagtt tgactgcaag    3240
gcctgggcct acttctctga tgtggacctg gagaaggatg tgcactctgg cctgattggc    3300
cccctgctgg tgtgccacac caacaccctg aaccctgccc atggcaggca ggtgactgtg    3360 caggagttg ccctgttctt caccatcttt gatgaaacca gagctggta cttcactgag      3420 aacatggaga ggaactgcag ggcccctgc aacatccaga tggaggaccc caccttcaag     3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc ccctgggca tggcctctgg ccacatcagg     3840
gacttccaga tcactgcctc tggccagtat ggccagtggg ccccaagct ggccaggctg     3900 cactactctg gcagcatcaa tgcctggagc accaaggagc ccttcagctg gatcaaggtg    3960
gacctgctgg cccccatgat catccatggc atcaagaccc aggggccag gcagaagttc     4020 agcagcctgt acatcagcca gttcatcatc atgtacagcc tggatggcaa gaagtggcag    4080
acctacaggg gcaacagcac tggcacccg atggtgttct ttggcaatgt ggacagctct     4140
ggcatcaagc acaacatctt caaccccccc atcattgcca gatacatcag gctgcacccc   4200
acccactaca gcatcaggag cacccctgagg atggagctga tgggctgtga cctgaacagc   4260
tgcagcatgc ccctgggcat ggagagcaag gccatctctg atgcccagat cactgccagc   4320
agctacttca ccaacatgtt tgccacctgg agccccagca aggccaggct gcacctgcag    4380
ggcaggagca atgcctggag gccccaggtc aacaaccca aggagtggct gcaggtggac    4440
ttccagaaga ccatgaaggt gactgggtg accacccagg gggtgaagag cctgctgacc    4500
agcatgtatg tgaaggagtt cctgatcagc agcagccagg atggccacca gtggacccctg  4560
```

| | | |
|---|---|---|
| ttcttccaga atggcaaggt gaaggtgttc cagggcaacc aggacagctt cacccctgtg | 4620 | |
| gtgaacagcc tggacccccc cctgctgacc agatacctga ggattcaccc ccagagctgg | 4680 | |
| gtgcaccaga ttgccctgag gatggaggtg ctgggctgtg aggcccagga cctgtactga | 4740 | |
| aataaaagat ctttattttc attagatctg tgtgttggtt ttttgtgtga ggaaccccta | 4800 | |
| gtgatggagt tggccactcc ctctctgcgc gctcgctcgc tcactgaggc cgggcgacca | 4860 | |
| aaggtcgccc gacgcccggg ctttgcccgg gcggcctcag tgagcgagcg agcgcgcaga | 4920 | |
| gagggagtgg ccaa | 4934 | |

<210> SEQ ID NO 7
<211> LENGTH: 4934
<212> TYPE: DNA
<213> ORGANISM: Adeno-Associated Virus

<400> SEQUENCE: 7

| | | |
|---|---|---|
| ttggccactc cctctctgcg cgctcgctcg ctcactgagg ccgcccgggc aaagcccggg | 60 | |
| cgtcgggcga cctttggtcg cccggcctca gtgagcgagc gagcgcgcag agagggagtg | 120 | |
| gccaactcca tcactagggg ttcctgtttg ctgcttgcaa tgtttgccca ttttaggggtg | 180 | |
| gacacaggac gctgtggttt ctgagccagg gggcgactca gatcccagcc agtggactta | 240 | |
| gcccctgttt gctcctccga taactggggt gaccttggtt aatattcacc agcagcctcc | 300 | |
| cccgttgccc ctctggatcc actgcttaaa tacggacgag gacagggccc tgtctcctca | 360 | |
| gcttcaggca ccaccactga cctgggacag tgaatcgcca ccatgcagat tgagctgagc | 420 | |
| acctgcttct tcctgtgcct gctgagattc tgctttagtg ccaccagaag atactacctg | 480 | |
| ggtgcagtgg aactgtcatg ggactatatg caaagtgatc tcggtgagct gcctgtggac | 540 | |
| gcaaggtaaa ggctgtttgc tgcttgcaat gtttgcccat tttagggggg gatgtaagtc | 600 | |
| tgcttggagg aaggtgcaga catcgggtta ggatggttgt gatgctattc tgactttttc | 660 | |
| cttcttcac gcagatttcc tcctagagtg ccaaaatctt ttccattcaa cacctcagtc | 720 | |
| gtgtacaaaa agactctgtt tgtagaattc acggatcacc ttttcaacat cgctaagccc | 780 | |
| aggcccccct ggatgggcct gctgggcccc accatccagg ctgaggtgta tgacactgtg | 840 | |
| gtgatcaccc tgaagaacat ggccagccac cctgtgagcc tgcatgctgt ggggggtgagc | 900 | |
| tactggaagg cctctgaggg ggctgagtat gatgaccaga ccagccagag ggagaaggag | 960 | |
| gatgacaagg tgttccctgg gggcagccac acctatgtgt ggcaggtgct gaaggagaat | 1020 | |
| ggcccccatg cctctgaccc cctgtgcctg acctacagct acctgagcca tgtggacctg | 1080 | |
| gtgaaggacc tgaactctgg cctgattggg gccctgctgg tgtgcaggga gggcagcctg | 1140 | |
| gccaaggaga gacccagac cctgcacaag ttcatcctgc tgtttgctgt gtttgatgag | 1200 | |
| ggcaagagct ggcactctga accaagaac agcctgatgc aggacaggga tgctgcctct | 1260 | |
| gccagggcct ggcccaagat gcacactgtg aatggctatg tgaacaggag cctgcctggc | 1320 | |
| ctgattggct gccacaggaa gtctgtgtac tggcatgtga ttggcatggg caccacccct | 1380 | |
| gaggtgcaca gcatcttcct ggagggccac accttcctgg tcaggaacca caggcaggcc | 1440 | |
| agcctggaga tcagccccat caccttcctg actgcccaga ccctgctgat ggaccctggg | 1500 | |
| cagttcctgc tgttctgcca catcagcagc caccagcatg atggcatgga ggcctatgtg | 1560 | |
| aaggtggaca gctgccctga ggagccccag ctgaggatga gaacaatga ggaggctgag | 1620 | |
| gactatgatg atgacctgac tgactctgag atggatgtgg tgaggtttga tgatgacaac | 1680 | |

-continued

```
agccccagct tcatccagat caggtctgtg gccaagaagc acccaagac ctgggtgcac    1740 tacattgctg ctgaggagga ggactgggac tatgccccc tggtgctggc ccctgatgac    1800
aggagctaca agagccagta cctgaacaat ggcccccaga ggattggcag aagtacaag    1860 aaggtcaggt tcatggccta cactgatgaa accttcaaga ccagggaggc catccagcat    1920
gagtctggca tcctgggccc cctgctgtat ggggaggtgg gggacaccct gctgatcatc    1980
ttcaagaacc aggccagcag gccctacaac atctaccccc atggcatcac tgatgtgagg    2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga acaggagc     2340 tggtacctga ctgagaacat ccagaggttc ctgcccaacc tgctggggt gcagctggag    2400 gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg agaggctgt gggactatgg catgagcagc    2880
agcccccatg tgctgaggaa cagggccag tctggctctg tgcccagtt caagaaggtg    2940 gtgttccagg agttcactga tggcagcttc acccagcccc tgtacagagg ggagctgaat    3000
gagcacctgg gcctgctggg ccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg gagaaggatg tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta cttcactgag    3420 aacatggaga ggaactgcag ggccccctgc aacatccaga tggaggaccc caccttcaag    3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcacctg    3780 ttcctggtgt acagcaacaa gtgccagacc cccctgggca tggcctctgg ccacatcagg    3840
gacttccaga tcactgcctc tggccagtat ggccagtggg ccccaagct ggccaggctg    3900 cactactctg gcagcatcaa tgcctggagc accaaggagc ccttcagctg gatcaaggtg    3960
gacctgctgc ccccatgat catccatggc atcaagaccc aggggccag gcagaagttc    4020 agcagcctgt acatcagcca gttcatcatc atgtacagcc tggatggcaa gaagtggcag    4080
```

-continued

```
acctacaggg gcaacagcac tggcaccctg atggtgttct ttggcaatgt ggacagctct    4140
ggcatcaagc acaacatctt caaccccccc atcattgcca gatacatcag gctgcacccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca aggccaggct gcacctgcag    4380
ggcaggagca atgcctggag gccccaggtc aacaacccca aggagtggct gcaggtggac    4440
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccccctgt    4620
gtgaacagcc tggaccccccc cctgctgacc agatacctga ggattcaccc ccagagctgg    4680
gtgcaccaga ttgccctgag gatggaggtg ctgggctgtg aggcccagga cctgtactga    4740
aataaaagat ctttatttttc attagatctg tgtgttggtt ttttgtgtga ggaaccccta    4800
gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934
```

<210> SEQ ID NO 8
<211> LENGTH: 4934
<212> TYPE: DNA
<213> ORGANISM: Adeno-Associated Virus

<400> SEQUENCE: 8

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240 gccccctgttt gctcctccga taactggggt gaccttggtt aatattcacc agcagcctcc     300
cccgttgccc ctctggatcc actgcttaaa tacgacgag acagggccc tgtctcctca     360 gcttcaggca ccaccactga cctgggacag tgaatcgcca ccatgcagat tgagctgagc     420
acctgcttct tcctgtgcct gctgagattc tgctttagtg ccaccagaag atactacctg     480
ggtgcagtgg aactgtcatg ggactatatg caaagtgatc tcggtgagct gcctgtggac     540
gcaaggtaaa gcatgtcct gtagggtctg atcggggcca ggattgtggg gatgtaagtc     600
tgcttggagg aagccctaaa atgggcaaac attgcaagca gcaaacattc tgactttttc     660
ctttcttcac gcagatttcc tcctagagtg ccaaaatctt ttccattcaa cacctcagtc     720
gtgtacaaaa agactctgtt tgtagaattc acggatcacc ttttcaacat cgctaagccc     780 aggccccccct ggatgggcct gctgggcccc accatccagg ctgaggtgta tgacactgtg     840
gtgatcaccc tgaagaacat ggccagccac cctgtgagcc tgcatgctgt gggggtgagc     900
tactggaagg cctctgaggg ggctgagtat gatgaccaga ccagccagag ggagaaggag     960
gatgacaagg tgttccctgg gggcagccac acctatgtgt ggcaggtgct gaaggagaat    1020
ggccccatgg cctctgaccc cctgtgcctg acctacagct acctgagcca tgtggacctg    1080
gtgaaggacc tgaactctgg cctgattggg gccctgctgg tgtgcaggga gggcagcctg    1140
gccaaggaga gacccagac cctgcacaag ttcatcctgc tgtttgctgt gtttgatgag    1200
```

```
ggcaagagct ggcactctga aaccaagaac agcctgatgc aggacaggga tgctgcctct    1260
gccagggcct ggcccaagat gcacactgtg aatggctatg tgaacaggag cctgcctggc    1320
ctgattggct gccacaggaa gtctgtgtac tggcatgtga ttggcatggg caccacccct    1380
gaggtgcaca gcatcttcct ggagggccac accttcctgg tcaggaacca caggcaggcc    1440
agcctggaga tcagccccat caccttcctg actgcccaga ccctgctgat ggacctgggc    1500
cagttcctgc tgttctgcca catcagcagc caccagcatg atggcatgga ggcctatgtg    1560
aaggtggaca gctgccctga ggagccccag ctgaggatga agaacaatga ggaggctgag    1620
gactatgatg atgacctgac tgactctgag atggatgtgg tgaggtttga tgatgacaac    1680
agccccagct tcatccagat caggtctgtg gccaagaagc accccaagac ctgggtgcac    1740
tacattgctg ctgaggagga ggactgggac tatgcccccc tggtgctggc ccctgatgac    1800
aggagctaca gagccagta cctgaacaat ggcccccaga ggattggcag gaagtacaag    1860
aaggtcaggt tcatggccta cactgatgaa accttcaaga ccaggaggc catccagcat    1920 gagtctggca tcctgggccc cctgctgtat ggggaggtgg gggacaccct gctgatcatc    1980
ttcaagaacc aggccagcag gccctacaac atctacccc atggcatcac tgatgtgagg    2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga aacaggagc    2340 tggtacctga ctgagaacat ccagaggttc ctgcccaacc tgctggggt gcagctggag    2400 gaccctgagt ccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt cccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg agaggctgt gggactatgg catgagcagc    2880
agcccccatg tgctgaggaa cagggccag tctggctctg tgcccagtt caagaaggtg    2940 gtgttccagg agttcactga tggcagcttc acccagcccc tgtacagagg ggagctgaat    3000
gagcacctgg gcctgctggg cccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg ccccccacca aggatgagtt tgactgcaag    3240
gcctgggcct acttctctga tgtggacctg gagaaggatg tgcactctgg cctgattggc    3300
cccctgctgt tgtgccacac caacaccctg aaccctgccc atggcaggca ggtgactgtg    3360
caggagtttg ccctgttctt caccatcttt gatgaaacca gagctggta cttcactgag    3420 aacatggaga ggaactgcag ggccccctgc aacatccaga tggaggaccc caccttcaag    3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
```

-continued

```
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc ccctgggca tggcctctgg ccacatcagg    3840
gacttccaga tcactgcctc tggccagtat ggccagtggg ccccaagct ggccaggctg    3900
cactactctg gcagcatcaa tgcctggagc accaaggagc cttcagctg atcaaggtg    3960
gacctgctgg cccccatgat catccatggc atcaagaccc agggggccag gcagaagttc    4020
agcagcctgt acatcagcca gttcatcatc atgtacagcc tggatggcaa gaagtggcag    4080
acctacaggg gcaacagcac tggcaccctg atggtgttct ttggcaatgt ggacagctct    4140
ggcatcaagc acaacatctt caacccccc atcattgcca gatacatcag gctgcacccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca aggccaggct gcacctgcag    4380
ggcaggagca atgcctggag gccccaggtc aacaaccca aggagtggct gcaggtggac    4440
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt cacccctgtg    4620
gtgaacagcc tggaccccc cctgctgacc agatacctga ggattcaccc ccagagctgg    4680
gtgcaccaga ttgccctgag gatggaggtg ctgggctgtg aggccagga cctgtactga    4740
aataaagat cttatttc attagatctg tgtgttggtt ttttgtgtga ggaaccccta    4800
gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934
```

<210> SEQ ID NO 9
<211> LENGTH: 5511
<212> TYPE: DNA
<213> ORGANISM: Adeno-Associated Virus 2

<400> SEQUENCE: 9

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaaact cctgtgtgcc    480
tctgagcctg cagacgcgaa acgtcgactg acacaggac gctgtggttt ctgagccagg    540
gggcgactca gatcccagcc agtggactta gcccctgttt gctcctccga taactggggt    600
gaccttggtt aatattcacc agcagcctcc ccgttgccc ctctggatcc actgcttaaa    660
tacggacgag gacagggccc tgtctcctca gcttcaggca ccaccactga cctgggacag    720
```

```
tgaatcgtaa gtactagcag ctacaatcca gctaccattc tgcttttatt ttatggttgg    780
gataaggctg gattattctg agtccaagct aggccctttt gctaatcatg ttcataccte    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt    1140
cactgaccac ctgttcaaca ttgccaagcc caggccccc tggatgggcc tgctgggccc    1200
caccatccag gctgaggtgt atgacactgt ggtgatcacc ctgaagaaca tggccagcca   1260
ccctgtgagc ctgcatgctg tggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggccccatg gcctctgacc cctgtgcct    1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga gtctgtgta    1740
ctggcatgtg attggcatgg gcaccacccc tgaggtgcac agcatcttcc tggagggcca   1800
caccttcctg gtcaggaacc acaggcaggc cagcctggga tcagccccca tcaccttcct   1860
gactgcccag acctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg tgaggttttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgacccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattgggc ccagactgac ttcctgtctg tgttcttctc   2940
tggctacacc ttcaagcaca gatggtgta tgaggacacc ctgaccctgt tccccttctc   3000
tgggggagact gtgttcatga gcatggagaa cctggcctg tggattctgg gctgccacaa    3060
ctctgacttc aggaacaggg gcatgactgc cctgctgaaa gtctccagct gtgacaagaa   3120
```

```
cactggggac tactatgagg acagctatga ggacatctct gcctacctgc tgagcaagaa    3180
caatgccatt gagcccagga gcttcagcca gaaccccca gtgctgaaga ggcaccagag     3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540 cagagggag ctgaatgagc acctgggcct gctgggcccc tacatcaggg ctgaggtgga    3600
ggacaacatc atggtgacct tcaggaacca ggccagcagg ccctacagct tctacagcag   3660
cctgatcagc tatgaggagg accagaggca ggggctgag cccaggaaga actttgtgaa    3720
gcccaatgaa accaagacct acttctggaa ggtgcagcac acatggcccc caccaaggga   3780
tgagtttgac tgcaaggcct gggcctactt ctctgatgtg gacctggaga aggatgtgca   3840
ctctggcctg attggccccc tgctggtgtg ccacaccaac ccctgaacc ctgcccatgg    3900 caggcaggtg actgtgcagg agtttgccct gttcttcacc atctttgatg aaaccaagag   3960
ctggtacttc actgagaaca tggagaggaa ctgcagggcc cctgcaaca tccagatgga    4020 ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc ccctgttcc tggtgtacag caacaagtgc cagaccccc tgggcatggc     4380 ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620 tgcaagaag tggcagacct acagggggcaa cagcactggc accctgatgg tgttctttgg   4680
caatgtggac agctctggca tcaagcacaa catcttcaac cccccatca ttgccagata   4740 catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca ccccaagga    4980 gtggctgcag gtggacttcc agaagaccat gaaggtgact ggggtgacca cccaggggt    5040 gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga ccccccctg ctgaccagat acctgaggat    5220 tcaccccag agctgggtgc accagattgc cctgaggatg gaggtgctgg gctgtgaggc   5280
ccaggacctg tactgacctc gaggaataaa ggaaatttat tttcattgca atagtgtgtt   5340
ggttttttgt gtcacgtggc ggccgcagga acccctagtg atggagttgg ccactccctc   5400
tctgcgcgct cgctcgctca ctgaggccgg gcgaccaaag gtcgcccgac gcccgggctt   5460
```

```
tgcccgggcg gcctcagtga gcgagcgagc gcgcagagag ggagtggcca a         5511

<210> SEQ ID NO 10
<211> LENGTH: 5688
<212> TYPE: DNA
<213> ORGANISM: Adeno-Associated Virus 2

<400> SEQUENCE: 10
ttggccactc cctctctgcg cgctcgctcg ctcactgagg ccgcccgggc aaagcccggg   60
cgtcgggcga cctttggtcg cccggcctca gtgagcgagc gagcgcgcag agagggagtg  120
gccaactcca tcactagggg ttcctgcggc cgcacgcgtg ttttcgaccc ctctcacact  180
acctaaacca cgccaggaca acctctgctc ctctccaccg aaattccaag gggtcgagtg  240
gatgttggag gtggcatggg cccagagagg tctctgacct ctgccccagc tccaaggtca  300
gcaggcaggg agggctgtgt gtttgctgtt tgctgcttgc aatgtttgcc cattttaggg  360
acatgagtag gctgaagttt gttcagtgtg gacttcagag gcagcacaca aacagctgct  420
ggaggatggg aactgagggg ttggaagggg cagggtgag cccagaaact cctgtgtgcc   480
tctgagcctg cagacgcgaa acgtcgactg gacacaggac gctgtggttt ctgagccagg  540
gggcgactca gatcccagcc agtggactta gcccctgttt gctcctccga taactggggt  600
gaccttggtt aatattcacc agcagcctcc cccgttgccc ctctggatcc actgcttaaa  660 tacgacgag acagggccc tgtctcctca gcttcaggca ccaccactga cctgggacag  720
tgaatcgtaa gtactagcag ctacaatcca gctaccattc tgcttttatt ttatggttgg  780
gataaggctg gattattctg agtccaagct aggcccttt gctaatcatg ttcatacctc  840
ttatcttcct cccacagctc ctgggcaacg tgctggtctg tgtgctggcc catcactttg  900
gcaaagaatt gcgatcgcca ccatgcagat tgagctgagc acctgcttct tcctgtgcct  960
gctgaggttc tgcttctctg ccaccaggag atactacctg ggggctgtgg agctgagctg 1020
ggactacatg cagtctgacc tgggggagct gcctgtggat ccaggttcc ccccagagt  1080 gcccaagagc ttcccccttca acacctctgt ggtgtacaag aagaccctgt tgtggagtt  1140 cactgaccac ctgttcaaca ttgccaagcc caggcccccc tggatgggcc tgctgggccc  1200
caccatccag gctgaggtgt atgacactgt ggtgatcacc ctgaagaaca tggccagcca  1260
ccctgtgagc ctgcatgctg tgggggtgag ctactggaag gcctctgagg gggctgagta  1320
tgatgaccag accagccaga gggagaagga ggatgacaag gtgttccctg ggggcagcca  1380
cacctatgtg tggcaggtgc tgaaggagaa tggccccatg gcctctgacc cctgtgcct   1440 gacctacagc tacctgagcc atgtggacct ggtgaaggac ctgaactctg gcctgattgg  1500 ggcccctgctg gtgtgcaggg agggcagcct ggccaaggag aagacccaga ccctgcacaa  1560
gttcatcctg ctgtttgctg tgtttgatga gggcaagagc tggcactctg aaaccaagaa  1620
cagcctgatg caggacaggg atgctgcctc tgccagggcc tggccaaga tgcacactgt  1680 gaatggctat gtgaacagga gcctgcctgg cctgattggc tgccacagga agtctgtgta  1740
ctggcatgtg attggcatgg gcaccacccc tgaggtgcac agcatcttcc tggagggcca  1800
caccttcctg gtcaggaacc acaggcaggc cagcctggaa atcagcccca tcaccttcct  1860
gactgcccag accctgctga tggacctggg ccagttcctg ctgttctgcc acatcagcag  1920
ccaccagcat gatggcatgg aggcctatgt gaaggtggac agctgccctg aggagcccca  1980
gctgaggatg aagaacaatg aggaggctga ggactatgat gatgacctga ctgactctga  2040
gatggatgtg gtgaggtttg atgatgacaa cagccccagc ttcatccaga tcaggtctgt  2100
```

-continued

```
ggccaagaag caccccaaga cctgggtgca ctacattgct gctgaggagg aggactggga    2160
ctatgccccc ctggtgctgg cccctgatga caggagctac aagagccagt acctgaacaa    2220
tggcccccag aggattggca ggaagtacaa gaaggtcagg ttcatggcct acactgatga    2280
aaccttcaag accagggagg ccatccagca tgagtctggc atcctgggcc ccctgctgta    2340
tggggaggtg ggggacaccc tgctgatcat cttcaagaac caggccagca ggccctacaa    2400
catctacccc catggcatca ctgatgtgag gccctgtac agcaggaggc tgcccaaggg    2460
ggtgaagcac ctgaaggact tccccatcct gcctggggag atcttcaagt acaagtggac    2520
tgtgactgtg gaggatggcc ccaccaagtc tgaccccagg tgcctgacca gatactacag    2580
cagctttgtg aacatggaga gggacctggc ctctggcctg attggccccc tgctgatctg    2640
ctacaaggag tctgtggacc agaggggcaa ccagatcatg tctgacaaga ggaatgtgat    2700
cctgttctct gtgtttgatg agaacaggag ctggtacctg actgagaaca tccagaggtt    2760
cctgcccaac cctgctgggg tgcagctgga ggaccctgag ttccaggcca gcaacatcat    2820
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca gatggtgta tgaggacacc ctgaccctgt ccccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc ccatgtgct gaggaacagg gcccagtctg gctctgtgcc    3480
ccagttcaag aaggtggtgt tccaggagtt cactgatggc agcttcaccc agccctgta    3540
cagagggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggtgag cccaggaaga ctttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc    4380
ctctggccac atcagggact tccagatcac tgcctctggc cagtatggcc agtgggcccc    4440
```

-continued

```
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac ccccccatca ttgccagata    4740
catcaggctg cacccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttcaccaa catgtttgcc acctggagcc ccagcaaggc    4920
caggctgcac ctgcagggca ggagcaatgc ctggaggccc caggtcaaca ccccaagga    4980
gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg accctgttct tccagaatgg caaggtgaag gtgttccagg caaccagga    5160
cagcttcacc cctgtggtga acagcctgga cccccccctg ctgaccagat acctgaggat    5220
tcaccccag agctgggtgc accagattgc cctgaggatg gaggtgctgg gctgtgaggc    5280
ccaggacctg tactgacctc gaggtgtgcc ttctagttgc cagccatctg ttgtttgccc    5340
ctcccccgtg ccttccttga ccctggaagg tgccactccc actgtccttt cctaataaaa    5400
tgaggaaatt gcatcgcatt gtctgagtag gtgtcattct attctggggg gtggggtggg    5460
gcaggacagc aagggggagg attgggaaga caatagcagg catgctgggg atgcggtggg    5520
ctctatgggc acgtggcggc cgcaggaacc cctagtgatg gagttggcca ctccctctct    5580
gcgcgctcgc tcgctcactg aggccgggcg accaaaggtc gcccgacgcc cgggctttgc    5640
ccgggcggcc tcagtgagcg agcgagcgcg cagagaggga gtggccaa    5688
```

<210> SEQ ID NO 11
<211> LENGTH: 5613
<212> TYPE: DNA
<213> ORGANISM: Adeno-Associated Virus 2

<400> SEQUENCE: 11

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gccctgtttt gctcctccga taactggggt    600
gaccttggtt aatattcacc agcagcctcc ccgttgcccc tctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggcccttt gctaatcatg ttcatacctc    840
ttatcttcct cccacagctc ctgggcaacg tgctggtctg tgtgctggcc catcactttg    900
```

```
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt tgtggagtt    1140 cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggccccatg gcctctgacc cctgtgcct    1440 gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agagggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattgggc ccagactgac ttcctgtctg tgttcttctc   2940
tggctacacc ttcaagcaca agatggtgta tgaggacacc ctgaccctgt tcccttctc    3000 tggggagact gtgttcatga gcatggagaa ccctggcctg tggattctgg ctgccacaa    3060 ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaacccccca gtgctgaaga ggcaccagag   3240
```

```
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga actttgtgaa     3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcaggggcc ccctgcaaca tccagatgga   4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc     4380 ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca gacccaggg    4560 ggccaggcag aagttcagca gcctgtacat cagccagttc atcatcatgt acagcctgga    4620
tggcaagaag tggcagacct acaggggcaa cagcactggc accctgatgg tgttcttgg    4680 caatgtggac agctctggca tcaagcacaa catcttcaac cccccccatca ttgccagata    4740 catcaggctg caccccacc actacagcat caggagcacc ctgaggatgg agctgatggg     4800
ctgtgacctg aacagctgca gcatgcccct gggcatggag agcaaggcca tctctgatgc    4860
ccagatcact gccagcagct acttccacca catgtttgcc acctggagcc ccagcaaggc    4920
caggctgcac ctgcagggca ggagcaatgc ctggaggccc caggtcaaca ccccaagga    4980 gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg accctgttct tccagaatgg caaggtgaag gtgttccagg caaccagga    5160 cagcttcacc cctgtggtga acagcctgga ccccccctg ctgaccagat acctgaggat      5220 tcaccccag agctgggtgc accagattgc cctgaggatg gaggtgctgg gctgtgaggc     5280
ccaggacctg tactgacctc gaggcactgt cctttcctaa taaaatgagg aaattgcatc    5340
gcattgtctg agtaggtgtc attctattct gggggtggg gtggggcagg acagcaaggg    5400
ggaggattgg gaagacaata gcaggcatgc tgggggatgcg gtggtgctcta tgggcacgtg  5460 gcggccgcag gaaccctag tgatggagtt ggccactccc tctctgcgcg ctcgctcgct     5520
cactgaggcc gggcgaccaa aggtcgcccg acgcccgggc tttgcccggg cggcctcagt    5580
gagcgagcga gcgcgcagag agggagtggc caa                                 5613
```

<210> SEQ ID NO 12
<211> LENGTH: 5362
<212> TYPE: DNA
<213> ORGANISM: Adeno-Associated Virus 2

<400> SEQUENCE: 12

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgcggc | cgcacgcgtg | ttttcgactg | tttgctgttt | 180 |
| gctgcttgca | atgtttgccc | attttaggga | catgtttgct | gtttgctgct | tgcaatgttt | 240 |
| gcccatttta | gggacatgtt | tgctgtttgc | tgcttgcaat | gtttgcccat | tttagggaca | 300 |
| tgtttgctgt | ttgctgcttg | caatgtttgc | catttttagg | acaacgcga | aacgtcgact | 360 |
| ggacacagga | cgctgtggtt | tctgagccag | ggggcgactc | agatcccagc | cagtggactt | 420 |
| agccctgtt | tgctcctccg | ataactgggg | tgaccttggt | taatattcac | cagcagcctc | 480 |
| ccccgttgcc | cctctggatc | cactgcttaa | atacggacga | ggacagggcc | ctgtctcctc | 540 |
| agcttcaggc | accaccactg | acctgggaca | gtgaatcgta | agtactagca | gctacaatcc | 600 |
| agctaccatt | ctgcttttat | tttatggttg | ggataaggct | ggattattct | gagtccaagc | 660 |
| taggcccttt | tgctaatcat | gttcatacct | cttatcttcc | tcccacagct | cctgggcaac | 720 |
| gtgctggtct | gtgtgctggc | ccatcacttt | ggcaaagaat | tgcgatcgcc | accatgcaga | 780 |
| ttgagctgag | cacctgcttc | ttcctgtgcc | tgctgagctt | ctgcttctct | gccaccagga | 840 |
| gatactacct | gggggctgtg | agctgagct | gggactacat | gcagtctgac | ctgggggagc | 900 |
| tgcctgtgga | tgccaggttc | ccccccagag | tgcccaagag | cttcccctttc | aacacctctg | 960 |
| tggtgtacaa | gaagaccctg | tttgtggagt | tcactgacca | cctgttcaac | attgccaagc | 1020 |
| ccaggccccc | ctggatgggc | ctgctggggc | ccaccatcca | ggctgaggtg | tatgacactg | 1080 |
| tggtgatcac | cctgaagaac | atggccagcc | accctgtgag | cctgcatgct | gtggggtga | 1140 |
| gctactggaa | ggcctctgag | ggggctgagt | atgatgacca | gaccagccag | agggagaagg | 1200 |
| aggatgacaa | ggtgttccct | gggggcagcc | acacctatgt | gtggcaggtg | ctgaaggaga | 1260 |
| atggcccat | ggcctctgac | cccctgtgcc | tgacctacag | ctacctgagc | catgtggacc | 1320 |
| tggtgaagga | cctgaactct | ggcctgattg | ggcccctgct | ggtgtgcagg | gagggcagcc | 1380 |
| tggccaagga | gaagacccag | accctgcaca | agttcatcct | gctgtttgct | gtgtttgatg | 1440 |
| agggcaagag | ctggcactct | gaaaccaaga | acagcctgat | gcaggacagg | gatgctgcct | 1500 |
| ctgccagggc | ctggcccaag | atgcacactg | tgaatggcta | tgtgaacagg | agcctgcctg | 1560 |
| gcctgattgg | ctgccacagg | aagtctgtgt | actggcatgt | gattggcatg | gcaccaccc | 1620 |
| ctgaggtgca | cagcatcttc | ctggagggcc | acaccttcct | ggtcaggaac | cacaggcagg | 1680 |
| ccagcctgga | gatcagcccc | atcaccttcc | tgactgccca | gaccctgctg | atggaccgg | 1740 |
| gccagttcct | gctgttctgc | cacatcagca | gccaccagca | tgatggcatg | gaggcctatg | 1800 |
| tgaaggtgga | cagctgccct | gaggagcccc | agctgaggat | gaagaacaat | gaggaggctg | 1860 |
| aggactatga | tgatgacctg | actgactctg | agatggatgt | ggtgaggttt | gatgatgaca | 1920 |
| acagccccag | cttcatccag | atcaggtctg | tggccaagaa | gcaccccaag | acctgggtgc | 1980 |
| actacattgc | tgctgaggag | gaggactggg | actatgcccc | cctggtgctg | gcccctgatg | 2040 |
| acaggagcta | caagagccag | tacctgaaca | atggccccca | gaggattggc | aggaagtaca | 2100 |

| | |
|---|---|
| agaaggtcag gttcatggcc tacactgatg aaaccttcaa gaccagggag gccatccagc | 2160 |
| atgagtctgg catcctgggc cccctgctgt atggggaggt gggggacacc ctgctgatca | 2220 |
| tcttcaagaa ccaggccagc aggccctaca acatctaccc ccatggcatc actgatgtga | 2280 |
| ggcccctgta cagcaggagg ctgcccaagg gggtgaagca cctgaaggac ttccccatcc | 2340 |
| tgcctgggga gatcttcaag tacaagtgga ctgtgactgt ggaggatggc cccaccaagt | 2400 |
| ctgaccccag gtgcctgacc agatactaca gcagctttgt gaacatggag agggacctgg | 2460 |
| cctctggcct gattggcccc ctgctgatct gctacaagga gtctgtggac cagaggggca | 2520 |
| accagatcat gtctgacaag aggaatgtga tcctgttctc tgtgtttgat gagaacagga | 2580 |
| gctggtacct gactgagaac atccagaggt tcctgcccaa ccctgctggg gtgcagctgg | 2640 |
| aggaccctga gttccaggcc agcaacatca tgcacagcat caatggctat gtgtttgaca | 2700 |
| gcctgcagct gtctgtgtgc ctgcatgagg tggcctactg gtacatcctg agcattgggg | 2760 |
| cccagactga cttcctgtct gtgttcttct ctggctacac cttcaagcac aagatggtgt | 2820 |
| atgaggacac cctgaccctg ttccccttct ctggggagac tgtgttcatg agcatggaga | 2880 |
| accctggcct gtggattctg ggctgccaca ctctgactt caggaacagg ggcatgactg | 2940 |
| ccctgctgaa agtctccagc tgtgacaaga acactgggga ctactatgag acagctatg | 3000 |
| aggacatctc tgcctacctg ctgagcaaga acaatgccat tgagcccagg agcttcagcc | 3060 |
| agaacccccc agtgctgaag aggcaccaga gggagatcac caggaccacc ctgcagtctg | 3120 |
| accaggagga gattgactat gatgacacca tctctgtgga gatgaagaag gaggactttg | 3180 |
| acatctacga cgaggacgag aaccagagcc ccaggagctt ccagaagaag accaggcact | 3240 |
| acttcattgc tgctgtggag aggctgtggg actatggcat gagcagcagc ccccatgtgc | 3300 |
| tgaggaacag ggcccagtct ggctctgtgc cccagttcaa gaaggtggtg ttccaggagt | 3360 |
| tcactgatgg cagcttcacc cagcccctgt acagagggga gctgaatgag cacctgggcc | 3420 |
| tgctgggccc ctacatcagg gctgaggtgg aggacaacat catggtgacc ttcaggaacc | 3480 |
| aggccagcag gccctacagc ttctacagca gcctgatcag ctatgaggag gaccagaggc | 3540 |
| agggggctga gccaggaag aactttgtga agcccaatga aaccaagacc tacttctgga | 3600 |
| aggtgcagca ccacatggcc cccaccaagg atgagtttga ctgcaaggcc tgggcctact | 3660 |
| tctctgatgt ggacctggag aaggatgtgc actctggcct gattggcccc ctgctggtgt | 3720 |
| gccacaccaa caccctgaac cctgcccatg gcaggcaggt gactgtgcag gagtttgccc | 3780 |
| tgttcttcac catctttgat gaaaccaaga gctggtactt cactgagaac atggagagga | 3840 |
| actgcagggc cccctgcaac atccagatgg aggaccccac cttcaaggag aactacaggt | 3900 |
| tccatgccat caatggctac atcatggaca ccctgcctgg cctggtgatg gcccaggacc | 3960 |
| agaggatcag gtggtacctg ctgagcatgg gcagcaatga aacatccac agcatccact | 4020 |
| tctctggcca tgtgttcact gtgaggaaga aggaggagta caagatggcc ctgtacaacc | 4080 |
| tgtaccctgg ggtgtttgag actgtggaga tgctgcccag caaggctggc atctggaggg | 4140 |
| tggagtgcct gattggggag cacctgcatg ctggcatgag caccctgttc ctggtgtaca | 4200 |
| gcaacaagtg ccagaccccc ctgggcatgg cctctggcca tcagggac ttccagatca | 4260 |
| ctgcctctgg ccagtatggc cagtgggccc ccaagctggc caggctgcac tactctggca | 4320 |
| gcatcaatgc ctggagcacc aaggagccct tcagctggat caaggtggac ctgctggccc | 4380 |
| ccatgatcat ccatggcatc aagacccagg ggccaggca gaagttcagc agcctgtaca | 4440 |
| tcagccagtt catcatcatg tacagcctgg atggcaagaa gtggcagacc tacaggggca | 4500 |

-continued

```
acagcactgg caccctgatg gtgttctttg gcaatgtgga cagctctggc atcaagcaca      4560
acatcttcaa ccccccatc attgccagat acatcaggct gcaccccacc cactacagca       4620
tcaggagcac cctgaggatg gagctgatgg gctgtgacct gaacagctgc agcatgcccc      4680
tgggcatgga gagcaaggcc atctctgatg cccagatcac tgccagcagc tacttccacca    4740 acatgtttgc cacctggagc cccagcaagg ccaggctgca cctgcagggc aggagcaatg     4800
cctggaggcc ccaggtcaac aaccccaagg agtggctgca ggtggacttc cagaagacca    4860
tgaaggtgac tggggtgacc acccaggggg tgaagagcct gctgaccagc atgtatgtga    4920
aggagttcct gatcagcagc agccaggatg ccaccagtg gaccctgttc ttccagaatg     4980
gcaaggtgaa ggtgttccag ggcaaccagg acagcttcac ccctgtggtg aacagcctgg    5040 accccccct gctgaccaga tacctgagga ttcaccccca gagctgggtg caccagattg     5100
ccctgaggat ggaggtgctg ggctgtgagg cccaggacct gtactgacct cgaggaataa    5160
aggaaattta ttttcattgc aatagtgtgt tggttttttg tgtcacgtgg cggccgcagg    5220 aaccctagt gatggagttg gccactccct ctctgcgcgc tcgctcgctc actgaggccg     5280
ggcgaccaaa ggtcgcccga cgcccgggct tgcccgggc ggcctcagtg agcgagcgag     5340
cgcgcagaga gggagtggcc aa                                              5362
```

<210> SEQ ID NO 13
<211> LENGTH: 5464
<212> TYPE: DNA
<213> ORGANISM: Adeno-Associated Virus 2

<400> SEQUENCE: 13

```
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgactg tttgctgttt     180
gctgcttgca atgtttgccc attttaggga catgtttgct gtttgctgct tgcaatgttt    240
gcccatttta gggacatgtt tgctgttttgc tgcttgcaat gtttgcccat tttagggaca   300
tgtttgctgt ttgctgcttg caatgtttgc ccatttagg acaacgcga aacgtcgact       360 ggacacagga cgctgtggtt tctgagccag ggggcgactc agatcccagc cagtggactt     420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtactagca gctacaatcc   600
agctaccatt ctgcttttat tttatggttg ggataaggct ggattattct gagtccaagc    660
taggcccttt tgctaatcat gttcatacct cttatcttcc tcccacagct cctgggcaac    720
gtgctggtct gtgtgctggc ccatcacttt ggcaaagaat tgcgatcgcc accatgcaga   780
ttgagctgag cacctgcttc ttcctgtgcc tgctgaggtt ctgcttctct gccaccagga   840
gatactacct gggggctgtg gagctgagct gggactacat gcagtctgac ctggggagc     900 tgcctgtgga tgccaggttc ccccccagag tgcccaagag cttcccttc aacacctctg    960 tggtgtacaa gaagaccctg tttgtggagt tcactgacca cctgttcaac attgccaagc  1020
ccaggccccc ctggatgggc ctgctgggcc ccaccatcca ggctgaggtg tatgacactg   1080
tggtgatcac cctgaagaac atggccagcc acctgtgag cctgcatgct gtgggggtga   1140
gctactggaa ggcctctgag ggggctgagt atgatgacca gaccagccag agggagaagg  1200
```

```
aggatgacaa ggtgttccct gggggcagcc acacctatgt gtggcaggtg ctgaaggaga    1260
atggccccat ggcctctgac cccctgtgcc tgacctacag ctacctgagc catgtggacc    1320
tggtgaagga cctgaactct ggcctgattg gggccctgct ggtgtgcagg gagggcagcc    1380
tggccaagga gaagacccag accctgcaca agttcatcct gctgtttgct gtgtttgatg    1440
agggcaagag ctggcactct gaaaccaaga acagcctgat gcaggacagg gatgctgcct    1500
ctgccagggc ctggcccaag atgcacactg tgaatggcta tgtgaacagg agcctgcctg    1560
gcctgattgg ctgccacagg aagtctgtgt actggcatgt gattggcatg ggcaccaccc    1620
ctgaggtgca cagcatcttc ctggagggcc acaccttcct ggtcaggaac acacaggcagg   1680 ccagcctgga gatcagcccc atcaccttcc tgactgccca gaccctgctg atggacctgg    1740
gccagttcct gctgttctgc cacatcagca gccaccagca tgatggcatg gaggcctatg    1800
tgaaggtgga cagctgccct gaggagcccc agctgaggat gaagaacaat gaggaggctg    1860
aggactatga tgatgacctg actgactctg agatggatgt ggtgaggttt gatgatgaca    1920
acagccccag cttcatccag atcaggtctg tggccaagag caccccaag acctgggtgc     1980 actacattgc tgctgaggag gaggactggg actatgcccc cctggtgctg gcccctgatg    2040
acaggagcta aagagccag tacctgaaca atggccccca gaggattggc aggaagtaca     2100
agaaggtcag gttcatggcc tacactgatg aaaccttcaa gaccgggag gccatccagc     2160 atgagtctgg catcctgggc ccctgctgt atggggaggt gggggacacc ctgctgatca     2220
tcttcaagaa ccaggccagc aggccctaca acatctaccc ccatggcatc actgatgtga    2280
ggcccctgta cagcaggagg ctgcccaagg gggtgaagca cctgaaggac ttccccatcc    2340
tgcctgggga gatcttcaag tacaagtgga ctgtgactgt ggaggatggc cccaccaagt    2400
ctgaccccag gtgcctgacc agatactaca gcagctttgt gaacatggag agggacctgg    2460
cctctggcct gattggcccc ctgctgatct gctacaagga gtctgtggac cagaggggca    2520
accagatcat gtctgacaag aggaatgtga tcctgttctc tgtgtttgat gagaacagga    2580
gctggtacct gactgagaac atccagaggt tcctgcccaa ccctgctggg gtgcagctgg    2640
aggaccctga gttccaggcc agcaacatca tgcacagcat caatggctat gtgtttgaca    2700
gcctgcagct gtctgtgtgc ctgcatgagg tggcctactg gtacatcctg agcattgggg    2760
cccagactga cttcctgtct gtgttcttct ctggctacac cttcaagcac aagatggtgt    2820
atgaggacac cctgacccctg ttccccttct ctggggagac tgtgttcatg agcatggaga    2880
accctggcct gtggattctg ggctgccaca actctgactt caggaacagg ggcatgactg    2940
ccctgctgaa agtctccagc tgtgacaaga cactgggga ctactatgag acagctatg     3000 aggacatctc tgcctacctg ctgagcaaga caatgccat tgagcccagg agcttcagcc     3060 agaaccccc agtgctgaag aggcaccaga gggagatcac caggaccacc ctgcagtctg     3120
accaggagga gattgactat gatgacacca tctctgtgga gatgaagaag gaggactttg    3180
acatctacga cgaggacgag aaccagagcc ccaggagctt ccagaagaag accaggcact    3240
acttcattgc tgctgtggag aggctgtggg actatggcat gagcagcagc ccccatgtgc    3300
tgaggaacag ggcccagtct ggctctgtgc cccagttcaa gaaggtggtg ttccaggagt    3360
tcactgatgg cagcttcacc cagccectgt acagagggga gctgaatgag cacctgggcc    3420
tgctgggccc ctacatcagg gctgaggtgg aggacaacat catggtgacc ttcaggaacc    3480
aggccagcag gccctacagc ttctacagca gcctgatcag ctatgaggag gaccagaggc    3540 aggggggctga gcccaggaag aactttgtga agcccaatga aaccaagacc tacttctgga    3600
```

```
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg gcaggcaggt gactgtgcag gagtttgccc    3780
tgttcttcac catctttgat gaaaccaaga gctggtactt cactgagaac atggagagga    3840
actgcagggc ccctgcaac atccagatgg aggaccccac cttcaaggag aactacaggt     3900
tccatgccat caatggctac atcatggaca ccctgcctgg cctggtgatg gcccaggacc    3960
agaggatcag gtggtacctg ctgagcatgg gcagcaatga gaacatccac agcatccact    4020
tctctggcca tgtgttcact gtgaggaaga aggaggagta caagatgccc tgtacaacc     4080 tgtaccctgg ggtgtttgag actgtggaga tgctgcccag caaggctggc atctggaggg    4140
tggagtgcct gattggggag cacctgcatg ctggcatgag caccctgttc ctggtgtaca    4200
gcaacaagtg ccagaccccc ctgggcatgg cctctggcca catcagggac ttccagatca    4260
ctgcctctgg ccagtatggc cagtgggccc caagctggc caggctgcac tactctggca     4320
gcatcaatgc ctggagcacc aaggagccct tcagctggat caaggtggac ctgctggccc    4380
ccatgatcat ccatggcatc aagacccagg gggccaggca gaagttcagc agcctgtaca    4440
tcagccagtt catcatcatg tacagcctgg atggcaagaa gtggcagacc tacaggggca    4500
acagcactgg caccctgatg gtgttctttg gcaatgtgga cagctctggc atcaagcaca    4560
acatcttcaa ccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttcacca    4740
acatgtttgc cacctggagc cccagcaagg ccaggctgca cctgcagggc aggagcaatg    4800
cctggaggcc ccaggtcaac aaccccaagg agtggctgca ggtggacttc cagaagacca    4860
tgaaggtgac tgggggtgacc acccagggggg tgaagagcct gctgaccagc atgtatgtga    4920
aggagttcct gatcagcagc agccaggatg ccaccagtg gaccctgttc ttccagaatg    4980
gcaaggtgaa ggtgttccag ggcaaccagg acagcttcac ccctgtggtg aacagcctgg    5040
acccccccct gctgaccaga tacctgagga ttcacccca gagctgggtg caccagattg    5100
ccctgaggat ggaggtgctg gctgtgagg cccaggacct gtactgacct cgaggcactg    5160
tcctttccta ataaaatgag gaaattgcat cgcattgtct gagtaggtgt cattctattc    5220
tggggggtgg ggtggggcag gacagcaagg gggaggattg gaagacaat agcaggcatg    5280 ctggggatgc ggtgggctct atgggcacgt ggcggccgca ggaaccccta gtgatggagt    5340
tggccactcc ctctctgcgc gctcgctcgc tcactgaggc cgggcgacca aggtcgccc    5400 gacgcccggg ctttgcccgg gcggcctcag tgagcgagcg agcgcgcaga gagggagtgg    5460
ccaa                                                                5464
```

<210> SEQ ID NO 14
<211> LENGTH: 6354
<212> TYPE: DNA
<213> ORGANISM: Adeno-Associated Virus 2

<400> SEQUENCE: 14

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg tttaaacgtc gacaggttaa    180
```

-continued

| | |
|---|---|
| tttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa tttttaaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg gacacaggac gctgtggttt | 540 |
| ctgagccagg gggcgactca gatcccagcc agtggactta gccctgtttt gctcctccga | 600 |
| taactggggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgtaa gtactagcag ctacaatcca gctaccattc tgcttttatt | 780 |
| ttatggttgg gataaggctg gattattctg agtccaagct aggccctttt gctaatcatg | 840 |
| ttcatacctc ttatcttcct cccacagctc ctgggcaacg tgctggtctg tgtgctggcc | 900 |
| catcactttg gcaaagaatt gcgatcgcca ccatgcagat tgagctgagc acctgcttct | 960 |
| tcctgtgcct gctgaggttc tgcttctctg ccaccaggag atactacctg ggggctgtgg | 1020 |
| agctgagctg ggactacatg cagtctgacc tgggggagct gcctgtggat gccaggttcc | 1080 |
| cccccagagt gcccaagagc ttccccttca cacctctgt ggtgtacaag aagaccctgt | 1140 |
| ttgtggagtt cactgaccac ctgttcaaca ttgccaagcc caggcccccc tggatgggcc | 1200 |
| tgctgggccc caccatccag gctgaggtgt atgacactgt ggtgatcacc ctgaagaaca | 1260 |
| tggccagcca ccctgtgagc ctgcatgctg tgggggtgag ctactggaag gcctctgagg | 1320 |
| ggctgagtta tgatgaccag accagccaga gggagaagga ggatgacaag gtgttccctg | 1380 |
| ggggcagcca cacctatgtg tggcaggtgc tgaaggagaa tggcccatg gcctctgacc | 1440 |
| ccctgtgcct gacctacagc tacctgagcc atgtggacct ggtgaaggac ctgaactctg | 1500 |
| gcctgattgg ggccctgctg gtgtgcaggg agggcagcct ggccaaggag aagacccaga | 1560 |
| ccctgcacaa gttcatcctg ctgtttgctg tgtttgatga gggcaagagc tggcactctg | 1620 |
| aaaccaagaa cagcctgatg caggacaggg atgctgcctc tgccagggcc tggcccaaga | 1680 |
| tgcacactgt gaatggctat gtgaacagga gcctgcctgg cctgattggc tgccacagga | 1740 |
| agtctgtgta ctggcatgtg attggcatgg gcaccacccc tgaggtgcac agcatcttcc | 1800 |
| tggagggcca caccttcctg gtcaggaacc acaggcaggc cagcctggag atcagcccca | 1860 |
| tcaccttcct gactgcccag accctgctga tggacctggg ccagttcctg ctgttctgcc | 1920 |
| acatcagcag ccaccagcat gatggcatgg aggcctatgt gaaggtggac agctgccctg | 1980 |
| aggagcccca gctgaggatg aagaacaatg aggaggctga ggactatgat gatgacctga | 2040 |
| ctgactctga gatggatgtg gtgaggtttg atgatgacaa cagccccagc ttcatccaga | 2100 |
| tcaggtctgt ggccaagaag caccccaaga cctgggtgca ctacattgct gctgaggagg | 2160 |
| aggactggga ctatgccccc ctggtgctgg cccctgatga caggagctac aagagccagt | 2220 |
| acctgaacaa tggcccccag aggattggca ggaagtacaa gaaggtcagg ttcatggcct | 2280 |
| acactgatga aaccttcaag accagggagg ccatccagca tgagtctggc atcctgggcc | 2340 |
| ccctgctgta tggggaggtg ggggacaccc tgctgatcat cttcaagaac caggccagca | 2400 |
| ggccctacaa catctacccc catggcatca ctgatgtgag gcccctgtac agcaggaggc | 2460 |
| tgcccaaggg ggtgaagcac ctgaaggact tccccatcct gcctggggag atcttcaagt | 2520 |
| acaagtggac tgtgactgtg gaggatggcc ccaccaagtc tgaccccagg tgcctgacca | 2580 |

```
gatactacag cagctttgtg aacatggaga gggacctggc ctctggcctg attggcccc    2640 tgctgatctg ctacaaggag tctgtggacc agaggggcaa ccagatcatg tctgacaaga   2700
ggaatgtgat cctgttctct gtgtttgatg agaacaggag ctggtacctg actgagaaca   2760
tccagaggtt cctgcccaac cctgctgggg tgcagctgga ggaccctgag ttccaggcca   2820
gcaacatcat gcacagcatc aatggctatg tgtttgacag cctgcagctg tctgtgtgcc   2880
tgcatgaggt ggcctactgg tacatcctga gcattgggc ccagactgac ttcctgtctg    2940
tgttcttctc tggctacacc ttcaagcaca agatggtgta tgaggacacc ctgaccctgt   3000
tccccttctc tggggagact gtgttcatga gcatggagaa ccctggcctg tggattctgg   3060
gctgccacaa ctctgacttc aggaacaggg gcatgactgc cctgctgaaa gtctccagct   3120
gtgacaagaa cactggggac tactatgagg acagctatga ggacatctct gcctacctgc   3180
tgagcaagaa caatgccatt gagcccagga gcttcagcca gaaccccca gtgctgaaga    3240 ggcaccagag ggagatcacc aggaccaccc tgcagtctga ccaggaggag attgactatg   3300
atgacaccat ctctgtggag atgaagaagg aggactttga catctacgac gaggacgaga   3360
accagagccc caggagcttc cagaagaaga ccaggcacta cttcattgct gctgtggaga   3420
ggctgtggga ctatggcatg agcagcagcc cccatgtgct gaggaacagg gcccagtctg   3480
gctctgtgcc ccagttcaag aaggtggtgt tccaggagtt cactgatggc agcttcaccc   3540
agcccctgta cagaggggag ctgaatgagc acctgggcct gctgggcccc tacatcaggg   3600
ctgaggtgga ggacaacatc atggtgacct caggaaacca ggccagcagg ccctacagct   3660
tctacagcag cctgatcagc tatgaggagg accagaggca gggggctgag cccaggaaga   3720
actttgtgaa gcccaatgaa accaagacct acttctggaa ggtgcagcac cacatggccc   3780
ccaccaagga tgagtttgac tgcaaggcct gggcctactt ctctgatgtg gacctggaga   3840
aggatgtgca ctctggcctg attggccccc tgctggtgtg ccacaccaac ccctgaacc    3900 ctgcccatgg caggcaggtg actgtgcagg agtttgccct gttcttcacc atctttgatg   3960
aaaccaagag ctggtacttc actgagaaca tggagaggaa ctgcagggcc cctgcaaca    4020 tccagatgga ggaccccacc ttcaaggaga actacaggtt ccatgccatc aatggctaca   4080
tcatggacac cctgcctggc ctggtgatgg cccaggacca gaggatcagg tggtacctgc   4140
tgagcatggg cagcaatgag aacatccaca gcatccactt ctctggccat gtgttcactg   4200
tgaggaagaa ggaggagtac aagatggccc tgtacaacct gtaccctggg gtgtttgaga   4260
ctgtggagat gctgcccagc aaggctgcca tctggagggt ggagtgcctg attggggagc   4320
acctgcatgc tggcatgagc accctgttcc tggtgtacag caacaagtgc cagacccccc   4380
tgggcatggc ctctggccac atcagggact tccagatcac tgcctctggc cagtatggcc   4440
agtgggcccc caagctggcc aggctgcact actctggcag catcaatgcc tggagcacca   4500
aggagccctt cagctggatc aaggtggacc tgctggcccc catgatcatc catggcatca   4560
agacccaggg ggccaggcag aagttcagca gcctgtacat cagccagttc atcatcatgt   4620
acagcctgga tggcaagaag tggcagacct acaggggcaa cagcactggc accctgatgg   4680 tgttcttgg caatgtggac agctctggca tcaagcacaa catcttcaac cccccatca    4740 ttgccagata catcaggctg caccccaccc actacagcat caggagcacc ctgaggatgg   4800
agctgatggg ctgtgacctg aacagctgca gcatgccct gggcatggag agcaaggcca    4860
tctctgatgc ccagatcact gccagcagct acttcaccaa catgtttgcc acctggagcc   4920
```

| | |
|---|---|
| ccagcaaggc caggctgcac ctgcagggca ggagcaatgc ctggaggccc caggtcaaca | 4980 |
| accccaagga gtggctgcag gtggacttcc agaagaccat gaaggtgact ggggtgacca | 5040 |
| cccaggggt gaagagcctg ctgaccagca tgtatgtgaa ggagttcctg atcagcagca | 5100 |
| gccaggatgg ccaccagtgg accctgttct tccagaatgg caaggtgaag gtgttccagg | 5160 |
| gcaaccagga cagcttcacc cctgtggtga acagcctgga ccccccctg ctgaccagat | 5220 |
| acctgaggat tcaccccag agctgggtgc cagattgc cctgaggatg gaggtgctgg | 5280 |
| gctgtgaggc ccaggacctg tactgacctc gaggtgtgcc ttctagttgc cagccatctg | 5340 |
| ttgtttgccc ctccccgtg ccttccttga ccctggaagg tgccactccc actgtccttt | 5400 |
| cctaataaaa tgaggaaatt gcatcgcatt gtctgagtag gtgtcattct attctggggg | 5460 |
| gtggggtggg gcaggacagc aagggggagg attgggaaga caatagcagg catgctgggg | 5520 |
| atgcggtggg ctctatgggc acgtgcctc tcacactacc taaaccacgc caggacaacc | 5580 |
| tctgctcctc tccaccgaaa ttccaagggg tcgagtggat gttggaggtg gcatgggccc | 5640 |
| agagaggtct ctgacctctg ccccagctcc aaggtcagca ggcagggagg gctgtgtgtt | 5700 |
| tgctgtttgc tgcttgcaat gtttgccat tttagggaca tgagtaggct gaagtttgtt | 5760 |
| cagtgtggac ttcagaggca gcacacaaac agctgctgga ggatgggaac tgaggggttg | 5820 |
| gaaggggca gggtgagccc agaaactcct gtgtgcctct gagcctgcag ccctctcaca | 5880 |
| ctacctaaac cacgccagga caacctctgc tcctctccac cgaaattcca aggggtcgag | 5940 |
| tggatgttgg aggtggcatg ggcccagaga ggtctctgac ctctgcccca gctccaaggt | 6000 |
| cagcaggcag ggagggctgt gtgtttgctg tttgctgctt gcaatgtttg cccattttag | 6060 |
| ggacatgagt aggctgaagt tgttcagtg tggacttcag aggcagcaca caaacagctg | 6120 |
| ctggaggatg ggaactgagg ggttggaagg gggcagggtg agcccagaaa ctcctgtgtg | 6180 |
| cctctgagcc tgcagcacgt ggcggccgca ggaaccccta gtgatggagt tggccactcc | 6240 |
| ctctctgcgc gctcgctcgc tcactgaggc cgggcgacca aggtcgccc gacgcccggg | 6300 |
| ctttgcccgg gcggcctcag tgagcgagcg agcgcgcaga gagggagtgg ccaa | 6354 |

<210> SEQ ID NO 15
<211> LENGTH: 6308
<212> TYPE: DNA
<213> ORGANISM: Adeno-Associated Virus 2

<400> SEQUENCE: 15

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttaattttta aaaagcagtc | 180 |
| aaaagtccaa gtggcccttg gcagcattta ctctctctgt ttgctctggt taataatctc | 240 |
| aggagcacaa acattcctgg aggcaggaga agaaatcaac atcctggact atcctctgg | 300 |
| gcctgttaat ttttaaaaag cagtcaaaag tccagtggc ccttggcagc atttactctc | 360 |
| tctgtttgct ctggttaata atctcaggag cacaaacatt cctggaggca ggagaagaaa | 420 |
| tcaacatcct ggacttatcc tctgggccta ggcctgagcc tggtcaaaat tgaacctcct | 480 |
| cctgctctga gcagcctggg gggcagacta agcagagggc tgtgcagacc cacataaaga | 540 |
| gcctactgtg tgccaggcac ttcacccgag gcacttcaca agcatgcttg gaatgaaac | 600 |
| ttccaactct ttgggatgca ggtgaaacag ttcctggttc agagaggtga agcggcctgc | 660 |
| ctgaggcagc acagctcttc tttacagatg tgcttcccca cctctaccct gtctcacggc | 720 |

```
cccccatgcc agcctgacgg ttgtgtctgc ctcagtcatg ctccattttt ccatcgggac    780
catcaagagg gtgtttgtgt ctaaggctga ctgggtaact ttggatgagc ggtctctccg    840
ctctgagcct gtttcctcat ctgtcaaatg ggctctaacc cactctgatc tcccagggcg    900
gcagtaagtc ttcagcatca ggcattttgg ggtgactcag taaatggtag atcttgctac    960
cagtggaaca gccactaagg attctgcagt gagagcagag ggccagctaa gtggtactct   1020
cccagagact gtctgactca cgccaccccc tccaccttgg acacaggacg ctgtggtttc   1080
tgagccaggt acaatgactc ctttcggtaa gtgcagtgga agctgtacac tgcccaggca   1140
aagcgtccgg gcagcgtagg cgggcgactc agatcccagc cagtggactt agcccctgtt   1200
tgctcctccg ataactgggg tgaccttggt taatattcac cagcagcctc cccgttgcc    1260 cctctggatc cactgcttaa atacggacga ggacagggcc ctgtctcctc agcttcaggc   1320
accaccactg acctgggaca gtgaatcgta agtactagca gctacaatcc agctaccatt   1380
ctgcttttat tttatggttg ggataaggct ggattattct gagtccaagc taggcccttt   1440
tgctaatcat gttcatacct cttatcttcc tcccacagct cctgggcaac gtgctggtct   1500
gtgtgctggc ccatcacttt ggcaaagaat tgcgatcgcc accatgcaga ttgagctgag   1560
cacctgcttc ttcctgtgcc tgctgaggtt ctgcttctct gccaccagga gatactacct   1620
gggggctgtg gagctgagct gggactacat gcagtctgac ctgggggagc tgcctgtgga   1680
tgccaggttc ccccccagag tgcccaagag cttccccttc aacacctctg tggtgtacaa   1740
gaagaccctg tttgtggagt tcactgacca cctgttcaac attgccaagc caggccccc    1800 ctggatgggc ctgctgggcc ccaccatcca ggctgaggtg tatgacactg tggtgatcac   1860
cctgaagaac atggccagcc accctgtgag cctgcatgct gtgggggtga gctactggaa   1920
ggcctctgag ggggctgagt atgatgacca gaccagccag agggagaagg aggatgacaa   1980
ggtgttccct gggggcagcc acacctatgt gtggcaggtg ctgaaggaga atggcccat    2040 ggcctctgac cccctgtgcc tgacctacag ctacctgagc catgtggacc tggtgaagga   2100
cctgaactct ggcctgattg gggcctgct ggtgtgcagg gagggcagcc tggcaaggg    2160 gaagacccag accctgcaca agttcatcct gctgtttgct gtgtttgatg agggcaagag   2220
ctggcactct gaaaccaaga acagcctgat gcaggacagg gatgctgcct ctgccagggc   2280
ctggcccaag atgcacactg tgaatggcta tgtgaacagg agcctgcctg gcctgattgg   2340
ctgccacagg aagtctgtgt actggcatgt gattggcatg ggcaccaccc ctgaggtgca   2400
cagcatcttc ctggagggcc acaccttcct ggtcaggaac acaggcagg ccagcctgga    2460 gatcagcccc atcaccttcc tgactgccca gaccctgctg atggacctgg gccagttcct   2520
gctgttctgc cacatcagca gccaccagca tgatggcatg gaggcctatg tgaaggtgga   2580
cagctgccct gaggagcccc agctgaggat gaagaacaat gaggaggctg aggactatga   2640
tgatgacctg actgactctg agatggatgt ggtgaggttt gatgatgaca cagcccag    2700 cttcatccag atcaggtctg tggccaagaa gcaccccaag acctgggtgc actacattgc   2760
tgctgaggag gaggactggg actatgcccc cctggtgctg gccctgatg acaggagcta    2820 caagagccag tacctgaaca atggccccca gaggattggc aggaagtaca agaaggtcag   2880
gttcatggcc tacactgatg aaaccttcaa gaccagggag gccatccagc atgagtctgg   2940
catcctgggc cccctgctgt atgggagggt ggggacacc ctgctgatca tcttcaagaa    3000
ccaggccagc aggccctaca acatctaccc ccatggcatc actgatgtga ggcccctgta   3060
```

```
cagcaggagg ctgcccaagg gggtgaagca cctgaaggac ttccccatcc tgcctgggga    3120
gatcttcaag tacaagtgga ctgtgactgt ggaggatggc cccaccaagt ctgaccccag    3180
gtgcctgacc agatactaca gcagctttgt gaacatggag agggacctgg cctctggcct    3240
gattggcccc ctgctgatct gctacaagga gtctgtggac cagaggggca accagatcat    3300
gtctgacaag aggaatgtga tcctgttctc tgtgtttgat gagaacagga gctggtacct    3360
gactgagaac atccagaggt tcctgcccaa ccctgctggg gtgcagctgg aggaccctga    3420
gttccaggcc agcaacatca tgcacagcat caatggctat gtgtttgaca gcctgcagct    3480
gtctgtgtgc ctgcatgagg tggcctactg gtacatcctg agcattgggg cccagactga    3540
cttcctgtct gtgttcttct ctggctacac cttcaagcac aagatggtgt atgaggacac    3600
cctgaccctg ttccccttct ctggggagac tgtgttcatg agcatggaga ccctggcct    3660 gtggattctg ggctgccaca actctgactt caggaacagg ggcatgactg ccctgctgaa    3720
agtctccagc tgtgacaaga cactggggga ctactatgag gacagctatg aggacatctc    3780
tgcctacctg ctgagcaaga caatgccat tgagcccagg agcttcagcc agaaccccc    3840 agtgctgaag aggcaccaga gggagatcac caggaccacc ctgcagtctg accaggagga    3900
gattgactat gatgacacca tctctgtgga gatgaagaag gaggactttg acatctacga    3960
cgaggacgag aaccagagcc ccaggagctt ccagaagaag accaggcact acttcattgc    4020
tgctgtggag aggctgtggg actatggcat gagcagcagc ccccatgtgc tgaggaacag    4080
ggcccagtct ggctctgtgc cccagttcaa gaaggtggtg ttccaggagt cactgatgg    4140 cagcttcacc cagcccctgt acagagggga gctgaatgag cacctgggcc tgctgggccc    4200
ctacatcagg gctgaggtgg aggacaacat catggtgacc ttcaggaacc aggccagcag    4260
gccctacagc ttctacagca gcctgatcag ctatgaggag gaccagaggc aggggctga    4320 gcccaggaag aactttgtga gcccaatga aaccaagacc tacttctgga aggtgcagca    4380
ccacatggcc cccaccaagg atgagtttga ctgcaaggcc tgggcctact ctctgatgt    4440 ggacctggag aaggatgtgc actctggcct gattggcccc ctgctggtgt gccacaccaa    4500
caccctgaac cctgcccatg gcaggcaggt gactgtgcag gagtttgccc tgttcttcac    4560
catctttgat gaaaccaaga gctggtactt cactgagaac atggagagga actgcagggc    4620
cccctgcaac atccagatgg aggaccccac cttcaaggag aactacaggt tccatgccat    4680
caatggctac atcatggaca ccctgcctgg cctggtgatg gcccaggacc agaggatcag    4740
gtggtacctg ctgagcatgg gcagcaatga gaacatccac agcatccact ctctggcca    4800 tgtgttcact gtgaggaaga aggaggagta caagatggcc ctgtacaacc tgtaccctgg    4860
ggtgtttgag actgtggaga tgctgcccag caaggctggc atctggaggg tggagtgcct    4920
gattggggag cacctgcatg ctggcatgag caccctgttc ctggtgtaca gcaacaagtg    4980 ccagacccc ctgggcatgg cctctggcca catcaggac ttccagatca ctgcctctgg    5040
ccagtatggc cagtgggccc ccaagctggc caggctgcac tactctggca gcatcaatgc    5100
ctggagcacc aaggagccct tcagctggat caaggtggac ctgctggccc ccatgatcat    5160
ccatggcatc aagacccagg gggccaggca aagttcagc agcctgtaca tcagccagtt    5220
catcatcatg tacagcctgg atggcaagaa gtggcagacc tacaggggca acagcactgg    5280 cacccctgatg gtgttctttg gcaatgtgga cagctctggc atcaagcaca acatcttcaa    5340
cccccccatc attgccagat acatcaggct gcacccacc cactacagca tcaggagcac    5400
cctgaggatg gagctgatgg gctgtgacct gaacagctgc agcatgcccc tgggcatgga    5460
```

```
gagcaaggcc atctctgatg cccagatcac tgccagcagc tacttcacca acatgtttgc    5520
cacctggagc cccagcaagg ccaggctgca cctgcagggc aggagcaatg cctggaggcc    5580
ccaggtcaac aaccccaagg agtggctgca ggtggacttc agaagaccat gaaggtgac     5640 tggggtgacc acccaggggg tgaagagcct gctgaccagc atgtatgtga aggagttcct    5700
gatcagcagc agccaggatg ccaccagtg gaccctgttc ttccagaatg caaggtgaa     5760 ggtgttccag gcaaccagg acagcttcac ccctgtggtg aacagcctgg accccccct     5820 gctgaccaga tacctgagga ttcacccca gagctgggtg caccagattg ccctgaggat    5880
ggaggtgctg ggctgtgagg cccaggacct gtactgacct cgagctgtgc cttctagttg    5940
ccagccatct gttgtttgcc cctccccgt gccttccttg accctggaag gtgccactcc    6000
cactgtcctt tcctaataaa atgaggaaat tgcatcgcat tgtctgagta ggtgtcattc    6060
tattctgggg ggtggggtgg ggcaggacag caaggggag gattgggaag acaatagcag    6120
gcatgctggg gatgcggtgg gctctatgga ccggtgcggc cgcaggaacc cctagtgatg    6180
gagttggcca ctccctctct gcgcgctcgc tcgctcactg aggccgggcg accaaaggtc    6240
gcccgacgcc cgggctttgc ccgggcggcc tcagtgagcg agcgagcgcg cagagaggga    6300
gtggccaa                                                            6308
```

<210> SEQ ID NO 16
<211> LENGTH: 5635
<212> TYPE: DNA
<213> ORGANISM: Adeno-Associate Virus 2

<400> SEQUENCE: 16

```
ttggccactc cctctctgcg cgctcgctcg ctcactgagg ccgcccgggc aaagcccggg      60
cgtcgggcga ccttggtcg cccggcctca gtgagcgagc gagcgcgcag agagggagtg     120
gccaactcca tcactagggg ttcctgcggc cgcacgcgtg ttaattttta aaaagcagtc     180
aaaagtccaa gtggcccttg gcagcattta ctctctctgt ttgctctggt taataatctc     240
aggagcacaa acattcctgg aggcaggaga agaaatcaac atcctggact atcctctgg     300 gcctgttaat ttttaaaaag cagtcaaaag tccaagtggc ccttggcagc atttactctc     360
tctgtttgct ctggtaata atctcaggag cacaaacatt cctggaggca ggagaagaaa     420
tcaacatcct ggacttatcc tctgggccta gtcgactgga cacaggacgc tgtggtttct    480
gagccagggg gcgactcaga tcccagccag tggacttagc ccctgtttgc tcctccgata    540
actggggtga ccttggttaa tattcaccag cagcctcccc cgttgcccct ctggatccac    600
tgcttaaata cggacgagga cagggccctg tctcctcagc ttcaggcacc accactgacc    660
tgggacagtg aatcgtaagt actagcagct acaatccagc taccattctg cttttatttt    720
atggttggga taaggctgga ttattctgag tccaagctag gccttttgc taatcatgtt     780 catacctctt atcttcctcc cacagctcct gggcaacgtg ctggtctgtg tgctggccca    840
tcactttggc aaagaattgc gatcgccacc atgcagattg agctgagcac ctgcttcttc    900
ctgtgcctgc tgaggttctg cttctctgcc accaggagat actacctggg gctgtggag     960 ctgagctggg actacatgca gtctgacctg ggggagctgc ctgtggatgc caggttcccc   1020
cccagagtgc ccaagagctt cccttcaac acctctgtgg tgtacaagaa gaccctgttt    1080
gtggagttca ctgaccacct gttcaacatt gccaagccca ggcccccctg gatgggcctg   1140
ctgggcccca ccatccaggc tgaggtgtat gacactgtgg tgatcaccct gaagaacatg   1200
```

```
gccagccacc ctgtgagcct gcatgctgtg ggggtgagct actggaaggc ctctgagggg    1260
gctgagtatg atgaccagac cagccagagg gagaaggagg atgacaaggt gttccctggg    1320
ggcagccaca cctatgtgtg gcaggtgctg aaggagaatg gccccatggc ctctgacccc    1380
ctgtgcctga cctacagcta cctgagccat gtggacctgg tgaaggacct gaactctggc    1440
ctgattgggg ccctgctggt gtgcagggag ggcagcctgg ccaaggagaa gacccagacc    1500
ctgcacaagt tcatcctgct gtttgctgtg tttgatgagg gcaagagctg gcactctgaa    1560
accaagaaca gcctgatgca ggacagggat gctgcctctg ccagggcctg gcccaagatg    1620
cacactgtga atggctatgt gaacaggagc ctgcctggcc tgattggctg ccacaggaag    1680
tctgtgtact ggcatgtgat tggcatgggc accacccctg aggtgcacag catcttcctg    1740
gagggccaca ccttcctggt caggaaccac aggcaggcca gcctggagat cagccccatc    1800
accttcctga ctgcccagac cctgctgatg gacctgggcc agttcctgct gttctgccac    1860
atcagcagcc accagcatga tggcatggag gcctatgtga aggtggacag ctgccctgag    1920
gagccccagc tgaggatgaa gaacaatgag gaggctgagg actatgatga tgacctgact    1980
gactctgaga tggatgtggt gaggtttgat gatgacaaca gccccagctt catccagatc    2040
aggtctgtgg ccaagaagca ccccaagacc tgggtgcact acattgctgc tgaggaggag    2100
gactgggact atgccccccct ggtgctggcc cctgatgaca ggagctacaa gagccagtac    2160
ctgaacaatg gccccagag gattggcagg aagtacaaga aggtcaggtt catggcctac    2220
actgatgaaa ccttcaagac cagggaggcc atccagcatg agtctggcat cctgggcccc    2280
ctgctgtatg gggaggtggg ggacaccctg ctgatcatct tcaagaacca ggccagcagg    2340
ccctacaaca tctacccca tggcatcact gatgtgaggc cctgtacag caggaggctg    2400
cccaaggggg tgaagcacct gaaggacttc cccatcctgc ctggggagat cttcaagtac    2460
aagtggactg tgactgtgga ggatggcccc accaagtctg accccaggtg cctgaccaga    2520
tactacagca gctttgtgaa catggagagg gacctggcct ctggcctgat ggcccctg    2580
ctgatctgct acaaggagtc tgtggaccag aggggcaacc agatcatgtc tgacaagagg    2640
aatgtgatcc tgttctctgt gtttgatgag aacaggagct ggtacctgac tgagaacatc    2700
cagaggttcc tgcccaaccc tgctggggtg cagctggagg accctgagtt ccaggccagc    2760
aacatcatgc acagcatcaa tggctatgtg tttgacagcc tgcagctgtc tgtgtgcctg    2820
catgaggtgg cctactggta catcctgagc attggggccc agactgactt cctgtctgtg    2880
ttcttctctg gctacacctt caagcacaag atggtgtatg aggacaccct gacctgttc    2940
cccttctctg gggagactgt gttcatgagc atggagaacc ctggctgtg gattctgggc    3000
tgccacaact ctgacttcag gaacaggggc atgactgccc tgctgaaagt ctccagctgt    3060
gacaagaaca ctggggacta ctatgaggac agctatgagg acatctctgc ctacctgctg    3120
agcaagaaca atgccattga gcccaggagc ttcagccaga acccccagt gctgaagagg    3180
caccagaggg agatcaccag gaccacctg cagtctgacc aggaggagat tgactatgat    3240
gacaccatct ctgtggagat gaagaaggag gactttgaca tctacgacga ggacgagaac    3300
cagagcccca ggagcttcca gaagaagacc aggcactact cattgctgc tgtggagagg    3360
ctgtgggact atggcatgag cagcagcccc catgtgctga ggaacagggc ccagtctggc    3420
tctgtgcccc agttcaagaa ggtggtgttc caggagttca ctgatggcag cttcacccag    3480
cccctgtaca gaggggagct gaatgagcac ctggcctgc tgggcccta catcagggct    3540
gaggtggagg acaacatcat ggtgaccttc aggaaccagg ccagcaggcc ctacagcttc    3600
```

```
tacagcagcc tgatcagcta tgaggaggac cagaggcagg gggctgagcc caggaagaac    3660
tttgtgaagc ccaatgaaac caagacctac ttctggaagg tgcagcacca catggccccc    3720
accaaggatg agtttgactg caaggcctgg gcctacttct ctgatgtgga cctggagaag    3780
gatgtgcact ctggcctgat tggcccctg ctggtgtgcc acaccaacac cctgaaccct    3840
gcccatggca ggcaggtgac tgtgcaggag tttgccctgt tcttcaccat ctttgatgaa    3900
accaagagct ggtacttcac tgagaacatg gagaggaact gcagggcccc tgcaacatc    3960 cagatggagg accccacctt caaggagaac tacaggttcc atgccatcaa tggctacatc    4020
atggacaccc tgcctggcct ggtgatggcc caggaccaga ggatcaggtg gtacctgctg    4080
agcatgggca gcaatgagaa catccacagc atccacttct ctggccatgt gttcactgtg    4140
aggaagaagg aggagtacaa gatggccctg tacaacctgt accctggggt gtttgagact    4200
gtggagatgc tgcccagcaa ggctggcatc tggagggtgg agtgcctgat tggggagcac    4260
ctgcatgctg gcatgagcac cctgttcctg gtgtacagca caagtgcca gaccccctg    4320 ggcatggcct ctggccacat cagggacttc cagatcactg cctctggcca gtatggccag    4380
tgggccccca gctggccag gctgcactac tctggcagca tcaatgcctg gagcaccaag    4440
gagcccttca gctggatcaa ggtggacctg ctggcccca tgatcatcca tggcatcaag    4500
acccaggggg ccaggcagaa gttcagcagc ctgtacatca gccagttcat catcatgtac    4560
agcctggatg caagaagtg gcagacctac aggggcaaca gcactggcac cctgatggtg    4620
ttctttggca atgtggacag ctctggcatc aagcacaaca tcttcaaccc cccatcatt    4680 gccagataca tcaggctgca ccccacccac tacagcatca ggagcaccct gaggatggag    4740
ctgatgggct gtgacctgaa cagctgcagc atgcccctgg gcatggagag caaggccatc    4800
tctgatgccc agatcactgc cagcagctac ttcaccaaca tgtttgccac ctggagcccc    4860
agcaaggcca ggctgcacct gcaggcagg agcaatgcct ggaggcccca ggtcaacaac    4920
cccaaggagt ggctgcaggt ggacttccag aagaccatga aggtgactgg ggtgaccacc    4980
caggggtgta gagcctgct gaccagcatg tatgtgaagg agttcctgat cagcagcagc    5040
caggatggcc accagtggac cctgttcttc cagaatggca aggtgaaggt gttccagggc    5100
aaccaggaca gcttcacccc tgtggtgaac agcctggacc cccccctgct gaccagatac    5160
ctgaggattc accccagag ctgggtgcac agattgccc tgaggatgga ggtgctgggc    5220
tgtgaggccc aggacctgta ctgacctcga gctgtgcctt ctagttgcca gccatctgtt    5280
gtttgcccct ccccgtgcc ttccttgacc ctggaaggtg ccactcccac tgtccttttcc    5340 taataaatg aggaaattgc atcgcattgt ctgagtaggt gtcattctat tctggggggt    5400 gggtggggc aggacagcaa gggggaggat tggaagaca atagcaggca tgctgggat    5460 gcggtgggct ctatggaccg gtgcggccgc aggaaccct agtgatggag ttggccactc    5520
cctctctgcg cgctcgctcg ctcactgagg ccgcccgggc aaagcccggg    5580
gctttgcccg gcggcctca gtgagcgagc gagcgcgcag agagggagtg gccaa    5635
```

<210> SEQ ID NO 17
<211> LENGTH: 6962
<212> TYPE: DNA
<213> ORGANISM: Adeno-Associated Virus 2

<400> SEQUENCE: 17

```
ttggccactc cctctctgcg cgctcgctcg ctcactgagg ccgcccgggc aaagcccggg      60
```

```
cgtcgggcga cctttggtcg cccggcctca gtgagcgagc gagcgcgcag agagggagtg    120
gccaactcca tcactagggg ttcctgcggc cgcacgcgta ggctcagagg cacacaggag    180
tttctgggct caccctgccc ccttccaacc cctcagttcc catcctccag cagctgtttg    240
tgtgctgcct ctgaagtcca cactgaacaa acttcagcct actcatgtcc ctaaaatggg    300
caaacattgc aagcagcaaa cagcaaacac acagccctcc ctgcctgctg accttggagc    360
tggggcagag gtcagagacc tctctgggcc catgccacct ccaacatcca ctcgacccct    420
tggaatttcg gtggagagga gcagaggttg tcctggcgtg gtttaggtag tgtgagaggg    480
gtcgacaggc tcagaggcac acaggagttt ctgggctcac cctgcccct tccaacccct     540
cagttcccat cctccagcag ctgtttgtgt gctgcctctg aagtccacac tgaacaaact    600
tcagcctact catgtcccta aaatgggcaa acattgcaag cagcaaacag caaacacaca    660
gccctccctg cctgctgacc ttggagctgg ggcagaggtc agagacctct ctgggcccat    720
gccacctcca acatccactc gacccttgg aatttcggtg gagaggagca gaggttgtcc     780
tggcgtggtt taggtagtgt gagagggtc gacgttaatt tttaaaaagc agtcaaaagt     840
ccaagtggcc cttggcagca tttactctct ctgtttgctc tggttaataa tctcaggagc    900
acaaacattc ctggaggcag gagaagaaat caacatcctg gacttatcct ctgggcctgt    960
taattttaa aaagcagtca aaagtccaag tggcccttgg cagcatttac tctctctgtt     1020
tgctctggtt aataatctca ggagcacaaa cattcctgga ggcaggagaa gaatcaaca    1080
tcctggactt atcctctggg cctaggcctg aggctggtca aaattgaacc tcctcctgct    1140
ctgagcagcc tggggggcag actaagcaga gggctgtgca gacccacata aagagcctac    1200
tgtgtgccag gcacttcacc cgaggcactt cacaagcatg cttgggaatg aaacttccaa    1260
ctctttggga tgcaggtgaa acagttcctg gttcagagag gtgaagcggc ctgcctgagg    1320
cagcacagct cttctttaca gatgtgcttc cccacctcta ccctgtctca cggccccca    1380
tgccagcctg acgttgtgt ctgcctcagt catgctccat ttttccatcg ggaccatcaa    1440
gagggtgttt gtgtctaagg ctgactgggt aactttggat gagcggtctc tccgctctga    1500
gcctgttttcc tcatctgtca aatgggctct aacccactct gatctcccag gcggcagta    1560
agtcttcagc atcaggcatt tgggggtgac tcagtaaatg gtagatcttg ctaccagtgg    1620
aacagccact aaggattctg cagtgagagc agagggccag ctaagtggta ctctcccaga    1680
gactgtctga ctcacgccac ccctccacc ttggacacag gacgctgtgg tttctgagcc     1740
aggtacaatg actcctttcg gtaagtgcag tggaagctgt acactgccca ggcaaagcgt    1800
ccgggcagcg taggcgggcg actcagatcc cagccagtgg acttagcccc tgtttgctcc    1860
tccgataact ggggtgacct tggttaatat tcaccagcag cctcccccgt gcccctctg     1920
gatccactgc ttaaatacgg acgaggacag ggccctgtct cctcagcttc aggcaccacc    1980
actgacctgg gacagtgaat cgtaagtact agcagctaca atccagctac cattctgctt    2040
ttatttatg gttgggataa ggctggatta ttctgagtcc aagctaggcc ttttgctaa     2100
tcatgttcat acctcttatc ttcctcccac agctcctggg caacgtgctg gtctgtgtgc    2160
tggcccatca ctttggcaaa gaattgcgat cgccaccatg cagattgagc tgagcacctg    2220
cttcttcctg tgcctgctga ggttctgctt ctctgccacc aggagatact acctgggggc    2280
tgtggagctg agctgggact acatgcagtc tgacctgggg gagctgcctg tggatgccag    2340
gttcccccc agagtgccca agagcttccc cttcaacacc tctgtggtgt acaagaagac    2400
cctgtttgtg gagttcactg accacctgtt caacattgcc aagcccaggc cccctggat    2460
```

```
gggcctgctg ggccccacca tccaggctga ggtgtatgac actgtggtga tcaccctgaa    2520
gaacatggcc agccaccctg tgagcctgca tgctgtgggg gtgagctact ggaaggcctc    2580
tgagggggct gagtatgatg accagaccag ccagagggag aaggaggatg acaaggtgtt    2640
ccctggggga agccacacct atgtgtggca ggtgctgaag gagaatggcc ccatggcctc    2700
tgaccccctg tgcctgacct acagctacct gagccatgtg gacctggtga aggacctgaa    2760
ctctggcctg attggggccc tgctggtgtg caggagggc agcctggcca aggagaagac    2820
ccagaccctg cacaagttca tcctgctgtt tgctgtgttt gatgagggca gagctggca    2880 ctctgaaacc aagaacagcc tgatgcagga cagggatgct gcctctgcca gggcctggcc    2940
caagatgcac actgtgaatg ctatgtgaaa caggagcctg cctggcctga ttggctgcca    3000
caggaagtct gtgtactggc atgtgattgg catgggcacc accctgagg tgcacagcat    3060 cttcctggag ggccacacct tcctggtcag gaaccacagg caggccagcc tggagatcag    3120
ccccatcacc ttcctgactg cccagaccct gctgatggac ctgggccagt tcctgctgtt    3180
ctgccacatc agcagccacc agcatgatgg catggaggcc tatgtgaagg tggacagctg    3240
ccctgaggag ccccagctga ggatgaagaa caatgaggag gctgaggact atgatgatga    3300
cctgactgac tctgagatgg atgtggtgag gtttgatgat gacaacagcc ccagcttcat    3360
ccagatcagg tctgtggcca agaagcaccc caagacctgg gtgcactaca ttgctgctga    3420
ggaggaggac tgggactatg ccccctggt gctggcccct gatgacagga gctacaagag    3480
ccagtacctg aacaatggcc cccagaggat tggcaggaag tacaagaagg tcaggttcat    3540
ggcctacact gatgaaacct tcaagaccag ggaggccatc cagcatgagt ctggcatcct    3600 gggcccctg ctgtatgggg aggtggggga caccctgctg atcatcttca agaaccaggc    3660
cagcaggccc tacaacatct accccatgg catcactgat gtgaggcccc tgtacagcag    3720
gaggctgccc aaggggtga agcacctgaa ggacttcccc atcctgcctg ggagatctt    3780 caagtacaag tggactgtga ctgtggagga tggccccacc aagtctgacc ccaggtgcct    3840
gaccagatac tacagcagct tgtgaacat ggagagggac ctggcctctg gcctgattgg    3900 cccccctgctg atctgctaca aggagtctgt ggaccagagg ggcaaccaga tcatgtctga    3960
caagaggaat gtgatcctgt tctctgtgtt tgatgagaac aggagctggt acctgactga    4020
gaacatccag aggttcctgc ccaaccctgc tggggtgcag ctggaggacc ctgagttcca    4080
ggccagcaac atcatgcaca gcatcaatgg ctatgtgttt gacagcctgc agctgtctgt    4140
gtgcctgcat gaggtggcct actggtacat cctgagcatt ggggcccaga ctgacttcct    4200
gtctgtgttc ttctctggct acaccttcaa gcacaagatg gtgtatgagg cacccctgac    4260
cctgttcccc ttctctgggg agactgtgtt catgagcatg gagaaccctg gcctgtggat    4320
tctgggctgc cacaactctg acttcaggaa caggggcatg actgccctgc tgaaagtctc    4380
cagctgtgac aagaacactg gggactacta tgaggacagc tatgaggaca tctctgccta    4440
cctgctgagc aagaacaatg ccattgagcc caggagcttc agccagaacc ccccagtgct    4500
gaagaggcac cagagggaga tcaccaggac caccctgcag tctgaccagg aggagattga    4560
ctatgatgac accatctctg tggagatgaa gaaggaggac tttgacatct acgacgagga    4620
cgagaaccag agccccagga gcttccagaa gaagaccagg cactacttca ttgctgctgt    4680
ggagaggctg tgggactatg gcatgagcag cagcccccat gtgctgagga cagggccca    4740 gtctggctct gtgccccagt tcaagaaggt ggtgttccag gagttcactg atggcagctt    4800
```

```
cacccagccc ctgtacagag ggagctgaa tgagcacctg ggcctgctgg gcccctacat    4860
cagggctgag gtggaggaca acatcatggt gaccttcagg aaccaggcca gcaggcccta    4920
cagcttctac agcagcctga tcagctatga ggaggaccag aggcaggggg ctgagcccag    4980
gaagaacttt gtgaagccca atgaaaccaa gacctacttc tggaaggtgc agcaccacat    5040
ggccccccacc aaggatgagt tgactgcaa ggcctgggcc tacttctctg atgtggacct    5100
ggagaaggat gtgcactctg gcctgattgg cccctgctg gtgtgccaca ccaacaccct    5160
gaaccctgcc catggcaggc aggtgactgt gcaggagttt gccctgttct tcaccatctt    5220
tgatgaaacc aagagctggt acttcactga gaacatggag aggaactgca gggccccctg    5280
caacatccag atggaggacc ccaccttcaa ggagaactac aggttccatg ccatcaatgg    5340
ctacatcatg gacaccctgc ctggcctggt gatggcccag gaccagagga tcaggtggta    5400
cctgctgagc atgggcagca atgagaacat ccacagcatc cacttctctg ccatgtgtt    5460
cactgtgagg aagaaggagg agtacaagat ggccctgtac aacctgtacc ctggggtgtt    5520
tgagactgtg gagatgctgc ccagcaaggc tggcatctgg agggtggagt gcctgattgg    5580
ggagcacctg catgctggca tgagcaccct gttcctggtg tacagcaaca agtgccagac    5640
ccccctgggc atggcctctg gccacatcag ggacttccag atcactgcct ctggccagta    5700
tggccagtgg gcccccaagc tggccaggct gcactactct ggcagcatca atgcctggag    5760
caccaaggag ccccttcagct ggatcaaggt ggacctgctg gcccccatga tcatccatgg    5820
catcaagacc cagggggcca ggcagaagtt cagcagcctg tacatcagcc agttcatcat    5880
catgtacagc ctgatggcca agaagtggca gacctacagg gcaacagca ctggcaccct    5940
gatggtgttc tttggcaatg tggacagctc tggcatcaag cacaacatct tcaaccccc    6000
catcattgcc agatacatca ggctgcaccc caccactac agcatcagga gcaccctgag    6060
gatggagctg atgggctgtg acctgaacag ctgcagcatg ccctgggca tggagagcaa    6120
ggccatctct gatgcccaga tcactgccag cagctacttc accaacatgt tgccacctg    6180
gagccccagc aaggccaggc tgcacctgca gggcaggagc aatgcctgga ggccccaggt    6240
caacaaccccc aaggagtggc tgcaggtgga cttccagaag accatgaagg tgactggggt    6300
gaccacccag ggggtgaaga gcctgctgac cagcatgtat gtgaaggagt tcctgatcag    6360
cagcagccag gatggccacc agtggaccct gttcttccag aatggcaagg tgaaggtgtt    6420
ccagggcaac caggacagct tcacccctgt ggtgaacagc ctggacccc cctgctgac     6480
cagatacctg aggattcacc cccagagctg ggtgcaccag attgccctga ggatggaggt    6540
gctgggctgt gaggcccagg acctgtactg acctcgagct gtgccttcta gttgccagcc    6600
atctgttgtt tgcccctccc ccgtgccttc cttgaccctg gaaggtgcca ctcccactgt    6660
cctttcctaa taaaatgagg aaattgcatc gcattgtctg agtaggtgtc attctattct    6720
ggggggtggg gtggggcagg acagcaaggg ggaggattgg gaagacaata gcaggcatgc    6780
tggggatgcg gtgggctcta tggaccggtg cggccgcagg aaccctagt gatggagttg    6840
gccactccct ctctgcgcgc tcgctcgctc actgaggccg ggcgaccaaa ggtcgcccga    6900
cgcccgggct ttgcccgggc ggcctcagtg agcgagcgag cgcgcagaga gggagtggcc    6960
aa                                                                  6962
```

<210> SEQ ID NO 18
<211> LENGTH: 6289
<212> TYPE: DNA
<213> ORGANISM: Adeno-Associated Virus 2

<400> SEQUENCE: 18

```
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcctgcggc cgcacgcgta ggctcagagg cacacaggag   180
tttctgggct caccctgccc ccttccaacc cctcagttcc catcctccag cagctgtttg   240
tgtgctgcct ctgaagtcca cactgaacaa acttcagcct actcatgtcc ctaaaatggg   300
caaacattgc aagcagcaaa cagcaaacac acagccctcc ctgcctgctg accttggagc   360
tggggcagag gtcagagacc tctctgggcc catgccacct ccaacatcca ctcgacccct   420
tggaatttcg gtggagagga gcagaggttg tcctggcgtg gtttaggtag tgtgagaggg   480
gtcgacaggc tcagaggcac acaggagttt ctgggctcac cctgcccctt ccaacccct   540
cagttcccat cctccagcag ctgtttgtgt gctgcctctg aagtccacac tgaacaaact   600
tcagcctact catgtcccta aaatgggcaa acattgcaag cagcaaacag caaacacaca   660
gccctccctg cctgctgacc ttggagctgg ggcagaggtc agagacctct ctgggcccat   720
gccacctcca acatccactc gacccctggg aatttcggtg gagaggagca gaggttgtcc   780
tggcgtggtt taggtagtgt gagaggggtc gacgttaatt tttaaaaagc agtcaaaagt   840
ccaagtggcc cttggcagca tttactctct ctgtttgctc tggttaataa tctcaggagc   900
acaaacattc ctggaggcag gagaagaaat caacatcctg gacttatcct ctgggcctgt   960
taattttaa aaagcagtca aaagtccaag tggcccttgg cagcatttac tctctctgtt  1020
tgctctggtt aataatctca ggagcacaaa cattcctgga ggcaggagaa gaaatcaaca  1080
tcctggactt atcctctggg cctagtcgac tggacacagg acgctgtggt ttctgagcca  1140
gggggcgact cagatcccag ccagtggact tagcccctgt ttgctcctcc gataactggg  1200
gtgaccttgg ttaatattca ccagcagcct ccccgttgc ccctctggat ccactgctta  1260
aatacggacg aggacagggc cctgtctcct cagcttcagg caccaccact gacctgggac  1320
agtgaatcgt aagtactagc agctacaatc cagctaccat tctgctttta ttttatggtt  1380
gggataaggc tggattattc tgagtccaag ctaggcccctt ttgctaatca tgttcatacc  1440
tcttatcttc ctcccacagc tcctgggcaa cgtgctggtc tgtgtgctgg cccatcactt  1500
tggcaaagaa ttgcgatcgc caccatgcag attgagctga gcacctgctt cttcctgtgc  1560
ctgctgaggt tctgcttctc tgccaccagg agatactacc tgggggctgt ggagctgagc  1620
tgggactaca tgcagtctga cctggggag ctgcctgtgg atgccaggtt cccccccaga  1680
gtgcccaaga gcttccccctt caacacctct gtggtgtaca agaagaccct gtttgtggag  1740
ttcactgacc acctgttcaa cattgccaag cccaggcccc ctggatggg cctgctgggc  1800
cccaccatcc aggctgaggt gtatgacact gtggtgatca ccctgaagaa catggccagc  1860
caccctgtga gcctgcatgc tgtggggtg agctactgga aggcctctga ggggctgag  1920
tatgatgacc agaccagcca gagggagaag gaggatgaca aggtgttccc tggggcagc  1980
cacacctatg tgtggcaggt gctgaaggag aatggcccca tggcctctga cccctgtgc  2040
ctgacctaca gctacctgag ccatgtggac ctggtgaagg acctgaactc tggcctgatt  2100
ggggccctgc tggtgtgcag ggagggcagc ctggccaagg agaagaccca gaccctgcac  2160
aagttcatcc tgctgtttgc tgtgtttgat gagggcaaga gctggcactc tgaaaccaag  2220
aacagcctga tgcaggacag ggatgctgcc tctgccaggg cctggccaa gatgcacact  2280
```

-continued

```
gtgaatggct atgtgaacag gagcctgcct ggcctgattg gctgccacag gaagtctgtg    2340
tactggcatg tgattggcat gggcaccacc cctgaggtgc acagcatctt cctggagggc    2400
cacaccttcc tggtcaggaa ccacaggcag gccagcctgg agatcagccc catcaccttc    2460
ctgactgccc agaccctgct gatggacctg ggccagttcc tgctgttctg ccacatcagc    2520
agccaccagc atgatggcat ggaggcctat gtgaaggtgg acagctgccc tgaggagccc    2580
cagctgagga tgaagaacaa tgaggaggct gaggactatg atgatgacct gactgactct    2640
gagatggatg tggtgaggtt tgatgatgac aacagcccca gcttcatcca gatcaggtct    2700
gtggccaaga agcaccccaa gacctgggtg cactacattg ctgctgagga ggaggactgg    2760
gactatgccc ccctggtgct ggcccctgat gacaggagct acaagagcca gtacctgaac    2820
aatggccccc agaggattgg caggaagtac aagaaggtca ggttcatggc ctacactgat    2880
gaaaccttca agaccaggga ggccatccag catgagtctg gcatcctggg ccccctgctg    2940
tatggggagg tggggacac cctgctgatc atcttcaaga accaggccag caggccctac    3000
aacatctacc cccatggcat cactgatgtg aggcccctgt acagcaggag gctgcccaag    3060
ggggtgaagc acctgaagga cttccccatc ctgcctgggg agatcttcaa gtacaagtgg    3120
actgtgactg tggaggatgg cccccaccaag tctgacccca ggtgcctgac cagatactac    3180
agcagctttg tgaacatgga gagggacctg gcctctggcc tgattggccc cctgctgatc    3240
tgctacaagg agtctgtgga ccagagggc aaccagatca tgtctgacaa gaggaatgtg    3300
atcctgttct ctgtgtttga tgagaacagg agctggtacc tgactgagaa catccagagg    3360
ttcctgccca accctgctgg ggtgcagctg gaggaccctg agttccaggc cagcaacatc    3420
atgcacagca tcaatggcta tgtgtttgac agcctgcagc tgtctgtgtg cctgcatgag    3480
gtggcctact ggtacatcct gagcattggg gcccagactg acttcctgtc tgtgttcttc    3540
tctggctaca ccttcaagca caagatggtg tatgaggaca ccctgaccct gttccccttc    3600
tctggggaga ctgtgttcat gagcatggag aaccctggcc tgtggattct gggctgccac    3660
aactctgact tcaggaacag gggcatgact gccctgctga aagtctccag ctgtgacaag    3720
aacactgggg actactatga ggacagctat gaggacatct ctgcctacct gctgagcaag    3780
aacaatgcca ttgagcccag gagcttcagc cagaaccccc cagtgctgaa gaggcaccag    3840
agggagatca ccaggaccac cctgcagtct gaccaggagg agattgacta tgatgacacc    3900
atctctgtgg agatgaagaa ggaggacttt gacatctacg acgaggacga gaaccagagc    3960
cccaggagct tccagaagaa gaccaggcac tacttcattg ctgctgtgga gaggctgtgg    4020
gactatggca tgagcagcag cccccatgtg ctgaggaaca gggcccagtc tggctctgtg    4080
ccccagttca agaaggtggt gttccaggag ttcactgatg gcagcttcac ccagcccctg    4140
tacagagggg agctgaatga gcacctgggc ctgctgggcc cctacatcag ggctgaggtg    4200
gaggacaaca tcatggtgac cttcaggaac caggccagca ggccctacag cttctacagc    4260
agcctgatca gctatgagga ggaccagagg caggggctg agcccaggaa gaactttgtg    4320
aagcccaatg aaaccaagac ctacttctgg aaggtgcagc accacatggc ccccaccaag    4380
gatgagtttg actgcaaggc ctgggcctac ttctctgatg tggacctgga aaggatgtg    4440 cactctggcc tgattggccc cctgctggtg tgccacacca cacccctgaa ccctgcccat    4500
ggcaggcagg tgactgtgca ggagtttgcc ctgttcttca ccatctttga tgaaaccaag    4560
agctggtact tcactgagaa catggagagg aactgcaggg ccccctgcaa catccagatg    4620
gaggacccca ccttcaagga gaactacagg ttccatgcca tcaatggcta catcatggac    4680
```

-continued

```
accctgcctg gcctggtgat ggcccaggac cagaggatca ggtggtacct gctgagcatg    4740
ggcagcaatg agaacatcca cagcatccac ttctctggcc atgtgttcac tgtgaggaag    4800
aaggaggagt acaagatggc cctgtacaac ctgtaccctg gggtgtttga gactgtggag    4860
atgctgccca gcaaggctgg catctggagg gtggagtgcc tgattgggga gcacctgcat    4920
gctggcatga gcaccctgtt cctggtgtac agcaacaagt gccagacccc cctgggcatg    4980
gcctctggcc acatcaggga cttccagatc actgcctctg ccagtatgg ccagtgggcc     5040 cccaagctgg ccaggctgca ctactctggc agcatcaatg cctggagcac aaggagccc    5100 ttcagctgga tcaaggtgga cctgctggcc ccatgatca tccatggcat caagacccag     5160
ggggccaggc agaagttcag cagcctgtac atcagccagt tcatcatcat gtacagcctg    5220
gatggcaaga gtggcagac ctacagggg aacagcactg gcaccctgat ggtgttcttt      5280
ggcaatgtgg acagctctgg catcaagcac aacatcttca accccccat cattgccaga     5340 tacatcaggc tgcaccccac ccactacagc atcaggagca ccctgaggat ggagctgatg    5400
ggctgtgacc tgaacagctg cagcatgccc ctgggcatgg agagcaaggc catctctgat    5460
gcccagatca ctgccagcag ctacttcacc aacatgtttg ccacctggag ccccagcaag    5520
gccaggctgc acctgcaggg caggagcaat gcctggaggc cccaggtcaa caaccccaag    5580
gagtggctgc aggtggactt ccagaagacc atgaaggtga ctggggtgac cacccagggg    5640
gtgaagagcc tgctgaccag catgtatgtg aaggagttcc tgatcagcag cagccaggat    5700
ggccaccagt ggaccctgtt cttccagaat ggcaaggtga aggtgttcca gggcaaccag    5760
gacagcttca ccctgtggt gaacagcctg gaccccccc tgctgaccag ataccctgagg    5820 attcacccc agagctgggt gcaccagatt gccctgagga tggaggtgct gggctgtgag    5880
gcccaggacc tgtactgacc tcgagctgtg ccttctagtt gccagccatc tgttgtttgc    5940
ccctcccccg tgccttcctt gaccctggaa ggtgccactc ccactgtcct ttcctaataa    6000
aatgaggaaa ttgcatcgca ttgtctgagt aggtgtcatt ctattctggg gggtgggggtg   6060 gggcaggaca gcaaggggga ggattgggaa gacaatagca gcatgctgg ggatgcggtg     6120 ggctctatgg accggtgcgg ccgcaggaac ccctagtgat ggagttggcc actccctctc    6180
tgcgcgctcg ctcgctcact gaggccgggc gaccaaaggt cgcccgacgc ccgggctttg    6240
cccgggcggc ctcagtgagc gagcgagcgc gcagagaggg agtggccaa                6289
```

<210> SEQ ID NO 19
<211> LENGTH: 5430
<212> TYPE: DNA
<213> ORGANISM: Adeno-Associated Virus 2

<400> SEQUENCE: 19

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacgt ggacttagcc    180
cctgtttgct cctccgataa ctggggtgac cttggttaat attcaccagc agcctccccg    240
tggacttagc cctgtttgc tcctccgata actggggtga ccttggttaa tattcaccag    300
cagcctcccc acgcgaaacg tcgactggac acaggacgct gtggtttctg agccaggggg   360
cgactcagat cccagccagt ggacttagcc cctgtttgct cctccgataa ctggggtgac    420
cttggttaat attcaccagc agcctccccc gttgccctc tggatccact gcttaaatac     480
```

```
ggacgaggac agggccctgt ctcctcagct tcaggcacca ccactgacct gggacagtga    540
atcgtaagta ctagcagcta caatccagct accattctgc tttttatttta tggttgggat    600 aaggctggat tattctgagt ccaagctagg ccctttttgct aatcatgttc atacctctta    660
tcttcctccc acagctcctg gcaacgtgc tggtctgtgt gctggcccat cactttggca    720
aagaattgcg atcgccacca tgcagattga gctgagcacc tgcttcttcc tgtgcctgct    780
gaggttctgc ttctctgcca ccaggagata tacctgggg gctgtggagc tgagctggga    840
ctacatgcag tctgacctgg gggagctgcc tgtggatgcc aggttccccc ccagagtgcc    900
caagagcttc cccttcaaca cctctgtggt gtacaagaag accctgtttg tggagttcac   960
tgaccacctg ttcaacattg ccaagcccag gccccctgg atgggcctgc tgggccccac    1020
catccaggct gaggtgtatg acactgtggt gatcaccctg aagaacatgg ccagccaccc    1080
tgtgagcctg catgctgtgg gggtgagcta ctggaaggcc tctgaggggg ctgagtatga    1140
tgaccagacc agccagaggg agaaggagga tgacaaggtg ttccctgggg gcagccacac    1200
ctatgtgtgg caggtgctga aggagaatgg ccccatggcc tctgaccccc tgtgcctgac    1260
ctacagctac ctgagccatg tggacctggt gaaggacctg aactctggcc tgattggggc    1320
cctgctggtg tgcaggagg gcagcctggc caaggagaag acccagaccc tgcacaagtt    1380
catcctgctg tttgctgtgt ttgatgaggg caagagctgg cactctgaaa ccaagaacag    1440
cctgatgcag gacagggatg ctgcctctgc cagggcctgg cccaagatgc acactgtgaa    1500
tggctatgtg aacaggagcc tgcctggcct gattggctgc cacaggaagt ctgtgtactg    1560
gcatgtgatt ggcatgggca ccaccccctga ggtgcacagc atcttcctgg agggccacac    1620
cttcctggtc aggaaccaca ggcaggccag cctggagatc agccccatca ccttcctgac    1680
tgcccagacc ctgctgatgg acctgggcca gttcctgctg ttctgccaca tcagcagcca    1740
ccagcatgat ggcatggagg cctatgtgaa ggtggacagc tgccctgagg agccccagct    1800
gaggatgaag aacaatgagg aggctgagga ctatgatgat gacctgactg actctgagat    1860
ggatgtggtg aggtttgatg atgacaacag ccccagcttc atccagatca ggtctgtggc    1920
caagaagcac cccaagacct gggtgcacta cattgctgct gaggaggagg actgggacta    1980 tgccccctg gtgctggccc ctgatgacag gagctacaag agccagtacc tgaacaatgg    2040 ccccagagg attggcagga agtacaagaa ggtcaggttc atggcctaca ctgatgaaac    2100
cttcaagacc agggaggcca tccagcatga gtctggcatc ctgggccccc tgctgtatgg    2160
ggaggtgggg gacaccctgc tgatcatctt caagaaccag gccagcaggc cctacaacat    2220 ctaccccccat ggcatcactg atgtgaggcc cctgtacagc aggaggctgc caaggggggt    2280
gaagcacctg aaggacttcc ccatcctgcc tggggagatc ttcaagtaca gtgtgactgt    2340
gactgtggag gatggcccca ccaagtctga ccccaggtgc ctgaccagat actacagcag    2400
ctttgtgaac atggagaggg acctggcctc tggcctgatt ggccccctgc tgatctgcta    2460
caaggagtct gtgaccagag gggcaacca gatcatgtct gacaagagga atgtgatcct    2520
gttctctgtg tttgatgaga acaggagctg gtacctgact gagaacatcc agaggttcct    2580
gcccaaccct gctggggtgc agctggagga ccctgagttc caggcagca acatcatgca    2640 cagcatcaat ggctatgtgt tgacagcct gcagctgtct gtgtgcctgc atgaggtggc    2700
ctactggtac atcctgagca ttggggccca gactgacttc ctgtctgtgt tcttctctgg    2760
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
```

```
tgacttcagg aacaggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact tgtgaagcc    3540
caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggccccctgc tggtgtgcca caccaacacc ctgaaccctg ccatggcag    3720
gcaggtgact gtgcaggagt ttgccctgtt cttcaccatc tttgatgaaa ccaagagctg   3780
gtacttcact gagaacatgg agaggaactg cagggccccc tgcaacatcc agatggagga   3840
ccccaccttc aaggagaact acaggttcca tgccatcaat ggctacatca tggacaccct   3900
gcctggcctg gtgatggccc aggaccagag gatcaggtgg tacctgctga gcatgggcag   3960
caatgagaac atccacagca tccacttctc tggccatgtg ttcactgtga ggaagaagga   4020
ggagtacaag atggccctgt acaacctgta ccctgggtg tttgagactg tggagatgct    4080
gcccagcaag gctggcatct ggagggtgga gtgcctgatt ggggagcacc tgcatgctgg   4140
catgagcacc ctgttcctgg tgtacagcaa caagtgccag acccccctgg gcatggcctc   4200
tggccacatc agggacttcc agatcactgc ctctggccag tatggccagt gggccccaa    4260
gctggccagg ctgcactact ctggcagcat caatgcctgg agcaccaagg agcccttcag   4320
ctggatcaag gtggacctgc tggccccat gatcatccat ggcatcaaga cccaggggc     4380
caggcagaag ttcagcagcc tgtacatcag ccagttcatc atcatgtaca gcctggatgg   4440
caagaagtgg cagacctaca ggggcaacag cactggcacc ctgatggtgt cttttggcaa   4500
tgtggacagc tctggcatca gcacaacat cttcaacccc cccatcattg ccagatacat    4560
caggctgcac cccaccccact acagcatcag gagcaccctg aggatggagc tgatgggctg   4620
tgacctgaac agctgcagca tgcccctggg catggagagc aaggccatct ctgatgccca   4680
gatcactgcc agcagctact tcaccaacat gtttgccacc tggagcccca gcaaggccag   4740
gctgcacctg cagggcagga gcaatgcctg gaggccccag gtcaacaacc caaggagtg    4800
gctgcaggtg gacttccaga gaccatgaa ggtgactggg gtgaccaccc aggggggtgaa    4860
gagcctgctg accagcatgt atgtgaagga gttcctgatc agcagcagcc aggatggcca   4920
ccagtggacc ctgttcttcc agaatggcaa ggtgaaggtg ttccagggca accaggacag   4980
cttcacccct gtggtgaaca gcctggaccc ccccctgctg accagatacc tgaggattca   5040
cccccagagc tgggtgcacc agattgccct gaggatggag gtgctgggct gtgaggccca   5100
ggacctgtac tgacctcgag gcactgtcct ttcctaataa aatgaggaaa ttgcatcgca   5160
ttgtctgagt aggtgtcatt ctattctggg gggtggggtg gggcaggaca gcaagggga    5220
```

-continued

```
ggattgggaa gacaatagca ggcatgctgg ggatgcggtg ggctctatgg gcacgtggcg    5280
gccgcaggaa ccoctagtga tggagttggc cactccctct ctgcgcgctc gctcgctcac    5340
tgaggccggg cgaccaaagg tcgcccgacg cccgggcttt gcccgggcgg cctcagtgag    5400
cgagcgagcg cgcagagagg gagtggccaa                                     5430
```

<210> SEQ ID NO 20
<211> LENGTH: 5779
<212> TYPE: DNA
<213> ORGANISM: Adeno-Associated Virus 2

<400> SEQUENCE: 20

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacgt ggacttagcc    180
cctgtttgct cctccgataa ctggggtgac cttggttaat attcaccagc agcctccccg    240
tggacttagc ccctgtttgc tcctccgata actggggtga ccttggttaa tattcaccag    300
cagcctcccc acgcgaaacg tcgactggac acaggacgct gtggtttctg agccaggggg    360
cgactcagat cccagccagt ggacttagcc cctgtttgct cctccgataa ctggggtgac    420
cttggttaat attcaccagc agcctccccg ttgcccctc tggatccact gcttaaatac    480
ggacgaggac agggccctgt ctcctcagct tcaggcacca ccactgacct gggacagtga    540
atcgtaagta ctagcagcta caatccagct accattctgc ttttatttta tggttgggat    600
aaggctggat tattctgagt ccaagctagg ccctttttgct aatcatgttc atacctctta    660
tcttcctccc acagctcctg ggcaacgtgc tggtctgtgt gctggcccat cactttggca    720
aagaattgcg atcgccacca tgcagattga gctgagcacc tgcttcttcc tgtgcctgct    780
gaggttctgc ttctctgcca ccaggagata ctacctgggg gctgtggagc tgagctggga    840
ctacatgcag tctgacctgg gggagctgcc tgtggatgcc aggttccccc ccagagtgcc    900
caagagcttc cccttcaaca cctctgtggt gtacaagaag accctgtttg tggagttcac    960
tgaccacctg ttcaacattg ccaagcccag gcccccctgg atgggcctgc tgggccccac    1020
catccaggct gaggtgtatg acactgtggt gatcaccctg aagaacatgg ccagccaccc    1080
tgtgagcctg catgctgtgg gggtgagcta ctggaaggcc tctgaggggg ctgagtatga    1140
tgaccagacc agccagaggg agaaggagga tgacaaggtg ttccctgggg gcagccacac    1200
ctatgtgtgg caggtgctga aggagaatgg ccccatggcc tctgaccccc tgtgcctgac    1260
ctacagctac ctgagccatg tggacctggt gaaggacctg aactctggcc tgattggggc    1320
cctgctggtg tgcagggagg gcagcctggc caaggagaag acccagaccc tgcacaagtt    1380
catcctgctg tttgctgtgt tgatgagggg caagagctgg cactctgaaa ccaagaacag    1440
cctgatgcag gacagggatg ctgcctctgc cagggcctgg cccaagatgc acactgtgaa    1500
tggctatgtg aacaggagcc tgcctggcct gattggctgc cacaggaagt ctgtgtactg    1560
gcatgtgatt ggcatgggca ccaccectga ggtgcacagc atcttcctgg agggccacac    1620
cttcctggtc aggaaccaca ggcaggccag cctggagatc agccccatca ccttcctgac    1680
tgcccagacc ctgctgatgg acctgggcca gttcctgctg ttctgccaca tcagcagcca    1740
ccagcatgat ggcatggagg cctatgtgaa ggtggacagc tgccctgagg agcccagcct    1800
gaggatgaag aacaatgagg aggctgagga ctatgatgat gacctgactg actctgagat    1860
ggatgtggtg aggtttgatg atgacaacag ccccagcttc atccagatca ggtctgtggc    1920
```

```
caagaagcac cccaagacct gggtgcacta cattgctgct gaggaggagg actgggacta    1980
tgcccccctg gtgctggccc ctgatgacag gagctacaag agccagtacc tgaacaatgg    2040
cccccagagg attggcagga agtacaagaa ggtcaggttc atggcctaca ctgatgaaac    2100
cttcaagacc agggaggcca tccagcatga gtctggcatc ctgggccccc tgctgtatgg    2160
ggaggtgggg gacaccctgc tgatcatctt caagaaccag gccagcaggc cctacaacat    2220
ctacccccat ggcatcactg atgtgaggcc cctgtacagc aggaggctgc caagggggt    2280
gaagcacctg aaggacttcc ccatcctgcc tggggagatc ttcaagtaca agtggactgt    2340
gactgtggag gatggcccca ccaagtctga ccccaggtgc ctgaccagat actacagcag    2400
ctttgtgaac atggagaggg acctggcctc tggcctgatt ggccccctgc tgatctgcta    2460
caaggagtct gtggaccaga ggggcaacca gatcatgtct gacaagagga atgtgatcct    2520
gttctctgtg tttgatgaga acaggagctg gtacctgact gagaacatcc agaggttcct    2580
gcccaaccct gctggggtgc agctggagga ccctgagttc caggccagca acatcatgca    2640
cagcatcaat ggctatgtgt tgacagcct gcagctgtct gtgtgcctgc atgaggtggc    2700
ctactggtac atcctgagca ttggggccca gactgacttc ctgtctgtgt tcttctctgg    2760
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
tgacttcagg aacaggggca tgactgccct gctgaaagtc tccagctgtg acaagaacac    2940
tggggactac tatgaggaca gctatgagga catctctgcc tacctgctga gcaagaacaa    3000
tgccattgag cccaggagct tcagccagaa ccccccagtg ctgaagaggc accagaggga    3060
gatcaccagg accaccctgc agtctgacca ggaggagatt gactatgatg acaccatctc    3120
tgtggagatg aagaaggagg actttgacat ctacgacgag gacgagaacc agagcccag    3180
gagcttccag aagaagacca ggcactactt cattgctgct gtggagaggc tgtgggacta    3240
tggcatgagc agcagccccc atgtgctgag gaacagggcc cagtctggct ctgtgcccca    3300
gttcaagaag gtggtgttcc aggagttcac tgatggcagc ttcacccagc cctgtacag    3360
aggggagctg aatgagcacc tgggcctgct gggcccctac atcagggctg aggtggagga    3420
caacatcatg gtgaccttca ggaaccaggc cagcaggccc tacagcttct acagcagcct    3480
gatcagctat gaggaggacc agaggcaggg ggctgagccc aggaagaact tgtgaagcc    3540
caatgaaacc aagacctact tctggaaggt gcagcaccac atggcccca ccaaggatga    3600
gtttgactgc aaggcctggg cctacttctc tgatgtggac ctggagaagg atgtgcactc    3660
tggcctgatt ggccccctgc tggtgtgcca caccaacacc ctgaaccctg cccatggcag    3720
gcaggtgact gtgcaggagt ttgccctgtt cttcaccatc tttgatgaaa ccaagagctg    3780
gtacttcact gagaacatgg agaggaactg cagggcccc tgcaacatcc agatggagga    3840
ccccaccttc aaggagaact acaggttcca tgccatcaat ggctacatca tggacacccct    3900
gcctggcctg gtgatggccc aggaccagag gatcaggtgg tacctgctga gcatgggcag    3960
caatgagaac atccacagca tccacttctc tggccatgtg ttcactgtga ggaagaagga    4020
ggagtacaag atggccctgt acaacctgta ccctgggggtg tttgagactg tggagatgct    4080
gcccagcaag gctggcatct ggagggtgga gtgcctgatt ggggagcacc tgcatgctgg    4140
catgagcacc ctgttcctgg tgtacagcaa caagtgccag acccccctgg catggcctc    4200
tggccacatc agggacttcc agatcactgc ctctggccag tatggccagt gggccccaa    4260
```

| gctggccagg ctgcactact ctggcagcat caatgcctgg agcaccaagg agcccttcag | 4320 |
| ctggatcaag gtggacctgc tggcccccat gatcatccat ggcatcaaga cccaggggc | 4380 |
| caggcagaag ttcagcagcc tgtacatcag ccagttcatc atcatgtaca gcctggatgg | 4440 |
| caagaagtgg cagacctaca ggggcaacag cactggcacc ctgatggtgt tctttggcaa | 4500 |
| tgtggacagc tctggcatca agcacaacat cttcaacccc cccatcattg ccagatacat | 4560 |
| caggctgcac cccaccccact acagcatcag gagcaccctg aggatggagc tgatgggctg | 4620 |
| tgacctgaac agctgcagca tgcccctggg catggagagc aaggccatct ctgatgccca | 4680 |
| gatcactgcc agcagctact tcaccaacat gtttgccacc tggagcccca gcaaggccag | 4740 |
| gctgcacctg cagggcagga gcaatgcctg gaggccccag gtcaacaacc ccaaggagtg | 4800 |
| gctgcaggtg gacttccaga agaccatgaa ggtgactggg gtgaccaccc aggggtgaa | 4860 |
| gagcctgctg accagcatgt atgtgaagga gttcctgatc agcagcagcc aggatggcca | 4920 |
| ccagtggacc ctgttcttcc agaatggcaa ggtgaaggtg ttccagggca accaggacag | 4980 |
| cttcacccct gtggtgaaca gcctggaccc cccctgctg accagatacc tgaggattca | 5040 |
| cccccagagc tgggtgcacc agattgccct gaggatggag gtgctgggct gtgaggccca | 5100 |
| ggacctgtac tgacctcgag gcactgtcct ttcctaataa aatgaggaaa ttgcatcgca | 5160 |
| ttgtctgagt aggtgtcatt ctattctggg gggtggggtg gggcaggaca gcaaggggga | 5220 |
| ggattgggaa gacaatagca ggcatgctgg ggatgcggtg ggctctatgg gcactcgaca | 5280 |
| ggttaattt taaaaagcag tcaaagtcc aagtggccct tggcagcatt tactctctct | 5340 |
| gtttgctctg gttaataatc tcaggagcac aaacattcct ggaggcagga gaagaaatca | 5400 |
| acatcctgga cttatcctct gggcctctcc caccccag gagaggctca ggttaatttt | 5460 |
| taaaaagcag tcaaagtcc aagtggccct tggcagcatt tactctctct gtttgctctg | 5520 |
| gttaataatc tcaggagcac aaacattcct ggaggcagga gaagaaatca acatcctgga | 5580 |
| cttatcctct gggcctctcc caccccag gagaggctgt cgagtggcgg ccgcaggaac | 5640 |
| ccctagtgat ggagttggcc actccctctc tgcgcgctcg ctcgctcact gaggccgggc | 5700 |
| gaccaaaggt cgcccgacgc ccgggctttg cccgggcggc ctcagtgagc gagcgagcgc | 5760 |
| gcagagaggg agtggccaa | 5779 |

<210> SEQ ID NO 21
<211> LENGTH: 5962
<212> TYPE: DNA
<213> ORGANISM: Adeno-Associated Virus 2

<400> SEQUENCE: 21

| ttggccactc cctctctgcg cgctcgctcg ctcactgagg ccgccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaacca cgccaggaca acctctgctc ctctccaccg aaattccaag gggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |
| ggaggatggg aactgagggg ttggaagggg gcagggtgag cccagaaact cctgtgtgcc | 480 |
| tctgagcctg cagacgcgaa acgtcgactg gacacaggac gctgtggttt ctgagccagg | 540 |
| gggcgactca gatcccagcc agtggactta gcccctgttt gctcctccga taactgggt | 600 |

-continued

```
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggcccttt gctaatcatg ttcatacctc     840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt     1140
cactgaccac ctgttcaaca ttgccaagcc caggccccc tggatgggcc tgctgggccc    1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggcccccatg gcctctgacc cctgtgcct   1440
gacctacagc tacctgagcc atgtggacct ggtgaaggac ctgaactctg gcctgattgg   1500
ggccctgctg gtgtgcaggg agggcagcct ggccaaggaa aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc cctgctgta    2340
tgggaggtg ggggacaccc tgctgatcat cttcaagaac caggccagca ggccctacaa    2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgacccagg tgcctgacca gatactacag    2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
```

-continued

```
tggctacacc ttcaagcaca agatggtgta tgaggacacc ctgaccctgt tccccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag     3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggta ctgtgcagg agtttgccct gttcttcacc atctttgatg aaaccaagag    3960
ctggtacttc actgagaaca tggagaggaa ctgcagggcc ccctgcaaca tccagatgga    4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc    4380 ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac ccccccatca ttgccagata    4740
catcaggctg caccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttccaccaa catgtttgcc acctggagcc ccagcaaggc    4920
caggctgcac ctgcagggca ggagcaatgc ctggaggccc caggtcaaca ccccaagga    4980 gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccctgttct tccagaatgg caaggtgaag gtgttccagg gcaaccagga    5160
cagcttcacc cctgtggtga acagcctgga ccccccctg ctgaccagat acctgaggat    5220
tcacccccag agctgggtgc accagattgc cctgaggatg gaggtgctgg gctgtgaggc    5280
ccaggacctg tactgacctc gaggcactgt cctttcctaa taaaatgagg aaattgcatc    5340
```

```
gcattgtctg agtaggtgtc attctattct gggggtggg gtgggcagg acagcaaggg   5400 ggaggattgg gaagacaata gcaggcatgc tggggatgcg gtgggctcta tgggcactcg   5460
acaggttaat ttttaaaaag cagtcaaaag tccaagtggc ccttggcagc atttactctc   5520
tctgtttgct ctggttaata atctcaggag cacaaacatt cctggaggca ggagaagaaa   5580
tcaacatcct ggacttatcc tctgggcctc tccccacccc caggagaggc tcaggttaat   5640
ttttaaaaag cagtcaaaag tccaagtggc ccttggcagc atttactctc tctgtttgct   5700
ctggttaata atctcaggag cacaaacatt cctggaggca ggagaagaaa tcaacatcct   5760
ggacttatcc tctgggcctc tccccacccc caggagaggc tgtcgagtgg cggccgcagg   5820 aaccctagt gatggagttg ccactccct ctctgcgcgc tcgctcgctc actgaggccg   5880
ggcgaccaaa ggtcgcccga cgcccgggct tgcccgggc ggcctcagtg agcgagcgag   5940
cgcgcagaga gggagtggcc aa                                           5962
```

<210> SEQ ID NO 22
<211> LENGTH: 5919
<212> TYPE: DNA
<213> ORGANISM: Adeno-Associated Virus 2

<400> SEQUENCE: 22

```
ttggccactc cctctctgcg cgctcgctcg ctcactgagg ccgccgggc aaagcccggg     60 cgtcgggcga cctttggtcg cccggcctca gtgagcgagc gagcgcgcag agagggagtg   120
gccaactcca tcactagggg ttcctgcggc cgcacgcgta ggctcagagg cacacaggag   180
tttctgggct caccctgccc ccttccaacc cctcagttcc catcctccag cagctgtttg   240
tgtgctgcct ctgaagtcca cactgaacaa acttcagcct actcatgtcc ctaaaatggg   300
caaacattgc aagcagcaaa cagcaaacac acagccctcc ctgcctgctg accttggagc   360
tggggcagag gtcagagacc tctctggcc catgccacct ccaacatcca ctcgacccct   420
tggaatttcg gtggagagga gcagaggttg tcctggcgtg gtttaggtag tgtgagaggg   480
gtcgacgatc ttgctaccag tggaacagcc actaaggatt ctgcagtgag agcagagggc   540
cagctaagtg gtactctccc agagactgtc tgactcacgc cacccctcc accttggaca   600 caggacgctg tggttcctga gccaggtaca atgactcctt tcggtaagtg cagtggaagc   660
tgtacactgc ccaggcaaag cgtccgggca gcgtaggcgg gcgactcaga tcccagccag   720
tggacttagc ccctgtttgc tcctccgata actggggtga ccttggttaa tattcaccag   780
cagcctcccc cgttgcccct ctggatccac tgcttaaata cggacgagga cagggccctg   840
tctcctcagc ttcaggcacc accactgacc tgggacagtg aatcgtaagt atgcctttca   900
ctgcgagagg ttctggagag gcttctgagc tccccatggc ccaggcaggc agcaggtctg   960
gggcaggagg ggggttgtgg agtgggtatc cgcctgctga ggtgcagggc agatcatcat   1020
gtgccttgac tcggggcctg cccccccat ctctgtcttg caggacaatt gccgtcttct   1080
gtctcgtggg gcatcctcct gctggcaggc ctgtgctgcc tggtccctgt ctccctggct   1140
gaggaccggc caccatgcag attgagctga gcacctgctt cttcctgtgc ctgctgaggt   1200
tctgcttctc tgccaccagg agatactacc tgggggctgt ggagctgagc tgggactaca   1260
tgcagtctga cctgggggag ctgcctgtgg atgccaggtt cccccccaga gtgcccaaga   1320
gcttcccctt caacacctct gtggtgtaca agaagaccct gtttgtggag ttcactgacc   1380
acctgttcaa cattgccaag cccaggcccc cctggatggg cctgctgggc ccaccatcc   1440
```

```
aggctgaggt gtatgacact gtggtgatca ccctgaagaa catggccagc caccctgtga    1500
gcctgcatgc tgtggggtg agctactgga aggcctctga gggggctgag tatgatgacc     1560
agaccagcca gagggagaag gaggatgaca aggtgttccc tgggggcagc cacacctatg    1620
tgtggcaggt gctgaaggag aatggcccca tggcctctga cccctgtgc ctgacctaca     1680 gctacctgag ccatgtggac ctggtgaagg acctgaactc tggcctgatt ggggccctgc    1740
tggtgtgcag ggagggcagc ctggccaagg agaagaccca gaccctgcac aagttcatcc    1800
tgctgtttgc tgtgtttgat gagggcaaga gctggcactc tgaaaccaag aacagcctga    1860
tgcaggacag ggatgctgcc tctgccaggg cctggcccaa gatgcacact gtgaatggct    1920
atgtgaacag gagcctgcct ggcctgattg ctgccacag gaagtctgtg tactggcatg     1980
tgattggcat gggcaccacc cctgaggtgc acagcatctt cctggagggc cacaccttcc    2040
tggtcaggaa ccacaggcag gccagcctgg agatcagccc catcaccttc ctgactgccc    2100
agaccctgct gatggacctg gccagttcc tgctgttctg ccacatcagc agccaccagc     2160
atgatggcat ggaggcctat gtgaaggtgg acagctgccc tgaggagccc cagctgagga    2220
tgaagaacaa tgaggaggct gaggactatg atgatgacct gactgactct gagatggatg    2280
tggtgaggtt tgatgatgac aacagcccca gcttcatcca gatcaggtct gtggccaaga    2340
agcaccccaa gacctgggtg cactacattg ctgctgagga ggaggactgg gactatgccc    2400
ccctggtgct ggcccctgat gacaggagct acaagagcca gtacctgaac aatgcccccc    2460
agaggattgg caggaagtac aagaaggtca ggttcatggc ctacactgat gaaaccttca    2520
agaccaggga ggccatccag catgagtctg gcatcctggg ccccctgctg tatggggagg    2580 tggggacac cctgctgatc atcttcaaga accaggccag caggccctac aacatctacc     2640
cccatggcat cactgatgtg aggccctgt acagcaggag gctgcccaag ggggtgaagc     2700
acctgaagga cttcccccatc ctgcctgggg agatcttcaa gtacaagtgg actgtgactg   2760
tggaggatgg ccccaccaag tctgaccccca ggtgcctgac cagatactac agcagctttg   2820
tgaacatgga gagggacctg gcctctggcc tgattggccc cctgctgatc tgctacaagg    2880
agtctgtgga ccagagggc aaccagatca tgtctgacaa gaggaatgtg atcctgttct     2940
ctgtgtttga tgagaacagg agctggtacc tgactgagaa catccagagg ttcctgccca    3000
accctgctgg ggtgcagctg gaggaccctg agttccaggc cagcaacatc atgcacagca    3060
tcaatggcta tgtgtttgac agcctgcagc tgtctgtgtg cctgcatgag gtggcctact    3120
ggtacatcct gagcattggg gcccagactg acttcctgtc tgtgttcttc tctggctaca    3180
ccttcaagca caagatggtg tatgaggaca ccctgacct gttccccttc tctggggaga    3240
ctgtgttcat gagcatggag aaccctggcc tgtggattct gggctgccac aactctgact    3300
tcaggaacag gggcatgact gccctgctga aagtctccag ctgtgacaag aacactgggg    3360
actactatga ggacagctat gaggacatct ctgcctacct gctgagcaag aacaatgcca    3420
ttgagcccag gagcttcagc cagaaccccc cagtgctgaa gaggcaccag agggagatca    3480
ccaggaccac cctgcagtct gaccaggagg agattgacta tgatgacacc atctctgtgg    3540
agatgaagaa ggaggacttt gacatctacg acgaggacga gaaccagagc ccaggagct    3600 tccagaagaa gaccaggcac tacttcattg ctgctgtgga ggctgtggg gactatggca    3660 tgagcagcag ccccccatgtg ctgaggaaca gggcccagtc tggctctgtg ccccagttca    3720
agaaggtggt gttccaggag ttcactgatg gcagcttcac ccagccccctg tacagagggg   3780 agctgaatga gcacctgggc ctgctgggcc cctacatcag ggctgaggtg gaggacaaca    3840
```

```
tcatggtgac cttcaggaac caggccagca ggccctacag cttctacagc agcctgatca    3900
gctatgagga ggaccagagg caggggggctg agcccaggaa gaactttgtg aagcccaatg    3960
aaaccaagac ctacttctgg aaggtgcagc accacatggc ccccaccaag gatgagtttg    4020
actgcaaggc ctgggcctac ttctctgatg tggacctgga gaaggatgtg cactctggcc    4080
tgattggccc cctgctggtg tgccacacca caccctgaa ccctgcccat ggcaggcagg    4140
tgactgtgca ggagtttgcc ctgttcttca ccatctttga tgaaaccaag agctggtact    4200
tcactgagaa catggagagg aactgcaggg cccctgcaa catccagatg gaggacccca    4260
ccttcaagga gaactacagg ttccatgcca tcaatggcta catcatggac accctgcctg    4320
gcctggtgat ggcccaggac cagaggatca ggtggtacct gctgagcatg ggcagcaatg    4380
agaacatcca cagcatccac ttctctggcc atgtgttcac tgtgaggaag aaggaggagt    4440
acaagatggc cctgtacaac ctgtaccctg gggtgtttga actgtggag atgctgccca    4500 gcaaggctgg catctggagg gtggagtgcc tgattgggga gcacctgcat gctggcatga    4560
gcaccctgtt cctggtgtac agcaacaagt gccagacccc cctgggcatg gcctctggcc    4620
acatcaggga cttccagatc actgcctctg gccagtatgg ccagtgggcc ccaagctgg    4680 ccaggctgca ctactctggc agcatcaatg cctggagcac caaggagccc ttcagctgga    4740
tcaaggtgga cctgctggcc cccatgatca tccatggcat caagacccag ggggccaggc    4800
agaagttcag cagcctgtac atcagccagt tcatcatcat gtacagcctg gatggcaaga    4860
agtggcagac ctacaggggc aacagcactg gcaccctgat ggtgttcttt ggcaatgtgg    4920
acagctctgg catcaagcac aacatcttca accccccccat cattgccaga tacatcaggc    4980
tgcaccccac ccactacagc atcaggagca ccctgaggat ggagctgatg ggctgtgacc    5040
tgaacagctg cagcatgccc ctgggcatgg agagcaaggc catctctgat gcccagatca    5100
ctgccagcag ctacttcacc aacatgtttg ccacctggag ccccagcaag gccaggctgc    5160
acctgcaggg caggagcaat gcctggaggc ccaggtcaa caaccccaag gagtggctgc    5220
aggtggactt ccagaagacc atgaaggtga ctggggtgac cacccagggg gtgaagagcc    5280
tgctgaccag catgtatgtg aaggagttcc tgatcagcag cagccaggat ggccaccagt    5340
ggacccctgt ccttccagaat ggcaaggtga aggtgttcca gggcaaccag gacagcttca    5400 ccccctgtggt gaacagcctg accccccccc tgctgaccag atacctgagg attcaccccc    5460
agagctgggt gcaccagatt gccctgagga tggaggtgct gggctgtgag gcccaggacc    5520
tgtactgagc tcgagctgtg ccttctagtt gccagccatc tgttgtttgc ccctcccccg    5580
tgccttcctt gaccctggaa ggtgccactc ccactgtcct ttcctaataa aatgaggaaa    5640
ttgcatcgca ttgtctgagt aggtgtcatt ctattctggg gggtgggtg gggcaggaca    5700 gcaaggggga ggattgggaa gacaatagca ggcatgctgg ggatgcggtg ggctctatgg    5760
accggtgcgg ccgcaggaac ccctagtgat ggagttggcc actccctctc tgcgcgctcg    5820
ctcgctcact gaggccgggc gaccaaaggt cgcccgacgc ccgggctttg cccgggcggc    5880
ctcagtgagc gagcgagcgc gcagagaggg agtggccaa                          5919
```

<210> SEQ ID NO 23
<211> LENGTH: 5306
<212> TYPE: DNA
<213> ORGANISM: Adeno-Associated Virus 2

<400> SEQUENCE: 23

-continued

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttaaacgt cgaccctaaa     180
atgggcaaac attgcaagca gcaaacagca aactgacctt ggagctgggg cagaggtcag     240
agacctctct gggcactcga ccccttggaa tttcggtgga gaggagcaga ggtacacagc     300
cctccctgcc tgccccatgc cacctccaac atctgtcctg cgtggttta ggtagtgtga      360 gagggaatg actcctttcg gtaagtgcag tggaagctgt acactgccca ggcaaagcgt      420
ccgggcagcg taggcgggcg actcagatcc cagccagtgg acttagcccc tgtttgctcc     480
tccgataact ggggtgacct tggttaatat tcaccagcag cctccccgt tgccctctg       540 gatccactgc ttaaatacgg acgaggacag ggccctgtct cctcagcttc aggcaccacc     600
actgacctgg gacagtgaat cgcgatcgca ctgcttaaat acggacgagg acagggccct     660
gtctcctcag cttcaggcac caccactgac ctgggacagt gaatcgcgat cgccaccatg     720
cagattgagc tgagcacctg cttcttcctg tgcctgctga ggttctgctt ctctgccacc     780
aggagatact acctggggc tgtggagctg agctgggact acatgcagtc tgacctgggg     840
gagctgcctg tggatgccag gttccccccc agagtgccca gagcttccc cttcaacacc      900 tctgtggtgt acaagaagac cctgtttgtg gagttcactg accacctgtt caacattgcc     960
aagcccaggc cccctggat gggcctgctg gccccacca tccaggctga ggtgtatgac       1020
actgtggtga tcaccctgaa gaacatggcc agccaccctg tgagcctgca tgctgtgggg    1080
gtgagctact ggaaggcctc tgagggggct gagtatgatg accagaccag ccagagggag    1140
aaggaggatg acaaggtgtt ccctgggggc agccacacct atgtgtggca ggtgctgaag    1200
gagaatggcc ccatggcctc tgaccccctg tgcctgacct acagctacct gagccatgtg    1260
gacctggtga aggacctgaa ctctggcctg attggggccc tgctggtgtg cagggagggc    1320
agcctggcca aggagaagac ccagaccctg cacaagttca tcctgctgtt tgctgtgttt    1380
gatgagggca agagctggca ctctgaaacc aagaacagcc tgatgcagga cagggatgct    1440
gcctctgcca gggcctggcc caagatgcac actgtgaatg ctatgtgaa caggagcctg     1500 cctggcctga ttgctgcca caggaagtct gtgtactggc atgtgattgg catgggcacc    1560 accccctgagg tgcacagcat cttcctggag ggccacacct tcctggtcag gaaccacagg    1620
caggccagcc tggagatcag ccccatcacc ttcctgactg cccagaccct gctgatggac    1680
ctgggccagt cctgctgttt ctgccacatc agcagccacc agcatgatgg catggaggcc    1740
tatgtgaagg tggacagctg ccctgaggag ccccagctga ggatgaagaa caatgaggag    1800
gctgaggact atgatgatga cctgactgac tctgagatgg atgtggtgag gtttgatgat    1860
gacaacagcc ccagcttcat ccagatcagg tctgtggcca agaagcaccc caagacctgg    1920
gtgcactaca ttgctgctga ggaggaggac tgggactatg cccccctggt gctggcccct    1980
gatgacagga gctacaagag ccagtacctg aacaatggcc cccagaggat ggcaggaag     2040 tacaagaagg tcaggttcat ggcctacact gatgaaacct tcaagaccag ggaggccatc    2100
cagcatgagt ctggcatcct gggccccctg ctgtatgggg aggtggggga cccctgctg    2160 atcatcttca agaaccaggc cagcaggccc tacaacatct accccccatgg catcactgat   2220 gtgaggcccc tgtacagcag gaggctgccc aaggggtga agcacctgaa ggacttcccc     2280
atcctgcctg gggagatctt caagtacaag tggactgtga ctgtggagga tggccccacc    2340
aagtctgacc ccaggtgcct gaccagatac tacagcagct ttgtgaacat ggagagggac    2400
```

```
ctggcctctg gcctgattgg cccccctgctg atctgctaca aggagtctgt ggaccagagg   2460
ggcaaccaga tcatgtctga caagaggaat gtgatcctgt tctctgtgtt tgatgagaac   2520
aggagctggt acctgactga aacatccag aggttcctgc ccaaccctgc tggggtgcag   2580
ctggaggacc ctgagttcca ggccagcaac atcatgcaca gcatcaatgg ctatgtgttt   2640
gacagcctgc agctgtctgt gtgcctgcat gaggtggcct actggtacat cctgagcatt   2700
ggggcccaga ctgacttcct gtctgtgttc ttctctggct acaccttcaa gcacaagatg   2760
gtgtatgagg acaccctgac cctgttcccc ttctctgggg agactgtgtt catgagcatg   2820
gagaaccctg gcctgtggat tctgggctgc cacaactctg acttcaggaa caggggcatg   2880
actgccctgc tgaaagtctc cagctgtgac aagaacactg gggactacta tgaggacagc   2940
tatgaggaca tctctgccta cctgctgagc aagaacaatg ccattgagcc caggagcttc   3000
agccagaacc ccccagtgct gaagaggcac cagagggaga tcaccaggac caccctgcag   3060
tctgaccagg aggagattga ctatgatgac accatctctg tggagatgaa gaaggaggac   3120
tttgacatct acgacgagga cgagaaccag agccccagga gcttccagaa gaagaccagg   3180
cactacttca ttgctgctgt ggagaggctg tgggactatg gcatgagcag cagcccccat   3240
gtgctgagga cagggccca gtctggctct gtgccccagt tcaagaaggt ggtgttccag   3300
gagttcactg atggcagctt cacccagccc ctgtacagag gggagctgaa tgagcacctg   3360
ggcctgctgg gcccctacat cagggctgag gtggaggaca acatcatggt gaccttcagg   3420
aaccaggcca gcaggcccta cagcttctac agcagcctga tcagctatga ggaggaccag   3480
aggcaggggg ctgagcccag gaagaacttt gtgaagccca tgaaaccaa gacctacttc   3540 tggaaggtgc agcaccacat ggcccccacc aaggatgagt ttgactgcaa ggcctgggcc   3600
tacttctctg atgtggacct ggagaaggat gtgcactctg gcctgattgg ccccctgctg   3660
gtgtgccaca ccaacacccct gaaccctgcc catggcaggc aggtgactgt gcaggagttt   3720
gccctgttct tcaccatctt tgatgaaacc aagagctggt acttcactga aacatggag   3780 aggaactgca gggcccccctg caacatccag atggaggacc ccaccttcaa ggagaactac   3840
aggttccatg ccatcaatgg ctacatcatg gacacccctgc ctggcctggt gatggcccag   3900
gaccagagga tcaggtggta cctgctgagc atgggcagca atgagaacat ccacagcatc   3960
cacttctctg gccatgtgtt cactgtgagg aagaaggagg agtacaagat ggccctgtac   4020
aacctgtacc ctgggtgtt tgagactgtg gagatgctgc ccagcaaggc tggcatctgg   4080
agggtggagt gcctgattgg ggagcacctg catgctggag tgagcaccct gttcctggtg   4140
tacagcaaca agtgccagac ccccctgggc atggcctctg ccacatcag ggacttccag   4200 atcactgcct ctggccagta tggccagtgg gcccccaagc tggccaggct gcactactct   4260
ggcagcatca atgcctggag caccaaggag cccttcagct ggatcaaggt ggacctgctg   4320
gcccccatga tcatccatgg catcaagacc caggggcca gcagaagtt cagcagcctg   4380 tacatcagcc agttcatcat catgtacagc ctggatggca gaagtggca gacctacagg   4440 ggcaacagca ctggcaccct gatggtgttc tttggcaatg tggacagctc tggcatcaag   4500
cacaacatct tcaaccccccc catcattgcc agatacatca ggctgcaccc cacccactac   4560
agcatcagga gcaccctgag gatggagctg atgggctgtg acctgaacag ctgcagcatg   4620
cccctgggca tggagagcaa ggccatctct gatgcccaga tcactgccag cagctacttc   4680
accaacatgt ttgccaccctg gagccccagc aaggccaggc tgcacctgca gggcaggagc   4740
```

| | |
|---|---|
| aatgcctgga ggccccaggt caacaacccc aaggagtggc tgcaggtgga cttccagaag | 4800 |
| accatgaagg tgactggggt gaccacccag ggggtgaaga gcctgctgac cagcatgtat | 4860 |
| gtgaaggagt tcctgatcag cagcagccag gatggccacc agtggaccct gttcttccag | 4920 |
| aatggcaagg tgaaggtgtt ccagggcaac caggacagct tcacccctgt ggtgaacagc | 4980 |
| ctggaccccc ccctgctgac cagatacctg aggattcacc cccagagctg ggtgcaccag | 5040 |
| attgccctga ggatggaggt gctgggctgt gaggcccagg acctgtactg acctcgagga | 5100 |
| ataaaggaaa tttattttca ttgcaatagt gtgttggttt tttgtgtcac gtggcggccg | 5160 |
| caggaacccc tagtgatgga gttggccact ccctctctgc gcgctcgctc gctcactgag | 5220 |
| gccgggcgac caaaggtcgc ccgacgcccg ggctttgccc gggcggcctc agtgagcgag | 5280 |
| cgagcgcgca gagagggagt ggccaa | 5306 |

<210> SEQ ID NO 24
<211> LENGTH: 5461
<212> TYPE: DNA
<213> ORGANISM: Adeno-Associated Virus 2

<400> SEQUENCE: 24

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgactt tatttgccac | 180 |
| aaaaacccta tcagatgggc gtctttatca tttccattgt acagatgggg aaacaggctt | 240 |
| cggggtcggg gcatagccac ttactgacga ctccccaccc agcaagtggt tttgaacccg | 300 |
| gaccctctca cactacctaa accacgccag acaacctct gctcctctcc accgaaattc | 360 |
| caaggggtcg agtggatgtt ggaggtggca tgggcccaga gaggtctctg acctctgccc | 420 |
| cagctccaag gtcagcaggc agggagggct gtgtgtttgc tgtttgctgc ttgcaatgtt | 480 |
| tgcccatttt agggacatga gtaggctgaa gtttgttcag tgtggacttc agaggcagca | 540 |
| cacaaacagc tgctggagga tgggaactga ggggttggaa gggggcaggg tgagcccaga | 600 |
| aactcctgtg tgcctctgag cctgcagacg cgaaacgtcg actggacaca ggacgctgtg | 660 |
| gtttctgagc caggggggcga ctcagatccc agccagtgga cttagcccct gtttgctcct | 720 |
| ccgataactg gggtgacctt ggttaatatt caccagcagc ctccccgtt gcccctctgg | 780 |
| atccactgct taaatacgga cgaggacagg gccctgtctc ctcagcttca ggcaccacca | 840 |
| ctgacctggg acagtgaatc gcgatcgcca ccatgcagat tgagctgagc acctgcttct | 900 |
| tcctgtgcct gctgaggttc tgcttctctg ccaccaggag atactacctg ggggctgtgg | 960 |
| agctgagctg ggactacatg cagtctgacc tgggggagct gcctgtggat gccaggttcc | 1020 |
| cccccagagt gcccaagagc ttccccttca acacctctgt ggtgtacaag aagacccctg | 1080 |
| ttgtggagtt cactgaccac ctgttcaaca ttgccaagcc caggcccccc tggatgggcc | 1140 |
| tgctgggccc caccatccag gctgaggtgt atgacactgt ggtgatcacc ctgaagaaca | 1200 |
| tggccagcca ccctgtgagc ctgcatgctg tggggtgag ctactggaag gcctctgagg | 1260 |
| gggctgagta tgatgaccag accagccaga gggagaagga ggatgacaag gtgttccctg | 1320 |
| ggggcagcca cacctatgtg tggcaggtgc tgaaggagaa tggccccatg gcctctgacc | 1380 |
| ccctgtgcct gacctacagc tacctgagcc atgtggacct ggtgaaggac ctgaactctg | 1440 |
| gcctgattgg ggccctgctg gtgtgcaggg agggcagcct ggccaaggag aagacccaga | 1500 |
| ccctgcacaa gttcatcctg ctgtttgctg tgtttgatga gggcaagagc tggcactctg | 1560 |

```
aaaccaagaa cagcctgatg caggacaggg atgctgcctc tgccaggcc tggcccaaga      1620 tgcacactgt gaatggctat gtgaacagga gcctgcctgg cctgattggc tgccacagga     1680
agtctgtgta ctggcatgtg attggcatgg gcaccacccc tgaggtgcac agcatcttcc     1740
tggagggcca caccttcctg gtcaggaacc acaggcaggc cagcctggag atcagcccca     1800
tcaccttcct gactgcccag accctgctga tggacctggg ccagttcctg ctgttctgcc     1860
acatcagcag ccaccagcat gatggcatgg aggcctatgt gaaggtggac agctgccctg     1920
aggagcccca gctgaggatg aagaacaatg aggaggctga ggactatgat gatgacctga     1980
ctgactctga gatggatgtg gtgaggtttg atgatgacaa cagccccagc ttcatccaga     2040
tcaggtctgt ggccaagaag cacccccaaga cctgggtgca ctacattgct gctgaggagg     2100
aggactggga ctatgccccc ctggtgctgg cccctgatga caggagctac aagagccagt     2160
acctgaacaa tggcccccag aggattggca ggaagtacaa gaaggtcagg ttcatggcct     2220
acactgatga aaccttcaag accagggagg ccatccagca tgagtctggc atcctgggcc     2280
ccctgctgta tggggaggtg ggggacaccc tgctgatcat cttcaagaac caggccagca     2340
ggccctacaa catctacccc catggcatca ctgatgtgag gccctgtac agcaggaggc       2400 tgcccaaggg ggtgaagcac ctgaaggact cccccatcct gcctggggag atcttcaagt     2460
acaagtggac tgtgactgtg gaggatggcc ccaccaagtc tgaccccagg tgcctgacca     2520
gatactacag cagctttgtg aacatggaga gggacctggc ctctggcctg attggccccc     2580
tgctgatctg ctacaaggag tctgtggacc agagggcaa ccagatcatg tctgacaaga     2640
ggaatgtgat cctgttctct gtgtttgatg agaacaggag ctggtacctg actgagaaca     2700
tccagaggtt cctgcccaac cctgctgggg tgcagctgga ggaccctgag ttccaggcca     2760
gcaacatcat gcacagcatc aatggctatg tgtttgacag cctgcagctg tctgtgtgcc     2820
tgcatgaggt ggcctactgg tacatcctga gcattgggc ccagactgac ttcctgtctg      2880
tgttcttctc tggctacacc ttcaagcaca agatggtgta tgaggacacc ctgacctgt       2940 tccccttctc tggggagact gtgttcatga gcatggagaa ccctggcctg tggattctgg     3000
gctgccacaa ctctgacttc aggaacaggg gcatgactgc cctgctgaaa gtctccagct     3060
gtgacaagaa cactggggac tactatgagg acagctatga ggacatctct gcctacctgc     3120
tgagcaagaa caatgccatt gagcccagga gcttcagcca gaaccccca gtgctgaaga      3180 ggcaccagag ggagatcacc aggaccaccc tgcagtctga ccaggaggag attgactatg     3240
atgacaccat ctctgtggag atgaagaagg aggactttga catctacgac gaggacgaga     3300
accagagccc caggagcttc cagaagaaga ccaggcacta cttcattgct gctgtggaga     3360
ggctgtggga ctatgcatg agcagcagcc ccatgtgct gaggaacagg gcccagtctg       3420
gctctgtgcc ccagttcaag aaggtggtgt tccaggagtt cactgatggc agcttcaccc     3480
agcccctgta cagaggggag ctgaatgagc acctgggcct gctgggcccc tacatcaggg     3540
ctgaggtgga ggacaacatc atggtgacct tcaggaacca ggccagcagg ccctacagct     3600
tctacagcag cctgatcagc tatgaggagg accagaggca gggggctgag cccaggaaga     3660
actttgtgaa gcccaatgaa accaagacct acttctggaa ggtgcagcac cacatggccc     3720
ccaccaagga tgagtttgac tgcaaggcct gggcctactt ctctgatgtg gacctggaga     3780
aggatgtgca ctctggcctg attggccccc tgctggtgtg ccacaccaac accctgaacc     3840
ctgcccatgg caggcaggtg actgtgcagg agtttgccct gttcttcacc atctttgatg     3900
```

-continued

```
aaaccaagag ctggtacttc actgagaaca tggagaggaa ctgcagggcc ccctgcaaca      3960
tccagatgga ggaccccacc ttcaaggaga actacaggtt ccatgccatc aatggctaca      4020
tcatggacac cctgcctggc ctggtgatgg cccaggacca gaggatcagg tggtacctgc      4080
tgagcatggg cagcaatgag aacatccaca gcatccactt ctctggccat gtgttcactg      4140
tgaggaagaa ggaggagtac aagatggccc tgtacaacct gtaccctggg gtgtttgaga      4200
ctgtggagat gctgcccagc aaggctgcac tctggagggt ggagtgcctg attggggagc      4260
acctgcatgc tggcatgagc accctgttcc tggtgtacag caacaagtgc cagaccccccc      4320 tgggcatggc ctctgccac atcagggact tccagatcac tgcctctggc cagtatggcc      4380
agtgggcccc caagctggcc aggctgcact actctggcag catcaatgcc tggagcacca      4440
aggagccctt cagctggatc aaggtggacc tgctggcccc catgatcatc catggcatca      4500
agacccaggg ggccaggcag aagttcagca gcctgtacat cagccagttc atcatcatgt      4560
acagcctgga tggcaagaag tggcagacct cagggggcaa cagcactggc accctgatgg      4620
tgttctttgg caatgtggac agctctggca tcaagcacaa catcttcaac cccccatca      4680 ttgccagata catcaggctg caccccaccc actacagcat caggagcacc ctgaggatgg      4740
agctgatggg ctgtgacctg aacagctgca gcatgcccct gggcatggag agcaaggcca      4800
tctctgatgc ccagatcact gccagcagct acttcaccaa catgtttgcc acctggagcc      4860
ccagcaaggc caggctgcac ctgcagggca ggagcaatgc ctggaggccc caggtcaaca      4920
accccaagga gtggctgcag gtggacttcc agaagaccat gaaggtgact ggggtgacca      4980 cccaggggt gaagagcctg ctgaccagca tgtatgtgaa ggagttcctg atcagcagca      5040
gccaggatgg ccaccagtgg accctgttct tccagaatgg caaggtgaag gtgttccagg      5100
gcaaccagga cagcttcacc cctgtggtga acagcctgga ccccccctg ctgaccagat      5160 acctgaggat tcacccccag agctgggtgc accagattgc cctgaggatg gaggtgctgg      5220
gctgtgaggc ccaggacctg tactgacctc gaggaataaa ggaaatttat tttcattgca      5280
atagtgtgtt ggttttttgt gtcacgtggc ggccgcagga acccctagtg atggagttgg      5340
ccactccctc tctgcgcgct cgctcgctca ctgaggccgg gcgaccaaag gtcgcccgac      5400
gcccgggctt tgcccgggcg gcctcagtga gcgagcgagc gcgcagagag ggagtggcca      5460
a                                                                      5461
```

<210> SEQ ID NO 25
<211> LENGTH: 5327
<212> TYPE: DNA
<213> ORGANISM: Adeno-Associated Virus 2

<400> SEQUENCE: 25

```
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgaccc ctctcacact      180
acctaaacca cgccaggaca acctctgctc ctctccaccg aaattccaag gggtcgagtg      240
gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg gcagggtgag cccagaaaact cctgtgtgcc      480 tctgagcctg cagacgcgaa acgtcgactg gacacaggac gctgtggttt ctgagccagg      540
```

```
gggcgactca gatcccagcc agtggactta gcccctgttt gctcctccga taactgggt    600
gaccttggtt aatattcacc agcagcctcc cccgttgccc ctctggatcc actgcttaaa   660
tacggacgag gacagggccc tgtctcctca gcttcaggca ccaccactga cctgggacag   720
tgaatcgcga tcgccaccat gcagattgag ctgagcacct gcttcttcct gtgcctgctg   780
aggttctgct tctctgccac caggagatac tacctggggg ctgtggagct gagctgggac   840
tacatgcagt ctgacctggg ggagctgcct gtggatgcca ggttcccccc cagagtgccc   900
aagagcttcc ccttcaacac ctctgtggtg tacaagaaga ccctgtttgt ggagttcact   960
gaccacctgt tcaacattgc caagcccagg ccccctgga tgggcctgct gggccccacc    1020
atccaggctg aggtgtatga cactgtggtg atcaccctga gaacatggc cagccaccct    1080
gtgagcctgc atgctgtggg ggtgagctac tggaaggcct ctgaggggc tgagtatgat    1140
gaccagacca gccagaggga aaggaggat acaaggtgt tccctggggg cagccacacc     1200
tatgtgtggc aggtgctgaa ggagaatggc cccatggcct ctgacccct gtgcctgacc    1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gccccctgg tgctggcccc ctgatgacagg agctacaaga ccagtacct gaacaatggc    2040
ccccagagga ttggcaggaa gtacaagaag gtcaggttca tggcctacac tgatgaaacc   2100
ttcaagacca gggaggccat ccagcatgag tctggcatcc tgggcccct gctgtatggg    2160
gaggtggggg acaccctgct gatcatcttc aagaaccagg ccagcaggcc ctacaacatc   2220
tacccccatg gcatcactga tgtgaggccc ctgtacagca ggaggctgcc caaggggtg    2280
aagcacctga aggacttccc catcctgcct ggggagatct tcaagtacaa gtggactgtg   2340
actgtggagg atgcccccac caagtctgac cccaggtgcc tgaccagata ctacagcagc   2400
tttgtgaaca tggagaggga cctggcctct ggcctgattg gccccctgct gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
tacacccttca agcacaagat ggtgtatgag gacaccctga ccctgttccc cttctctggg   2820
gagactgtgt tcatgagcat ggagaaccct ggcctgtgga ttctgggctg ccacaactct   2880
```

```
gacttcagga acaggggcat gactgccctg ctgaaagtct ccagctgtga caagaacact    2940
ggggactact atgaggacag ctatgaggac atctctgcct acctgctgag caagaacaat    3000
gccattgagc ccaggagctt cagccagaac cccccagtgc tgaagaggca ccagagggag    3060
atcaccagga ccaccctgca gtctgaccag gaggagattg actatgatga caccatctct    3120
gtggagatga agaaggagga ctttgacatc tacgacgagg acgagaacca gagccccagg    3180
agcttccaga agaagaccag gcactacttc attgctgctg tggagaggct gtgggactat    3240
ggcatgagca gcagcccca tgtgctgagg aacagggccc agtctggctc tgtgcccag    3300
ttcaagaagg tggtgttcca ggagttcact gatggcagct tcacccagcc cctgtacaga    3360
ggggagctga atgagcacct gggcctgctg ggcccctaca tcagggctga ggtggaggac    3420
aacatcatgg tgaccttcag gaaccaggcc agcaggccct acagcttcta cagcagcctg    3480
atcagctatg aggaggacca gaggcagggg gctgagccca ggaagaactt tgtgaagccc    3540
aatgaaacca agacctactt ctggaaggtg cagcaccaca tggcccccac caaggatgag    3600
tttgactgca aggcctgggc ctacttctct gatgtggacc tggagaagga tgtgcactct    3660
ggcctgattg gcccctgct ggtgtgccac accaacaccc tgaaccctgc ccatggcagg    3720
caggtgactg tgcaggagtt tgccctgttc ttcaccatct ttgatgaaac caagagctgg    3780
tacttcactg agaacatgga gaggaactgc agggcccct gcaacatcca gatggaggac    3840
cccaccttca aggagaacta caggttccat gccatcaatg ctacatcat ggacaccctg    3900
cctggcctgg tgatggccca ggaccagagg atcaggtggt acctgctgag catgggcagc    3960
aatgagaaca tccacagcat ccacttctct ggccatgtgt tcactgtgag gaagaaggag    4020
gagtacaaga tggccctgta caacctgtac cctggggtgt tgagactgt ggagatgctg    4080
cccagcaagg ctggcatctg gagggtggag tgcctgattg gggagcacct gcatgctggc    4140
atgagcaccc tgttcctggt gtacagcaac aagtgccaga ccccctgggg catggcctct    4200
ggccacatca gggacttcca gatcactgcc tctggccagt atggccagtg ggccccaag    4260
ctggccaggc tgcactactc tggcagcatc aatgcctgga gcaccaagga gcccttcagc    4320
tggatcaagg tggacctgct ggcccccatg atcatccatg gcatcaagac caggggggcc    4380
aggcagaagt tcagcagcct gtacatcagc cagttcatca tcatgtacag cctggatggc    4440
aagaagtggc agacctacag gggcaacagc actggcaccc tgatggtgtt ctttggcaat    4500
gtggacagct ctggcatcaa gcacaacatc ttcaacccc ccatcattgc cagatacatc    4560
aggctgcacc ccacccacta cagcatcagg agcaccctga ggatggagct gatgggctgt    4620
gacctgaaca gctgcagcat gccctgggc atggagagca aggccatctc tgatgcccag    4680
atcactgcca gcagctactt caccaacatg tttgccacct ggagcccag caaggccagg    4740
ctgcacctgc agggcaggag caatgcctgg aggccccagg tcaacaaccc caaggagtgg    4800
ctgcaggtgg acttccagaa gaccatgaag gtgactgggg tgaccaccca ggggggtgaag    4860
agcctgctga ccagcatgta tgtgaaggag ttcctgatca gcagcagcca ggatggccac    4920
cagtggaccc tgttcttcca gaatggcaag gtgaaggtgt tccagggcaa ccaggacagc    4980
ttcacccctg tggtgaacag cctggaccc ccctgctga ccagatacct gaggattcac    5040
ccccagagct gggtgcacca gattgccctg aggatggagg tgctgggctg tgaggcccag    5100
gacctgtact gacctcgagg aataaaggaa atttattttc attgcaatag tgtgttggtt    5160
ttttgtgtca cgtggcggcc gcaggaaccc ctagtgatgg agttggccac tccctctctg    5220
cgcgctcgct cgctcactga ggccgggcga ccaaaggtcg cccgacgccc gggctttgcc    5280
```
cgggcggcct cagtgagcga gcgagcgcgc agagagggag tggccaa       5327

<210> SEQ ID NO 26
<211> LENGTH: 5309
<212> TYPE: DNA
<213> ORGANISM: Adeno-Associated Virus 2

<400> SEQUENCE: 26

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgcggc | cgcacgcgtc | tgcaggctca | gaggcacaca | 180 |
| ggagtttctg | gctcaccct | gcccccttcc | aacccctcag | ttcccatcct | ccagcagctg | 240 |
| tttgtgtgct | gcctctgaag | tccacactga | acaaacttca | gcctactcat | gtccctaaaa | 300 |
| tgggcaaaca | ttgcaagcag | caaacagcaa | acacacagcc | ctccctgcct | gctgaccttg | 360 |
| gagctggggc | agaggtcaga | gacctctctg | ggcccatgcc | acctccaaca | tccactcgac | 420 |
| cccttggaat | tcggtggag | aggagcagag | gttgtcctgg | cgtggtttag | gtagtgtgag | 480 |
| aggggtcgac | tggacacagg | acgctgtggt | ttctgagcca | gggggcgact | cagatcccag | 540 |
| ccagtggact | tagcccctgt | ttgctcctcc | gataactggg | gtgaccttgg | ttaatattca | 600 |
| ccagcagcct | ccccgttgc | ccctctggat | ccactgctta | aatacggacg | aggacagggc | 660 |
| cctgtctcct | cagcttcagg | caccaccact | gacctgggac | agtgaatcgc | gatcgccacc | 720 |
| atgcagattg | agctgagcac | ctgcttcttc | ctgtgcctgc | tgaggttctg | cttctctgcc | 780 |
| accaggagat | actacctggg | ggctgtggag | ctgagctggg | actacatgca | gtctgacctg | 840 |
| ggggagctgc | ctgtggatgc | caggttcccc | cccagagtgc | caagagctt | ccccttcaac | 900 |
| acctctgtgg | tgtacaagaa | gaccctgttt | gtggagttca | ctgaccacct | gttcaacatt | 960 |
| gccaagccca | ggccccctg | gatgggcctg | ctgggcccca | ccatccaggc | tgaggtgtat | 1020 |
| gacactgtgg | tgatcaccct | gaagaacatg | gccagccacc | ctgtgagcct | gcatgctgtg | 1080 |
| ggggtgagct | actggaaggc | ctctgagggg | gctgagtatg | atgaccagac | cagccagagg | 1140 |
| gagaaggagg | atgacaaggt | gttccctggg | ggcagccaca | cctatgtgtg | gcaggtgctg | 1200 |
| aaggagaatg | gccccatggc | ctctgacccc | ctgtgcctga | cctacagcta | cctgagccat | 1260 |
| gtggacctgg | tgaaggacct | gaactctggc | ctgattgggg | ccctgctggt | gtgcaggag | 1320 |
| ggcagcctgg | ccaaggagaa | gacccagacc | ctgcacaagt | tcatcctgct | gtttgctgtg | 1380 |
| tttgatgagg | gcaagagctg | gcactctgaa | accaagaaca | gcctgatgca | ggacagggat | 1440 |
| gctgcctctg | ccagggcctg | gcccaagatg | cacactgtga | atggctatgt | gaacaggagc | 1500 |
| ctgcctggcc | tgattggctg | ccacaggaag | tctgtgtact | ggcatgtgat | tggcatgggc | 1560 |
| accacccctg | aggtgcacag | catcttcctg | gagggccaca | ccttcctggt | caggaaccac | 1620 |
| aggcaggcca | gctggagat | cagccccatc | accttcctga | ctgcccagac | cctgctgatg | 1680 |
| gacctgggcc | agttcctgct | gttctgccac | atcagcagcc | accagcatga | tggcatggag | 1740 |
| gcctatgtga | aggtggacag | ctgccctgag | gagcccagc | tgaggatgaa | gaacaatgag | 1800 |
| gaggctgagg | actatgatga | tgacctgact | gactctgaga | tggatgtggt | gaggtttgat | 1860 |
| gatgacaaca | gccccagctt | catccagatc | aggtctgtgg | ccaagaagca | ccccaagacc | 1920 |
| tgggtgcact | acattgctgc | tgaggaggag | gactgggact | atgccccct | ggtgctggcc | 1980 |
| cctgatgaca | ggagctacaa | gagccagtac | ctgaacaatg | gccccagag | gattggcagg | 2040 |

```
aagtacaaga aggtcaggtt catggcctac actgatgaaa ccttcaagac cagggaggcc    2100
atccagcatg agtctggcat cctgggcccc ctgctgtatg gggaggtggg ggacaccctg    2160
ctgatcatct tcaagaacca ggccagcagg ccctacaaca tctaccccca tggcatcact    2220
gatgtgaggc ccctgtacag caggaggctg cccaaggggg tgaagcacct gaaggacttc    2280
cccatcctgc ctggggagat cttcaagtac aagtggactg tgactgtgga ggatggcccc    2340
accaagtctg accccaggtg cctgaccaga tactacagca gctttgtgaa catggagagg    2400
gacctggcct ctggcctgat tggcccctg ctgatctgct acaaggagtc tgtggaccag    2460
aggggcaacc agatcatgtc tgacaagagg aatgtgatcc tgttctctgt gtttgatgag    2520
aacaggagct ggtacctgac tgagaacatc cagaggttcc tgcccaaccc tgctggggtg    2580
cagctggagg accctgagtt ccaggccagc aacatcatgc acagcatcaa tggctatgtg    2640
tttgacagcc tgcagctgtc tgtgtgcctg catgaggtgg cctactggta catcctgagc    2700 attgggccc agactgactt cctgtctgtg ttcttctctg gctacacctt caagcacaag    2760
atggtgtatg aggacaccct gaccctgttc cccttctctg gggagactgt gttcatgagc    2820
atggagaacc ctggcctgtg gattctgggc tgccacaact ctgacttcag aacaggggc    2880 atgactgccc tgctgaaagt ctccagctgt gacaagaaca ctggggacta ctatgaggac    2940
agctatgagg acatctctgc ctacctgctg agcaagaaca atgccattga gcccaggagc    3000
ttcagccaga cccccccagt gctgaagagg caccagaggg agatcaccag gaccaccctg    3060
cagtctgacc aggaggagat tgactatgat gacaccatct ctgtggagat gaagaaggag    3120
gactttgaca tctacgacga ggacgagaac cagagcccca ggagcttcca gaagaagacc    3180
aggcactact tcattgctgc tgtggagagg ctgtgggact atggcatgag cagcagcccc    3240
catgtgctga ggaacagggc ccagtctggc tctgtgcccc agttcaagaa ggtggtgttc    3300
caggagttca ctgatggcag cttcacccag ccctgtaca gaggggagct gaatgagcac    3360
ctgggcctgc tgggccccta catcagggct gaggtggagg acaacatcat ggtgaccttc    3420
aggaaccagg ccagcaggcc ctacagcttc tacagcagcc tgatcagcta tgaggaggac    3480
cagaggcagg ggctgagcc aggaagaac tttgtgaagc ccaatgaaac caagacctac    3540
ttctggaagg tgcagcacca catggccccc accaaggatg agtttgactg caaggcctgg    3600
gcctacttct ctgatgtgga cctggagaag gatgtgcact ctggcctgat tggcccctg    3660 ctggtgtgcc acaccaacac cctgaaccct gcccatggca ggcaggtgac tgtgcaggag    3720
tttgccctgt tcttcaccat cttttgatgaa accaagagct ggtacttcac tgagaacatg    3780
gagaggaact gcagggcccc ctgcaacatc cagatggagg accccacctt caaggagaac    3840
tacaggttcc atgccatcaa tggctacatc atggacaccc tgcctggcct ggtgatggcc    3900
caggaccaga ggatcaggtg gtacctgctg agcatgggca gcaatgagaa catccacagc    3960
atccacttct ctggccatgt gttcactgtg aggaagaagg aggagtacaa gatggccctg    4020
tacaacctgt accctgggt gttttgagact gtggagatgc tgcccagcaa ggctggcatc    4080
tggagggtgg agtgcctgat tggggagcac ctgcatgctg gcatgagcac cctgttcctg    4140
gtgtacagca caagtgcca gaccccctg ggcatggcct ctggccacat cagggacttc    4200
cagatcactg cctctggcca gtatggccag tgggccccca gctggccag ctgcactac    4260 tctggcagca tcaatgcctg gagcaccaag gagcccttca gctggatcaa ggtggacctg    4320
ctggccccca tgatcatcca tggcatcaag acccagggg ccaggcagaa gttcagcagc    4380
ctgtacatca gccagttcat catcatgtac agcctggatg gcaagaagtg gcagacctac    4440
```

```
agggggcaaca gcactggcac cctgatggtg ttctttggca atgtggacag ctctggcatc    4500
aagcacaaca tcttcaaccc ccccatcatt gccagataca tcaggctgca ccccacccac    4560
tacagcatca ggagcaccct gaggatggag ctgatgggct gtgacctgaa cagctgcagc    4620
atgcccctgg gcatggagag caaggccatc tctgatgccc agatcactgc cagcagctac    4680
ttcaccaaca tgtttgccac ctggagcccc agcaaggcca ggctgcacct gcagggcagg    4740
agcaatgcct ggaggcccca ggtcaacaac cccaaggagt ggctgcaggt ggacttccag    4800
aagaccatga aggtgactgg ggtgaccacc caggggtga agagcctgct gaccagcatg    4860
tatgtgaagg agttcctgat cagcagcagc aggatggcc accagtggac cctgttcttc    4920
cagaatggca aggtgaaggt gttccagggc aaccaggaca gcttcacccc tgtggtgaac    4980
agcctggacc cccccctgct gaccagatac ctgaggattc accccagag ctgggtgcac    5040
cagattgccc tgaggatgga ggtgctgggc tgtgaggccc aggacctgta ctgacctcga    5100
ggaataaagg aaatttattt tcattgcaat agtgtgttgg ttttttgtgt cacgtggcgg    5160
ccgcaggaac ccctagtgat ggagttggcc actccctctc tgcgcgctcg ctcgctcact    5220
gaggccgggc gaccaaaggt cgcccgacgc ccgggctttg cccgggcggc ctcagtgagc    5280
gagcgagcgc gcagagaggg agtggccaa                                      5309
```

<210> SEQ ID NO 27
<211> LENGTH: 5532
<212> TYPE: DNA
<213> ORGANISM: Adeno-Associated Virus 2

<400> SEQUENCE: 27

```
ttggccactc cctctctgcg cgctcgctcg ctcactgagg ccgccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacgacgag gacagggccc tgtctcctca gcttcaggca ccaccactga cctgggacag    720
tgaatcgtaa gtatgccttt cactgcgaga ggttctggag aggcttctga gctccccatg    780
gcccaggcag gcagcaggtc tggggcagga gggggttgt ggagtgcctt gactcggggc    840
ctggcccccc catctctgtc ttgcaggaca attgccgtct tctgtctcgt ggggcatcct    900
cctgctggca ggcctgtgct gcctggtccc tgcgatcgcc accatgcaga ttgagctgag    960
cacctgcttc ttcctgtgcc tgctgaggtt ctgcttctct gccaccagga gatactacct   1020
gggggctgtg gagctgagct gggactacat gcagtctgac ctgggggagc tgcctgtgga   1080
tgccaggttc ccccccagag tgcccaagag cttcccctttc aacacctctg tggtgtacaa   1140
gaagaccctg tttgtggagt tcactgacca cctgttcaac attgccaagc caggccccc    1200
```

```
ctggatgggc ctgctgggcc ccaccatcca ggctgaggtg tatgacactg tggtgatcac    1260
cctgaagaac atggccagcc accctgtgag cctgcatgct gtgggggtga gctactggaa    1320
ggcctctgag ggggctgagt atgatgacca gaccagccag agggagaagg aggatgacaa    1380
ggtgttccct gggggcagcc acacctatgt gtggcaggtg ctgaaggaga atggccccat    1440
ggcctctgac cccctgtgcc tgacctacag ctacctgagc catgtggacc tggtgaagga    1500
cctgaactct ggcctgattg gggccctgct ggtgtgcagg gagggcagcc tggccaagga    1560
gaagacccag accctgcaca agttcatcct gctgtttgct gtgtttgatg agggcaagag    1620
ctggcactct gaaaccaaga acagcctgat gcaggacagg gatgctgcct ctgccagggc    1680
ctggcccaag atgcacactg tgaatggcta tgtgaacagg agcctgcctg gcctgattgg    1740
ctgccacagg aagtctgtgt actggcatgt gattggcatg ggcaccaccc ctgaggtgca    1800
cagcatcttc ctggagggcc acaccttcct ggtcaggaac acaggcagg ccagcctgga     1860 gatcagcccc atcaccttcc tgactgccca gaccctgctg atggacctgg gccagttcct    1920
gctgttctgc cacatcagca gccaccagca tgatggcatg gaggcctatg tgaaggtgga    1980
cagctgccct gaggagcccc agctgaggat gaagaacaat gaggaggctg aggactatga    2040
tgatgacctg actgactctg agatggatgt ggtgaggttt gatgatgaca cagccccag    2100 cttcatccag atcaggtctg tggccaagaa gcaccccaag acctgggtgc actacattgc    2160
tgctgaggag gaggactggg actatgcccc cctggtgctg gcccctgatg acaggagcta    2220
caagagccag tacctgaaca atggcccca gaggattggc aggaagtaca agaaggtcag     2280
gttcatggcc tacactgatg aaaccttcaa gaccagggag gccatccagc atgagtctgg    2340
catcctgggc cccctgctgt atggggaggt gggggacacc ctgctgatca tcttcaagaa    2400
ccaggccagc aggccctaca acatctaccc ccatggcatc actgatgtga ggcccctgta    2460
cagcaggagg ctgcccaagg gggtgaagca cctgaaggac ttccccatcc tgcctgggga    2520
gatcttcaag tacaagtgga ctgtgactgt ggaggatggc cccaccaagt ctgaccccag    2580
gtgcctgacc agatactaca gcagctttgt gaacatggag agggacctgg cctctggcct    2640
gattggcccc ctgctgatct gctacaagga gtctgtggac cagaggggca accagatcat    2700
gtctgacaag aggaatgtga tcctgttctc tgtgtttgat gagaacagga gctggtacct    2760
gactgagaac atccagaggt tcctgcccaa ccctgctggg gtgcagctgg aggccctga    2820 gttccaggcc agcaacatca tgcacagcat caatggctat gtgtttgaca gcctgcagct    2880
gtctgtgtgc ctgcatgagg tggcctactg gtacatcctg agcattgggg cccagactga    2940
cttcctgtct gtgttcttct ctggctacac cttcaagcac aagatggtgt atgaggacac    3000
cctgaccctg ttccccttct ctggggagac tgtgttcatg agcatggaga ccctggcct    3060 gtggattctg ggctgccaca actctgactt caggaacagg gcatgactg ccctgctgaa     3120 agtctccagc tgtgacaaga acactgggga ctactatgag gacagctatg aggacatctc    3180
tgcctacctg ctgagcaaga caatgccat gagcccagg agcttcagcc agaaccccc      3240 agtgctgaag aggcaccaga gggagatcac caggaccacc ctgcagtctg accaggagga    3300
gattgactat gatgacacca tctctgtgga gatgaagaag gaggactttg acatctacga    3360
cgaggacgag aaccagagcc caggagctt ccagaagaag accaggcact acttcattgc     3420
tgctgtggag aggctgtggg actatggcat gagcagcagc ccccatgtgc tgaggaacag    3480
ggcccagtct ggctctgtgc cccagttcaa gaaggtggtg ttccaggagt tcactgatgg    3540
cagcttcacc cagccccctgt acagagggga gctgaatgag cacctgggcc tgctgggccc    3600
```

```
ctacatcagg gctgaggtgg aggacaacat catggtgacc ttcaggaacc aggccagcag    3660
gccctacagc ttctacagca gcctgatcag ctatgaggag gaccgagggc aggggggctga    3720 gcccaggaag aactttgtga agcccaatga aaccaagacc tacttctgga aggtgcagca    3780
ccacatggcc cccaccaagg atgagtttga ctgcaaggcc tgggcctact tctctgatgt    3840
ggacctggag aaggatgtgc actctggcct gattggcccc ctgctggtgt gccacaccaa    3900
caccctgaac cctgcccatg gcaggcaggt gactgtgcag gagtttgccc tgttcttcac    3960
catctttgat gaaaccaaga gctggtactt cactgagaac atggagagga actgcagggc    4020
cccctgcaac atccagatgg aggaccccac cttcaaggag aactacaggt tccatgccat    4080
caatggctac atcatggaca ccctgcctgg cctggtgatg gcccaggacc agaggatcag    4140
gtggtacctg ctgagcatgg gcagcaatga aaacatccac agcatccact ctctggccca    4200
tgtgttcact gtgaggaaga aggaggagta caagatggcc ctgtacaacc tgtaccctgg    4260
ggtgtttgag actgtggaga tgctgcccag caaggctggc atctggaggg tggagtgcct    4320
gattggggag cacctgcatg ctggcatgag caccctgttc ctggtgtaca gcaacaagtg    4380 ccagacccccc ctgggcatgg cctctggcca catcagggac ttccagatca ctgcctctgg    4440
ccagtatggc cagtgggccc ccaagctggc caggctgcac tactctggca gcatcaatgc    4500
ctggagcacc aaggagccct tcagctggat caaggtggac ctgctggccc ccatgatcat    4560
ccatggcatc aagacccagg gggccaggca gaagttcagc agcctgtaca tcagccagtt    4620
catcatcatg tacagcctgg atggcaagaa gtggcagacc tacaggggca acagcactgg    4680
caccctgatg gtgttctttg gcaatgtgga cagctctggc atcaagcaca acatcttcaa    4740 ccccccccatc attgccagat acatcaggct gcaccccacc cactacagca tcaggagcac    4800
cctgaggatg gagctgatgg gctgtgacct gaacagctgc agcatgcccc tgggcatgga    4860
gagcaaggcc atctctgatg cccagatcac tgccagcagc tacttcacca acatgtttgc    4920
cacctggagc cccagcaagg ccaggctgca cctgcagggc aggagcaatg cctggaggcc    4980
ccaggtcaac aaccccaagg agtggctgca ggtggacttc cagaagacca tgaaggtgac    5040
tggggtgacc acccagggg tgaagagcct gctgaccagc atgtatgtga aggagttcct    5100
gatcagcagc agccaggatg ccaccagtg accctgttc ttccagaatg caaggtgaa    5160 ggtgttccag ggcaaccagg acagcttcac ccctgtggtg aacagctgg accccccccct    5220 gctgaccaga tacctgagga ttcacccccca gagctgggtg caccagattg ccctgaggat    5280
ggaggtgctg ggctgtgagg cccaggacct gtactgacct cgaggaataa ggaaatttat    5340
ttttcattgc aatagtgtgt tggtttttg tgtcacgtgg cggccgcagg aaccccctagt    5400 gatgagttg gccactccct ctctgcgcgc tcgctcgctc actgaggccg ggcgaccaaa    5460
ggtcgcccga cgcccgggct ttgcccgggc ggcctcagtg agcgagcgag cgcgcagaga    5520
gggagtggcc aa                                                       5532

<210> SEQ ID NO 28
<211> LENGTH: 5877
<212> TYPE: DNA
<213> ORGANISM: Adeno-Associated Virus 2

<400> SEQUENCE: 28
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
```

```
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540
agtggccctt ggcagcattt actctctctg tttgctctgg ttaataatct caggagcaca    600
aacattcctg gaggcaggag aagaaatcaa catcctggac ttatcctctg ggcctctccc    660
cacccccagg agaggctcag gttaattttt aaaaagcagt caaaagtcca agtggccctt    720
ggcagcattt actctctctg tttgctctgg ttaataatct caggagcaca aacattcctg    780
gaggcaggag aagaaatcaa catcctggac ttatcctctg ggcctctccc cacccccagg    840
agaggctgtc gactggacac aggacgctgt ggtttctgag ccaggggcg actcagatcc    900 cagccagtgg acttagcccc tgtttgctcc tccgataact ggggtgacct tggttaatat    960
tcaccagcag cctcccccgt tgcccctctg atccactgc ttaaatacgg acgaggacag   1020
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggagggg gttgtggagt gccttgactc ggggcctggc cccccatct    1200 ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccctggg ttgggcctgct   1560 gggccccacc atccaggctg aggtgtatga cactgtggtg atcaccctga gaacatggc   1620 cagccaccct gtgagcctgc atgctgtggg gtgagctac tggaaggcct ctgaggggc    1680 tgagtatgat gaccagacca gcagaggga aaggaggat gacaaggtgt ccctgggggg   1740
cagccacacc tatgtgtggc aggtgctgaa ggagaatggc cccatggcct ctgacccct    1800 gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt tgctgtgtt tgatgagggc aagagctggc actctgaaac    1980
caagaacagc ctgatgcagg acagggatgc tgcctctgcc agggcctggc caagatgca    2040 cactgtgaat ggctatgtga acaggagcct gcctggcctg attggctgcc acaggaagtc   2100
tgtgtactgg catgtgattg gcatgggcac cacccctgag gtgcacagca tcttcctgga   2160
gggccacacc ttcctggtca ggaaccacag gcaggccagc ctggagatca gccccatcac   2220
cttcctgact gccagacccc tgctgatgga cctgggccag ttcctgctgt tctgtcacat    2280
cagcagccac cagcatgatg gcatggaggc ctatgtgaag gtggacagct gccctgagga   2340 gcccagctg aggatgaaga acaatgagga ggctgaggac tatgatgatg acctgactga    2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
```

```
ctgggactat gccccctgg tgctggcccc tgatgacagg agctacaaga gccagtacct    2580
gaacaatggc ccccagagga ttggcaggaa gtacaagaag gtcaggttca tggcctacac    2640
tgatgaaacc ttcaagacca gggaggccat ccagcatgag tctggcatcc tgggccccct    2700
gctgtatggg gaggtggggg acaccctgct gatcatcttc aagaaccagg ccagcaggcc    2760
ctacaacatc taccccatg gcatcactga tgtgaggccc ctgtacagca ggaggctgcc    2820
caaggggtg aagcacctga aggacttccc catcctgcct ggggagatct tcaagtacaa    2880
gtggactgtg actgtggagg atggccccac caagtctgac cccaggtgcc tgaccagata    2940
ctacagcagc tttgtgaaca tggagaggga cctggcctct ggcctgattg ccccctgct    3000
gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctggggtgca gctggaggac cctgagttcc aggccagcaa    3180
catcatgcac agcatcaatg ctatgtgtt tgacagcctg cagctgtctg tgtgcctgca    3240
tgaggtggcc tactggtaca tcctgagcat tggggcccag actgacttcc tgtctgtgtt    3300
cttctctggc tacaccttca gcacaagat ggtgtatgag acaccctga ccctgttccc    3360
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgcccag ttcaagaagg tggtgttcca ggagttcact gatggcagct tcacccagcc    3900
cctgtacaga ggggagctga atgagcacct gggcctgctg gcccctaca tcagggctga    3960
ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggccccac    4140
caaggatgag tttgactgca aggcctgggc ctacttctct gatgtggacc tggagaagga    4200
tgtgcactct ggcctgattg cccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga gagaactgc agggccccct gcaacatcca    4380
gatggaggac cccaccttca aggagaacta caggttccat gccatcaatg ctacatcat    4440
ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggcctgta caacctgtac cctggggtgt ttgagactgt    4620
ggagatgctg cccagcaagg ctggcatctg gagggtggag tgcctgattg gggagcacct    4680
gcatgctggc atgagcaccc tgttcctggt gtacagcaac aagtgccaga ccccctggg    4740
catggcctct ggccacatca gggacttcca gatcactgcc tctggccagt atggccagtg    4800
ggccccaag ctggccaggc tgcactactc tggcagcatc aatgcctgga gcaccaagga    4860
```

```
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggacccc ccctgctga ccagatacct   5580 gaggattcac ccccagagct gggtgcacca gattgccctg aggatggagg tgctgggctg   5640
tgaggcccag gacctgtact gacctcgagg aataaaggaa atttattttc attgcaatag   5700
tgtgttggtt ttttgtgtca cgtggcggcc gcaggaaccc ctagtgatgg agttggccac   5760
tccctctctg cgcgctcgct cgctcactga ggccgggcga ccaaaggtcg cccgacgccc   5820
gggctttgcc cggcggcct cagtgagcga gcgagcgcgc agagagggag tggccaa     5877

<210> SEQ ID NO 29
<211> LENGTH: 6054
<212> TYPE: DNA
<213> ORGANISM: Adeno-Associated Virus 2

<400> SEQUENCE: 29
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540 agtgccctt ggcagcattt actctctctg tttgctctgg ttaataatct caggagcaca    600
aacattcctg gaggcaggag aagaaatcaa catcctggac ttatcctctg ggcctctccc    660
cacccccagg agaggctcag gttaattttt aaaaagcagt caaaagtcca agtgccctt    720 ggcagcattt actctctctg tttgctctgg ttaataatct caggagcaca aacattcctg    780
gaggcaggag aagaaatcaa catcctggac ttatcctctg ggcctctccc cacccccagg    840
agaggctgtc gactgacac aggacgctgt ggtttctgag ccaggggcg actcagatcc    900 cagccagtgg acttagcccc tgtttgctcc tccgataact ggggtgacct tggttaatat    960
tcaccagcag cctcccccgt tgcccctctg gatccactgc ttaaatacgg acgaggacag   1020
ggccctgtct cctcagcttc aggcaccacc actgacctgg gacagtgaat cgtaagtatg   1080 ccttttcactg cgagaggttc tggagaggct tctgagctcc ccatggccca ggcaggcagc   1140
```

-continued

```
aggtctgggg caggaggggg gttgtggagt gccttgactc ggggcctggc ccccccatct    1200
ctgtcttgca ggacaattgc cgtcttctgt ctcgtggggc atcctcctgc tggcaggcct    1260
gtgctgcctg gtccctgcga tcgccaccat gcagattgag ctgagcacct gcttcttcct    1320
gtgcctgctg aggttctgct tctctgccac caggagatac tacctggggg ctgtggagct    1380
gagctgggac tacatgcagt ctgacctggg ggagctgcct gtggatgcca ggttcccccc    1440
cagagtgccc aagagcttcc ccttcaacac ctctgtggtg tacaagaaga ccctgtttgt    1500
ggagttcact gaccacctgt tcaacattgc caagcccagg ccccctgga tgggcctgct    1560 gggccccacc atccaggctg aggtgtatga cactgtggtg atcaccctga gaacatggc    1620 cagccaccct gtgagcctgc atgctgtggg ggtgagctac tggaaggcct ctgaggggc    1680 tgagtatgat gaccagacca gccagaggga aaggaggat gacaaggtgt tccctggggg    1740
cagccacacc tatgtgtggc aggtgctgaa ggagaatggc cccatggcct ctgaccccct    1800
gtgcctgacc tacagctacc tgagccatgt ggacctggtg aaggacctga actctggcct    1860
gattggggcc ctgctggtgt gcagggaggg cagcctggcc aaggagaaga cccagaccct    1920
gcacaagttc atcctgctgt ttgctgtgtt tgatgagggc aagagctggc actctgaaac    1980
caagaacagc ctgatgcagg acagggatgc tgcctctgcc agggcctggc ccaagatgca    2040
cactgtgaat ggctatgtga acaggagcct gcctggcctg attggctgcc acaggaagtc    2100
tgtgtactgg catgtgattg gcatgggcac caccctgag gtgcacagca tcttcctgga    2160
gggccacacc ttcctggtca ggaaccacag gcaggccagc ctggagatca gccccatcac    2220
cttcctgact gcccagaccc tgctgatgga cctgggccag ttcctgctgt ctgccacat    2280 cagcagccac cagcatgatg gcatggaggc ctatgtgaag gtggacagct gccctgagga    2340
gccccagctg aggatgaaga acaatgagga ggctgaggac tatgatgatg acctgactga    2400
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gccccctgg tgctggcccc tgatgacagg agctacaaga gccagtacct    2580
gaacaatggc ccccagagga ttggcaggaa gtacaagaag gtcaggttca tggcctacac    2640
tgatgaaacc ttcaagacca gggaggccat ccagcatgag tctggcatcc tgggcccct    2700 gctgtatggg gaggtggggg acccctgct gatcatcttc aagaaccagg ccagcaggcc    2760
ctacaacatc tacccccatg gcatcactga tgtgaggccc ctgtacagca ggaggctgcc    2820
caagggggtg aagcacctga aggacttccc catcctgcct ggggagatct tcaagtacaa    2880
gtggactgtg actgtggagg atggccccac caagtctgac cccaggtgcc tgaccagata    2940
ctacagcagc tttgtgaaca tggagaggga cctggcctct ggcctgattg ccccctgct    3000 gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctggggtgca gctggaggac cctgagttcc aggccagcaa    3180
catcatgcac agcatcaatg gctatgtgtt tgacagcctg cagctgtctg tgtgcctgca    3240
tgaggtggcc tactggtaca tcctgagcat tggggcccag actgacttcc tgtctgtgtt    3300
cttctctggc tacaccttca agcacaagat ggtgtatgag gacaccctga ccctgttccc    3360
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
```

```
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga atgagcacct gggcctgctg gcccctaca tcagggctga     3960 ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggcccccac    4140
caaggatgag tttgactgca aggcctgggc ctacttctct gatgtggacc tggagaagga    4200
tgtgcactct ggcctgattg ccccctgct ggtgtgccac accaacaccc tgaaccctgc     4260
ccatggcagg caggtgactg tgcaggagtt tgccctgttc ttcaccatct ttgatgaaac    4320
caagagctgg tacttcactg agaacatgga gagaactgc agggcccct gcaacatcca      4380 gatggaggac cccaccttca aggagaacta caggttccat gccatcaatg ctacatcat     4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctggc atgagcaccc tgttcctggt gtacagcaac aagtgccaga cccccctggg    4740
catggcctct ggccacatca gggacttcca gatcactgcc tctggccagt atggccagtg    4800 gggcccccaag ctggccaggc tgcactactc tggcagcatc aatgcctgga gcaccaagga   4860
gcccttcagc tggatcaagg tggacctgct ggcccccatg atcatccatg gcatcaagac    4920 ccaggggcc aggcagaagt tcagcagcct gtacatcagc cagttcatca tcatgtacag     4980
cctggatggc aagaagtggc agacctacag gggcaacagc actggcaccc tgatggtgtt    5040
ctttggcaat gtggacagct ctggcatcaa gcacaacatc ttcaacccc catcattgc      5100 cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggcccccagg tcaacaaccc   5340 caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcacccctg tggtgaacag cctggacccc ccctgctga ccagatacct    5580 gaggattcac ccccagagct gggtgcacca gattgccctg aggatggagg tgctgggctg    5640
tgaggcccag gacctgtact gacctcgagg tgtgccttct agttgccagc catctgttgt    5700
ttgcccctcc cccgtgcctt ccttgaccct ggaaggtgcc actcccactg tccttccta    5760 ataaaatgag gaaattgcat cgcattgtct gagtaggtgt cattctattc tggggggtgg    5820
ggtggggcag gacagcaagg gggaggattg ggaagacaat agcaggcatg ctggggatgc    5880
```

```
ggtgggctct atgggcacgt ggcggccgca ggaaccccta gtgatggagt tggccactcc      5940
ctctctgcgc gctcgctcgc tcactgaggc cgggcgacca aggtcgccc gacgcccggg      6000 cttttgcccgg gcggcctcag tgagcgagcg agcgcgcaga gagggagtgg ccaa           6054

<210> SEQ ID NO 30
<211> LENGTH: 6054
<212> TYPE: DNA
<213> ORGANISM: Adeno-Associated Virus 2

<400> SEQUENCE: 30
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg      120
gccaactcca tcactagggg ttcctgcggc cgcacgcgtg ttttcgaccc ctctcacact      180
acctaaacca cgccaggaca acctctgctc ctctccaccg aaattccaag gggtcgagtg      240
gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg gcagggtgag cccagaaact cctgtgtgcc      480
tctgagcctg cagacgcgaa acgtcgaagc ctctcctggg ggtggggaga ggcccagagg      540
ataagtccag gatgttgatt tcttctcctg cctccaggaa tgtttgtgct cctgagatta      600
ttaaccagag caaacagaga gagtaaatgc tgccaagggc cacttggact tttgactgct      660
ttttaaaaat taacctgagc ctctcctggg ggtggggaga ggcccagagg ataagtccag      720
gatgttgatt tcttctcctg cctccaggaa tgtttgtgct cctgagatta ttaaccagag      780
caaacagaga gagtaaatgc tgccaagggc cacttggact tttgactgct ttttaaaaat      840
taacctggtc gactggacac aggacgctgt ggtttctgag ccaggggcg actcagatcc      900 cagccagtgg acttagcccc tgtttgctcc tccgataact ggggtgacct tggttaatat      960
tcaccagcag cctccccgt tgcccctctg gatccactgc ttaaatacgg acgaggacag      1020
ggccctgtct cctcagcttc aggcaccacc actgacctgg acagtgaat cgtaagtatg      1080 cctttcactg cgagaggttc tggagaggct tctgagctcc ccatggccca ggcaggcagc      1140
aggtctgggg caggaggggg gttgtggagt gccttgactc ggggcctggc cccccatct      1200 ctgtcttgca ggacaattgc cgtcttctgt ctcgtgggc atcctcctgc tggcaggcct      1260
gtgctgcctg gtccctgcga tcgccaccat gcagattgag ctgagcacct gcttcttcct      1320
gtgcctgctg aggttctgct tctctgccac caggagatac tacctggggg ctgtggagct      1380
gagctgggac tacatgcagt ctgacctggg ggagctgcct gtggatgcca ggttcccccc      1440
cagagtgccc aagagcttcc ccttcaacac ctctgtggtg tacaagaaga cctgtttgt      1500 ggagttcact gaccacctgt tcaacattgc caagccaggg cccccctgga tgggcctgct      1560
gggccccacc atccaggctg aggtgtatga cactgtggtg atcaccctga gaacatggc      1620 cagccaccct gtgagcctgc atgctgtggg ggtgagctac tggaaggcct ctgagggggc      1680
tgagtatgat accagacca gccagaggga gaaggaggat gacaaggtgt ccctggggg     1740 cagccacacc tatgtgtggc aggtgctgaa ggagaatggc cccatggcct ctgaccccct      1800
gtgcctgacc tacagctacc tgagccatgt ggacctggtg aaggacctga actctggcct      1860
gattggggcc ctgctggtgt gcagggaggg cagcctggcc aaggagaaga cccagaccct      1920
```

```
gcacaagttc atcctgctgt tgctgtgtt tgatgagggc aagagctggc actctgaaac      1980
caagaacagc ctgatgcagg acagggatgc tgcctctgcc agggcctggc ccaagatgca      2040
cactgtgaat ggctatgtga acaggagcct gcctggcctg attggctgcc acaggaagtc      2100
tgtgtactgg catgtgattg gcatgggcac caccctgag gtgcacagca tcttcctgga       2160
gggccacacc ttcctggtca ggaaccacag gcaggccagc ctggagatca gccccatcac      2220
cttcctgact gcccagaccc tgctgatgga cctgggccag ttcctgctgt tctgccacat      2280
cagcagccac cagcatgatg gcatggaggc ctatgtgaag gtggacagct gccctgagga      2340
gccccagctg aggatgaaga acaatgagga ggctgaggac tatgatgatg acctgactga      2400
ctctgagatg gatgtggtga ggtttgatga tgacaacagc cccagcttca tccagatcag      2460
gtctgtggcc aagaagcacc ccaagacctg ggtgcactac attgctgctg aggaggagga      2520
ctgggactat gcccccctgg tgctggcccc tgatgacagg agctacaaga ccagtacct       2580 gaacaatggc ccccagagga ttggcaggaa gtacaagaag gtcaggttca tggcctacac      2640
tgatgaaacc ttcaagacca gggaggcat ccagcatgag tctggcatcc tgggcccct       2700 gctgtatggg gaggtggggg acaccctgct gatcatcttc aagaaccagg ccagcaggcc      2760
ctacaacatc tacccccatg gcatcactga tgtgaggccc ctgtacagca ggaggctgcc      2820 caaggggtg aagcacctga aggacttccc catcctgcct ggggagatct tcaagtacaa       2880
gtggactgtg actgtggagg atggccccac caagtctgac cccaggtgcc tgaccagata      2940
ctacagcagc tttgtgaaca tggagaggga cctggcctct ggcctgattg cccccctgct      3000
gatctgctac aaggagtctg tggaccagag gggcaaccag atcatgtctg acaagaggaa      3060
tgtgatcctg ttctctgtgt tgatgagaa caggagctgg tacctgactg agaacatcca       3120
gaggttcctg cccaaccctg ctggggtgca gctggaggac cctgagttcc aggccagcaa      3180
catcatgcac agcatcaatg gctatgtgtt tgacagcctg cagctgtctg tgtgcctgca      3240
tgaggtggcc tactgtgtac acctgagcat tgggcccag actgacttcc tgtctgtgtt       3300
cttctctggc tacaccttca gcacaagat ggtgtatgag acaccctga ccctgttccc        3360 cttctctggg gagactgtgt tcatgagcat ggagaaccct ggcctgtgga ttctgggctg      3420
ccacaactct gacttcagga acaggggcat gactgccctg ctgaaagtct ccagctgtga      3480
caagaacact ggggactact atgaggacag ctatgaggac atctctgcct acctgctgag      3540
caagaacaat gccattgagc ccaggagctt cagccagaac ccccagtgc tgaagaggca      3600 ccagaggag atcaccagga ccaccctgca gtctgaccag gaggagattg actatgatga       3660
caccatctct gtggagatga agaaggagga ctttgacatc tacgacgagg acgagaacca      3720
gagccccagg agcttccaga agaagaccag gcactacttc attgctgctg tggagaggct      3780
gtgggactat ggcatgagca gcagccccca tgtgctgagg aacagggccc agtctggctc      3840
tgtgccccag ttcaagaagg tggtgttcca ggagttcact gatggcagct tcacccagcc      3900
cctgtacaga ggggagctga tgagcacct gggcctgctg gcccctaca tcagggctga       3960 ggtggaggac aacatcatgg tgaccttcag gaaccaggcc agcaggccct acagcttcta      4020
cagcagcctg atcagctatg aggaggacca gaggcagggg gctgagccca ggaagaactt      4080
tgtgaagccc aatgaaacca gacctactt ctggaaggtg cagcaccaca tggcccccac      4140
caaggatgag tttgactgca aggcctgggc ctacttctct gatgtggacc tggagaagga      4200
tgtgcactct ggcctgattg ccccctgct ggtgtgccac accaacaccc tgaaccctgc       4260
ccatggcagg caggtgactg tgcaggagtt tgccctgttc ttcaccatct ttgatgaaac      4320
```

```
caagagctgg tacttcactg agaacatgga gggaactgc agggccccct gcaacatcca    4380
gatggaggac cccaccttca aggagaacta caggttccat gccatcaatg ctacatcat    4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctggc atgagcaccc tgttcctggt gtacagcaac aagtgccaga ccccctggg    4740 catggcctct ggccacatca gggacttcca gatcactgcc tctggccagt atggccagtg    4800 ggccccccaag ctggccaggc tgcactactc tggcagcatc aatgcctgga gcaccaagga    4860
gcccttcagc tggatcaagg tggacctgct ggccccccatg atcatccatg catcaagac    4920 ccaggggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaacccccc ccatcattgc    5100 cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggcccccagg tcaacaaccc    5340 caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcacccctg tggtgaacag cctggacccc cccctgctga ccagataccct    5580 gaggattcac ccccagagct gggtgcacca gattgccctg aggatggagg tgctgggctg    5640
tgaggcccag gacctgtact gacctcgagg tgtgccttct agttgccagc catctgttgt    5700 ttgccccctcc cccgtgcctt ccttgaccct ggaaggtgcc actcccactg tcctttccta    5760
ataaaatgag gaaattgcat cgcattgtct gagtaggtgt cattctattc tggggggtgg    5820
ggtggggcag gacagcaagg gggaggattg gaagacaat agcaggcatg ctggggatgc    5880
ggtgggctct atgggcacgt gcggccgca ggaaccccta gtgatggagt tggccactcc    5940
ctctctgcgc gctcgctcgc tcactgaggc cgggcgacca aaggtcgccc gacgcccggg    6000 ctttgccccgg gcggcctcag tgagcgagcg agcgcgcaga gagggagtgg ccaa         6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact    180 acctaaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
```

```
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gccctgttt gctcctccga taactggggt     600
gaccttggtt aatattcacc agcagcctcc cccgttgccc ctctggatcc actgcttaaa    660
tacgacgag  gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgttgt  ggagttcact    960
gaccacctgt tcaacattgc caagcccagg ccccctgga tgggcctgct gggccccacc    1020
atccaggctg aggtgtatga cactgtggtg atcaccctga gaacatggc  cagccaccct   1080
gtgagcctgc atgctgtggg ggtgagctac tggaaggcct ctgaggggc  tgagtatgat   1140
gaccagacca gccagaggga aaggaggat  gacaaggtgt ccctgggggg cagccacacc   1200
tatgtgtggc aggtgctgaa ggagaatggc cccatggcct ctgaccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc caagatgca  cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct ccctgagga  gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggcccct  gctgtatggg   2160
gaggtgggg  acaccctgct gatcatcttc aagaaccagg ccagcaggcc ctacaacatc   2220
tacccccatg gcatcactga tgtgaggccc ctgtacagca ggaggctgcc caaggggtg   2280
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg cccctgct  gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
agcatcaatg gctatgtgtt tgacagcctg cagctgtctg tgcctgca  tgaggtggcc   2700
tactggtaca tcctgagcat tggggcccag actgacttcc tgtctgtgtt cttctctggc   2760
```

```
tacaccttca agcacaagat ggtgtatgag gacaccctga ccctgttccc cttctctggg   2820
gagactgtgt tcatgagcat ggagaaccct ggcctgtgga ttctgggctg ccacaactct   2880
gacttcagga acaggggcat gactgccctg ctgaaagtct ccagctgtga caagaacact   2940
ggggactact atgaggacag ctatgaggac atctctgcct acctgctgag caagaacaat   3000
gccattgagc ccaggagctt cagccagaac cccccagtgc tgaagaggca ccagagggag   3060
atcaccagga ccaccctgca gtctgaccag gaggagattg actatgatga caccatctct   3120
gtggagatga agaaggagga ctttgacatc tacgacgagg acgagaacca gagccccagg   3180
agcttccaga agaagaccag gcactacttc attgctgctg tggagaggct gtgggactat   3240
ggcatgagca gcagcccca tgtgctgagg aacagggccc agtctggctc tgtgccccag   3300
ttcaagaagg tggtgttcca ggagttcact gatggcagct tcacccagcc cctgtacaga   3360
ggggagctga atgagcacct gggcctgctg ggcccctaca tcagggctga ggtggaggac   3420
aacatcatgg tgaccttcag gaaccaggcc agcaggccct acagcttcta cagcagcctg   3480
atcagctatg aggaggacca gaggcagggg gctgagccca ggaagaactt tgtgaagccc   3540
aatgaaacca agacctactt ctggaaggtg cagcaccaca tggcccccac caaggatgag   3600
tttgactgca aggcctgggc ctacttctct gatgtggacc tggagaagga tgtgcactct   3660
ggcctgattg gcccctgct ggtgtgccac accaacaccc tgaaccctgc ccatggcagg   3720
caggtgactg tgcaggagtt tgccctgttc ttcaccatct ttgatgaaac caagagctgg   3780
tacttcactg agaacatgga gaggaactgc agggcccct gcaacatcca gatggaggac   3840
cccaccttca aggagaacta caggttccat gccatcaatg ctacatcat ggacaccctg   3900 cctggcctgg tgatggccca ggaccagagg atcaggtggt acctgctgag catgggcagc   3960
aatgagaaca tccacagcat ccacttctct ggccatgtgt tcactgtgag gaagaaggag   4020
gagtacaaga tggcccctgta caacctgtac cctggggtgt ttgagactgt ggagatgctg   4080
cccagcaagg ctggcatctg gagggtggag tgcctgattg gggagcacct gcatgctggc   4140
atgagcaccc tgttcctggt gtacagcaac aagtgccaga ccccctggg catggcctct   4200 ggccacatca gggacttcca gatcactgcc tctggccagt atggccagtg ggcccccaag   4260
ctggccaggc tgcactactc tggcagcatc aatgcctgga gcaccaagga gcccttcagc   4320
tggatcaagg tggacctgct ggcccccatg atcatccatg gcatcaagac caggggggcc   4380
aggcagaagt tcagcagcct gtacatcagc cagttcatca tcatgtacag cctggatggc   4440
aagaagtggc agacctacag gggcaacagc actggcaccc tgatggtgtt ctttggcaat   4500
gtggacagct ctggcatcaa gcacaacatc ttcaaccccc ccatcattgc cagatacatc   4560
aggctgcacc ccaccacta cagcatcagg agcaccctga ggatggagct gatggctgt   4620 gacctgaaca gctgcagcat gcccctgggc atggagagca aggccatctc tgatgcccag   4680
atcactgcca gcagctactt caccaacatg tttgccacct ggagcccag caaggccagg   4740 ctgcacctgc agggcaggag caatgcctgg aggccccagg tcaacaaccc caaggagtgg   4800
ctgcaggtgg acttccagaa gaccatgaag gtgactgggg tgaccaccca gggggtgaag   4860
agcctgctga ccagcatgta tgtgaaggag ttcctgatca gcagcagcca ggatggccac   4920
cagtggaccc tgttcttcca gaatggcaag gtgaaggtgt tccagggcaa ccaggacagc   4980
ttcacccctg tggtgaacag cctggaccc ccctgctga ccagatacct gaggattcac   5040
ccccagagct gggtgcacca gattgccctg aggatggagg tgctgggctg tgaggcccag   5100
```

```
gacctgtact gacctcgagg tgtgccttct agttgccagc catctgttgt ttgcccctcc    5160
cccgtgcctt ccttgaccct ggaaggtgcc actcccactg tcctttccta ataaaatgag    5220
gaaattgcat cgcattgtct gagtaggtgt cattctattc tggggggtgg ggtggggcag    5280
gacagcaagg gggaggattg ggaagacaat agcaggcatg ctgggatgc ggtgggctct     5340 atgggcacgt ggcggccgca ggaacccta gtgatggagt tggccactcc ctctctgcgc     5400
gctcgctcgc tcactgaggc cgggcgacca aggtcgccc gacgcccggg ctttgcccgg     5460
gcggcctcag tgagcgagcg agcgcgcaga gagggagtgg ccaa                     5504

<210> SEQ ID NO 32
<211> LENGTH: 5507
<212> TYPE: DNA
<213> ORGANISM: Adeno-Associated Virus 2

<400> SEQUENCE: 32
ttggccactc cctctctgcg cgctcgctcg ctcactgagg ccgccgggc aaagcccggg       60 cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaaact cctgtgtgcc    480 tctgagcctg cagacgcgaa acgtcgacga tcttgctacc agtggaacag ccactaagga    540
ttctgcagtg agagcagagg gccagctaag tggtactctc ccagagactg tctgactcac    600 gccacccct ccaccttgga cacaggacgc tgtggtttct gagccaggta caatgactcc    660
tttcggtaag tgcagtggaa gctgtacact gcccaggcaa agcgtccggg cagcgtaggc    720
gggcgactca gatcccagcc agtggactta gcccctgttt gctcctccga taactggggt    780
gaccttggtt aatattcacc agcagcctcc ccgttgccc ctctggatcc actgcttaaa     840
tacggacgag gacagggccc tgtctcctca gcttcaggca ccaccactga cctgggacag    900
tgaatcgcga tcgccaccat gcagattgag ctgagcaccct gcttcttcct gtgcctgctg    960
aggttctgct tctctgccac caggagatac tacctggggg ctgtggagct gagctgggac    1020
tacatgcagt ctgacctggg ggagctgcct gtggatgcca ggttcccccc cagagtgccc    1080
aagagcttcc ccttcaacac ctctgtggtg tacaagaaga ccctgttttgt ggagttcact    1140 gaccacctgt tcaacattgc caagcccagg ccccccctgga tgggcctgct gggcccccacc    1200 atccaggctg aggtgtatga cactgtggtg atcaccctga gaacatggc cagccaccct     1260 gtgagcctgc atgctgtggg ggtgagctac tggaaggcct ctgaggggc tgagtatgat    1320 gaccagacca gccagggga agggaggat gacaaggtgt cccctggggg cagccacacc    1380
tatgtgtggc aggtgctgaa ggagaatggc cccatggcct ctgaccccct gtgcctgacc    1440
tacagctacc tgagccatgt ggacctggtg aaggacctga actctggcct gattggggcc    1500
ctgctggtgt gcagggaggg cagcctggcc aaggagaaga cccagaccct gcacaagttc    1560
atcctgctgt ttgctgtgtt tgatgagggc aagagctggc actctgaaac caagaacagc    1620
ctgatgcagg acagggatgc tgcctctgcc agggcctgg ccaagatgca cactgtgaat    1680
ggctatgtga acaggagcct gcctggcctg attggctgcc acaggaagtc tgtgtactgg    1740
```

```
catgtgattg gcatgggcac cacccctgag gtgcacagca tcttcctgga gggccacacc      1800
ttcctggtca ggaaccacag gcaggccagc ctggagatca gccccatcac cttcctgact      1860
gcccagaccc tgctgatgga cctgggccag ttcctgctgt tctgccacat cagcagccac      1920
cagcatgatg gcatggaggc ctatgtgaag gtggacagct gccctgagga gccccagctg      1980
aggatgaaga acaatgagga ggctgaggac tatgatgatg acctgactga ctctgagatg      2040
gatgtggtga ggtttgatga tgacaacagc cccagcttca tccagatcag gtctgtggcc      2100
aagaagcacc ccaagacctg ggtgcactac attgctgctg aggaggagga ctgggactat      2160 gccccctgg tgctggcccc tgatgacagg agctacaaga ccagtacct gaacaatggc       2220 ccccagagga ttggcaggaa gtacaagaag gtcaggttca tggcctacac tgatgaaacc      2280
ttcaagacca gggaggccat ccagcatgag tctggcatcc tgggcccct gctgtatggg       2340 gaggtggggg acaccctgct gatcatcttc aagaaccagg ccagcaggcc ctacaacatc      2400 taccccatg gcatcactga tgtgaggccc ctgtacagca ggaggctgcc caaggggtg       2460 aagcacctga aggacttccc catcctgcct ggggagatct tcaagtacaa gtggactgtg      2520 actgtggagat atggccccac caagtctgac cccaggtgcc tgaccagata ctacagcagc     2580
tttgtgaaca tggagaggga cctggcctct ggcctgattg gcccctgct gatctgctac       2640 aaggagtctg tggaccagag gggcaaccag atcatgtctg acaagaggaa tgtgatcctg      2700
ttctctgtgt ttgatgagaa caggagctgg tacctgactg agaacatcca gaggttcctg      2760
cccaaccctg ctggggtgca gctggaggac cctgagttcc aggccagcaa catcatgcac     2820
agcatcaatg gctatgtgtt tgacagcctg cagctgtctg tgtgcctgca tgaggtggcc     2880
tactggtaca tcctgagcat tggggcccag actgacttcc tgtctgtgtt cttctctggc     2940
tacaccttca agcacaagat ggtgtatgag gacaccctga ccctgttccc cttctctggg     3000
gagactgtgt tcatgagcat ggagaaccct ggcctgtgga ttctgggctg ccacaactct     3060
gacttcagga acagggcat gactgccctg ctgaaagtct ccagctgtga caagaacact     3120
ggggactact atgaggacag ctatgaggac atctctgcct acctgctgag caagaacaat     3180
gccattgagc ccaggagctt cagccagaac cccccagtgc tgaagaggca ccagagggag     3240
atcaccagga ccaccctgca gtctgaccag gaggagattg actatgatga ccatcttctct    3300 gtggagatga agaaggagga cttttgacatc tacgacgagg acgagaacca gagccccagg   3360
agcttccaga agaaccag gcactacttc attgctgctg tggagaggct gtgggactat        3420
ggcatgagca gcagccccca tgtgctgagg aacagggccc agtctggctc tgtgccccag     3480
ttcaagaagg tggtgttcca ggagttcact gatggcagct tcacccagcc cctgtacaga     3540
ggggagctga atgagcacct gggcctgctg ggcccctaca tcagggctga ggtggaggac     3600
aacatcatgg tgaccttcag gaaccaggcc agcaggccct acagcttcta cagcagcctg     3660
atcagctatg aggaggacca gaggcagggg gctgagccca ggaagaactt tgtgaagccc      3720
aatgaaacca gacctactt ctggaaggtg cagcaccaca tggcccccac caaggatgag      3780
tttgactgca aggcctgggc ctacttctct gatgtggacc tggagaagga tgtgcactct     3840
ggcctgattg gccccctgct ggtgtgccac accaacaccc tgaaccctgc catggcagg      3900 caggtgactg tgcaggagtt tgccctgttc ttcaccatct ttgatgaaac caagagctgg      3960
tacttcactg agaacatgga gaggaactgc agggcccct gcaacatcca gatggaggac      4020
cccaccttca aggagaacta caggttccat gccatcaatg gctacatcat ggacaccctg      4080
```

```
cctggcctgg tgatggccca ggaccagagg atcaggtggt acctgctgag catgggcagc    4140
aatgagaaca tccacagcat ccacttctct ggccatgtgt tcactgtgag gaagaaggag    4200
gagtacaaga tggccctgta caacctgtac cctggggtgt ttgagactgt ggagatgctg    4260
cccagcaagg ctggcatctg gagggtggag tgcctgattg gggagcacct gcatgctggc    4320
atgagcaccc tgttcctggt gtacagcaac aagtgccaga ccccctggg catggcctct    4380 ggccacatca gggacttcca gatcactgcc tctggccagt atggccagtg ggcccccaag    4440
ctggccaggc tgcactactc tggcagcatc aatgcctgga gcaccaagga gcccttcagc    4500
tggatcaagg tggacctgct ggcccccatg atcatccatg gcatcaagac caggggggcc    4560
aggcagaagt tcagcagcct gtacatcagc cagttcatca tcatgtacag cctggatggc    4620
aagaagtggc agacctacag ggcaacagc actggcaccc tgatggtgtt ctttggcaat    4680
gtggacagct ctggcatcaa gcacaacatc ttcaacccccc ccatcattgc cagatacatc    4740
aggctgcacc ccaccctcta cagcatcagg agcaccctga ggatggagct gatgggctgt    4800
gacctgaaca gctgcagcat gccctgggc atggagagca aggccatctc tgatgcccag    4860
atcactgcca gcagctactt caccaacatg tttgccacct ggagcccag caaggccagg    4920 ctgcacctgc agggcaggag caatgcctgg aggccccagg tcaacaaccc caaggagtgg    4980
ctgcaggtgg acttccagaa gaccatgaag gtgactgggg tgaccacca gggggtgaag    5040 agcctgctga ccagcatgta tgtgaaggag ttcctgatca gcagcagcca ggatggccac    5100
cagtggaccc tgttcttcca gaatggcaag gtgaaggtgt tccagggcaa ccaggacagc    5160
ttcacccctg tggtgaacag cctggaccccc ccctgctga ccagatacct gaggattcac    5220
ccccagagct gggtgcacca gattgccctg aggatggagg tgctgggctg tgaggcccag    5280
gacctgtact gacctcgagg aataaaggaa atttattttc attgcaatag tgtgttggtt    5340
ttttgtgtca cgtggcggcc gcaggaaccc ctagtgatgg agttggccac tccctctctg    5400
cgcgctcgct cgctcactga ggccgggcga ccaaaggtcg cccgacgccc gggctttgcc    5460
cgggcggcct cagtgagcga gcgagcgcgc agagagggag tggccaa                 5507
```

<210> SEQ ID NO 33
<211> LENGTH: 5311
<212> TYPE: DNA
<213> ORGANISM: Adeno-Associated Virus 2

<400> SEQUENCE: 33

```
ttggccactc cctctctgcg cgctcgctcg ctcactgagg ccgccgggc aaagcccggg      60 cgtcgggcga cctttggtcg cccggcctca gtgagcgagc gagcgcgcag agagggagtg    120
gccaactcca tcactagggg ttcctgcggc cgcacgcgtg ttttcgacgc agagaggtct    180
ctgacctctg ccccagctcc aaggtcagca ggcagggagg gctgtgtgtt tgctgtttgc    240
tgcttgcaat gtttgcccat tttagggaca tgagtaggct gaagtttgtt cagtgtggac    300
ttcagaggca gcacacaaac agccagagag gtctctgacc tctgccccag ctccaaggtc    360
agcaggcagg gagggctgtg tgtttgctgt ttgctgcttg caatgtttgc ccattttagg    420
gacatgagta ggctgaagtt tgttcagtgt ggacttcaga ggcagcacac aaacagcacg    480
cgaaacgtcg actggacaca ggacgctgtg gtttctgagc caggggggcga ctcagatccc    540 agccagtgga cttagcccct gtttgctcct ccgataactg gggtgacctt ggttaatatt    600
caccagcagc ctccccccgtt gccccctctgg atccactgct taaatacgga cgaggacagg    660
gccctgtctc ctcagcttca ggcaccacca ctgacctggg acagtgaatc gcgatcgcca    720
```

```
ccatgcagat tgagctgagc acctgcttct tcctgtgcct gctgaggttc tgcttctctg      780
ccaccaggag atactacctg ggggctgtgg agctgagctg ggactacatg cagtctgacc      840 tggggagct gcctgtggat gccaggttcc cccccagagt gcccaagagc ttccccttca       900
acacctctgt ggtgtacaag aagaccctgt ttgtggagtt cactgaccac ctgttcaaca     960
ttgccaagcc caggcccccc tggatgggcc tgctgggccc caccatccag gctgaggtgt     1020
atgacactgt ggtgatcacc ctgaagaaca tggccagcca cctgtgagc ctgcatgctg     1080 tgggggtgag ctactggaag gcctctgagg gggctgagta tgatgaccag accagccaga    1140
gggagaagga ggatgacaag gtgttccctg ggggcagcca cacctatgtg tggcaggtgc     1200
tgaaggagaa tggccccatg gcctctgacc ccctgtgcct gacctacagc tacctgagcc    1260
atgtggacct ggtgaaggac ctgaactctg gcctgattgg ggccctgctg gtgtgcaggg    1320
agggcagcct ggccaaggag aagacccaga ccctgcacaa gttcatcctg ctgtttgctg    1380
tgtttgatga gggcaagagc tggcactctg aaaccaagaa cagcctgatg caggacaggg    1440
atgctgcctc tgccagggcc tggcccaaga tgcacactgt gaatggctat gtgaacagga    1500
gcctgcctgg cctgattggc tgccacagga agtctgtgta ctggcatgtg attggcatgg    1560
gcaccacccc tgaggtgcac agcatcttcc tggagggcca ccttcctg gtcaggaacc      1620 acaggcaggc cagcctggag atcagcccca tcaccttcct gactgcccag accctgctga    1680
tggacctggg ccagttcctg ctgttctgcc acatcagcag ccaccagcat gatggcatgg    1740
aggcctatgt gaaggtggac agctgccctg aggagcccca gctgaggatg aagaacaatg    1800
aggaggctga ggactatgat gatgacctga ctgactctga gatggatgtg gtgaggtttg    1860
atgatgacaa cagccccagc ttcatccaga tcaggtctgt ggccaagaag caccccaaga    1920
cctgggtgca ctacattgct gctgaggagg aggactggga ctatgccccc ctggtgctgg    1980
cccctgatga caggagctac aagagccagt acctgaacaa tggccccag aggattggca    2040 ggaagtacaa gaaggtcagg ttcatggcct acactgatga aaccttcaag accagggagg    2100
ccatccagca tgagtctggc atcctgggcc cctgctgta tggggaggtg gggacaccc    2160 tgctgatcat cttcaagaac caggccagca ggccctacaa catctacccc catggcatca    2220
ctgatgtgag gccctgtac agcaggaggc tgcccaaggg ggtgaagcac ctgaaggact    2280
tccccatcct gcctggggag atcttcaagt acaagtggac tgtgactgtg gaggatggcc    2340
ccaccaagtc tgaccccagg tgcctgacca gatactacag cagctttgtg aacatggaga    2400
gggacctggc ctctggcctg attggcccc tgctgatctg ctacaaggag tctgtggacc    2460 agagggcaa ccagatcatg tctgacaaga ggaatgtgat cctgttctct gtgtttgatg    2520
agaacaggag ctggtacctg actgagaaca tccagaggtt cctgcccaac cctgctgggg    2580
tgcagctgga ggaccctgag ttccaggcca gcaacatcat gcacagcatc aatggctatg    2640 tgttttgacag cctgcagctg tctgtgtgcc tgcatgaggt ggcctactgg tacatcctga    2700 gcattgggc ccagactgac ttcctgtctg tgttcttctc tggctacacc ttcaagcaca    2760
agatggtgta tgaggacacc ctgacctgt tccccttctc tggggagact gtgttcatga    2820 gcatggaaa ccctggcctg tggattctgg gctgccacaa ctctgacttc aggaacaggg    2880
gcatgactgc cctgctgaaa gtctccagct gtgacaagaa cactggggac tactatgagg    2940
acagctatga ggacatctct gcctacctgc tgagcaagaa caatgccatt gagcccagga    3000
gcttcagcca gaaccccca gtgctgaaga ggcaccagag ggagatcacc aggaccaccc    3060
```

```
tgcagtctga ccaggaggag attgactatg atgacaccat ctctgtggag atgaagaagg   3120
aggactttga catctacgac gaggacgaga accagagccc caggagcttc agaagaaga    3180 ccaggcacta cttcattgct gctgtggaga ggctgtggga ctatggcatg agcagcagcc   3240
cccatgtgct gaggaacagg gcccagtctg gctctgtgcc ccagttcaag aaggtggtgt   3300
tccaggagtt cactgatggc agcttcaccc agcccctgta cagaggggag ctgaatgagc   3360
acctgggcct gctgggcccc tacatcaggg ctgaggtgga ggacaacatc atggtgacct   3420
tcaggaacca ggccagcagg ccctacagct tctacagcag cctgatcagc tatgaggagg   3480
accagaggca gggggctgag cccaggaaga actttgtgaa gcccaatgaa accaagacct   3540
acttctggaa ggtgcagcac cacatggccc ccaccaagga tgagtttgac tgcaaggcct   3600
gggcctactt ctctgatgtg gacctggaga aggatgtgca ctctggcctg attggccccc   3660
tgctggtgtg ccacaccaac accctgaacc ctgcccatgg caggcaggtg actgtgcagg   3720
agtttgccct gttcttcacc atctttgatg aaaccaagag ctggtacttc actgagaaca   3780
tggagaggaa ctgcagggcc ccctgcaaca tccagatgga ggaccccacc ttcaaggaga   3840
actacaggtt ccatgccatc aatggctaca tcatggacac cctgcctggc ctggtgatgg   3900
cccaggacca gaggatcagg tggtacctgc tgagcatggg cagcaatgag aacatccaca   3960
gcatccactt ctctggccat gtgttcactg tgaggaagaa ggaggagtac aagatggccc   4020
tgtacaacct gtaccctggg gtgtttgaga ctgtggagat gctgcccagc aaggctggca   4080
tctggagggt ggagtgcctg attggggagc acctgcatgc tggcatgagc acctgttcc    4140 tggtgtacag caacaagtgc cagaccccc tgggcatggc ctctggccac atcagggact   4200
tccagatcac tgcctctggc cagtatggcc agtgggcccc caagctggcc aggctgcact   4260
actctggcag catcaatgcc tggagcacca aggagccctt cagctggatc aaggtggacc   4320
tgctggcccc catgatcatc catggcatca gacccaggg ggccaggcag aagttcagca    4380
gcctgtacat cagccagttc atcatcatgt acagcctgga tggcaagaag tggcagacct   4440 acagggggcaa cagcactggc accctgatgg tgttctttgg caatgtggac agctctggca   4500
tcaagcacaa catcttcaac cccccccatca ttgccagata catcaggctg cacccccaccc   4560 actacagcat caggagcacc ctgaggatgg agctgatggg ctgtgacctg aacagctgca   4620
gcatgcccct gggcatggag agcaaggcca tctctgatgc ccagatcact gccagcagct   4680
acttcaccaa catgtttgcc acctggagcc ccagcaaggc caggctgcac ctgcagggca   4740
ggagcaatgc ctggaggccc caggtcaaca ccccaagga gtggctgcag gtggacttcc   4800
agaagaccat gaaggtgact ggggtgacca cccagggggt gaagagcctg ctgaccagca   4860
tgtatgtgaa ggagttcctg atcagcagca gccaggatgg ccaccagtgg accctgttct   4920
tccagaatgg caaggtgaag gtgttccagg caaccagga cagcttcacc cctgtggtga    4980
acagcctgga cccccccctg ctgaccagat acctgaggat tcacccccag agctgggtgc   5040
accagattgc cctgaggatg gaggtgctgg gctgtgaggc ccaggacctg tactgacctc   5100
gaggaataaa ggaaatttat tttcattgca atagtgtgtt ggttttttgt gtcacgtggc   5160
ggccgcagga ccccctagtg atggagttgg ccactccctc tctgcgcgct cgctcgctca   5220
ctgaggccgg gcgaccaaag gtcgcccgac gcccgggctt tgcccgggcg gcctcagtga   5280
gcgagcgagc gcgcagagag ggagtggcca a                                  5311

<210> SEQ ID NO 34
<211> LENGTH: 5156
```

```
<212> TYPE: DNA
<213> ORGANISM: Adeno-Associated Virus 2

<400> SEQUENCE: 34
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgacca gagaggtctc     180
tgacctctgc cccagctcca aggtcagcag gcagggaggg ctgtgtgttt gctgtttgct     240
gcttgcaatg tttgcccatt ttagggacat gagtaggctg aagtttgttc agtgtggact     300
tcagaggcag cacacaaaca gcacgcgaaa cgtcgactgg acacaggacg ctgtggtttc     360
tgagccaggg ggcgactcag atcccagcca gtggacttag cccctgtttg ctcctccgat     420
aactggggtg accttggtta atattcacca gcagcctccc ccgttgcccc tctggatcca     480
ctgcttaaat acggacgagg acagggccct gtctcctcag cttcaggcac caccactgac     540
ctgggacagt gaatcgcgat cgccaccatg cagattgagc tgagcacctg cttcttcctg     600
tgcctgctga ggttctgctt ctctgccacc aggagatact acctgggggc tgtggagctg     660
agctgggact acatgcagtc tgacctgggg gagctgcctg tggatgccag gttccccccc     720
agagtgccca gagcttccc cttcaacacc tctgtggtgt acaagaagac cctgtttgtg     780
gagttcactg accacctgtt caacattgcc aagcccaggc cccctggat gggcctgctg     840
ggccccacca tccaggctga ggtgtatgac actgtggtga tcaccctgaa gaacatggcc     900
agccacctg tgagcctgca tgctgtgggg gtgagctact ggaaggcctc tgagggggct     960
gagtatgatg accagaccag ccagagggag aaggaggatg acaaggtgtt ccctgggggc    1020
agccacacct atgtgtggca ggtgctgaag gagaatggcc ccatggcctc tgaccccctg    1080
tgcctgacct acagctacct gagccatgtg gacctggtga aggacctgaa ctctggcctg    1140
attggggccc tgctggtgtg cagggagggc agcctggcca aggagaagac ccagaccctg    1200
cacaagttca tcctgctgtt tgctgtgttt gatgagggca gagctggca ctctgaaacc    1260
aagaacagcc tgatgcagga cagggatgct gcctctgcca gggcctggcc caagatgcac    1320
actgtgaatg gctatgtgaa caggagcctg cctggcctga ttggctgcca caggaagtct    1380
gtgtactggc atgtgattgg catgggcacc acccctgagg tgcacagcat cttcctggag    1440
ggccacacct tcctggtcag gaaccacagg caggccagcc tggagatcag ccccatcacc    1500
ttcctgactg cccagaccct gctgatggac ctgggccagt tcctgctgtt ctgccacatc    1560
agcagccacc agcatgatgg catggaggcc tatgtgaagg tggacagctg ccctgaggag    1620
ccccagctga ggatgaagaa caatgaggag gctgaggact atgatgatga cctgactgac    1680
tctgagatga tgtggtgag gtttgatgat gacaacagcc cagcttcat ccagatcagg    1740
tctgtggcca agaagcaccc caagacctgg gtgcactaca ttgctgctga ggaggaggac    1800
tgggactatg ccccctggt gctggcccct gatgacagga gctacaagag ccagtacctg    1860
aacaatggcc cccagaggat tggcaggaag tacaagaagg tcaggttcat ggcctacact    1920
gatgaaacct tcaagaccag ggaggccatc cagcatgagt ctggcatcct gggcccctg    1980
ctgtatgggg aggtggggga caccctgctg atcatcttca agaaccaggc cagcaggccc    2040
tacaacatct accccatgg catcactgat gtgaggcccc tgtacagcag gaggctgccc    2100
aagggggtga agcacctgaa ggacttcccc atcctgcctg ggagatctt caagtacaag    2160
tggactgtga ctgtggagga tggccccacc aagtctgacc ccaggtgcct gaccagatac    2220
```

```
tacagcagct ttgtgaacat ggagagggac ctggcctctg gcctgattgg cccctgctg      2280 atctgctaca aggagtctgt ggaccagagg ggcaaccaga tcatgtctga caagaggaat      2340
gtgatcctgt tctctgtgtt tgatgagaac aggagctggt acctgactga gaacatccag      2400
aggttcctgc ccaaccctgc tggggtgcag ctggaggacc ctgagttcca ggccagcaac      2460
atcatgcaca gcatcaatgg ctatgtgttt gacagcctgc agctgtctgt gtgcctgcat      2520
gaggtggcct actggtacat cctgagcatt ggggcccaga ctgacttcct gtctgtgttc      2580
ttctctggct acaccttcaa gcacaagatg gtgtatgagg acaccctgac cctgttcccc      2640
ttctctgggg agactgtgtt catgagcatg gagaaccctg gcctgtggat tctgggctgc      2700
cacaactctg acttcaggaa caggggcatg actgccctgc tgaaagtctc cagctgtgac      2760
aagaacactg gggactacta tgaggacagc tatgaggaca tctctgccta cctgctgagc      2820
aagaacaatg ccattgagcc caggagcttc agccagaacc ccccagtgct gaagaggcac      2880
cagagggaga tcaccaggac caccctgcag tctgaccagg aggagattga ctatgatgac      2940
accatctctg tggagatgaa gaaggaggac tttgacatct acgacgagga cgagaaccag      3000
agccccagga gcttccagaa gaagaccagg cactacttca ttgctgctgt ggagaggctg      3060
tgggactatg gcatgagcag cagcccccat gtgctgagga caggggccca gtctggctct      3120
gtgccccagt tcaagaaggt ggtgttccag gagttcactg atggcagctt cacccagccc      3180
ctgtacagag gggagctgaa tgagcacctg ggcctgctgg gccctacat cagggctgag      3240 gtggaggaca acatcatggt gaccttcagg aaccaggcca gcaggcccta cagcttctac      3300
agcagcctga tcagctatga ggaggaccag aggcagggg ctgagcccag gaagaacttt      3360
gtgaagccca tgaaaccaa gacctacttc tggaaggtgc agcaccacat ggcccccacc      3420
aaggatgagt ttgactgcaa ggcctgggcc tacttctctg atgtggacct ggagaaggat      3480
gtgcactctg gcctgattgg cccctgctg gtgtgccaca ccaacaccct gaaccctgcc      3540
catggcaggc aggtgactgt gcaggagttt gccctgttct tcaccatctt tgatgaaacc      3600
aagagctggt acttcactga gaacatggag aggaactgca gggccccctg caacatccag      3660
atggaggacc ccaccttcaa ggagaactac aggttccatg ccatcaatgg ctacatcatg      3720
gacaccctgc ctggcctggt gatggcccag gaccagagga tcaggtggta cctgctgagc      3780
atgggcagca atgagaacat ccacagcatc cacttctctg gccatgtgtt cactgtgagg      3840
aagaaggagg agtacaagat ggcctgtac aacctgtacc ctgggggtgtt tgagactgtg      3900 gagatgctgc ccagcaaggc tggcatctgg agggtggagt gcctgattgg ggagcacctg      3960
catgctggca tgagcaccct gttcctggtg tacagcaaca agtgccagac cccctgggc      4020 atggcctctg ccacatcag ggacttccag atcactgcct ctggccagta tggccagtgg      4080
gcccccaagc tggccaggct gcactactct ggcagcatca atgcctggag caccaaggag      4140
cccttcagct ggatcaaggt ggacctgctg gcccccatga tcatccatgg catcaagacc      4200 caggggggcca ggcagaagtt cagcagcctg tacatcagcc agttcatcat catgtacagc      4260
ctggatggca gaagtgggca gacctacagg ggcaacagca ctggcaccct gatggtgttc      4320
tttggcaatg tggacagctc tggcatcaag cacaacatct tcaacccccc catcattgcc      4380
agatacatca ggctgcaccc cacccactac agcatcagga gcacctgag gatggagctg      4440 atgggctgtg acctgaacag ctgcagcatg cccctgggca tggagagcaa ggccatctct      4500
gatgcccaga tcactgccag cagctacttc accaacatgt tgccacctg gagccccagc      4560 aaggccaggc tgcacctgca gggcaggagc aatgcctgga ggccccaggt caacaaccc      4620
```

```
aaggagtggc tgcaggtgga cttccagaag accatgaagg tgactggggt gaccacccag   4680
ggggtgaaga gcctgctgac cagcatgtat gtgaaggagt tcctgatcag cagcagccag   4740
gatggccacc agtggaccct gttcttccag aatggcaagg tgaaggtgtt ccagggcaac   4800
caggacagct tcaccctgt ggtgaacagc ctggaccccc ccctgctgac cagatacctg   4860
aggattcacc cccagagctg ggtgcaccag attgccctga ggatggaggt gctgggctgt   4920
gaggcccagg acctgtactg acctcgagga ataaaggaaa tttattttca ttgcaatagt   4980
gtgttggttt tttgtgtcac gtggcggccg caggaacccc tagtgatgga gttggccact   5040
ccctctctgc gcgctcgctc gctcactgag gccgggcgac caaaggtcgc ccgacgcccg   5100
ggctttgccc gggcggcctc agtgagcgag cgagcgcgca gagagggagt ggccaa      5156
```

<210> SEQ ID NO 35
<211> LENGTH: 5178
<212> TYPE: DNA
<213> ORGANISM: Adeno-Associated Virus 2

<400> SEQUENCE: 35

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc atttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg acaacgcga aacgtcgact    360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgcg atcgccacca tgcagattga    600
gctgagcacc tgcttcttcc tgtgcctgct gaggttctgc ttctctgcca ccaggagata    660
ctacctgggg gctgtggagc tgagctggga ctacatgcag tctgacctgg gggagctgcc    720
tgtggatgcc aggttccccc ccagagtgcc aagagcttc cccttcaaca cctctgtggt    780
gtacaagaag accctgtttg tggagttcac tgaccacctg ttcaacattg ccaagcccag    840
gcccccctgg atgggcctgc tgggccccac catccaggct gaggtgtatg acactgtggt    900
gatcaccctg aagaacatgg ccagccaccc tgtgagcctg catgctgtgg gggtgagcta    960
ctggaaggcc tctgaggggg ctgagtatga tgaccagacc agccagaggg agaaggagga   1020
tgacaaggtg ttccctgggg gcagccacac ctatgtgtgg caggtgctga aggagaatgg   1080
ccccatggcc tctgaccccc tgtgcctgac ctacagctac ctgagccatg tggacctggt   1140
gaaggacctg aactctggcc tgattggggc cctgctggtg tgcagggagg cagcctggc   1200 caaggagaag acccagaccc tgcacaagtt catcctgctg tttgctgtgt tgatgaggg   1260 caagagctgg cactctgaaa ccaagaacag cctgatgcag gacagggatg ctgcctctgc   1320
cagggcctgg cccaagatgc acactgtgaa tggctatgtg aacaggagcc tgcctggcct   1380
gattggctgc cacaggaagt ctgtgtactg gcatgtgatt ggcatgggca ccacccctga   1440
ggtgcacagc atcttcctgg agggccacac cttcctggtc aggaaccaca ggcaggccag   1500
cctggagatc agccccatca ccttcctgac tgcccagacc ctgctgatgg acctgggcca   1560
```

```
gttcctgctg ttctgccaca tcagcagcca ccagcatgat ggcatggagg cctatgtgaa    1620
ggtggacagc tgccctgagg agccccagct gaggatgaag aacaatgagg aggctgagga    1680
ctatgatgat gacctgactg actctgagat ggatgtggtg aggtttgatg atgacaacag    1740
ccccagcttc atccagatca ggtctgtggc caagaagcac cccaagacct gggtgcacta    1800
cattgctgct gaggaggagg actgggacta tgccccctg gtgctggccc ctgatgacag    1860
gagctacaag agccagtacc tgaacaatgg cccccagagg attggcagga agtacaagaa    1920
ggtcaggttc atggcctaca ctgatgaaac cttcaagacc agggaggcca tccagcatga    1980
gtctggcatc ctgggccccc tgctgtatgg ggaggtgggg gacaccctgc tgatcatctt    2040
caagaaccag gccagcaggc cctacaacat ctaccccat ggcatcactg atgtgaggcc    2100
cctgtacagc aggaggctgc caagggggt gaagcacctg aaggacttcc ccatcctgcc    2160
tggggagatc ttcaagtaca gtggactgt gactgtggag gatggcccca ccaagtctga    2220
ccccaggtgc ctgaccagat actacagcag ctttgtgaac atggagaggg acctggcctc    2280
tggcctgatt ggccccctgc tgatctgcta caaggagtct gtggaccaga ggggcaacca    2340
gatcatgtct gacaagagga atgtgatcct gttctctgtg tttgatgaga acaggagctg    2400
gtacctgact gagaacatcc agaggttcct gcccaaccct gctggggtgc agctggagga    2460
ccctgagttc caggccagca acatcatgca cagcatcaat ggctatgtgt ttgacagcct    2520
gcagctgtct gtgtgcctgc atgaggtggc ctactggtac atcctgagca ttggggccca    2580
gactgacttc ctgtctgtgt tcttctctgg ctacaccttc aagcacaaga tggtgtatga    2640
ggacaccctg accctgttcc ccttctctgg ggagactgtg ttcatgagca tggagaaccc    2700
tggcctgtgg attctgggct gccacaactc tgacttcagg aacaggggca tgactgccct    2760
gctgaaagtc tccagctgtg acaagaacac tggggactac tatgaggaca gctatgagga    2820
catctctgcc tacctgctga gcaagaacaa tgccattgag cccaggagct tcagccagaa    2880
cccccccagt ctgaagaggc accagaggga gatcaccagg accaccctgc agtctgacca    2940
ggaggagatt gactatgatg acaccatctc tgtggagatg aagaaggagg actttgacat    3000
ctacgacgag gacgagaacc agagcccag gagcttccag aagaagacca ggcactactt    3060
cattgctgct gtggagaggc tgtgggacta tggcatgagc agcagccccc atgtgctgag    3120
gaacagggcc cagtctggct ctgtgcccca gttcaagaag gtggtgttcc aggagttcac    3180
tgatggcagc ttcacccagc ccctgtacag aggggagctg aatgagcacc tgggcctgct    3240
gggcccctac atcagggctg aggtggagga caacatcatg gtgaccttca ggaaccaggc    3300
cagcaggccc tacagcttct acagcagcct gatcagctat gaggaggacc agaggcaggg    3360
ggctgagccc aggaagaact tgtgaagcc aatgaaacc aagacctact ctggaaggt    3420
gcagcaccac atggccccca ccaaggatga gttgactgc aaggcctggg cctacttctc    3480
tgatgtggac ctggagaagg atgtgcactc tggcctgatt ggccccctgc tggtgtgcca    3540
caccaacacc ctgaaccctg cccatggcag gcaggtgact gtgcaggagt ttgccctgtt    3600
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tccacttctc    3840
tggccatgtg ttcactgtga ggaagaagga ggagtacaag atggcccctgt acaacctgta    3900
ccctgggggtg tttgagactg tggagatgct gcccagcaag gctggcatct ggaggtgga    3960
```

| | |
|---|---|
| gtgcctgatt ggggagcacc tgcatgctgg catgagcacc ctgttcctgg tgtacagcaa | 4020 |
| caagtgccag acccccctgg gcatggcctc tggccacatc agggacttcc agatcactgc | 4080 |
| ctctggccag tatggccagt gggcccccaa gctggccagg ctgcactact ctggcagcat | 4140 |
| caatgcctgg agcaccaagg agcccttcag ctggatcaag gtggacctgc tggcccccat | 4200 |
| gatcatccat ggcatcaaga cccagggggc caggcagaag ttcagcagcc tgtacatcag | 4260 |
| ccagttcatc atcatgtaca gcctggatgg caagaagtgg cagacctaca ggggcaacag | 4320 |
| cactggcacc ctgatggtgt tctttggcaa tgtggacagc tctggcatca agcacaacat | 4380 |
| cttcaacccc cccatcattg ccagatacat caggctgcac cccacccact acagcatcag | 4440 |
| gagcaccctg aggatggagc tgatgggctg tgacctgaac agctgcagca tgcccctggg | 4500 |
| catggagagc aaggccatct ctgatgccca gatcactgcc agcagctact tcaccaacat | 4560 |
| gtttgccacc tggagcccca gcaaggccag gctgcacctg cagggcagga gcaatgcctg | 4620 |
| gaggcccag gtcaacaacc ccaaggagtg gctgcaggtg gacttccaga agaccatgaa | 4680 |
| ggtgactggg gtgaccaccc aggggggtgaa gagcctgctg accagcatgt atgtgaagga | 4740 |
| gttcctgatc agcagcagcc aggatggcca ccagtggacc ctgttcttcc agaatggcaa | 4800 |
| ggtgaaggtg ttccagggca accaggacag cttcacccct gtggtgaaca gcctggaccc | 4860 |
| cccctgctg accagatacc tgaggattca ccccagagc tgggtgcacc agattgccct | 4920 |
| gaggatggag gtgctgggct gtgaggccca ggacctgtac tgacctcgag aataaagga | 4980 |
| aatttatttt cattgcaata gtgtgttggt tttttgtgtc acgtggcggc cgcaggaacc | 5040 |
| cctagtgatg gagttggcca ctccctctct gcgcgctcgc tcgctcactg aggccgggcg | 5100 |
| accaaaggtc gcccgacgcc cgggctttgc ccgggcggcc tcagtgagcg agcgagcgcg | 5160 |
| cagagaggga gtggccaa | 5178 |

<210> SEQ ID NO 36
<211> LENGTH: 5160
<212> TYPE: DNA
<213> ORGANISM: Adeno-Associated Virus 2

<400> SEQUENCE: 36

| | |
|---|---|
| ttggccactc cctctctgcg cgctcgctcg ctcactgagg ccgccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtt gtccctaaaa tgggcaaaca | 180 |
| ttgcaagcag caaacagcaa acatgtccct aaaatgggca acattgcaa gcagcaaaca | 240 |
| gcaaacatgt ccctaaaatg ggcaaacatt gcaagcagca acagcaaac atgtccctaa | 300 |
| aatgggcaaa cattgcaagc agcaaacagc aaacagtcga ctggacacag gacgctgtgg | 360 |
| tttctgagcc aggggggcgac tcagatccca gccagtggac ttagcccctg tttgctcctc | 420 |
| cgataactgg ggtgaccttg gttaatattc accagcagcc tccccgttg ccctctgga | 480 |
| tccactgctt aaatacggac gaggacaggg ccctgtctcc tcagcttcag gcaccaccac | 540 |
| tgacctggga cagtgaatcg cgatcgccac catgcagatt gagctgagca cctgcttctt | 600 |
| cctgtgcctg ctgaggttct gcttctctgc caccaggaga tactacctgg ggctgtgga | 660 |
| gctgagctgg gactacatgc agtctgacct gggggagctg cctgtggatg ccaggttccc | 720 |
| ccccagagtg cccaagagct tcccccttcaa cacctctgtg gtgtacaaga gaccctgtt | 780 |
| tgtggagttc actgaccacc tgttcaacat tgccaagccc aggccccct ggatgggcct | 840 |

```
gctgggcccc accatccagg ctgaggtgta tgacactgtg gtgatcaccc tgaagaacat    900
ggccagccac cctgtgagcc tgcatgctgt gggggtgagc tactggaagg cctctgaggg    960
ggctgagtat gatgaccaga ccagccagag ggagaaggag gatgacaagg tgttccctgg   1020
gggcagccac acctatgtgt ggcaggtgct gaaggagaat ggccccatgg cctctgaccc   1080
cctgtgcctg acctacagct acctgagcca tgtggacctg gtgaaggacc tgaactctgg   1140
cctgattggg gccctgctgg tgtgcaggga gggcagcctg gccaaggaga agacccagac   1200
cctgcacaag ttcatcctgc tgtttgctgt gtttgatgag ggcaagagct ggcactctga   1260
aaccaagaac agcctgatgc aggacaggga tgctgcctct gccagggcct ggcccaagat   1320
gcacactgtg aatggctatg tgaacaggag cctgcctggc ctgattggct gccacaggaa   1380
gtctgtgtac tggcatgtga ttggcatggg caccacccct gaggtgcaca gcatcttcct   1440
ggagggccac accttcctgg tcaggaacca caggcaggcc agcctggaga tcagccccat   1500
caccttcctg actgcccaga ccctgctgat ggacctgggc cagttcctgc tgttctgcca   1560
catcagcagc caccagcatg atggcatgga ggcctatgtg aaggtggaca gctgccctga   1620
ggagccccag ctgaggatga agaacaatga ggaggctgag gactatgatg atgacctgac   1680
tgactctgag atggatgtgg tgaggtttga tgatgacaac agcccagct tcatccagat   1740
caggtctgtg gccaagaagc acccaagac ctgggtgcac tacattgctg ctgaggagga   1800
ggactgggac tatgccccc tggtgctggc ccctgatgac aggagctaca agagccagta   1860
cctgaacaat ggcccccaga ggattggcag gaagtacaag aaggtcaggt tcatggccta   1920
cactgatgaa accttcaaga ccagggaggc catccagcat gagtctggca tcctgggccc   1980
cctgctgtat ggggaggtgg gggacaccct gctgatcatc ttcaagaacc aggccagcag   2040
gccctacaac atctaccccc atggcatcac tgatgtgagg ccctgtaca gcaggaggct   2100
gcccaagggg gtgaagcacc tgaaggactt ccccatcctg cctggggaga tcttcaagta   2160
caagtggact gtgactgtgg aggatggccc caccaagtct gacccccaggt gcctgaccag   2220
atactacagc agctttgtga acatggagag ggacctggcc tctggcctga ttggcccct   2280
gctgatctgc tacaaggagt ctgtggacca gaggggcaac cagatcatgt ctgacaagag   2340
gaatgtgatc ctgttctctg tgtttgatga acaggagc tggtacctga ctgagaacat   2400
ccagaggttc ctgcccaacc tgctgggggt gcagctggag gacctgagt ccaggccag   2460
caacatcatg cacagcatca atggctatgt gtttgacagc ctgcagctgt ctgtgtgcct   2520
gcatgaggtg gcctactggt acatcctgag cattggggcc cagactgact tcctgtctgt   2580
gttcttctct ggctacacct tcaagcacaa gatggtgtat gaggacaccc tgaccctgtt   2640
cccctttctct ggggagactg tgttcatgag catggagaac cctggcctgt ggattctggg   2700
ctgccacaac tctgacttca ggaacagggg catgactgcc ctgctgaaag tctccagctg   2760
tgacaagaac actggggact actatgagga cagctatgag gacatctctg cctacctgct   2820
gagcaagaac aatgccattg agcccaggag cttcagccag aacccccag tgctgaagag   2880
gcaccagagg gagatcacca ggaccaccct gcagtctgac caggaggaga ttgactatga   2940
tgacaccatc tctgtggaga tgaagaagga ggactttgac atctacgacg aggacgagaa   3000
ccagagcccc aggagcttcc agaagaagac caggcactac ttcattgctg ctgtgggaga   3060
gctgtgggac tatggcatga gcagcagccc catgtgctgt aggaacaggg cccagtctgg   3120
ctctgtgccc cagttcaaga aggtggtgtt ccaggagttc actgatggca gcttcaccca   3180
gccccctgtac agagggagc tgaatgagca cctgggcctg ctgggccct acatcagggc   3240
```

```
tgaggtggag gacaacatca tggtgacctt caggaaccag gccagcaggc cctacagctt    3300
ctacagcagc ctgatcagct atgaggagga ccagaggcag ggggctgagc ccaggaagaa    3360
ctttgtgaag cccaatgaaa ccaagaccta cttctggaag gtgcagcacc acatggcccc    3420
caccaaggat gagtttgact gcaaggcctg ggcctacttc tctgatgtgg acctggagaa    3480
ggatgtgcac tctggcctga ttggccccct gctggtgtgc cacaccaaca ccctgaaccc    3540
tgcccatggc aggcaggtga ctgtgcagga gtttgccctg ttcttcacca tctttgatga    3600
aaccaagagc tggtacttca ctgagaacat ggagaggaac tgcagggccc cctgcaacat    3660
ccagatggag gaccccacct tcaaggagaa ctacaggttc catgccatca atggctacat    3720
catggacacc ctgcctggcc tggtgatggc ccaggaccag aggatcaggt ggtacctgct    3780
gagcatgggc agcaatgaga acatccacag catccacttc tctggccatg tgttcactgt    3840
gaggaagaag gaggagtaca agatggccct gtacaacctg taccctgggg tgtttgagac    3900
tgtggagatg ctgcccagca aggctggcat ctggagggtg gagtgcctga ttggggagca    3960
cctgcatgct ggcatgagca ccctgttcct ggtgtacagc aacaagtgcc agaccccccct   4020 gggcatggcc tctggccaca tcagggactt ccagatcact gcctctggcc agtatggcca    4080
gtgggccccc aagctggcca ggctgcacta ctctggcagc atcaatgcct ggagcaccaa    4140
ggagcccttc agctggatca aggtggacct gctggccccc atgatcatcc atggcatcaa    4200
gacccagggg gccaggcaga agttcagcag cctgtacatc agccagttca tcatcatgta    4260
cagcctggat ggcaagaagt ggcagaccta caggggcaac agcactggca ccctgatggt    4320
gttcttcggc aatgtggaca gctctggcat caagcacaac atcttcaacc ccccatcat    4380 tgccagatac atcaggctgc accccaccca ctacagcatc aggagcaccc tgaggatgga    4440
gctgatgggc tgtgacctga acagctgcag catgcccctg ggcatggaga gcaaggccat    4500
ctctgatgcc cagatcactg ccagcagcta cttcaccaac atgtttgcca cctggagccc    4560
cagcaaggcc aggctgcacc tgcagggcag gagcaatgcc tggaggcccc aggtcaacaa    4620
ccccaaggag tggctgcagg tggacttcca gaagaccatg aaggtgactg gggtgaccac    4680 ccaggggggtg aagagcctgc tgaccagcat gtatgtgaag gagttcctga tcagcagcag    4740
ccaggatggc caccagtgga cccctgttctt ccagaatggc aaggtgaagg tgttccaggg    4800
caaccaggac agcttcaccc ctgtggtgaa cagcctggac ccccccctgc tgaccagata    4860
cctgaggatt cacccccaga gctgggtgca ccagattgcc ctgaggatgg aggtgctggg    4920
ctgtgaggcc caggacctgt actgacctcg aggaataaag gaaatttatt ttcattgcaa    4980
tagtgtgttg gttttttgtg tcacgtggcg gccgcaggaa ccccctagtga tggagttggc    5040 cactccctct ctgcgcgctc gctcgctcac tgaggccggg cgaccaaagg tcgcccgacg    5100
cccgggcttt gcccgggcgg cctcagtgag cgagcgagcg cgcagagagg gagtggccaa    5160
```

<210> SEQ ID NO 37
<211> LENGTH: 5383
<212> TYPE: DNA
<213> ORGANISM: Adeno-Associated Virus 2

<400> SEQUENCE: 37

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
```

-continued

```
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg acaacgcga aacgtcgact    360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtatgcctt tcactgcgag    600
aggttctgga gaggcttctg agctccccat ggcccaggca ggcagcaggt ctggggcagg    660 agggggggttg tggagtgcct tgactcgggg cctggccccc ccatctctgt cttgcaggac    720
aattgccgtc ttctgtctcg tggggcatcc tcctgctggc aggcctgtgc tgcctggtcc    780
ctgcgatcgc caccatgcag attgagctga gcacctgctt cttcctgtgc ctgctgaggt    840
tctgcttctc tgccaccagg agatactacc tgggggctgt ggagctgagc tgggactaca    900
tgcagtctga cctgggggag ctgcctgtgg atgccaggtt ccccccagga gtgcccaaga    960
gcttcccctt caacacctct gtggtgtaca agaagaccct gtttgtggag ttcactgacc   1020
acctgttcaa cattgccaag cccaggcccc cctggatggg cctgctgggc ccaccatcc    1080 aggctgaggt gtatgacact gtggtgatca ccctgaagaa catggccagc caccctgtga   1140
gcctgcatgc tgtgggggtg agctactgga aggcctctga gggggctgag tatgatgacc   1200
agaccagcca gagggagaag gaggatgaca aggtgttccc tggggcagc cacacctatg   1260 tgtggcaggt gctgaaggag aatggcccca tggcctctga cccctgtgc ctgacctaca   1320 gctacctgag ccatgtggac ctggtgaagg acctgaactc tggcctgatt ggggccctgc   1380
tggtgtgcag ggagggcagc ctggccaagg agaagaccca gaccctgcac aagttcatcc   1440
tgctgtttgc tgtgtttgat gagggcaaga gctggcactc tgaaaccaag aacagcctga   1500
tgcaggacag ggatgctgcc tctgccaggg cctggcccaa gatgcacact gtgaatggct   1560
atgtgaacag gagcctgcct ggcctgattg gctgccacag gaagtctgtg tactggcatg   1620
tgattggcat gggcaccacc cctgaggtgc acagcatctt cctggagggc acaccttcc   1680 tggtcaggaa ccacaggcag gccagcctgg agatcagccc catcaccttc ctgactgccc   1740
agaccctgct gatggacctg gccagttcc tgctgttctg ccacatcagc agccaccagc   1800
atgatggcat ggaggcctat gtgaaggtgg acagctgccc tgaggagccc cagctgagga   1860
tgaagaacaa tgaggaggct gaggactatg atgatgacct gactgactct gagatggatg   1920
tggtgaggtt tgatgatgac aacagcccca gcttcatcca gatcaggtct gtggccaaga   1980
agcaccccaa gacctgggtg cactacattg ctgctgagga ggaggactgg gactatgccc   2040
ccctggtgct ggcccctgat gacaggagct acaagagcca gtacctgaac aatggccccc   2100
agaggattgg caggaagtac aagaaggtca ggttcatggc ctacactgat gaaaccttca   2160
agaccaggga ggccatccag catgagtctg gcatcctggg cccctgctg tatgggag   2220 tgggggacac cctgctgatc atcttcaaga accaggccag caggccctac aacatctacc   2280 cccatgcat cactgatgtg aggccctgt acagcaggag gctgcccaag ggggtgaagc   2340
acctgaagga cttcccatc ctgcctgggg agatcttcaa gtacaagtgg actgtgactg   2400
tggaggatgg ccccaccaag tctgaccca ggtgcctgac cagatactac agcagctttg   2460
tgaacatgga gagggacctg gcctctgcc tgattggccc cctgctgatc tgctacaagg   2520
agtctgtgga ccagagggc aaccagatca tgtctgacaa gaggaatgtg atcctgttct   2580
```

```
ctgtgtttga tgagaacagg agctggtacc tgactgagaa catccagagg ttcctgccca      2640
accctgctgg ggtgcagctg gaggaccctg agttccaggc cagcaacatc atgcacagca      2700
tcaatggcta tgtgtttgac agcctgcagc tgtctgtgtg cctgcatgag gtggcctact      2760
ggtacatcct gagcattggg gcccagactg acttcctgtc tgtgttcttc tctggctaca      2820
ccttcaagca caagatggtg tatgaggaca ccctgaccct gttccccttc tctggggaga      2880
ctgtgttcat gagcatggag aaccctggcc tgtggattct gggctgccac aactctgact      2940
tcaggaacag gggcatgact gccctgctga agtctccag ctgtgacaag aacactgggg       3000
actactatga ggacagctat gaggacatct ctgcctacct gctgagcaag aacaatgcca      3060
ttgagcccag gagcttcagc cagaaccccc cagtgctgaa gaggcaccag agggagatca      3120
ccaggaccac cctgcagtct gaccaggagg agattgacta tgatgacacc atctctgtgg      3180
agatgaagaa ggaggacttt gacatctacg acgaggacga gaaccagagc cccaggagct      3240
tccagaagaa gaccaggcac tacttcattg ctgctgtgga gaggctgtgg gactatggca      3300
tgagcagcag ccccccatgtg ctgaggaaca gggcccagtc tggctctgtg ccccagttca      3360
agaaggtggt gttccaggag ttcactgatg gcagcttcac ccagccctg tacagagggg        3420
agctgaatga gcacctgggc ctgctggggcc cctacatcag ggctgaggtg gaggacaaca      3480
tcatggtgac cttcaggaac caggccagca ggccctacag cttctacagc agcctgatca      3540
gctatgagga ggaccagagg caggggctg agcccaggaa gaactttgtg aagcccaatg        3600
aaaccaagac ctacttctgg aaggtgcagc accacatggc cccaccaag gatgagtttg       3660
actgcaaggc ctgggcctac ttctctgatg tggacctgga aaggatgtg cactctggcc        3720
tgattggccc cctgctggtg tgccacacca acacctgaa ccctgcccat ggcaggcagg       3780
tgactgtgca ggagtttgcc ctgttcttca ccatctttga tgaaaccaag agctggtact      3840
tcactgagaa catggagagg aactgcaggg cccctgcaa catccagatg gaggacccca      3900
ccttcaagga gaactacagg ttccatgcca tcaatggcta catcatggac accctgcctg      3960
gcctggtgat ggcccaggac cagaggatca ggtggtacct gctgagcatg ggcagcaatg      4020
agaacatcca cagcatccac ttctctggcc atgtgttcac tgtgaggaag aaggaggagt      4080
acaagatggc cctgtacaac ctgtaccctg gggtgtttga gactgtggag atgctgccca      4140
gcaaggctgg catctggagg gtggagtgcc tgattgggga gcacctgcat gctggcatga      4200
gcaccctgtt cctggtgtac agcaacaagt gccagacccc cctgggcatg gcctctggcc      4260
acatcaggga cttccagatc actgcctctg ccagtatggg ccagtgggcc ccaagctgg       4320
ccaggctgca ctactctggc agcatcaatg cctggagcac caaggagccc ttcagctgga      4380
tcaaggtgga cctgctggcc cccatgatca tccatgcat caagacccag ggggccaggc       4440
agaagttcag cagcctgtac atcagccagt tcatcatcat gtacagcctg atggcaaga      4500
agtggcagac ctacagggc aacagcactg gcaccctgat ggtgttcttt ggcaatgtgg       4560
acagctctgg catcaagcac aacatcttca acccccccat cattgccaga tacatcaggc      4620
tgcacccac ccactacagc atcaggagca cctgaggat ggagctgatg gctgtgacc         4680
tgaacagctg cagcatgccc ctgggcatgg agagcaaggc catctctgat gcccagatca      4740
ctgccagcag ctacttcacc aacatgtttg ccacctggag ccccagcaag gccaggctgc      4800
acctgcaggg caggagcaat gcctggaggc ccaggtcaa caaccccaag gagtggctgc      4860
aggtggactt ccagaagacc atgaaggtga ctggggtgac cacccagggg gtgaagagcc      4920
```

```
tgctgaccag catgtatgtg aaggagttcc tgatcagcag cagccaggat ggccaccagt   4980
ggaccctgtt cttccagaat ggcaaggtga aggtgttcca gggcaaccag acagcttca    5040 cccctgtggt gaacagcctg accccccccc tgctgaccag atacctgagg attcacccc   5100 agagctgggt gcaccagatt gccctgagga tggaggtgct gggctgtgag gcccaggacc   5160
tgtactgacc tcgaggaata aaggaaattt attttcattg caatagtgtg ttggtttttt   5220
gtgtcacgtg gcggccgcag gaaccccctag tgatggagtt ggccactccc tctctgcgcg   5280
ctcgctcgct cactgaggcc gggcgaccaa aggtcgcccg acgcccgggc tttgcccggg   5340
cggcctcagt gagcgagcga gcgcgcagag agggagtggc caa                     5383
```

<210> SEQ ID NO 38
<211> LENGTH: 5728
<212> TYPE: DNA
<213> ORGANISM: Adeno-Associated Virus 2

<400> SEQUENCE: 38

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttaggaca    300 tgtttgctgt ttgctgcttg caatgtttgc cattttagg acaacgcga aacgtcgaca    360 ggttaatttt taaaaagcag tcaaaagtcc aagtggccct tggcagcatt tactctctct   420
gtttgctctg gttaataatc tcaggagcac aaacattcct ggaggcagga agaaaatca    480 acatcctgga cttatcctct gggcctctcc ccaccccag agaggctca ggttaatttt     540 taaaaagcag tcaaaagtcc aagtggccct tggcagcatt tactctctct gtttgctctg   600
gttaataatc tcaggagcac aaacattcct ggaggcagga agaaaatca acatcctgga    660 cttatcctct gggcctctcc ccaccccag agaggctgt cgactggaca caggacgctg    720
tggtttctga gccaggggc gactcagatc ccagccagtg gacttagccc ctgtttgctc    780
ctccgataac tggggtgacc ttggttaata ttcaccagca gcctcccccg ttgcccctct   840
ggatccactg cttaaatacg gacgaggaca gggccctgtc tcctcagctt caggcaccac   900
cactgacctg ggacagtgaa tcgtaagtat gcctttcact gcgagaggtt ctggagaggc   960
ttctgagctc cccatggccc aggcaggcag caggtctggg gcaggagggg ggttgtggag   1020
tgccttgact cggggcctgg ccccccatc tctgtcttgc aggacaattg ccgtcttctg    1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgttg tggagttcac tgaccacctg ttcaacattg   1380
ccaagcccag gccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg gcagccacac ctatgtgtgg caggtgctga   1620
aggagaatgg ccccatggcc tctgaccccc tgtgcctgac ctacagctac ctgagccatg   1680
```

```
tggacctggt gaaggacctg aactctggcc tgattggggc cctgctggtg tgcagggagg    1740
gcagcctggc caaggagaag acccagaccc tgcacaagtt catcctgctg tttgctgtgt    1800
ttgatgaggg caagagctgg cactctgaaa ccaagaacag cctgatgcag gacagggatg    1860
ctgcctctgc cagggcctgg cccaagatgc acactgtgaa tggctatgtg aacaggagcc    1920
tgcctggcct gattggctgc acaggaagt ctgtgtactg gcatgtgatt ggcatgggca    1980
ccaccccctga ggtgcacagc atcttcctgg agggccacac cttcctggtc aggaaccaca    2040
ggcaggccag cctggagatc agccccatca ccttcctgac tgcccagacc ctgctgatgg    2100
acctgggcca gttcctgctg ttctgccaca tcagcagcca ccagcatgat ggcatggagg    2160
cctatgtgaa ggtggacagc tgccctgagg agccccagct gaggatgaag aacaatgagg    2220
aggctgagga ctatgatgat gacctgactg actctgagat ggatgtggtg aggtttgatg    2280
atgacaacag ccccagcttc atccagatca ggtctgtggc caagaagcac cccaagacct    2340
gggtgcacta cattgctgct gaggaggagg actgggacta tgccccccctg gtgctggccc    2400
ctgatgacag gagctacaag agccagtacc tgaacaatgg ccccagagg attggcagga    2460
agtacaagaa ggtcaggttc atggcctaca ctgatgaaac cttcaagacc agggaggcca    2520
tccagcatga gtctggcatc ctgggccccc tgctgtatgg ggaggtgggg gacaccctgc    2580
tgatcatctt caagaaccag gccagcaggc cctacaacat ctaccccat ggcatcactg    2640
atgtgaggcc cctgtacagc aggaggctgc ccaagggggt gaagcacctg aaggacttcc    2700
ccatcctgcc tgggagatc ttcaagtaca gtggactgt gactgtggag atggccccca    2760
ccaagtctga ccccaggtgc ctgaccagat actacagcag ctttgtgaac atggagaggg    2820
acctggcctc tggcctgatt ggccccctgc tgatctgcta caaggagtct gtggaccaga    2880
ggggcaacca gatcatgtct gacaagagga atgtgatcct gttctctgtg tttgatgaga    2940
acaggagctg gtacctgact gagaacatcc agaggttcct gcccaaccct gctggggtgc    3000
agctggagga ccctgagttc caggccagca acatcatgca cagcatcaat ggctatgtgt    3060
ttgacagcct gcagctgtct gtgtgcctgc atgaggtggc ctactggtac atcctgagca    3120
ttggggccca gactgacttc ctgtctgtgt tcttctctgg ctacaccttc aagcacaaga    3180
tggtgtatga ggacaccctg acctgttcc ccttctctgg ggagactgtg ttcatgagca    3240
tggagaaccc tggcctgtgg attctgggct gccacaactc tgacttcagg aacagggca    3300
tgactgccct gctgaaagtc tccagctgtg acaagaacac tggggactac tatgaggaca    3360
gctatgagga catctctgcc tacctgctga gcaagaacaa tgccattgag cccaggagct    3420
tcagccagaa ccccccagtg ctgaagaggc accagaggga gatcaccagg accaccctgc    3480
agtctgacca ggaggagatt gactatgatg acaccatctc tgtggagatg aagaaggagg    3540
actttgacat ctacgacgag gacgagaacc agagccccag gagcttccag aagaagacca    3600
ggcactactt cattgctgct gtggagaggc tgtgggacta tggcatgagc agcagccccc    3660
atgtgctgag gaacagggcc cagtctggct ctgtgccccca gttcaagaag gtggtgttcc    3720
aggagttcac tgatggcagc ttcacccagc ccctgtacag aggggagctg aatgagcacc    3780
tgggcctgct gggcccctac atcagggctg aggtggagga acatcatg gtgaccttca    3840
ggaaccaggc cagcaggccc tacagcttct acagcagcct gatcagctat gaggaggacc    3900
agaggcaggg ggctgagccc aggaagaact ttgtgaagcc caatgaaacc aagacctact    3960
tctggaaggt gcagcaccac atggcccccca ccaaggatga gtttgactgc aaggcctggg    4020
```

-continued

```
cctacttctc tgatgtggac ctggagaagg atgtgcactc tggcctgatt ggcccctgc    4080
tggtgtgcca caccaacacc ctgaaccctg cccatggcag gcaggtgact gtgcaggagt    4140
ttgccctgtt cttcaccatc tttgatgaaa ccaagagctg gtacttcact gagaacatgg    4200
agaggaactg cagggccccc tgcaacatcc agatggagga ccccaccttc aaggagaact    4260
acaggttcca tgccatcaat ggctacatca tggacaccct gcctggcctg gtgatggccc    4320
aggaccagag gatcaggtgg tacctgctga gcatgggcag caatgagaac atccacagca    4380
tccacttctc tggccatgtg ttcactgtga ggaagaagga ggagtacaag atggccctgt    4440
acaacctgta ccctggggtg tttgagactg tggagatgct gcccagcaag gctggcatct    4500
ggagggtgga gtgcctgatt ggggagcacc tgcatgctgg catgagcacc ctgttcctgg    4560
tgtacagcaa caagtgccag accccctgg gcatggcctc tggccacatc agggacttcc    4620
agatcactgc ctctggccag tatggccagt gggcccccaa gctggccagg ctgcactact    4680
ctggcagcat caatgcctgg agcaccaagg agcccttcag ctggatcaag gtggacctgc    4740
tggcccccat gatcatccat ggcatcaaga cccagggggc caggcagaag ttcagcagcc    4800
tgtacatcag ccagttcatc atcatgtaca gcctggatgg caagaagtgg cagacctaca    4860
ggggcaacag cactggcacc ctgatggtgt tctttggcaa tgtggacagc tctggcatca    4920
agcacaacat cttcaacccc ccatcattg ccagatacat caggctgcac cccacccact    4980
acagcatcag gagcaccctg aggatggagc tgatgggctg tgacctgaac agctgcagca    5040
tgccccctggg catggagagc aaggccatct ctgatgccca gatcactgcc agcagctact    5100
tcaccaacat gtttgccacc tggagcccca gcaaggccag gctgcacctg cagggcagga    5160
gcaatgcctg gaggcccag gtcaacaacc caaggagtg gctgcaggtg gacttccaga    5220
agaccatgaa ggtgactggg gtgaccaccc aggggtgaa gagcctgctg accagcatgt    5280
atgtgaagga gttcctgatc agcagcagcc aggatggcca ccagtggacc ctgttcttcc    5340
agaatggcaa ggtgaaggtg ttccagggca accaggacag cttcacccct gtggtgaaca    5400
gcctggaccc cccctgctg accagatacc tgaggattca ccccagagc tgggtgcacc    5460
agattgccct gaggatggag gtgctgggct gtgaggccca ggacctgtac tgacctcgag    5520
gaataaagga aatttatttt cattgcaata gtgtgttggt ttttgtgtc acgtggcggc    5580
cgcaggaacc cctagtgatg gagttggcca ctccctctct gcgcgctcgc tcgctcactg    5640
aggccgggcg accaaaggtc gcccgacgcc cgggctttgc ccgggcggcc tcagtgagcg    5700
agcgagcgcg cagagaggga gtggccaa                                       5728
```

<210> SEQ ID NO 39  
<211> LENGTH: 5905  
<212> TYPE: DNA  
<213> ORGANISM: Adeno-Associated Virus 2

<400> SEQUENCE: 39

```
ttggccactc cctctctgcg cgctcgctcg ctcactgagg ccgcccgggc aaagcccggg      60
cgtcgggcga cctttggtcg cccggcctca gtgagcgagc agcgcgcag agagggagtg     120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgccat tttagggaca    300
tgtttgctgt ttgctgcttg caatgtttgc ccatttttagg acaacgcgca aacgtcgaca    360
ggttaatttt taaaaagcag tcaaaagtcc aagtggccct tggcagcatt tactctctct    420
```

```
gtttgctctg gttaataatc tcaggagcac aaacattcct ggaggcagga gaagaaatca    480
acatcctgga cttatcctct gggcctctcc ccaccccag gagaggctca ggttaatttt     540
taaaaagcag tcaaaagtcc aagtggccct tggcagcatt tactctctct gtttgctctg   600
gttaataatc tcaggagcac aaacattcct ggaggcagga gaagaaatca acatcctgga   660
cttatcctct gggcctctcc ccaccccag gagaggctgt cgactggaca caggacgctg    720
tggtttctga gccaggggc gactcagatc cagccagtg gacttagccc ctgtttgctc     780
ctccgataac tggggtgacc ttggttaata ttcaccagca gcctccccg ttgcccctct    840 ggatccactg cttaaatacg gacgaggaca gggccctgtc tcctcagctt caggcaccac   900
cactgacctg ggacagtgaa tcgtaagtat gcctttcact gcgagaggtt ctggagaggc   960
ttctgagctc cccatggccc aggcaggcag caggtctggg gcaggagggg ggttgtggag  1020
tgccttgact cggggcctgg ccccccatc tctgtcttgc aggacaattg ccgtcttctg   1080
tctcgtgggg catcctcctg ctggcaggcc tgtgctgcct ggtccctgcg atcgccacca  1140
tgcagattga gctgagcacc tgcttcttcc tgtgcctgct gaggttctgc ttctctgcca  1200
ccaggagata ctacctgggg gctgtggagc tgagctggga ctacatgcag tctgacctgg  1260
gggagctgcc tgtggatgcc aggttccccc ccagagtgcc caagagcttc cccttcaaca  1320
cctctgtggt gtacaagaag accctgtttg tggagttcac tgaccacctg ttcaacattg  1380
ccaagcccag gcccccctgg atgggcctgc tgggccccac catccaggct gaggtgtatg  1440
acactgtggt gatcaccctg aagaacatgg ccagccaccc tgtgagcctg catgctgtgg  1500
gggtgagcta ctggaaggcc tctgaggggg ctgagtatga tgaccagacc agccagaggg  1560
agaaggagga tgacaaggtg ttccctgggg gcagccacac ctatgtgtgg caggtgctga  1620
aggagaatgg ccccatggcc tctgaccccc tgtgcctgac ctacagctac ctgagccatg  1680
tggacctggt gaaggacctg aactctggcc tgattgggc cctgctggtg tgcagggagg  1740
gcagcctggc caaggagaag acccagaccc tgcacaagtt catcctgctg tttgctgtgt  1800
ttgatgaggg caagagctgg cactctgaaa ccaagaacag cctgatgcag gacagggatg  1860
ctgcctctgc cagggcctgg cccaagatgc acactgtgaa tggctatgtg aacaggagcc  1920
tgcctggcct gattggctgc cacaggaagt ctgtgtactg gcatgtgatt ggcatgggca  1980 ccaccccctga ggtgcacagc atcttcctgg agggccacac cttcctggtc aggaaccaca  2040
ggcaggccag cctggagatc agccccatca ccttcctgac tgcccagacc ctgctgatgg  2100
acctgggcca gttcctgctg ttctgccaca tcagcagcca ccagcatgat ggcatggagg  2160
cctatgtgaa ggtggacagc tgccctgagg agcccagct gaggatgaag aacaatgagg  2220
aggctgagga ctatgatgat gacctgactg actctgagat ggatgtggtg aggtttgatg  2280
atgacaacag ccccagcttc atccagatca ggtctgtggc caagaagcac cccaagacct  2340
gggtgcacta cattgctgct gaggaggagg actgggacta tgccccctg gtgctggccc   2400 ctgatgacag gagctacaag agccagtacc tgaacaatgg cccccagagg attggcagga  2460
agtacaagaa ggtcaggttc atggcctaca ctgatgaaac cttcaagacc agggaggcca  2520
tccagcatga gtctggcatc ctgggccccc tgctgtatgg ggaggtgggg gacaccctgc  2580
tgatcatctt caagaaccag gccagcaggc cctacaacat ctacccccat ggcatcactg  2640
atgtgaggcc cctgtacagc aggaggctgc caagggggt gaagcacctg aaggacttcc   2700
ccatcctgcc tggggagatc ttcaagtaca agtggactgt gactgtggag gatggccccc  2760
```

```
ccaagtctga ccccaggtgc ctgaccagat actacagcag ctttgtgaac atggagaggg    2820
acctggcctc tggcctgatt ggccccctgc tgatctgcta caaggagtct gtggaccaga    2880
ggggcaacca gatcatgtct gacaagagga atgtgatcct gttctctgtg tttgatgaga    2940
acaggagctg gtacctgact gagaacatcc agaggttcct gcccaaccct gctggggtgc    3000
agctggagga ccctgagttc caggccagca acatcatgca cagcatcaat ggctatgtgt    3060
ttgacagcct gcagctgtct gtgtgcctgc atgaggtggc ctactggtac atcctgagca    3120
ttggggccca gactgacttc ctgtctgtgt tcttctctgg ctacaccttc aagcacaaga    3180
tggtgtatga ggacaccctg accctgttcc ccttctctgg ggagactgtg ttcatgagca    3240
tggagaaccc tggcctgtgg attctgggct gccacaactc tgacttcagg aacagggca    3300 tgactgccct gctgaaagtc tccagctgtg acaagaacac tggggactac tatgaggaca    3360
gctatgagga catctctgcc tacctgctga gcaagaacaa tgccattgag cccaggagct    3420
tcagccagaa ccccccagtg ctgaagaggc accagaggga gatcaccagg accaccctgc    3480
agtctgacca ggaggagatt gactatgatg acaccatctc tgtggagatg aagaaggagg    3540
actttgacat ctacgacgag gacgagaacc agagccccag gagcttccag aagaagacca    3600
ggcactactt cattgctgct gtggagaggc tgtgggacta tggcatgagc agcagccccc    3660
atgtgctgag gaacagggcc cagtctggct ctgtgcccca gttcaagaag gtggtgttcc    3720
aggagttcac tgatggcagc ttcacccagc ccctgtacag gggggagctg aatgagcacc    3780
tgggcctgct gggcccctac atcagggctg aggtggagga caacatcatg gtgaccttca    3840
ggaaccaggc cagcaggccc tacagcttct acagcagcct gatcagctat gaggaggacc    3900
agaggcaggg ggctgagccc aggaagaact tgtgaagcc caatgaaacc aagacctact    3960
tctggaaggt gcagcaccac atggcccccca ccaaggatga gtttgactgc aaggcctggg    4020
cctacttctc tgatgtggac ctggagaagg atgtgcactc tggcctgatt ggccccctgc    4080
tggtgtgcca caccaacacc ctgaaccctg cccatggcag gcaggtgact gtgcaggagt    4140
ttgccctgtt cttcaccatc tttgatgaaa ccaagagctg gtacttcact gagaacatgg    4200
agaggaactg cagggcccc tgcaacatcc agatggagga ccccaccttc aaggagaact    4260
acaggttcca tgccatcaat ggctacatca tggacaccct gcctggcctg gtgatggccc    4320
aggaccagag gatcaggtgg tacctgctga gcatgggcag caatgagaac atccacagca    4380
tccacttctc tggccatgtg ttcactgtga ggaagaagga ggagtacaag atggcctgt    4440 acaacctgta ccctgggtg tttgagactg tggagatgct gcccagcaag gctggcatct    4500
ggagggtgga gtgcctgatt ggggagcacc tgcatgctgg catgagcacc ctgttcctgg    4560
tgtacagcaa caagtgccag acccccctgg gcatggcctc tggccacatc agggacttcc    4620
agatcactgc ctctggccag tatggccagt gggcccccaa gctggccagg ctgcactact    4680
ctggcagcat caatgcctgg agcaccaagg agcccttcag ctggatcaag gtggacctgc    4740 tggccccat gatcatccat ggcatcaaga cccaggggc caggcagaag ttcagcagcc    4800
tgtacatcag ccagttcatc atcatgtaca gcctggatgg caagaagtgg cagacctaca    4860
ggggcaacag cactggcacc ctgatggtgt tcttttggcaa tgtggacagc ctggcatca    4920 agcacaacat cttcaacccc cccatcattg ccagatacat caggctgcac cccacccact    4980
acagcatcag gagcacctg aggatggagc tgatgggctg tgacctgaac agctgcagca    5040
tgcccctggg catggagagc aaggcctct ctgatgccca tcactgcc agcagctact    5100 tcaccaacat gtttgccacc tggagcccca gcaaggccag gctgcacctg cagggcagga    5160
```

-continued

```
gcaatgcctg gaggccccag gtcaacaacc ccaaggagtg gctgcaggtg gacttccaga      5220
agaccatgaa ggtgactggg gtgaccaccc aggggtgaa gagcctgctg accagcatgt      5280
atgtgaagga gttcctgatc agcagcagcc aggatggcca ccagtggacc ctgttcttcc      5340
agaatggcaa ggtgaaggtg ttccagggca accaggacag cttcacccct gtggtgaaca      5400
gcctggaccc ccccctgctg accagatacc tgaggattca ccccagagc tgggtgcacc       5460 agattgccct gaggatggag gtgctgggct gtgaggccca ggacctgtac tgacctcgag      5520
gtgtgccttc tagttgccag ccatctgttg tttgcccctc cccgtgcct tccttgaccc       5580 tggaaggtgc cactcccact gtcctttcct aataaaatga ggaaattgca tcgcattgtc      5640
tgagtaggtg tcattctatt ctggggggtg gggtggggca ggacagcaag ggggaggatt      5700
gggaagacaa tagcaggcat gctggggatg cggtgggctc tatgggcacg tggcggccgc      5760
aggaacccct agtgatggag ttggccactc cctctctgcg cgctcgctcg ctcactgagg      5820
ccgggcgacc aaaggtcgcc cgacgcccgg gctttgcccg gcggcctca gtgagcgagc       5880 gagcgcgcag agagggagtg gccaa                                            5905
```

```
<210> SEQ ID NO 40
<211> LENGTH: 5355
<212> TYPE: DNA
<213> ORGANISM: Adeno-Associated Virus 2

<400> SEQUENCE: 40
```

```
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgactg tttgctgttt      180
gctgcttgca atgtttgccc atttaggga catgtttgct gtttgctgct tgcaatgttt       240
gcccatttta gggacatgtt tgctgtttgc tgcttgcaat gtttgcccat tttagggaca      300
tgtttgctgt ttgctgcttg caatgtttgc ccattttagg gacaacgcga acgtcgact       360 ggacacagga cgctgtggtt tctgagccag ggggcgactc agatcccagc cagtggactt      420
agcccctgtt tgctcctccg ataactgggg tgaccttggt taatattcac cagcagcctc      480
ccccgttgcc cctctggatc cactgcttaa atacggacga ggacagggcc ctgtctcctc      540
agcttcaggc accaccactg acctgggaca gtgaatcgcg atcgccacca tgcagattga      600
gctgagcacc tgcttcttcc tgtgcctgct gaggttctgc ttctctgcca ccaggagata      660
ctacctgggg gctgtggagc tgagctggga ctacatgcag tctgacctgg gggagctgcc      720
tgtggatgcc aggttccccc ccagagtgcc caagagcttc cccttcaaca cctctgtggt      780
gtacaagaag accctgtttg tggagttcac tgaccacctg ttcaacattg ccaagcccag      840 gccccctgg atgggcctgc tgggccccac catccaggct gaggtgtatg acactgtggt      900
gatcaccctg aagaacatgg ccagccaccc tgtgagcctg catgctgtgg gggtgagcta      960
ctggaaggcc tctgaggggg ctgagtatga tgaccagacc agccagaggg agaaggagga     1020
tgacaaggtg ttccctgggg gcagccacac ctatgtgtgg caggtgctga aggagaatgg     1080
ccccatggcc tctgaccccc tgtgcctgac ctacagctac ctgagccatg tggacctggt     1140
gaaggacctg aactctggcc tgattggggc cctgctggtg tgcagggagg cagcctggc      1200 caaggagaag acccagaccc tgcacaagtt catcctgctg tttgctgtgt ttgatgaggg     1260
caagagctgg cactctgaaa ccaagaacag cctgatgcag gacagggatg ctgcctctgc     1320
```

```
cagggcctgg cccaagatgc acactgtgaa tggctatgtg aacaggagcc tgcctggcct    1380
gattggctgc cacaggaagt ctgtgtactg catgtgatt  ggcatgggca ccacccctga    1440
ggtgcacagc atcttcctgg agggccacac cttcctggtc aggaaccaca ggcaggccag    1500
cctggagatc agccccatca ccttcctgac tgcccagacc ctgctgatgg acctgggcca    1560
gttcctgctg ttctgccaca tcagcagcca ccagcatgat ggcatggagg cctatgtgaa    1620
ggtggacagc tgccctgagg agccccagct gaggatgaag aacaatgagg aggctgagga    1680
ctatgatgat gacctgactg actctgagat ggatgtggtg aggtttgatg atgacaacag    1740
cccccagcttc atccagatca ggtctgtggc caagaagcac cccaagacct gggtgcacta    1800
cattgctgct gaggaggagg actgggacta tgccccctg  gtgctggccc ctgatgacag    1860
gagctacaag agccagtacc tgaacaatgg ccccccagagg attggcagga agtacaagaa    1920
ggtcaggttc atggcctaca ctgatgaaac cttcaagacc agggaggcca tccagcatga    1980
gtctggcatc ctgggccccc tgctgtatgg ggaggtgggg gacaccctgc tgatcatctt    2040
caagaaccag gccagcaggc cctacaacat ctaccccat  ggcatcactg atgtgaggcc    2100
cctgtacagc aggaggctgc ccaagggggt gaagcacctg aaggacttcc ccatcctgcc    2160
tggggagatc ttcaagtaca gtggactgt  gactgtggag gatggccccca ccaagtctga    2220
ccccaggtgc ctgaccagat actacagcag cttttgtgaac atggagaggg  acctggcctc    2280
tggcctgatt ggccccctgc tgatctgcta caaggagtct gtggaccaga ggggcaacca    2340
gatcatgtct gacaagagga atgtgatcct gttctctgtg tttgatgaga caggagctg     2400
gtacctgact gagaacatcc agaggttcct gcccaaccct gctggggtgc agctggagga    2460
ccctgagttc caggccagca acatcatgca cagcatcaat ggctatgtgt tgacagcct    2520
gcagctgtct gtgtgcctgc atgaggtggc ctactggtac atcctgagca ttgggggccca    2580
gactgacttc ctgtctgtgt tcttctctgg ctacaccttc aagcacaaga tggtgtatga    2640
ggacaccctg accctgttcc ccttctctgg ggagactgtg ttcatgagca tggagaaccc    2700
tggcctgtgg attctgggct gccacaactc tgacttcagg aacaggggca tgactgccct    2760
gctgaaagtc tccagctgtg acaagaacac tggggactac tatgaggaca gctatgagga    2820
catctctgcc tacctgctga gcaagaacaa tgccattgag cccaggagct tcagccagaa    2880
ccccccagtg ctgaagaggc accagaggga gatcaccagg accaccctgc agtctgacca    2940
ggaggagatt gactatgatg acaccatctc tgtggagatg aagaaggagg actttgacat    3000
ctacgacgag gacgagaacc agagcccag  gagcttccag aagaagacca ggcactactt    3060
cattgctgct gtggagaggc tgtgggacta tggcatgagc agcagccccc atgtgctgag    3120
gaacagggcc cagtctggct ctgtgcccca gttcaagaag gtggtgttcc aggagttcac    3180
tgatggcagc ttcacccagc ccctgtacag aggggagctg aatgagcacc tgggcctgct    3240
gggcccctac atcagggctg aggtggagga caacatcatg gtgaccttca ggaaccaggc    3300
cagcaggccc tacagcttct acagcagcct gatcagctat gaggaggacc agaggcaggg    3360
ggctgagccc aggaagaact ttgtgaagcc caatgaaacc aagacctact tctggaaggt    3420
gcagcaccac atggccccca ccaaggatga gtttgactgc aaggcctggg cctacttctc    3480
tgatgtggac ctggagaagg atgtgcactc tggcctgatt ggccccctgc tggtgtgcca    3540
caccaacacc ctgaaccctg cccatggcag gcaggtgact gtgcaggagt ttgccctgtt    3600
cttcaccatc tttgatgaaa ccaagagctg gtacttcact gagaacatgg agaggaactg    3660
cagggccccc tgcaacatcc agatggagga ccccacctcc aaggagaact acaggttcca    3720
```

```
tgccatcaat ggctacatca tggacaccct gcctggcctg gtgatggccc aggaccagag    3780
gatcaggtgg tacctgctga gcatgggcag caatgagaac atccacagca tccacttctc    3840
tggccatgtg ttcactgtga ggaagaagga ggagtacaag atggccctgt acaacctgta    3900
ccctggggtg tttgagactg tggagatgct gcccagcaag gctggcatct ggagggtgga    3960
gtgcctgatt ggggagcacc tgcatgctgg catgagcacc ctgttcctgg tgtacagcaa    4020
caagtgccag acccccctgg gcatggcctc tggccacatc agggacttcc agatcactgc    4080
ctctggccag tatggccagt gggcccccaa gctggccagg ctgcactact ctggcagcat    4140
caatgcctgg agcaccaagg agcccttcag ctggatcaag gtggacctgc tggccccat    4200 gatcatccat ggcatcaaga cccagggggc caggcagaag ttcagcagcc tgtacatcag    4260
ccagttcatc atcatgtaca gcctggatgg caagaagtgg cagacctaca ggggcaacag    4320
cactggcacc ctgatggtgt ctttggcaa tgtggacagc tctggcatca agcacaacat    4380
cttcaacccc cccatcattg ccagatacat caggctgcac cccacccact acagcatcag    4440
gagcacactg aggatggagc tgatgggctg tgacctgaac agctgcagca tgccccctggg    4500 catggagagc aaggccatct ctgatgccca gatcactgcc agcagctact tcaccaacat    4560
gtttgccacc tggagcccca gcaaggccag gctgcacctg cagggcagga gcaatgcctg    4620
gaggccccag gtcaacaacc caaggagtg gctgcaggtg gacttccaga gaccatgaa    4680 ggtgactggg gtgaccaccc aggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca accaggacag cttcacccct gtggtgaaca gcctggaccc    4860 cccccctgctg accagatacc tgaggattca ccccagagc tgggtgcacc agattgccct    4920
gaggatggag gtgctgggct gtgaggccca ggacctgtac tgacctcgag gtgtgccttc    4980
tagttgccag ccatctgttg tttgcccctc cccgtgcct tccttgaccc tggaaggtgc    5040
cactcccact gtcctttcct aataaaatga ggaaattgca tcgcattgtc tgagtaggtg    5100
tcattctatt ctgggggtg gggtggggca ggacagcaag ggggaggatt gggaagacaa    5160
tagcaggcat gctggggatg cggtgggctc tatgggcacg tggcggccgc aggaaccct    5220 agtgatggag ttggccactc cctctctgcg cgctcgctcg ctcactgagg ccgggcgacc    5280
aaaggtcgcc cgacgcccgg gctttgcccg ggcggcctca gtgagcgagc gagcgcgcag    5340
agagggagtg gccaa                                                    5355
```

<210> SEQ ID NO 41
<211> LENGTH: 5618
<212> TYPE: DNA
<213> ORGANISM: Adeno-Associated Virus 2

<400> SEQUENCE: 41

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgacca gagaggtctc     180
tgacctctgc cccagctcca aggtcagcag gcagggaggc tgtgtgtttt gctgtttgct     240
gcttgcaatg tttgcccatt ttagggacat gagtaggctg aagtttgttc agtgtggact     300
tcagaggcag cacacaaaca gccagagagg tctctgacct ctgccccagc tccaaggtca     360
gcaggcaggg agggctgtgt gtttgctgtt tgctgcttgc aatgtttgcc cattttaggg     420
```

```
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gccccagctc    660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga aacgtcgact ggacacagga cgctgtggtt tctgagccag ggggcgactc    840
agatcccagc cagtggactt agcccctgtt tgctcctccg ataactgggg tgaccttggt    900
taatattcac cagcagcctc ccccgttgcc cctctggatc cactgcttaa atacggacga    960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gccccctgg atgggcctgc tgggcccccac catccaggct   1320
gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg gcagcctggc caaggagaag acccagaccc tgcacaagtt catcctgctg   1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccacccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agcccagct gaggatgaag   2100
aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgcccccctg   2280
gtgctggccc ctgatgacag gagctacaag agccagtacc tgaacaatgg ccccccagagg   2340
attggcagga agtacaagaa ggtcaggttc atggcctaca ctgatgaaac cttcaagacc   2400
agggaggcca tccagcatga gtctggcatc ctgggccccc tgctgtatgg ggaggtgggg   2460
gacaccctgc tgatcatctt caagaaccag gccagcaggc cctacaacat ctaccccat   2520
ggcatcactg atgtgagggc cctgtacagc aggaggctgc caaggggggt gaagcacctg   2580
aaggacttcc ccatcctgcc tggggagatc ttcaagtaca agtggactgt gactgtggag   2640
gatggcccca caagtctga ccccaggtgc ctgaccagat actacagcag ctttgtgaac   2700
atggagaggg acctggcctc tggcctgatt ggccccctgc tgatctgcta caaggagtct   2760
gtggaccaga ggggcaacca gatcatgtct gacaagagga atgtgatcct gttctctgtg   2820
```

```
tttgatgaga acaggagctg gtacctgact gagaacatcc agaggttcct gcccaaccct      2880 gctgggtgc  agctggagga ccctgagttc caggccagca acatcatgca cagcatcaat     2940
ggctatgtgt ttgacagcct gcagctgtct gtgtgcctgc atgaggtggc ctactggtac     3000
atcctgagca ttggggccca gactgacttc ctgtctgtgt tcttctctgg ctacaccttc     3060
aagcacaaga tggtgtatga ggacaccctg accctgttcc ccttctctgg ggagactgtg     3120
ttcatgagca tggagaaccc tggcctgtgg attctgggct gccacaactc tgacttcagg     3180
aacaggggca tgactgccct gctgaaagtc tccagctgtg acaagaacac tggggactac     3240
tatgaggaca gctatgagga catctctgcc tacctgctga gcaagaacaa tgccattgag     3300
cccaggagct tcagccagaa ccccccagtg ctgaagaggc accagaggga gatcaccagg     3360
accaccctgc agtctgacca ggaggagatt gactatgatg acaccatctc tgtggagatg     3420
aagaaggagg actttgacat ctacgacgag gacgagaacc agagcccag  gagcttccag     3480 aagaagacca ggcactactt cattgctgct gtggagaggc tgtgggacta tggcatgagc     3540
agcagccccc atgtgctgag gaacagggcc cagtctggct ctgtgcccca gttcaagaag     3600
gtggtgttcc aggagttcac tgatggcagc ttcacccagc ccctgtacag aggggagctg     3660
aatgagcacc tgggcctgct gggcccctac atcagggctg aggtggagga caacatcatg     3720
gtgaccttca ggaaccaggc cagcaggccc tacagcttct acagcagcct gatcagctat     3780
gaggaggacc agaggcaggg ggctgagccc aggaagaact tgtgaagcc  caatgaaacc     3840 aagacctact tctggaaggt gcagcaccac atggccccca ccaaggatga gtttgactgc     3900
aaggcctggg cctacttctc tgatgtggac ctggagaagg atgtgcactc tggcctgatt     3960 ggcccctgc  tggtgtgcca caccaacacc ctgaaccctg ccatggcag  gcaggtgact     4020 gtgcaggagt ttgccctgtt cttcaccatc tttgatgaaa ccaagagctg gtacttcact     4080
gagaacatgg agaggaactg cagggccccc tgcaacatcc agatggagga ccccaccttc     4140
aaggagaact acaggttcca tgccatcaat ggctacatca tggacaccct gcctggcctg     4200
gtgatggccc aggaccagag gatcaggtgg tacctgctga gcatgggcag caatgagaac     4260
atccacagca tccacttctc tggccatgtg ttcactgtga ggaagaagga ggagtacaag     4320
atggccctgt acaacctgta ccctggggtg tttgagactg tggagatgct gcccagcaag     4380
gctggcatct ggagggtgga gtgcctgatt ggggagcacc tgcatgctgg catgagcacc     4440
ctgttcctgg tgtacagcaa caagtgccag accccctgg  gcatggcctc tggccacatc     4500
agggacttcc agatcactgc ctctggccag tatggccagt gggccccaa  gctggccagg     4560 ctgcactact ctggcagcat caatgcctgg agcaccaagg agcccttcag ctggatcaag     4620
gtggacctgc tggcccccat gatcatccat ggcatcaaga cccagggggc caggcagaag     4680
ttcagcagcc tgtacatcag ccagttcatc atcatgtaca gcctggatgg caagaagtgg     4740
cagacctaca gggcaacag  cactggcacc ctgatggtgt ctttggcaa  tgtggacagc     4800 tctggcatca agcacaacat cttcaacccc cccatcattg ccagatacat caggctgcac     4860
cccacccact acagcatcag gagcaccctg aggatggagc tgatgggctg tgacctgaac     4920
agctgcagca tgcccctggg catggagagc aaggccatct ctgatgccca gatcactgcc     4980
agcagctact tcaccaacat gtttgccacc tggagcccca gcaaggccag gctgcacctg     5040
cagggcagga gcaatgcctg gaggccccag gtcaacaacc ccaaggagtg gctgcaggtg     5100
gacttccaga agaccatgaa ggtgactggg gtgaccaccc agggggtgaa gagcctgctg     5160
```

```
accagcatgt atgtgaagga gttcctgatc agcagcagcc aggatggcca ccagtggacc    5220
ctgttcttcc agaatggcaa ggtgaaggtg ttccagggca accaggacag cttcacccct    5280
gtggtgaaca gcctggaccc ccccctgctg accagatacc tgaggattca ccccagagc    5340 tgggtgcacc agattgccct gaggatggag gtgctgggct gtgaggccca ggacctgtac    5400
tgacctcgag gaataaagga aatttatttt cattgcaata gtgtgttggt ttttgtgtc    5460 acgtggcggc cgcaggaacc cctagtgatg gagttggcca ctccctctct gcgcgctcgc    5520
tcgctcactg aggccgggcg accaaaggtc gcccgacgcc cgggctttgc ccgggcggcc    5580
tcagtgagcg agcgagcgcg cagagaggga gtggccaa                           5618
```

<210> SEQ ID NO 42
<211> LENGTH: 5993
<212> TYPE: DNA
<213> ORGANISM: Adeno-Associated Virus 2

<400> SEQUENCE: 42

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtt tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg acacaggac gctgtggttt    540 ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttccccc    900 cagagtgccc aagagcttcc ccttcaacac ctctgtggtg tacaagaaga cctgtttgt    960 ggagttcact gaccacctgt tcaacattgc aagcccagg cccccctgga tgggcctgct   1020
gggccccacc atccaggctg aggtgtatga cactgtggtg atcaccctga gaacatggc   1080 cagccaccct gtgagcctgc atgctgtggg ggtgagctac tggaaggcct gagggggc    1140 tgagtatgat gaccagacca gccagaggga aaggaggat gacaaggtgt ccctgggggg   1200
cagccacacc tatgtgtggc aggtgctgaa ggagaatggc cccatggcct gtacccccct   1260
gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc ccaagatgca   1500
cactgtgaat ggctatgtga acaggagcct gcctggcctg attggctgcc acaggaagtc   1560
tgtgtactgg catgtgattg gcatgggcac caccctgaag gtgcacagca tcttcctgga   1620
gggccacacc ttcctggtca ggaaccacag gcaggccagc ctggagatca gccccatcac   1680
```

```
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga acaatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggaga   1980 ctgggactat gccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggcccct   2160 gctgtatggg gaggtggggg acaccctgct gatcatcttc aagaaccagg ccagcaggcc   2220
ctacaacatc taccccatg gcatcactga tgtgaggccc ctgtacagca ggaggctgcc   2280 caaggggtg aagcacctga aggacttccc catcctgcct ggggagatct tcaagtacaa   2340
gtggactgtg actgtggagg atggcccac caagtctgac cccaggtgcc tgaccagata   2400
ctacagcagc tttgtgaaca tggagaggga cctggcctct ggcctgattg gcccctgct   2460 gatctgctac aaggagtctg tggaccagag gggcaaccag atcatgtctg acaagaggaa   2520
tgtgatcctg ttctctgtgt tgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca agcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga cttttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg gcccctaca tcagggctga   3420 ggtggaggac aacatcatgg tgaccttcag gaaccaggcc agcaggccct acagcttcta   3480
cagcagcctg atcagctatg aggaggacca gaggcagggg gctgagccca ggaagaactt   3540
tgtgaagccc aatgaaacca gacctacttt ctggaaggtg cagcaccaca tggccccac   3600 caaggatgag tttgactgca aggcctgggc ctacttctct gatgtggacc tggagaagga   3660
tgtgcactct ggcctgattg gcccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggcccct gcaacatcca   3840 gatggaggac cccaccttca aggagaacta caggttccat gccatcaatg gctacatcat   3900
ggacaccctg cctggcctgg tgatggccca ggaccagagg atcaggtggt acctgctgag   3960
catgggcagc aatgagaaca tccacagcat ccacttctct ggccatgtgt tcactgtgag   4020
```

| gaagaaggag gagtacaaga tggccctgta caacctgtac cctggggtgt ttgagactgt | 4080 |
| ggagatgctg cccagcaagg ctggcatctg gagggtggag tgcctgattg gggagcacct | 4140 |
| gcatgctggc atgagcaccc tgttcctggt gtacagcaac aagtgccaga ccccctggg | 4200 |
| catggcctct ggccacatca gggacttcca gatcactgcc tctggccagt atggccagtg | 4260 |
| ggcccccaag ctggccaggc tgcactactc tggcagcatc aatgcctgga gcaccaagga | 4320 |
| gcccttcagc tggatcaagg tggacctgct ggccccatg atcatccatg gcatcaagac | 4380 |
| ccagggggcc aggcagaagt tcagcagcct gtacatcagc cagttcatca tcatgtacag | 4440 |
| cctggatggc aagaagtggc agacctacag gggcaacagc actggcaccc tgatggtgtt | 4500 |
| cttttggcaat gtggacagct ctggcatcaa gcacaacatc ttcaaccccc ccatcattgc | 4560 |
| cagatacatc aggctgcacc ccacccacta cagcatcagg agcacctga ggatggagct | 4620 |
| gatgggctgt gacctgaaca gctgcagcat gcccctgggc atggagagca aggccatctc | 4680 |
| tgatgcccag atcactgcca gcagctactt caccaacatg tttgccacct ggagccccag | 4740 |
| caaggccagg ctgcacctgc agggcaggag caatgcctgg aggccccagg tcaacaaccc | 4800 |
| caaggagtgg ctgcaggtgg acttccagaa gaccatgaag gtgactgggg tgaccaccca | 4860 |
| gggggtgaag agcctgctga ccagcatgta tgtgaaggag ttcctgatca gcagcagcca | 4920 |
| ggatggccac cagtggaccc tgttcttcca gaatggcaag gtgaaggtgt tccagggcaa | 4980 |
| ccaggacagc ttcaccctg tggtgaacag cctggacccc ccctgctga ccagatacct | 5040 |
| gaggattcac ccccagagct gggtgcacca gattgccctg aggatggagg tgctgggctg | 5100 |
| tgaggcccag gacctgtact gacctcgagg aataaaggaa atttatttc attgcaatag | 5160 |
| tgtgttggtt ttttgtgtca cgtgccctct cacactacct aaaccacgcc aggacaacct | 5220 |
| ctgctcctct ccaccgaaat tccaagggt cgagtggatg ttggaggtgg catgggccca | 5280 |
| gagaggtctc tgacctctgc cccagctcca aggtcagcag gcagggaggg ctgtgtgttt | 5340 |
| gctgtttgct gcttgcaatg tttgcccatt ttagggacat gagtaggctg aagtttgttc | 5400 |
| agtgtggact tcagaggcag cacacaaaca gctgctggag gatgggaact gaggggttgg | 5460 |
| aaggggcag ggtgagccca gaaactcctg tgtgcctctg agcctgcagc ctctctcacac | 5520 |
| tacctaaaacc acgccaggac aacctctgct cctctccacc gaaattccaa ggggtcgagt | 5580 |
| ggatgttgga ggtggcatgg gcccagagag gtctctgacc tctgccccag ctccaaggtc | 5640 |
| agcaggcagg gagggctgtg tgtttgctgt ttgctgcttg caatgtttgc ccattttagg | 5700 |
| gacatgagta ggctgaagtt tgttcagtgt ggacttcaga ggcagcacac aaacagctgc | 5760 |
| tggaggatgg gaactgaggg gttggaaggg gcagggtga gcccagaaac tcctgtgtgc | 5820 |
| ctctgagcct gcagcacgtg gcggccgcag gaacccctag tgatggagtt ggccactccc | 5880 |
| tctctgcgcg ctcgctcgct cactgaggcc gggcgaccaa aggtcgcccg acgcccgggc | 5940 |
| tttgcccggg cggcctcagt gagcgagcga gcgcgcagag agggagtggc caa | 5993 |

```
<210> SEQ ID NO 43
<211> LENGTH: 5337
<212> TYPE: DNA
<213> ORGANISM: Adeno-Associated Virus 2

<400> SEQUENCE: 43
```

| ttggccactc cctctctgcg cgctcgctcg ctcactgagg ccgccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg tttaaacgtc gacaggttaa | 180 |

-continued

```
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa ttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gccctgtttt gctcctccga    600
taactggggt gaccttggtt aatattcacc agcagcctcc cccgttgccc ctctggatcc    660
actgcttaaa tacgacgag acagggccc tgtctcctca gcttcaggca ccaccactga    720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttcccccc    900
cagagtgccc aagagcttcc ccttcaacac ctctgtggtg tacaagaaga ccctgtttgt    960
ggagttcact gaccacctgt tcaacattgc caagcccagg ccccctggaa tgggcctgct   1020
gggccccacc atccaggctg aggtgtatga cactgtggtg atcaccctga agaacatggc   1080
cagccaccct gtgagcctgc atgctgtggg ggtgagctac tggaaggcct ctgagggggc   1140
tgagtatgat gaccagacca gccagaggga aaggaggat gacaaggtgt ccctggggg   1200
cagccacacc tatgtgtggc aggtgctgaa ggagaatggc cccatggcct ctgacccct   1260
gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc caagatgca   1500
cactgtgaat ggctatgtga acaggagcct gcctggcctg attggctgcc acaggaagtc   1560
tgtgtactgg catgtgattg gcatgggcac caccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga caatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagaa   1980
ctgggactat gcccccctgg tgctggcccc tgatgacagg agctacaaga ccagtacct   2040
gaacaatggc ccccagagga ttggcaggaa gtacaagaag gtcaggttca tggcctacac   2100
tgatgaaacc ttcaagacca gggaggcat ccagcatgag tctggcatcc tgggcccct   2160
gctgtatggg gaggtggggg acaccctgct gatcatcttc aagaaccagg ccagcaggcc   2220
ctacaacatc taccccccatg gcatcactga tgtgaggccc ctgtacagca ggaggctgcc   2280
caaggggtg aagcacctga aggacttccc catcctgcct ggggagatct tcaagtacaa   2340
gtggactgtg actgtggagg atggccccac caagtctgac cccaggtgcc tgaccagata   2400
ctacagcagc tttgtgaaca tggagaggga cctggcctct ggcctgattg ccccctgct   2460
gatctgctac aaggagtctg tggaccagag gggcaaccag atcatgtctg acaagaggaa   2520
```

```
tgtgatcctg ttctctgtgt ttgatgagaa caggagctgg tacctgactg agaacatcca    2580
gaggttcctg cccaaccctg ctggggtgca gctggaggac cctgagttcc aggccagcaa    2640
catcatgcac agcatcaatg ctatgtgtt tgacagcctg cagctgtctg tgtgcctgca     2700
tgaggtggcc tactggtaca tcctgagcat gggcccag actgacttcc tgtctgtgtt     2760
cttctctggc tacaccttca agcacaagat ggtgtatgag acaccctga ccctgttccc    2820 cttctctggg gagactgtgt tcatgagcat ggagaaccct ggcctgtgga ttctgggctg    2880
ccacaactct gacttcagga acaggggcat gactgccctg ctgaaagtct ccagctgtga    2940
caagaacact ggggactact atgaggacag ctatgaggac atctctgcct acctgctgag    3000
caagaacaat gccattgagc ccaggagctt cagccagaac cccccagtgc tgaagaggca    3060
ccagagggag atcaccagga ccaccctgca gtctgaccag gaggagattg actatgatga    3120
caccatctct gtggagatga agaaggagga cttttgacatc tacgacgagg acgagaacca    3180
gagccccagg agcttccaga agaagaccag gcactacttc attgctgctg tggagaggct    3240
gtgggactat ggcatgagca gcagccccca tgtgctgagg aacagggccc agtctggctc    3300
tgtgccccag ttcaagaagg tggtgttcca ggagttcact gatggcagct tcacccagcc    3360
cctgtacaga ggggagctga atgagcacct gggcctgctg gcccctaca tcagggctga    3420 ggtggaggac aacatcatgg tgaccttcag gaaccaggcc agcaggccct acagcttcta    3480
cagcagcctg atcagctatg aggaggacca gaggcagggg gctgagccca ggaagaactt    3540
tgtgaagccc aatgaaacca agacctactt ctggaaggtg cagcaccaca tggcccccac    3600
caaggatgag tttgactgca aggcctgggc ctacttctct gatgtggacc tggagaagga    3660
tgtgcactct ggcctgattg gcccctgct ggtgtgccac accaacaccc tgaaccctgc     3720
ccatggcagg caggtgactg tgcaggagtt tgccctgttc ttcaccatct ttgatgaaac    3780
caagagctgg tacttcactg agaacatgga gaggaactgc agggcccct gcaacatcca    3840 gatggaggac cccaccttca aggagaacta caggttccat gccatcaatg ctacatcat    3900 ggacaccctg cctggcctgg tgatggccca ggaccagagg atcaggtggt acctgctgag    3960
catgggcagc aatgagaaca tccacagcat ccacttctct ggccatgtgt tcactgtgag    4020
gaagaaggag gagtacaaga tggccctgta caacctgtac cctggggtgt tgagactgt    4080 ggagatgctg cccagcaagg ctggcatctg gagggtggag tgcctgattg gggagcacct    4140
gcatgctggc atgagcaccc tgttcctggt gtacagcaac aagtgccaga ccccctggg    4200 catgccctct ggccacatca gggacttcca gatcactgcc tctggccagt atggccagtg    4260
ggcccccaag ctggccaggc tgcactactc tggcagcatc aatgcctgga gcaccaagga    4320
gcccttcagc tggatcaagg tggacctgct ggcccccatg atcatccatg gcatcaagac    4380 ccaggggcc aggcagaagt tcagcagcct gtacatcagc cagttcatca tcatgtacag    4440
cctggatggc aagaagtggc agacctacag gggcaacagc actggcaccc tgatggtgtt    4500 cttttggcaat gtggacagct ctggcatcaa gcacaacatc ttcaaccccc ccatcattgc    4560
cagatacatc aggctgcacc ccacccacta cagcatcagg agcaccctga ggatggagct    4620
gatgggctgt gacctgaaca gctgcagcat gcccctgggc atggagagca aggccatctc    4680
tgatgcccag atcactgcca gcagctactt caccaacatg tttgccacct ggagccccag    4740
caaggccagg ctgcacctgc agggcaggag caatgcctgg aggcccccagg tcaacaaccc    4800 caaggagtgg ctgcaggtgg acttccagaa gaccatgaag gtgactgggg tgaccaccca    4860
gggggtgaag agcctgctga ccagcatgta tgtgaaggag ttcctgatca gcagcagcca    4920
```

-continued

| | | |
|---|---|---|
| ggatggccac cagtggaccc tgttcttcca gaatggcaag gtgaaggtgt tccagggcaa | 4980 | |
| ccaggacagc ttcacccctg tggtgaacag cctggacccc ccctgctga ccagatacct | 5040 | |
| gaggattcac ccccagagct gggtgcacca gattgccctg aggatggagg tgctgggctg | 5100 | |
| tgaggcccag gacctgtact gacctcgagg aataaaggaa attattttc attgcaatag | 5160 | |
| tgtgttggtt ttttgtgtca cgtggcggcc gcaggaaccc ctagtgatgg agttggccac | 5220 | |
| tccctctctg cgcgctcgct cgctcactga ggccgggcga ccaaaggtcg cccgacgccc | 5280 | |
| gggctttgcc cgggcggcct cagtgagcga gcgagcgcgc agagagggag tggccaa | 5337 | |

<210> SEQ ID NO 44
<211> LENGTH: 5542
<212> TYPE: DNA
<213> ORGANISM: Adeno-Associated Virus 2

<400> SEQUENCE: 44

| | | |
|---|---|---|
| ttggccactc cctctctgcg cgctcgctcg ctcactgagg ccgcccgggc aaagcccggg | 60 | |
| cgtcgggcga cctttggtcg cccggcctca gtgagcgagc gagcgcgcag agagggagtg | 120 | |
| gccaactcca tcactagggg ttcctgcggc cgcacgcgtg tttaaacgtc gacaggttaa | 180 | |
| tttttaaaaa gcagtcaaaa gtccaagtgg cccttggcag catttactct ctctgtttgc | 240 | |
| tctggttaat aatctcagga gcacaaacat tcctggaggc aggagaagaa atcaacatcc | 300 | |
| tggacttatc ctctgggcct ctccccaccc ccaggagagg ctcaggttaa tttttaaaaa | 360 | |
| gcagtcaaaa gtccaagtgg cccttggcag catttactct ctctgtttgc tctggttaat | 420 | |
| aatctcagga gcacaaacat tcctggaggc aggagaagaa atcaacatcc tggacttatc | 480 | |
| ctctgggcct ctccccaccc ccaggagagg ctgtcgactg gacacaggac gctgtggttt | 540 | |
| ctgagccagg gggcgactca gatcccagcc agtggactta gcccctgttt gctcctccga | 600 | |
| taactggggt gaccttggtt aatattcacc agcagcctcc cccgttgccc ctctggatcc | 660 | |
| actgcttaaa tacggacgag gacagggccc tgtctcctca gcttcaggca ccaccactga | 720 | |
| cctgggacag tgaatcgtaa gtatgccttt cactgcgaga ggttctggag aggcttctga | 780 | |
| gctccccatg gcccaggcag gcagcaggtc tgggcagga ggggggttgt ggagtgcctt | 840 | |
| gactcggggc ctggccccc catctctgtc ttgcaggaca attgccgtct tctgtctcgt | 900 | |
| ggggcatcct cctgctggca ggcctgtgct gcctggtccc tgcgatcgcc accatgcaga | 960 | |
| ttgagctgag cacctgcttc ttcctgtgcc tgctgaggtt ctgcttctct gccaccagga | 1020 | |
| gatactacct gggggctgtg agctgagct gggactacat gcagtctgac ctgggggagc | 1080 | |
| tgcctgtgga tgccaggttc ccccccagag tgcccaagag cttcccttc aacacctctg | 1140 | |
| tggtgtacaa gaagaccctg tttgtggagt tcactgacca cctgttcaac attgccaagc | 1200 | |
| ccaggccccc ctggatgggc ctgctgggcc ccaccatcca ggctgaggtg tatgacactg | 1260 | |
| tggtgatcac cctgaagaac atggccagc acctgtgag cctgcatgct gtggggtga | 1320 | |
| gctactggaa ggcctctgag ggggctgagt atgatgacca gaccagccag agggagaagg | 1380 | |
| aggatgacaa ggtgttccct gggggcagcc acacctatgt gtggcaggtg ctgaaggaga | 1440 | |
| atggccccat ggcctctgac cccctgtgcc tgacctacag ctacctgagc catgtggacc | 1500 | |
| tggtgaagga cctgaactct ggcctgattg ggcccctgct ggtgtgcagg gagggcagcc | 1560 | |
| tggccaagga aagacccag accctgcaca agttcatcct gctgtttgct gtgtttgatg | 1620 | |
| agggcaagag ctggcactct gaaaccaaga acagcctgat gcaggacagg gatgctgcct | 1680 | |

-continued

```
ctgccagggc ctggcccaag atgcacactg tgaatggcta tgtgaacagg agcctgcctg    1740
gcctgattgg ctgccacagg aagtctgtgt actggcatgt gattggcatg ggcaccaccc    1800
ctgaggtgca cagcatcttc ctggagggcc acaccttcct ggtcaggaac cacaggcagg    1860
ccagcctgga gatcagcccc atcaccttcc tgactgccca gaccctgctg atggacctgg    1920
gccagttcct gctgttctgc cacatcagca gccaccagca tgatggcatg gaggcctatg    1980
tgaaggtgga cagctgccct gaggagcccc agctgaggat gaagaacaat gaggaggctg    2040
aggactatga tgatgacctg actgactctg agatggatgt ggtgaggttt gatgatgaca    2100
acagccccag cttcatccag atcaggtctg tggccaagaa gcaccccaag acctgggtgc    2160
actacattgc tgctgaggag gaggactggg actatgcccc cctggtgctg gcccctgatg    2220
acaggagcta caagagccag tacctgaaca atggccccca gaggattggc aggaagtaca    2280
agaaggtcag gttcatggcc tacactgatg aaaccttcaa gaccagggag gccatccagc    2340
atgagtctgg catcctgggc cccctgctgt atgggaggt ggggacacc ctgctgatca    2400
tcttcaagaa ccaggccagc aggccctaca acatctaccc ccatggcatc actgatgtga    2460
ggcccctgta cagcaggagg ctgcccaagg gggtgaagca cctgaaggac ttccccatcc    2520
tgcctgggga gatcttcaag tacaagtgga ctgtgactgt ggaggatggc cccaccaagt    2580
ctgaccccag gtgcctgacc agatactaca gcagctttgt gaacatggag agggacctgg    2640
cctctggcct gattggcccc tgctgatct gctacaagga gtctgtggac cagaggggca    2700
accagatcat gtctgacaag aggaatgtga tcctgttctc tgtgtttgat gagaacagga    2760
gctggtacct gactgagaac atccagaggt tcctgcccaa ccctgctggg gtgcagctgg    2820
aggaccctga gttccaggcc agcaacatca tgcacagcat caatggctat gtgtttgaca    2880
gcctgcagct gtctgtgtgc ctgcatgagg tggcctactg gtacatcctg agcattgggg    2940
cccagactga cttcctgtct gtgttcttct ctggctacac cttcaagcac aagatggtgt    3000
atgaggacac cctgacctg ttccccttct ctggggagac tgtgttcatg agcatggaga    3060
accctggcct gtggattctg ggctgccaca actctgactt caggaacagg ggcatgactg    3120
ccctgctgaa agtctccagc tgtgacaaga acactgggga ctactatgag acagcagtatg    3180
aggacatctc tgcctacctg ctgagcaaga caatgccat tgagcccagg agcttcagcc    3240
agaaccccc agtgctgaag aggcaccaga gggagatcac caggaccacc ctgcagtctg    3300
accaggagga gattgactat gatgacacca tctctgtgga gatgaagaag gaggactttg    3360
acatctacga cgaggacgag aaccagagcc caggagctt ccagaagaag accaggcact    3420
acttcattgc tgctgtggag aggctgtggg actatggcat gagcagcagc ccccatgtgc    3480
tgaggaacag ggcccagtct ggctctgtgc ccagttcaa gaaggtggtg ttccaggagt    3540
tcactgatgg cagcttcacc cagccctgt acagagggga gctgaatgag cacctgggcc    3600
tgctgggccc ctacatcagg gctgaggtgg aggacaacat catggtgacc ttcaggaacc    3660
aggccagcag gccctacagc ttctacagca gcctgatcag ctatgaggag gaccagggcc    3720
agggggctga gccaggaag aactttgtga gcccaatga accaagacc tacttctgga    3780
aggtgcagca ccacatggcc cccaccaagg atgagtttga ctgcaaggcc tgggcctact    3840
tctctgatgt ggacctggag aaggatgtgc actctggcct gattggcccc ctgctggtgt    3900
gccacaccaa caccctgaac cctgcccatg caggcaggt gactgtgcag gagtttgccc    3960
tgttcttcac catctttgat gaaaccaaga gctggtactt cactgagaac atggagagga    4020
actgcagggc cccctgcaac atccagatgg aggacccac cttcaaggag aactacaggt    4080
```

```
tccatgccat caatggctac atcatggaca ccctgcctgg cctggtgatg gcccaggacc    4140
agaggatcag gtggtacctg ctgagcatgg gcagcaatga gaacatccac agcatccact    4200
tctctggcca tgtgttcact gtgaggaaga aggaggagta caagatggcc ctgtacaacc    4260
tgtaccctgg ggtgtttgag actgtggaga tgctgcccag caaggctggc atctggaggg    4320
tggagtgcct gattggggag cacctgcatg ctggcatgag caccctgttc ctggtgtaca    4380
gcaacaagtg ccagaccccc ctgggcatgg cctctggcca catcagggac ttccagatca    4440
ctgcctctgg ccagtatggc cagtgggccc ccaagctggc caggctgcac tactctggca    4500
gcatcaatgc ctggagcacc aaggagccct cagctggat caaggtggac ctgctggccc    4560
ccatgatcat ccatggcatc aagacccagg ggccaggca aagttcagc agcctgtaca    4620 tcagccagtt catcatcatg tacagcctgg atggcaagaa gtggcagacc tacaggggca    4680
acagcactgg caccctgatg gtgttctttg gcaatgtgga cagctctggc atcaagcaca    4740
acatcttcaa cccccccatc attgccagat acatcaggct gcaccccacc cactacagca    4800
tcaggagcac cctgaggatg gagctgatgg gctgtgacct gaacagctgc agcatgcccc    4860
tgggcatgga gagcaaggcc atctctgatg cccagatcac tgccagcagc tacttcacca    4920
acatgtttgc cacctggagc cccagcaagg ccaggctgca cctgcagggc aggagcaatg    4980
cctggaggcc ccaggtcaac aaccccaagg agtggctgca ggtggacttc agaagaccca    5040
tgaaggtgac tggggtgacc acccagggg tgaagagcct gctgaccagc atgtatgtga    5100
aggagttcct gatcagcagc agccaggatg gccaccagtg gacccctgttc ttccagaatg    5160 gcaaggtgaa ggtgttccag ggcaaccagg acagcttcac ccctgtggtg aacagcctgg    5220 accccccct gctgaccaga tacctgagga ttcaccccca gagctgggtg caccagattg    5280
ccctgaggat ggaggtgctg gctgtgagg cccaggacct gtactgacct cgaggaataa    5340
aggaaattta ttttcattgc aatagtgtgt tggtttttg tgtcacgtgg cggccgcagg    5400
aacccctagt gatggagttg ccactcccct ctctgcgcgc tcgctcgctc actgaggccg    5460
ggcgaccaaa ggtcgcccga cgcccgggct tgcccgggc ggcctcagtg agcgagcgag    5520
cgcgcagaga gggagtggcc aa                                            5542
```

<210> SEQ ID NO 45
<211> LENGTH: 5126
<212> TYPE: DNA
<213> ORGANISM: Adeno-Associated Virus 2

<400> SEQUENCE: 45

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ggaggctgct ggtgaatatt    180
aaccaaggtc accccagtta tcggaggagc aaacaggggc taagtccacg ggaggctgc    240 tggtgaatat taaccaaggt cacccagtt atcggaggag caaacagggg ctaagtccac    300
ggtcgactgg acacaggacg ctgtggtttc tgagccaggg ggcgactcag atcccagcca    360
gtggacttag cccctgtttg ctcctccgat aactgggtg accttggtta atattcacca    420
gcagcctccc ccgttgcccc tctggatcca ctgcttaaat acggacgagg acagggccct    480
gtctcctcag cttcaggcac caccactgac ctgggacagt gaatcgcgat cgccaccatg    540
cagattgagc tgagcacctg cttcttcctg tgcctgctga ggttctgctt ctctgccacc    600
```

```
aggagatact acctgggggc tgtggagctg agctgggact acatgcagtc tgacctgggg   660
gagctgcctg tggatgccag gttccccccc agagtgccca agagcttccc cttcaacacc   720
tctgtggtgt acaagaagac cctgtttgtg gagttcactg accacctgtt caacattgcc   780
aagcccaggc cccctggat gggcctgctg ggccccacca tccaggctga ggtgtatgac    840
actgtggtga tcaccctgaa gaacatggcc agccaccctg tgagcctgca tgctgtgggg   900
gtgagctact ggaaggcctc tgagggggct gagtatgatg accagaccag ccagagggag   960
aaggaggatg acaaggtgtt ccctgggggc agccacacct atgtgtggca ggtgctgaag  1020
gagaatggcc ccatggcctc tgaccccctg tgcctgacct acagctacct gagccatgtg  1080
gacctggtga aggacctgaa ctctggcctg attggggccc tgctggtgtg cagggagggc  1140
agcctggcca aggagaagac ccagaccctg cacaagttca tcctgctgtt tgctgtgttt  1200
gatgagggca agagctggca ctctgaaacc aagaacagcc tgatgcagga cagggatgct  1260
gcctctgcca gggcctggcc caagatgcac actgtgaatg ctatgtgaa caggagcctg   1320 cctggcctga ttgctgccca caggaagtct gtgtactggc atgtgattgg catgggcacc  1380 accccctgagg tgcacagcat cttcctggag ggccacacct tcctggtcag gaaccacagg  1440
caggccagcc tggagatcag ccccatcacc ttcctgactg cccagaccct gctgatggac  1500
ctgggccagt tcctgctgtt ctgccacatc agcagccacc agcatgatgg catggaggcc  1560
tatgtgaagg tggacagctg ccctgaggag ccccagctga ggatgaagaa caatgaggag  1620
gctgaggact atgatgatga cctgactgac tctgagatgg atgtggtgag gtttgatgat  1680
gacaacagcc ccagcttcat ccagatcagg tctgtggcca agaagcaccc caagacctgg  1740
gtgcactaca ttgctgctga ggaggaggac tgggactatg ccccctggt gctggcccct   1800 gatgacagga gctacaagag ccagtacctg aacaatggcc cccagaggat ggcaggaag   1860 tacaagaagg tcaggttcat ggcctacact gatgaaacct tcaagaccag ggaggccatc  1920
cagcatgagt ctggcatcct gggccccctg ctgtatgggg aggtggggga cacctgctg   1980 atcatcttca gaaccaggc cagcaggccc tacaacatct acccccatgg catcactgat   2040
gtgaggcccc tgtacagcag gaggctgccc aaggggggtga agcacctgaa ggacttcccc  2100
atcctgcctg gggagatctt caagtacaag tggactgtga ctgtggagga tggccccacc  2160
aagtctgacc ccaggtgcct gaccagatac tacagcagct tgtgaacat ggagagggac   2220 ctggcctctg gcctgattgg ccccctgctg atctgctaca aggagtctgt ggaccagagg  2280
ggcaaccaga tcatgtctga caagaggaat gtgatcctgt tctctgtgtt tgatgagaac  2340
aggagctggt acctgactga gaacatccag aggttcctgc ccaaccctgc tggggtgcag  2400
ctggaggacc ctgagttcca ggccagcaac atcatgcaca gcatcaatgg ctatgtgttt  2460
gacagcctgc agctgtctgt gtgcctgcat gaggtggcct actggtacat cctgagcatt  2520
ggggcccaga ctgacttcct gtctgtgttc ttctctggct acaccttcaa gcacaagatg  2580
gtgtatgagg acaccctgac cctgttcccc ttctctgggg agactgtgtt catgagcatg  2640
gagaaccctg gctgtggat tctgggctgc acaactctg acttcaggaa cagggcatg    2700 actgccctgc tgaaagtctc cagctgtgac aagaacactg ggactacta tgaggacagc  2760 tatgaggaca tctctgccta cctgctgagc aagaacaatg ccattgagcc caggagcttc  2820
agccagaacc ccccagtgct gaagaggcac cagagggaga tcaccaggac caccctgcag  2880
tctgaccagg aggagattga ctatgatgac accatctctg tggagatgaa gaaggaggac  2940
tttgacatct acgacgagga cgagaaccag agccccagga gcttccagaa gaagaccagg  3000
```

-continued

```
cactacttca ttgctgctgt ggagaggctg tgggactatg gcatgagcag cagcccccat    3060
gtgctgagga acagggccca gtctggctct gtgcccagt  tcaagaaggt ggtgttccag    3120
gagttcactg atggcagctt cacccagccc ctgtacagag gggagctgaa tgagcacctg    3180
ggcctgctgg gccctacat  cagggctgag gtggaggaca acatcatggt gaccttcagg    3240
aaccaggcca gcaggcccta cagcttctac agcagcctga tcagctatga ggaggaccag    3300
aggcagggg  ctgagcccag gaagaacttt gtgaagccca tgaaaccaa  gacctacttc    3360
tggaaggtgc agcaccacat ggcccccacc aaggatgagt ttgactgcaa ggcctgggcc    3420
tacttctctg atgtggacct ggagaaggat gtgcactctg gcctgattgg cccctgctg    3480
gtgtgccaca ccaacaccct gaaccctgcc catggcaggc aggtgactgt gcaggagttt    3540
gccctgttct tcaccatctt tgatgaaacc aagagctggt acttcactga gaacatggag    3600
aggaactgca gggcccctg  caacatccag atggaggacc ccaccttcaa  ggagaactac    3660
aggttccatg ccatcaatgg ctacatcatg gacaccctgc ctggcctggt gatggcccag    3720
gaccagagga tcaggtggta cctgctgagc atgggcagca atgagaacat ccacagcatc    3780
cacttctctg gccatgtgtt cactgtgagg aagaaggagg agtacaagat ggccctgtac    3840
aacctgtacc ctggggtgtt tgagactgtg gagatgctgc ccagcaaggc tggcatctgg    3900
agggtggagt gcctgattgg ggagcacctg catgctggca tgagcaccct gttcctggtg    3960
tacagcaaca agtgccagac cccctgggc  atggcctctg gccacatcag ggacttccag    4020
atcactgcct ctggccagta tggccagtgg gcccccaagc tggccaggct gcactactct    4080
ggcagcatca atgcctggag caccaaggag cccttcagct ggatcaaggt ggacctgctg    4140
gcccccatga tcatccatgg catcaagacc caggggcca ggcagaagtt cagcagcctg    4200
tacatcagcc agttcatcat catgtacagc ctggatggca gaagtggca  gacctacagg    4260
ggcaacagca ctggcaccct gatggtgttc tttggcaatg tggacagctc tggcatcaag    4320
cacaacatct tcaacccccc catcattgcc agatacatca ggctgcaccc cacccactac    4380
agcatcagga gcaccctgag gatggagctg atgggctgtg acctgaacag ctgcagcatg    4440
cccctgggca tggagagcaa ggccatctct gatgcccaga tcactgccag cagctacttc    4500
accaacatgt ttgccacctg gagccccagc aaggccaggc tgcacctgca gggcaggagc    4560
aatgcctgga ggccccaggt caacaaccc  aaggagtggc tgcaggtgga cttccagaag    4620
accatgaagg tgactggggt gaccacccag ggggtgaaga gcctgctgac cagcatgtat    4680
gtgaaggagt tcctgatcag cagcagccag gatggccacc agtggacccct gttcttccag    4740
aatggcaagg tgaaggtgtt ccagggcaac caggacagct tcacccctgt ggtgaacagc    4800
ctggacccc  ccctgctgac cagatacctg aggattcacc cccagagctg ggtgcaccag    4860
attgccctga ggatggaggt gctgggctgt gaggcccagg acctgtactg acctcgagga    4920
ataaaggaaa tttattttca ttgcaatagt gtgttggttt tttgtgtcac gtggcggccg    4980
caggaaccc  tagtgatgga gttggccact ccctctctgc gcgctcgctc gctcactgag    5040
gccgggcgac caaaggtcgc ccgacgcccg ggctttgccc gggcggcctc agtgagcgag    5100
cgagcgcgca gagagggagt ggccaa                                        5126
```

ADENO-ASSOCIATED VIRUS FACTOR VIII VECTORS

This application is a continuation of U.S. patent application Ser. No. 15/294,310, now U.S. Pat. No. 10,463,718 filed Oct. 14, 2016, and U.S. patent application Ser. No. 14/842,648 now U.S. Pat. No. 9,504,762, filed Sep. 10, 2014, which claim priority to the U.S. Provisional Patent Application Ser. No. 61/877,042, filed Sep. 12, 2013, which are incorporated by reference herein their entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII. The invention also relates to methods of making the herein described AAV FVIII vectors and associated therapeutic uses of thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., New Engl. J. Med. 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., Blood, 117:798-807, 2011, and McIntosh et al., Blood 121:3335-3344, 2013).

While AAV vectors have been reported in the literature having AAV genomes of >5.0 kb, in many of these cases the 5' or 3' ends of the encoded genes appear to be truncated (see Hirsch et al., Molec. Ther. 18-6-8, 2010, and Ghosh et al., Biotech. Genet. Engin. Rev. 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein useful in gene therapy approaches for the treatment of hemophilia A. As such, the present invention relates to AAV vectors that encode functionally active FVIII such that either the AAV virions encapsidate the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. Moreover, to avoid capsid directed immune response, AAV vectors should have the highest possible transduction/expression activity of the target protein per capsid particle. This invention also relates to the production of completely AAV FVIII vectors with high expression activity. Finally, the present invention relates to methods for producing the herein described AAV Factor VIII vectors and associated methods for using the same.

SUMMARY OF INVENTION

The present invention provides AAV vectors encoding functionally active FVIII (referred to herein as "AAV FVIII vectors"). The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, allowing for blood coagulation to occur and decreasing the time that it takes for blood to clot in a subject suffering from Hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa.

As used herein, an "AAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements, i.e., one or more promoters and/or enhancers, and a polyadenylation sequence, and, optionally, one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., J. Virol. 79(1):364-379 (2005) which is herein incorporated by reference in its entirety.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII having the B domain replaced by the 14 amino acid SQ sequence, i.e., encoding FVIII SQ. The SQ sequence is disclosed in Ward et al., Blood, 117:798-807, 2011, and McIntosh et al., Blood 121:3335-3344, 2013. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121: 3335-3344, 2013). This sequence is referred herein as the "UCL SQ FVIII."

In a first aspect, the AAV vector of the invention comprises Proto 1, which is depicted schematically in FIG. 2A, and comprises the nucleic acid sequence set forth in SEQ ID NO: 1.

In a second aspect, the AAV vector of the invention comprises Proto 1S, which is depicted schematically in FIG. 2B, and comprises the nucleic acid sequence set forth in SEQ ID NO: 2.

In a third aspect, the AAV vector of the invention comprises Proto 2S, which is depicted schematically in FIG. 2C, and comprises the nucleic acid sequence set forth in SEQ ID NO: 3.

In a fourth aspect, the AAV vector of the invention comprises Proto 3S, which is depicted schematically in FIG. 2D, and comprises the nucleic acid sequence set forth in SEQ ID NO: 4.

In another embodiment, the AAV vector of the invention comprises a nucleic acid encoding FVIII lacking the entire B domain, including the SQ sequence, and the a3 domain, which is located just N-terminal to the light chain or C domain. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121:3335-3344, 2013).

In a first aspect, the AAV vector of the invention comprises Proto 4, which is depicted schematically in FIG. 3A, and comprises the nucleic acid sequence set forth in SEQ ID NO: 5.

In a second aspect, the AAV vector of the invention comprises Proto 5, which is depicted schematically in FIG. 3B, and comprises the nucleic acid sequence set forth in SEQ ID NO: 6.

In a third aspect, the AAV vector of the invention comprises Proto 6, which is depicted schematically in FIG. 3C, and comprises the nucleic acid sequence set forth in SEQ ID NO: 7.

In a fourth aspect, the AAV vector of the invention comprises Proto 7, which is depicted schematically in FIG. 3D, and comprises the nucleic acid sequence set forth in SEQ ID NO: 8.

In another embodiment, the AAV vector of the invention comprises a nucleic acid comprising an AAV2 5' inverted terminal repeat (ITR), a liver-specific transcription regulatory region, a codon-optimized functionally active FVIII coding region, optionally one or more introns, a polyadenylation sequence, and an AAV2 3' ITR. In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding regions encodes the FVIII SQ variant. In another preferred embodiment, the liver specific transcription regulatory region comprises a a1 microglobulin enhancer sequence and the 186 base human alpha anti-trypsin (AAT) proximal promoter.

In a first aspect, the AAV vector of the invention comprises Construct 100ATG comprising the nucleic acid sequence forth in SEQ ID NO: 9.

In a second aspect, the AAV vector of the invention comprises Construct 100ATG bGH poly A comprising the nucleic acid sequence set forth in SEQ ID NO: 10.

In a third aspect, the AAV vector of the invention comprises Construct 100ATG short bGH polyA sequence set forth in SEQ ID NO: 11.

In a fourth aspect, the AAV vector of the invention comprises Construct 103ATG comprising the nucleic acid sequence forth in SEQ ID NO: 12.

In a fifth aspect, the AAV vector of the invention comprises Construct 103ATG short bGH poly A comprising the nucleic acid sequence set forth in SEQ ID NO: 13.

In a sixth aspect, the AAV vector of the invention comprises Construct 105ATG bGH poly A comprising the nucleic acid sequence set forth in SEQ ID NO: 14.

In a seventh aspect, the AAV vector of the invention comprises Construct DC172ATG FVIII comprising the nucleic acid sequence set forth in SEQ ID NO: 15.

In an eighth aspect, the AAV vector of the invention comprises Construct DC172ATG FVIII hAAT comprising the nucleic acid sequence set forth in SEQ ID NO: 16.

In a ninth aspect, the AAV vector of the invention comprises Construct DC172 2xHCR ATG FVIII comprising the nucleic acid sequence set forth in SEQ ID NO: 17.

In a tenth aspect, the AAV vector of the invention comprises Construct DC172 2×HCR ATG FVIII hAAT comprising the nucleic acid sequence set forth in SEQ ID NO: 18.

In an eleventh aspect, the AAV vector of the invention comprises Construct 2× SerpinA hAAT ATG FVIII comprising the nucleic acid sequence set forth in SEQ ID NO: 19.

In a twelfth aspect, the AAV vector of the invention comprises Construct 2× SerpinA hAAT ATG FVIII 2× μ-globulin enhancer comprising the nucleic acid sequence set forth in SEQ ID NO: 20.

In a thirteenth aspect, the AAV vector of the invention Construct 100ATG short polyA 2× μ-globulin enhancer comprising the nucleic acid sequence set forth in SEQ ID NO: 21.

In a fourteenth aspect, the AAV vector of the invention comprises Construct Factor VIII-BMN001 comprising the nucleic acid sequence set forth in SEQ ID NO: 22.

In a fifteenth aspect, the AAV vector of the invention comprises Construct Factor VIII-BMN002 sequence set forth in SEQ ID NO: 23.

In a sixteenth aspect, the AAV vector of the invention comprises Construct 99 comprising the nucleic acid sequence set forth in SEQ ID NO: 24.

In a seventeenth aspect, the AAV vector of the invention comprises Construct 100 comprising the nucleic acid sequence set forth in SEQ ID NO: 25.

In an eighteenth aspect, the AAV vector of the invention comprises Construct 100 reverse orientation comprising the nucleic acid sequence set forth in SEQ ID NO: 26.

In a nineteenth aspect, the AAV vector of the invention Construct 100AT comprising the nucleic acid sequence set forth in SEQ ID NO: 27.

In a twentieth aspect, the AAV vector of the invention Construct 100AT 2× MG comprising the nucleic acid sequence set forth in SEQ ID NO: 28.

In a twenty-first aspect, the AAV vector of the invention comprises Construct 100AT 2× MG bGH polyA comprising the nucleic acid sequence set forth in SEQ ID NO: 29.

In a twenty-second aspect, the AAV vector of the invention comprises Construct 100AT 2× MG (reverse) bGH polyA comprising the nucleic acid sequence set forth in SEQ ID NO: 30.

In a twenty-third aspect, the AAV vector of the invention comprises Construct 100 bGH polyA comprising the nucleic acid sequence set forth in SEQ ID NO: 31.

In a twenty-fourth aspect, the AAV vector of the invention comprises Construct 100-400 comprising the nucleic acid sequence set forth in SEQ ID NO: 32.

In a twenty-fifth aspect, the AAV vector of the invention comprises Construct 101 comprising the nucleic acid sequence set forth in SEQ ID NO: 33.

In a twenty-sixth aspect, the AAV vector of the invention comprises Construct 102 sequence comprising the nucleic acid sequence set forth in SEQ ID NO: 34.

In a twenty-seventh aspect, the AAV vector of the invention comprises Construct 103 comprising the nucleic acid sequence set forth in SEQ ID NO: 35.

In a twenty-ninth aspect, the AAV vector of the invention comprises Construct 103 reverse orientation comprising the nucleic acid sequence set forth in SEQ ID NO: 36.

In a thirtieth aspect, the AAV vector of the invention comprises Construct 103AT comprising the nucleic acid sequence set forth in SEQ ID NO: 37.

In a thirty-first aspect, the AAV vector of the invention comprises Construct 103AT 2×MG comprising the nucleic acid sequence set forth in SEQ ID NO: 38.

In a thirty-second aspect, the AAV vector of the invention comprises Construct 103AT 2×MG bGH polyA comprising the nucleic acid sequence set forth in SEQ ID NO: 39.

In a thirty-third aspect, the AAV vector of the invention comprises the Construct 103 bGH polyA comprising the nucleic acid sequence set forth in SEQ ID NO: 40.

In a thirty-fourth aspect, the AAV vector of the invention comprises Construct 104 comprising the nucleic acid comprising the nucleic acid sequence set forth in SEQ ID NO: 41.

In a thirty-fifth aspect, the AAV vector of the invention comprises Construct 105 comprising the nucleic acid sequence set forth in SEQ ID NO: 42.

In a thirty-sixth aspect, the AAV vector of the invention comprises Construct 106 comprising the nucleic acid sequence set forth in SEQ ID NO: 43.

In a thirty-seventh aspect, the AAV vector of the invention comprises Construct 106AT comprising the nucleic acid sequence set forth in SEQ ID NO: 44.

In a thirty-eighth aspect, the AAV vector of the invention comprises Construct 2× SerpinA hAAT comprising the nucleic acid sequence set forth in SEQ ID NO: 45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation.

The AAV vectors of the invention in single strand is less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand ranges from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particle comprising any of the AAV vectors of the invention. The methods comprise the steps of culturing a cell that has been transfected with any of the AAV vectors of the invention and recovering recombinant AAV from the supernatant of the transfected cell.

The cells of the invention are any cell type are susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NSO, SP2/0, PER.C6, Vero, RD, BHK, HT 1080, A549, Cos-7, ARPE-19 and MRC-5 cells, and including mammalian cells such as HEK293, HeLa, CHO, NSO, SP2/0, PER.C6, Vero, RD, BHK, HT 1080, A549, Cos-7, ARPE-19 and MRC-5 cells.

The invention also provides for a viral particle comprising any of the AAV vectors of the invention or any viral particle produced by the forgoing methods of the invention.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient an effective amount of any of the AAV vectors of the invention, or a viral particle of the invention or a viral particles produced by a method of the invention.

In a further embodiment, the invention provides for a use of any of the AAV vectors of the invention for preparation of a medicament for the treatment of hemophilia A. In one aspect, the medicament comprises an amount of AAV vector that expresses human FVIII in an amount effective to treat hemophilia A.

In another embodiment, the invention provides for a composition comprising any of the AAV vectors of the invention for the treatment of hemophilia A. In one aspect, the composition comprises an amount of AAV vector that expresses human FVIII in an amount effective to treat hemophilia A.

In another embodiment, the AAV vectors of the invention are used to produce AAV viral particles that are useful to treat a patient suffering from Hemophilia A.

DESCRIPTION OF DRAWINGS

FIG. 2A provides a schematic of the Proto 1 vector. Starting from the UCL SQ vector (see FIG. 1), the extraneous wild-type AAV2 viral sequences were deleted, and sequences corresponding to restriction sites between the human AAT 5' UTR and the human FVIII coding region, and between the human FVIII termination codon and the synthetic polyadenylation sequence, were removed. FIG. 2B provides a schematic of the Proto 1S vector. Starting from the Proto 1 vector, 10 bases at the 3' end of the AAV2 5'ITR and 10 bases at the 5' end of the 3' ITR were deleted. FIG. 2C provides a schematic of the Proto 2S vector. Starting from the Proto 1S vector, the human ApoE/C1 enhancer and human AAT promoter distal X region were moved into a 100 base synthetic intron that was inserted between exons 1 and 2 of the human FVIII sequence. As indicated by the arrows, the orientation of the human ApoE/C1 enhancer and human AAT promoter distal X region are reversed compared to their orientation in Proto 1S. FIG. 2D provides a schematic of the Proto 3S vector. Starting from Proto 2S, the human AAT promoter distal X region is replaced by a second copy of the human ApoE/C1 enhancer in the reverse orientation.

FIG. 3A provides a schematic of the Proto 4 vector. Starting from the Proto 1 vector, the SQ sequence and a3 domain were deleted. FIG. 3B provides a schematic of the Proto 5 vector. Starting from the Proto 4 vector, a 129 base FVIII intron was inserted between exons 1 and 2 of the human Factor VIII sequence. FIG. 3C provides a schematic of the Proto 6 vector. Starting from the Proto 5 vector, a second copy of the human ApoE/C1 enhancer was inserted in the forward orientation into the FVIII intron. FIG. 3R provides a schematic of the Proto 7 vector. Starting from the Proto 5 vector, a second copy of the human ApoE/C1 enhancer was inserted in the reverse orientation into the FVIII intron.

FIG. 4A provides a schematic of Construct 100ATG. FIG. 4B provides a schematic of Construct 100ATG bGH polyA. FIG. 4C provides a schematic of Construct 100ATG short bGH poly A. FIG. 4D provides a schematic of Construct 103ATG. FIG. 4E provides a schematic of Construct 103ATG short bGH poly A. FIG. 4F provides a schematic of Construct 105ATG bGH polyA. FIG. 4G provides a schematic of Construct DC172ATG FVIII. FIG. 4H provides a schematic of Construct DC172ATG FVIII hAAT. FIG. 4I provides a schematic of Construct DC172 2×HCR ATG FVIII. FIG. 4J provides a schematic of Construct DC172 2×HCR ATG FVIII hAAT. FIG. 4K provides a schematic of Construct 2× SerpinA hAAT ATG FVIII. FIG. 4AA provides a schematic of Construct 103. FIG. 4BB provides a schematic of Construct 103 reverse orientation. FIG. 4CC provides a schematic of Construct 103AT. FIG. 4DD provides a schematic of Construct 103AT 2× MG. FIG. 4EE provides a schematic of Construct 103AT 2× MG bGH poly A. FIG. 4FF provides a schematic of 103 sbGH poly A. FIG. 4GG provides a schematic of Construct 104. FIG. 4HH provides a schematic of Construct 105. FIG. 4II provides a schematic of Construct 106. FIG. 4JJ provides a schematic of Construct 106AT. FIG. 4KK provides a schematic of Construct 2× SerpinA hAAT.

DETAILED DESCRIPTION

Oversized AAV vectors are randomly truncated at the 5' ends and lack a 5' AAV ITR. Because AAV is a single-stranded DNA virus, and packages either the sense or antisense strand, the sense strand in oversized AAV vectors lacks the 5' AAV ITR and possibly portions of the 5' end of the target protein-coding gene, and the antisense strand in oversized AAV vectors lacks the 3' ITR and possibly portions of the 3' end of the target protein-coding gene. A functional transgene is produced in oversized AAV vector infected cells by annealing of the sense and antisense truncated genomes within the target cell.

The invention provides for AAV vectors encoding functionally active FVIII, i.e., completely packaged AAV FVIII vectors or AAV FVIII vectors with high expression activity. The AAV FVIII vectors of the invention have improved expression/particle, as well as improved AAV virus production yield and simplified purification. Introducing one or more introns into the FVIII protein-coding region enhances expression. Reconfiguring the number and positioning of enhancers also enhances expression.

UCL SQ Vector

Figure 1:
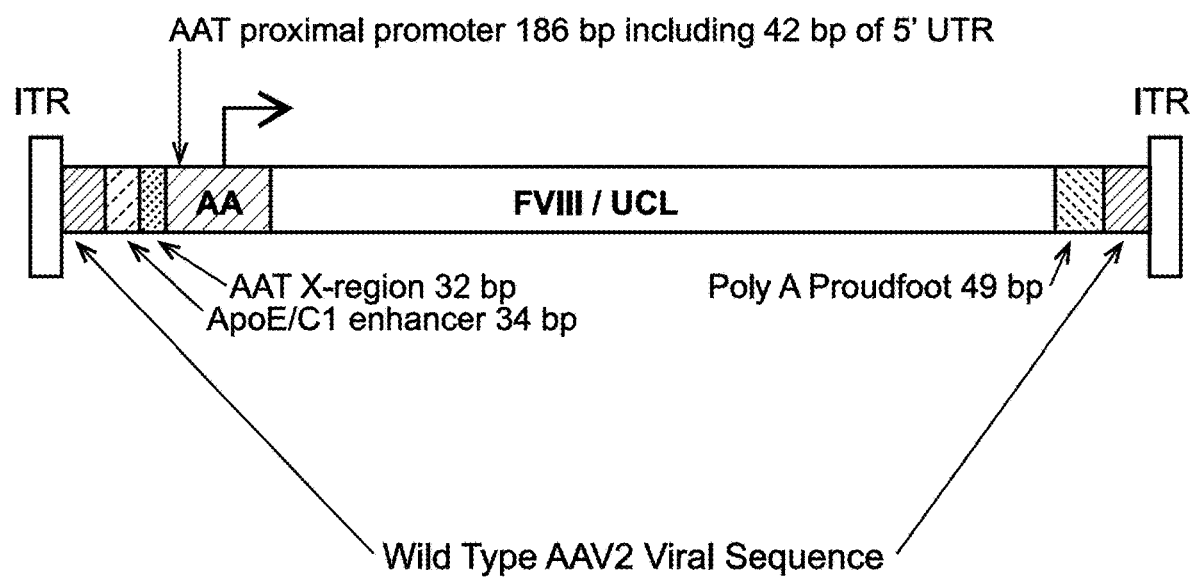
FIG. 1 provides a schematic of the UCL SQ vector. From left to right, the UCL SQ vector comprises the AAV2 5' ITR, wild-type AAV2 viral sequence, the 34 base human ApoE/C1 enhancer, the 32 base human AAT promoter distal X region, the 186 base human AAT promoter, including 42 bases of 5' UTR sequence, the codon-optimized human FVIII SQ sequence (see Nathwani et al., US Pat. App. Pub. No. 2013/0024960A1, published Jan. 24, 2013, which is incorporated herein by reference in its entirety, and McIntosh et al., Blood 121:3335-3344, 2013), the 49 bases synthetic polyadenylation sequence, wild-type AAV2 viral sequence, and the AAV2 3'ITR. The UCL SQ vector is 5081 bases in length.

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

As shown in Nathwani et al., US Pat. App. Pub. No. 2013/0024960A1, published Jan. 24, 2013, and McIntosh et al., Blood 121:3335-3344, 2013, the UCL SQ vector expresses functionally active FVIII in vitro and in vivo.

Proto 1, Proto 1S, Proto 2S and Proto 3S Vectors

To avoid the problem of over-sized AAV vectors and/or to increase the expression of the AAV vectors, the invention provides completely packaged, smaller, i.e., less than 5.0 kb, AAV vectors encoding the FVIII SQ variant. The 4970 bp nucleotide sequence of sequence of Proto 1 is set forth in SEQ ID NO: 1.

To generate the AAV vector Proto 1, sequences that appear to be unnecessary for production of functionally active FVIII were deleted as compared to the UCL SQ vector. As shown in Example 1, 110 bases of extraneous DNA were removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector is 4970 bases in length. When designed, it was unknown whether the Proto 1 vector would be capable of expressing functional FVIII polypeptide, either in vitro or in vivo.

To generate the AAV vector Proto 1S, 10 bases at the 3' end of the AAV2 5'ITR, and 10 bases at the 5' end of the AAV32 3'ITR, were removed from the Proto 1 vector. The resultant Proto 1S vector is 4950 bases in length. The nucleotide sequence of sequence of Proto 1S is set forth in SEQ ID NO: 2.

To generate the AAV vector Proto 2S, a synthetic 100 base intron was inserted between exons 1 and 2 of the codon-optimized FVIII SQ sequence in the Proto 1S vector. The 34 bases ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO: 3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO: 4.

Proto 4, Proto S, Proto 6 and Proto 7 Vectors

To reduce the size of AAV vectors and/or increase the expression of the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO: 5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO: 6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO: 7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO: 8.

Additional AAV FVIII Vectors With Improved Promoter/Enhancer Sequences

Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the µ-globulin enhancer or fragments thereof, the human alpha 1 antitrypsin promoter (hAAT) or fragments thereof, Serpin A enhancer or fragments thereof, the LP1 promoter enhancer or fragments thereof or macroglobulin enhancer or fragment thereof. These constructs comprise a polyadenylation sequence such as the bGH poly A sequence or the synthetic rabbit β-globin poly A sequence.

In some embodiment, the constructs comprise an intron or fragments of an intron such as a hAAT intron or a human β-globin intron.

Construct 100ATG is 5511 bases in length. This construct is set forth in SEQ ID NO: 9 in which bases 1-145 are the 5'AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5352 are a synthetic rabbit β-globin poly A and bases 5367-5511 are the 3' AAV2 ITR.

Construct 100ATG bGH poly A is 5688 bases in length. This construct is set forth in SEQ ID NO: 10 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5529 are a bGH poly A and bases 5544-5688 are the 3' AAV2 ITR.

Construct 100ATG short bGH poly A is 5613 bases in length. This construct is set forth in SEQ ID NO: 11 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5454 are a short bGH poly A and bases 5469-5613 are the 3' AAV2 ITR.

Construct 103ATG is 5362 bases in length. This construct is set forth in SEQ ID NO: 12 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5203 are a synthetic rabbit β-globin poly A and bases 5218-5362 are the 3' AAV2 ITR.

Construct 103ATG short bGH poly A is 5464 bases in length. This construct is set forth in SEQ ID NO: 13 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5305 are a bGH short poly A and bases 5320-5464 are the 3' AAV2 ITR.

Construct 105ATG bGH polyA is 6354 bases in length. This construct is set forth in SEQ ID NO: 14 in which bases 1-145 are the 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are a codon optimized SQ FVIII, bases 5315-5539 are a bGH poly A, bases 5546-6195 are two copies (2×) of a 325 bp ApoE HCR and bases 6210-6354 are the 3' AAV2 ITR.

Construct DC172ATG FVIII is 6308 bases in length. This construct is set forth in SEQ ID NO: 15 in which bases 1-145 are the 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are a codon optimized SQ FVIII, bases 5926-6149 are a bGH poly A and bases 6164-6308 are the 3' AAV2 ITR.

Construct DC172ATG FVIII hAAT is 5635 bases in length. This construct is set forth as SEQ ID NO: 16 in which bases 1-145 are the 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are a codon optimized SQ FVIII, bases 5253-5476 are a bGH poly A and bases 5490-5635 are the 3' AAV2 ITR.

Construct DC172 2×HCR ATG FVIII is 6962 bases in length. This construct is set forth in SEQ ID NO: 17 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are a codon optimized SQ FVIII, bases 6580-6803 are a bGH poly A and bases 6818-6962 are the 3' AAV2 ITR.

Construct DC172 2×HCR ATG FVIII hAAT is 6289 bases in length. This construct is set forth in SEQ ID NO: 18 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are a codon optimized SQ FVIII, bases 5907-6130 are a bGH poly A and bases 6245-6289 are the 3' AAV2 ITR.

Construct 2× SerpinA hAAT ATG FVIII is 5430 bases in length. This construct is set forth in SEQ ID NO: 19 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, and bases 5286-5430 are the 3'AAV2 ITR.

Construct 2× SerpinA hAAT ATG FVIII 2× μ-globulin enhancer is 5779 bases in length. This construct is set forth in SEQ ID NO: 20 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, bases 5279-5618 are two copies (2×) of a 170 bp μ-globulin enhancer and bases 5635-5779 are the 3' AAV2 ITR.

Construct 100ATG short bGH poly A 2× μ-globulin enhancer is 5962 bases in length. This construct is set forth in SEQ ID NO: 21 in which bases 1-145 are the 5' AAV2 ITR, bases 160-502 are an ApoE HCR, bases 509-726 are a hAAT promoter, bases 727-910 are a modified human β-globin $2^{nd}$ intron, bases 923-5296 are a codon optimized SQ FVIII, bases 5305-5454 are a short bGH poly A, bases 5462-5801 are two copies (2×) of a 170 bp microglobulin enhancer and bases 5818-5962 are the 3' AAV2 ITR.

Construct Factor VIII-BMN001 is 5919 bases in length. This construct is set forth in SEQ ID NO: 22 in which bases 1-145 are the 5' AAV2 ITR, bases 160-480 are an ApoE HCR, bases 487-884 are a 398 bp hAAT promoter, bases 885-1145 are a truncated hAAT intron, bases 1155-5528 are a codon optimized SQ FVIII, bases 5537-5760 are a bGH poly A and bases 5775-5919 are the 3' AAV2 ITR.

Construct FVIII-BMN002 is 5306 bases in length. This construct is set forth in SEQ ID NO: 23 in which bases 1-145 are the 5' AAV2 ITR, bases 175-705 are an LP1 promoter/enhancer, bases 718-5091 are a codon optimized SQ FVIII, bases 5100-5147 are a synthetic rabbit β-globin poly A and bases 5162-5306 are the 3' AAV2 ITR.

Construct 99 is 5461 bases in length. This construct is set forth in SEQ ID NO: 24 in which bases 1-145 are the 5' AAV2 ITR, bases 169-627 are an ApoE HCR/MAR, bases 634-866 are a hAAT promoter, bases 873-5246 are a codon optimized SQ FVIII, bases 5255-5302 are a synthetic rabbit β-globin poly A and bases 5317-5461 are the 3' AAV2 ITR.

Construct 100 is 5327 bases in length. This construct is set forth in SEQ ID NO: 25 in which bases 1-145 are the 5' AAV2 ITR, bases 169-493 are an ApoE HCR, bases 509-726 are a hAAT promoter, bases 739-5112 are a codon optimized SQ FVIII, bases 5121-5168 are a synthetic rabbit β-globin poly A and bases 5183-5327 are the 3' AAV2 ITR.

Construct 100 reverse orientation is 5309 bases in length. This construct is set forth in SEQ ID NO: 26 in which bases 1-145 are the 5' AAV2 ITR, bases 160-484 are an ApoE HCR in reverse orientation, bases 491-708 are a hAAT promoter, bases 721-5094 are a codon optimized SQ FVIII, bases 5103-5150 are a synthetic rabbit β-globin poly A and bases 5165-5309 are the 3' AAV2 ITR.

Construct 100AT is 5532 bases in length. This construct is set forth in SEQ ID NO: 27 in which bases 1-145 are the 5' AAV2 ITR, bases 169-493 are an ApoE HCR, bases 509-726 are a hAAT promoter, bases 727-931 are a hAAT intron, bases 944-5317 are a codon optimized SQ FVIII, bases 5326-5373 are a synthetic rabbit β-globin poly A and bases 5388-5532 are the 3' AAV2 ITR.

Construct 100AT 2× MG is 5877 bases in length. This construct is set forth in SEQ ID NO: 28 in which bases 1-145 are the 5' AAV2 ITR, bases 169-493 are an ApoE HCR, bases 508-847 are two copies (2×) of a 170 bp µ-globulin enhancer, bases 854-1071 are a hAAT promoter, bases 1072-1276 are a hAAT intron, bases 1289-5662 are a codon optimized SQ FVIII, bases 5671-5718 are a synthetic rabbit β-globin poly A and bases 5733-5877 are the 3' AAV2 ITR.

Construct 100AT 2× MG bGH poly A is 6054 bases in length. This construct is set forth in SEQ ID NO: 29 in which bases 1-145 are the 5' AAV2 ITR, bases 169-493 are an ApoE HCR, bases 508-847 are two copies (2×) of a 170 bp µ-globulin enhancer, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100AT 2× MG (reverse) bGH poly A is 6054 bases in length. This construct is set forth in SEQ ID NO: 30 in which bases 1-145 are the 5' AAV2 ITR, bases 169-493 are an ApoE HCR, bases 508-847 are two copies (2×) of a 170 bp µ-globulin enhancer in reverse orientation, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100 bGH poly A is 5504 bases in length. This construct is set forth in SEQ ID NO: 31 in which bases 1-145 are the 5' AAV2 ITR, bases 169-493 are an ApoE HCR, bases 509-726 are a hAAT promoter, bases 739-5112 are a codon optimized SQ FVIII, base pairs 5121-5345 are a bGH poly A and bases 5360-5504 are the 3' AAV2 ITR.

Construct 100-400 is 5507 bases in length. This construct is set forth in SEQ ID NO: 32 in which bases 1-145 are the 5' AAV2 ITR, bases 169-493 are an ApoE HCR, bases 512-906 are a 398 bp hAAT promoter, bases 919-5292 are a codon optimized SQ FVIII, bases 5301-5348 are a synthetic rabbit β-globin poly A and bases 5363-5507 are the 3' AAV2 ITR.

Construct 101 is 5311 base in length. This construct is set forth in SEQ ID NO: 33 in which bases 1-145 are the 5' AAV2 ITR, bases 170-477 are two copies (2×) of a 154 bp ApoE HCR, bases 493-710 are a hAAT promoter, bases 723-5096 are a codon optimized SQ FVIII, bases 5105-5152 are a synthetic rabbit β-globin poly A and bases 5167-5311 are the 3' AAV2 ITR.

Construct 102 is 5156 bases in length. This construct is set forth in SEQ ID NO: 34 in which bases 1-145 are the 5' AAV2 ITR, bases 169-322 are a 154 bp ApoE HCR, bases 338-555 are a hAAT promoter, bases 568-4941 are a codon optimized SQ FVIII, bases 4950-4997 are a synthetic rabbit β-globin poly A and bases 5012-5156 are the 3' AAV2 ITR.

Construct 103 is 5178 bases in length. This construct is set forth in SEQ ID NO: 35 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5019 are a synthetic rabbit β-globin poly A and bases 5034-5178 are the 3' AAV2 ITR.

Construct 103 reverse orientation is 5160 bases in length. This construct is set forth in SEQ ID NO: 36 in which bases 1-145 are the 5' AAV2 ITR, bases 160-335 are four copies (4×) of a 44 bp ApoE HCR in reverse orientation, bases 342-559 are a hAAT promoter, bases 572-4945 are a codon optimized SQ FVIII, bases 4954-5001 are a synthetic rabbit β-globin poly A and bases 5016-5160 are the 3' AAV2 ITR.

Construct 103AT is 5383 bases in length. This construct is set forth in SEQ ID NO: 37 in which bases 1-145 are the 5' AAV2 ITR, bases 169-344 are four copies (4×) of a 44 bp ApoE HCR, bases 360-577 are a hAAT promoter, bases 578-782 are a hAAT intron, bases 795-4374 are a codon optimized SQ FVIII, bases 5177-5224 are a synthetic rabbit β-globin poly A and bases 5239-5383 are the 3' AAV2 ITR.

Construct 103AT 2× MG is 5728 bases in length. This construct is set forth in SEQ ID NO: 38 in which bases 1-145 are the 5' AAV2 ITR, bases 169-344 are four copies (4×) of a 44 bp ApoE HCR, bases 359-698 are two copies (2×) of a 170 bp µ-globulin enhancer, bases 705-922 are a hAAT promoter, bases 923-1127 are a hAAT intron, bases 1140-5513 are a codon optimized SQ FVIII, bases 5522-5569 are a synthetic rabbit β-globin poly A and bases 5584-5728 are the 3' AAV2 ITR.

Construct 103AT 2× MG bGH poly A is 5905 bases in length. This construct is set forth in SEQ ID NO: 39 in which bases 1-145 are the 5' AAV2 ITR, bases 169-344 are four copies (4×) of a 44 bp ApoE HCR, bases 359-698 are two copies (2×) of a 170 bp µ-globulin enhancer, bases 705-922 are a hAAT promoter, bases 923-1127 are a hAAT intron, bases 1140-5513 are a codon optimized SQ FVIII, bases 5522-5746 are a synthetic rabbit β-globin poly A and bases 5761-5905 are the 5' AAV2 ITR.

Construct 103 bGH poly A is 5355 bases in length. This construct is set forth in SEQ ID NO: 40 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5196 are a synthetic rabbit β-globin poly A and bases 5211-5355 are the 3' AAV2 ITR.

Construct 104 is 5618 bases in length. This construct is set forth in SEQ ID NO: 41 in which bases 1-145 are the 5' AAV2 ITR, bases 169-784 are four copies (4×) of a 154 bp ApoE HCR, bases 800-1017 are a hAAT promoter, bases 1030-5403 are a codon optimized SQ FVIII, bases 5412-5459 are a synthetic rabbit β-globin poly A and bases 5474-5618 are the 3' AAV2 ITR.

Construct 105 is 5993 bases in length. This construct is set forth in SEQ ID NO: 42 in which bases 1-145 are the 5' AAV2 ITR, bases 173-512 are two copies (2×) of a 170 bp µ-globulin enhancer, bases 519-736 are a hAAT promoter, bases 749-5122 are a codon optimized SQ FVIII, bases 5131-5178 are a synthetic rabbit β-globin poly A, bases 5185-5834 are two copies (2×) of an ApoE HCR and bases 5849-5993 are the 3' AAV2 ITR.

Construct 106 is 5337 bases in length. This construct is set forth in SEQ ID NO: 43 in which bases 1-145 are the 5' AAV2 ITR, bases 173-512 are two copies (2×) of a 170 bp µ-globulin enhancer, bases 519-736 are a hAAT promoter, bases 749-5122 are a codon optimized SQ FVIII, bases 5131-5178 are a synthetic rabbit β-globin poly A and bases 5193-5337 are the 3' AAV2 ITR.

Construct 106AT is 5542 bases in length. This construct is set forth in SEQ ID NO: 44 in which bases 1-145 are the 5' AAV2 ITR, bases 173-512 are two copies (2×) of a 170 bp μ-globulin enhancer, bases 519-736 are a hAAT promoter, bases 737-941 are a hAAT intron, bases 954-5327 are a codon optimized SQ FVIII, bases 5336-5383 are a synthetic rabbit β-globin poly A and bases 5398-5542 are the 3' AAV2 ITR.

Construct 2× SerpinA hAAT is 5126 base. This construct is set forth in SEQ ID NO: 45 in which bases 1-145 are the 5' AAV2 ITR, bases 160-301 are an ApoE HCR, bases 308-525 are a hAAT promoter, bases 538-4911 are a codon optimized SQ FVIII, bases 4920-4967 are a synthetic rabbit β-globin poly A and bases 4982-5126 are the 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chlorini et al., J. Vir. 71: 6823-33 (1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, NJ (1995); O'Reilly et al., BACULOVIRUS EXPRESSION VECTORS, A LABORATORY MANUAL, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kirnbauer et al., Vir. 219:37-44 (1996); Zhao et al., Vir. 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally Autographa californica multicapsid nucleopolyhedrovirus (AcMNPV) or Bombyx mori (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be reduced using any invertebrate cell type which allows for production of AAV or biologic products and which can be maintained in culture. For example, the insect cell line used can be from *Spodoptera frugiperda*, such as SF9, SF21, SF900+, drosophila cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (BmNPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NSO, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the UCL SQ vector, and preferably 1.5-fold, 2-fold, 3-fold, 4-fold, or 5-fold or more expression and/or activity as compared to the UCL SQ vector.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the UCL SQ vector.

Other aspects and advantages of the present invention will be understood upon consideration of the following illustrative examples.

EXAMPLES

Example 1

Generation of Proto 1, Proto 1S, Proto 2S and Proto 3S Vectors

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

Figure 2A:
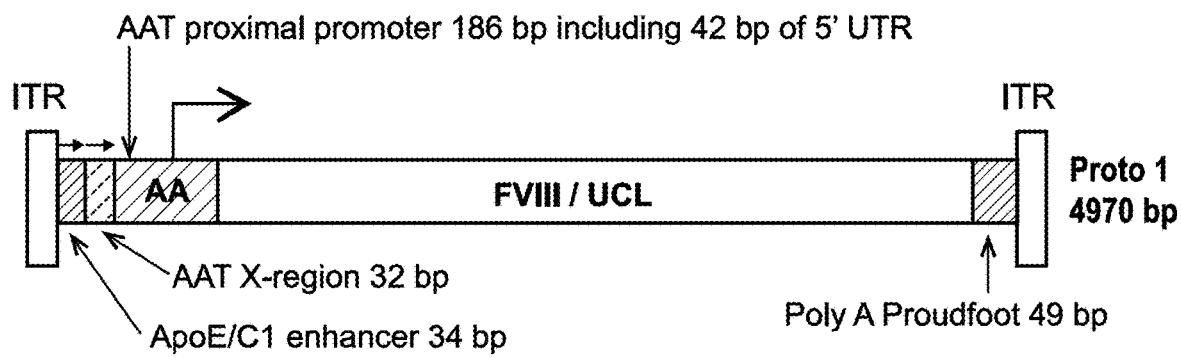
FIGS. 2A-2D provide schematics and sequences of the Proto 1, Proto 1S, Proto 2S and Proto 3S vectors.

To obtain a vector that is smaller than the UCL SQ vector, DNA sequences believed by the inventors herein to be unnecessary for FVIII expression and/or activity, or for AAV virion production, were removed from the UCL SQ vector sequence. Extraneous DNA sequence was removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector, which is 4970 bases in length, is shown in schematic form in FIG. 2A, and the sequence is set forth in SEQ ID NO: 1. Proto 1 produced infectious virus and encodes a functional Factor VIII polypeptide.

Figure 2B:
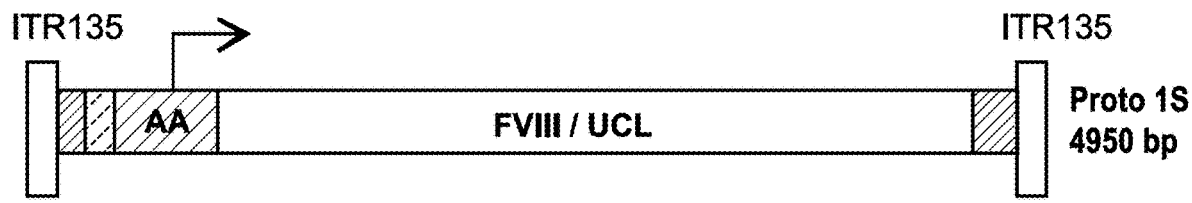

Sequences adjacent to the hairpin loop in the AAV2 ITR may also be dispensable in recombinant AAV vectors (see Srivastava et al., U.S. Pat. No. 6,521,225; Wang et al., J. Virol. 70:1668-1677, 1996; and Wang et al., J. Virol. 71:3077-3082, 1997). To further reduce the size of the Proto 1 vector, 10 bases of AAV2 sequence was removed directly 3' to the hairpin loop in the AAV2 5'ITR and 10 bases of AAV2 sequence was removed directly 5' to the hairpin loop in the AAV2 3'ITR. The resultant Proto 1S vector, which is 4950 bases in length, is shown in schematic form in FIG. 2B, and the sequence is set forth in SEQ ID NO: 2.

In an effort to increase the expression of the FVIII SQ variant in the Proto 1S vector, a 100 base synthetic intron was inserted between exons 1 and 2 in the codon-optimized FVIII sequence. It is known that insertion of an intron can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in Gray et al., U.S. Pat. No. 8,030,065 (FIX expression) and in Nathwani et al., US Pat. App. Pub. No. 2013/0024960 (FVIII expression), both of which are incorporated herein by reference in their entirety. The 32 base human AAT promoter distal X region, described in Di Simone et al., EMBO J. 6:2759-2766, 1987, is located within a regulatory domain that enhances expression of a heterologous promoter.

Figure 2C:
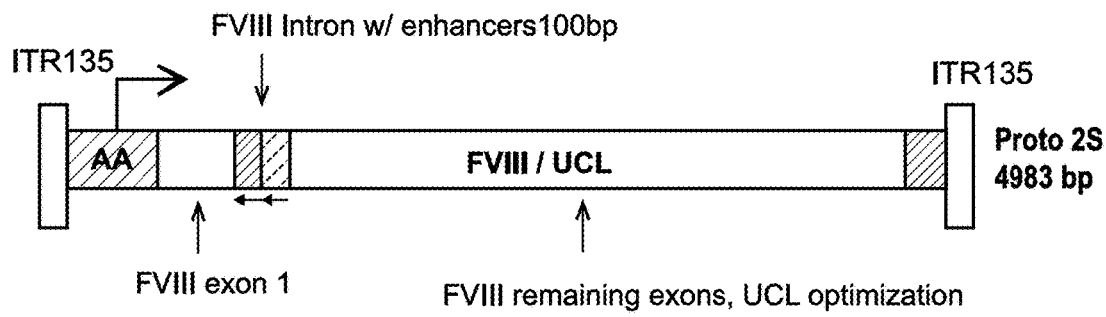

In another attempt to further increase the expression of the FVIII SQ variant in the Proto 1S vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 15. The resultant Proto 2S vector, which is 4983 bases in length, is shown in schematic form in FIG. 2C, and the sequence set forth in SEQ ID NO: 3.

Figure 2D:
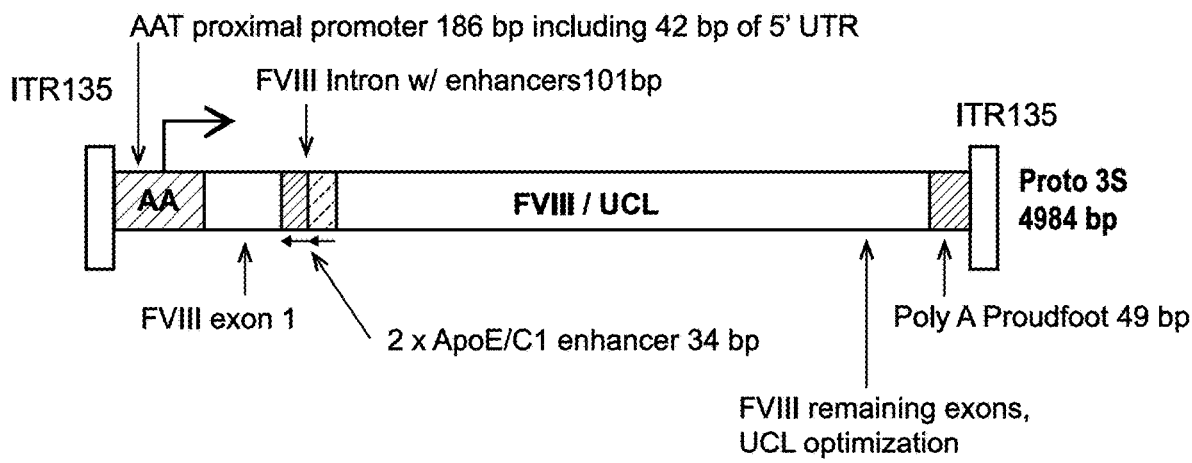

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO: 4.

The Proto 1, Proto 1S, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
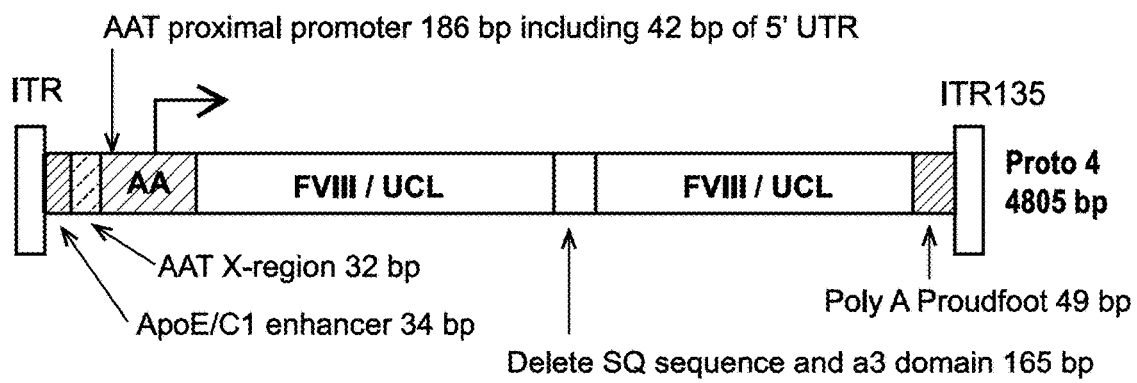
FIGS. 3A-3D provide schematics of the Proto 4, Proto 5, Proto 6 and Proto 7 vectors.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO: 5.

Figure 3B:
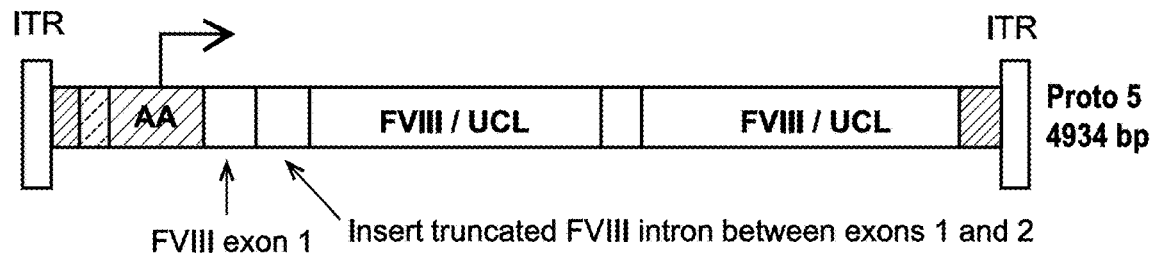

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO: 6.

Figure 3C:
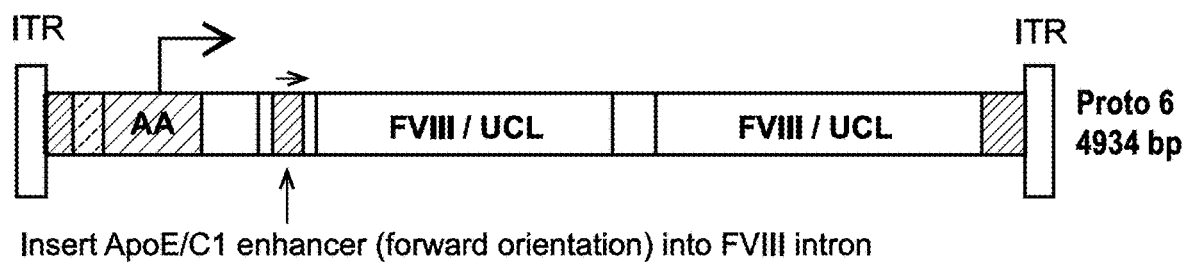

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO: 7.

Figure 3D:
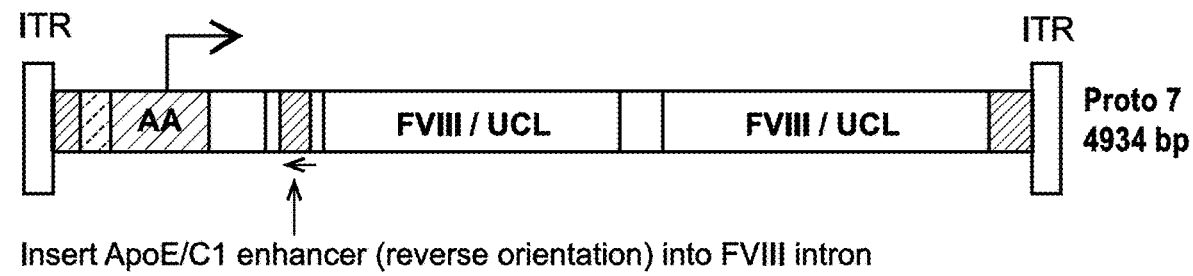
Figure 4A:
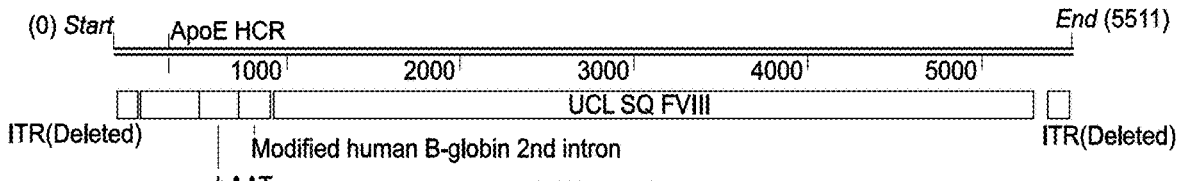
FIGS. 4A-4KK provide schematics of the AAV FVIII vectors with improved promoter/enhancer sequences.
Figure 4B:
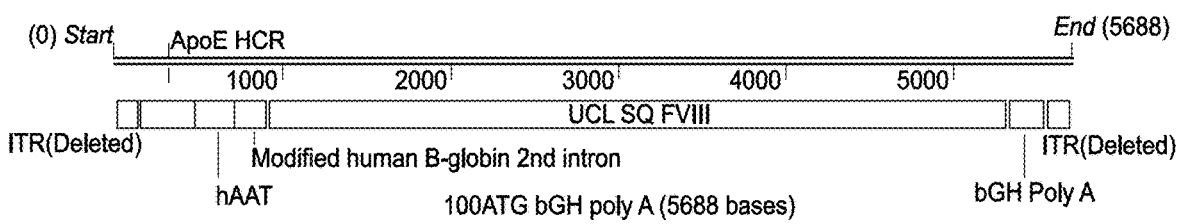
Figure 4C:
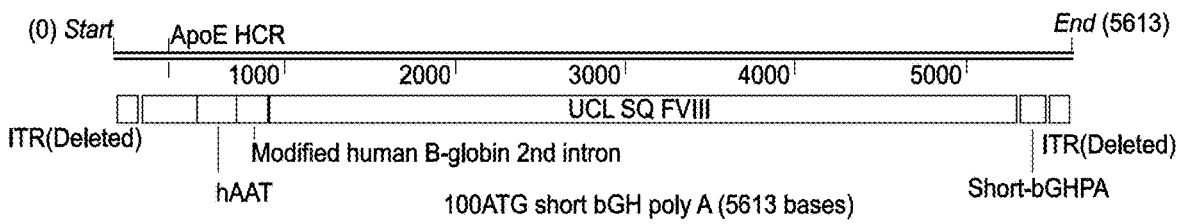
Figure 4D:
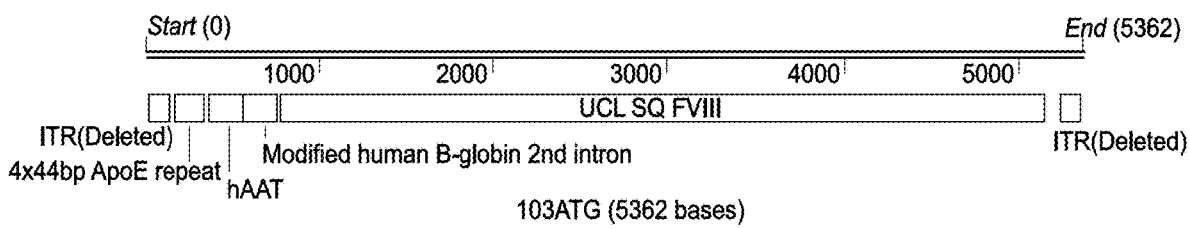
Figure 4E:
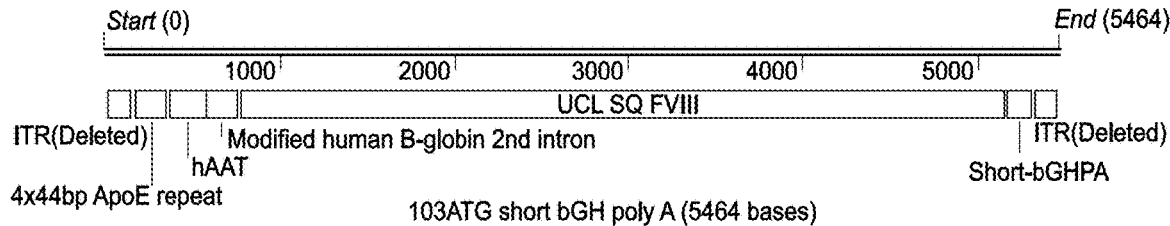
Figure 4F:
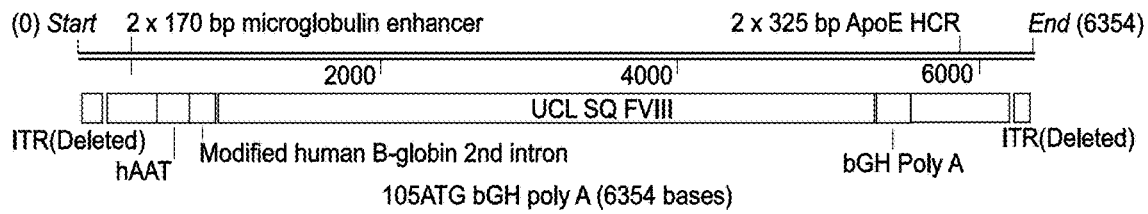
Figure 4G:
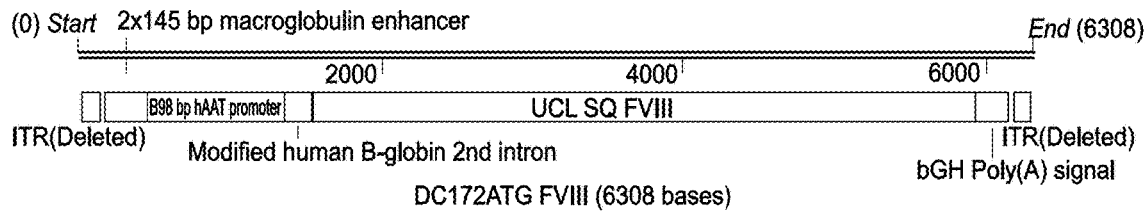
Figure 4H:
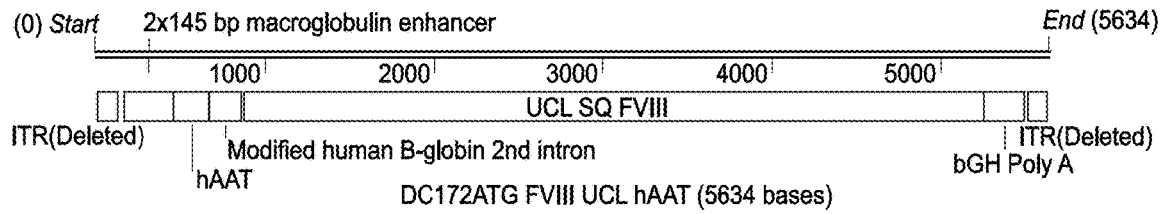
Figure 4I:
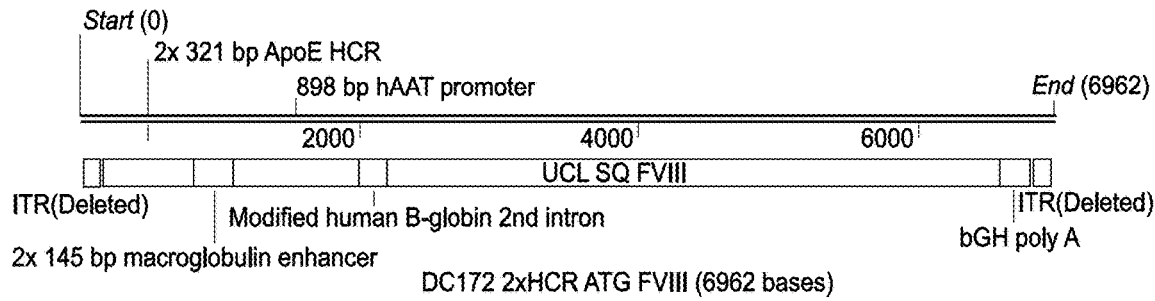
Figure 4J:
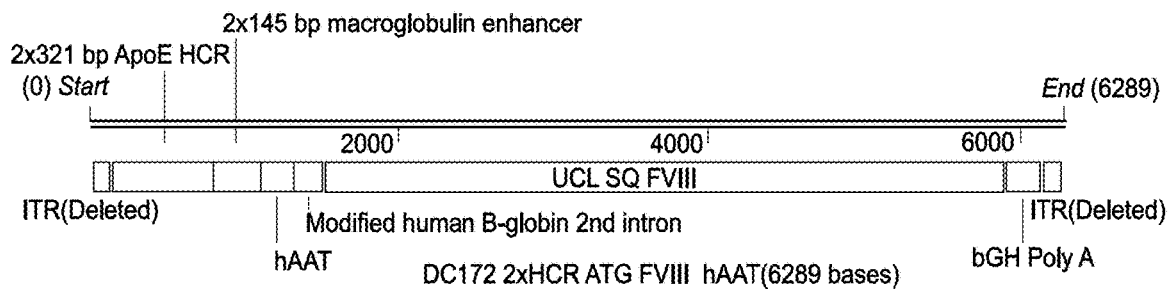
Figure 4K:
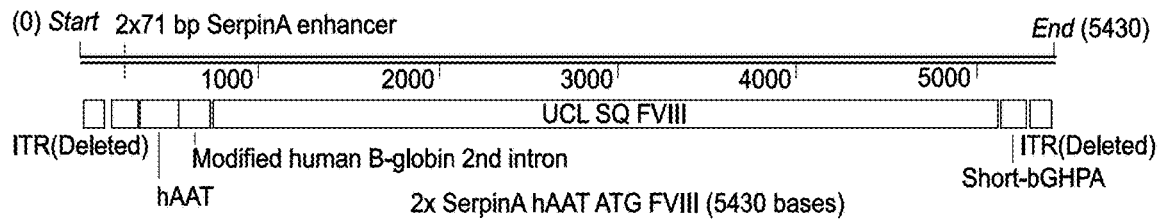
Figure 4L:
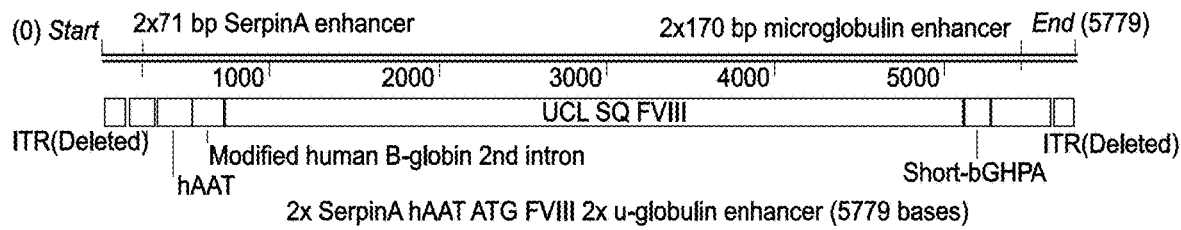
FIG. 4L provides a schematic of Construct 2× SerpinA hAAT ATG FVIII 2× μg-globulin enhancer.
Figure 4M:
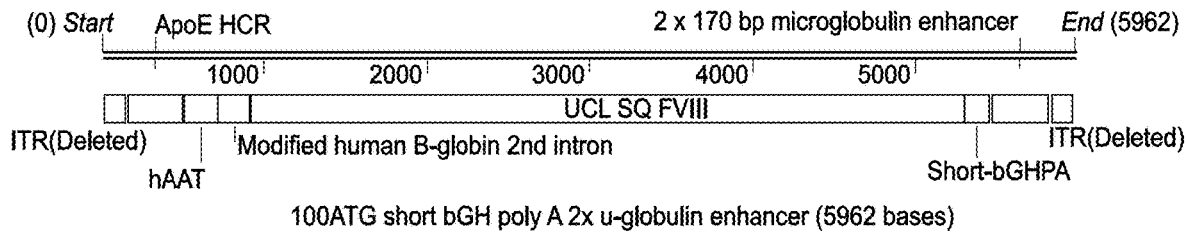
FIG. 4M provides a schematic of Construct 100ATG short bGH poly A 2× μg-globulin enhancer.
Figure 4N:
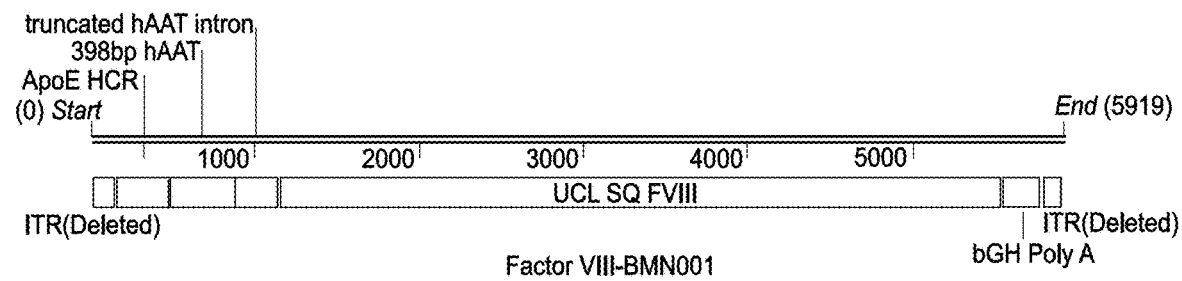
FIG. 4N provides a schematic of Construct Factor VIII-BMN001.
Figure 4O:
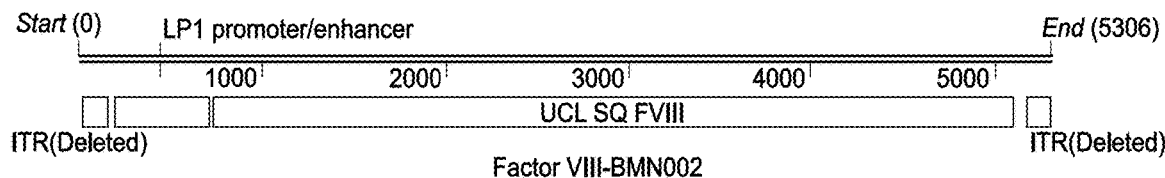
FIG. 4O provides a schematic of Construct FVIII-BMN002.
Figure 4P:
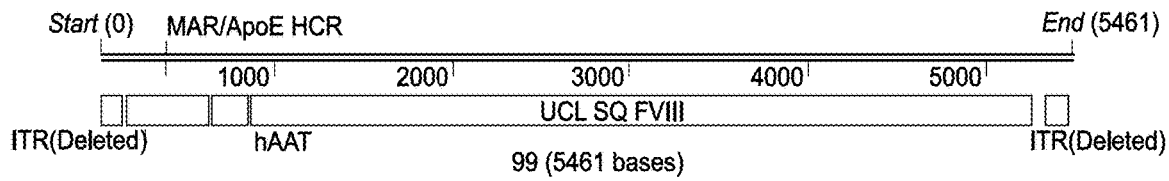
FIG. 4P provides a schematic of Construct 99.
Figure 4Q:
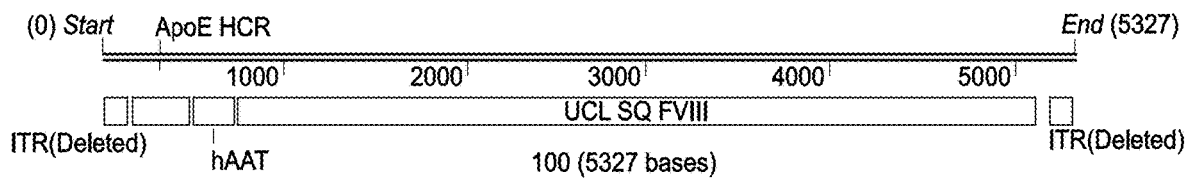
FIG. 4Q provides a schematic of Construct 100.
Figure 4R:
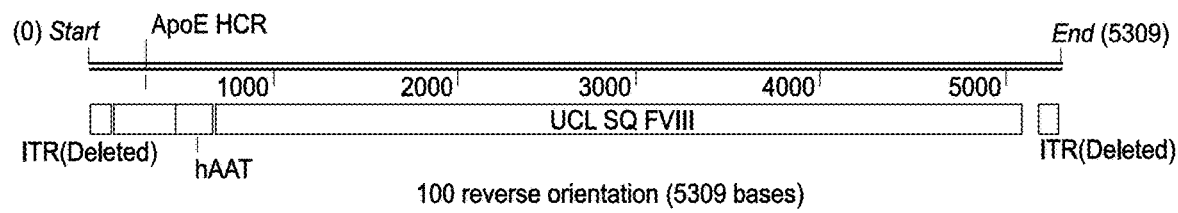
FIG. 4R provides a schematic of Construct 100 reverse orientation.
Figure 4S:
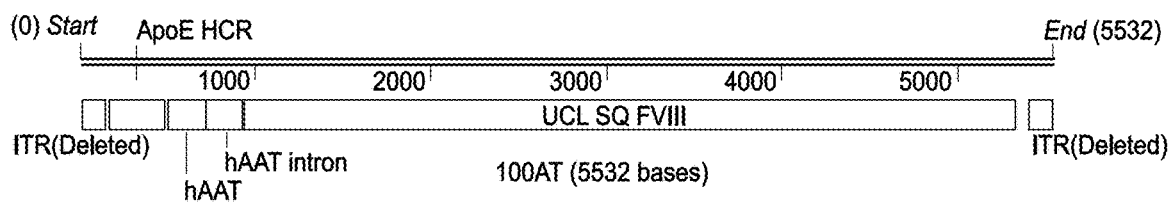
FIG. 4S provides a schematic of Construct 100AT.
Figure 4T:
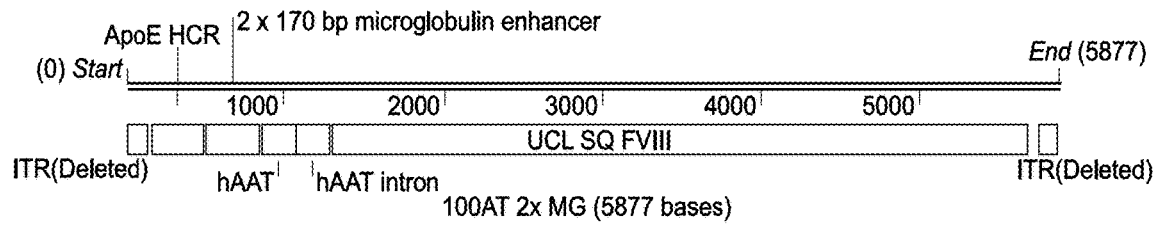
FIG. 4T provides a schematic of Construct 100AT 2× MG.
Figure 4U:
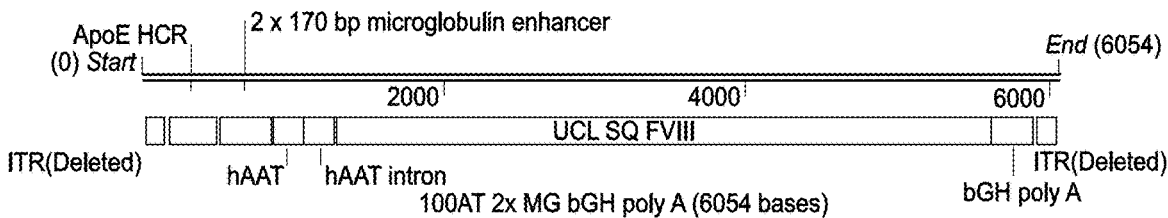
FIG. 4U provides a schematic of Construct 100AT 2× MG bGH polyA.
Figure 4V:
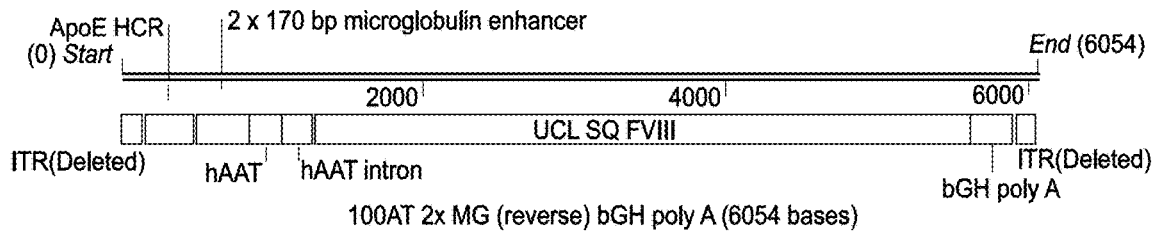
FIG. 4V provides a schematic of Construct 100AT 2× MG (reverse) bGH poly A.
Figure 4W:
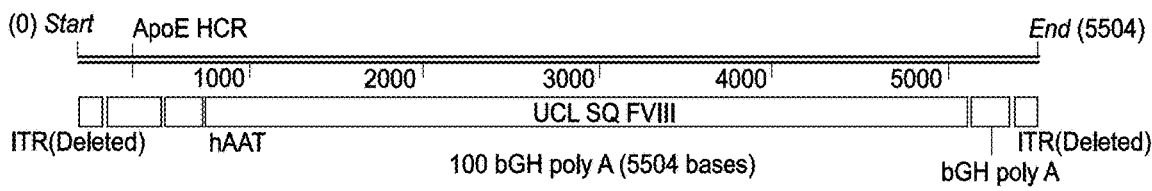
FIG. 4W provides a schematic of Construct 100 bGH poly A.
Figure 4X:
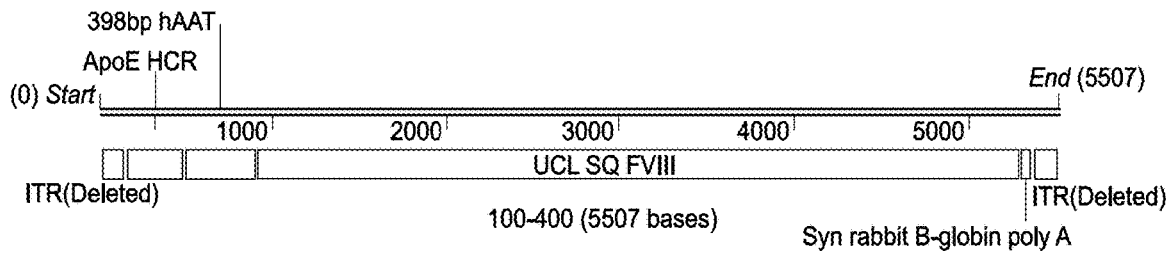
FIG. 4X provides a schematic of Construct 100-400.
Figure 4Y:
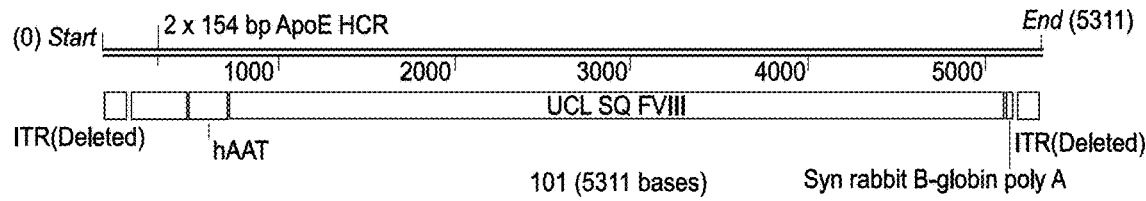
FIG. 4Y provides a schematic of Construct 101.
Figure 4Z:
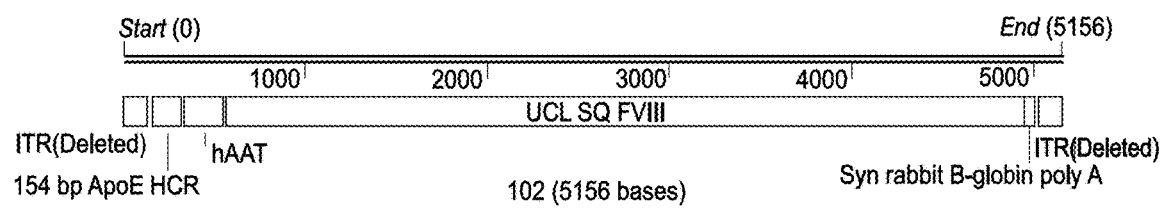
FIG. 4Z provides a schematic of Construct 102.
Figure 4A:
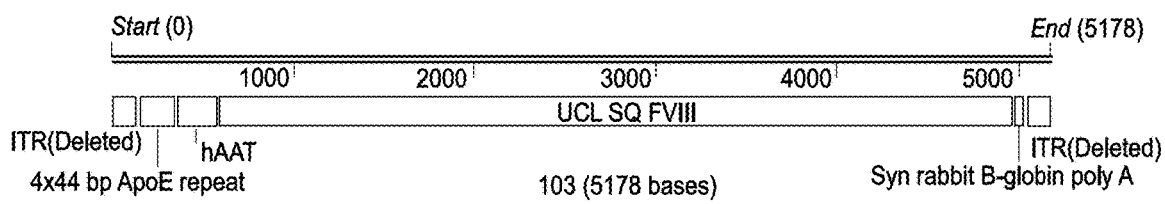
Figure 4B:
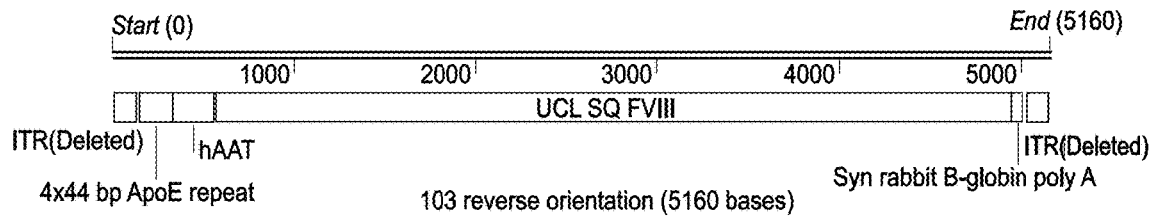
Figure 4C:
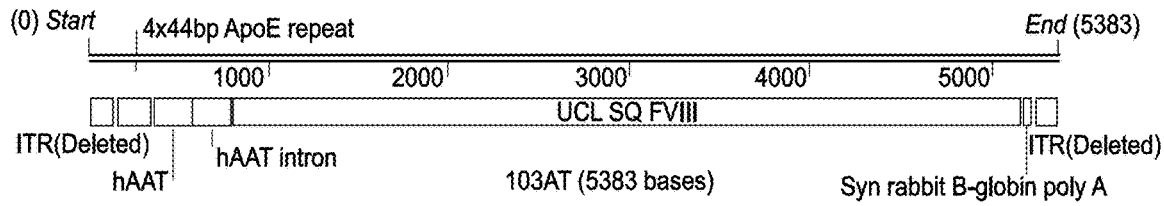
Figure 4D:
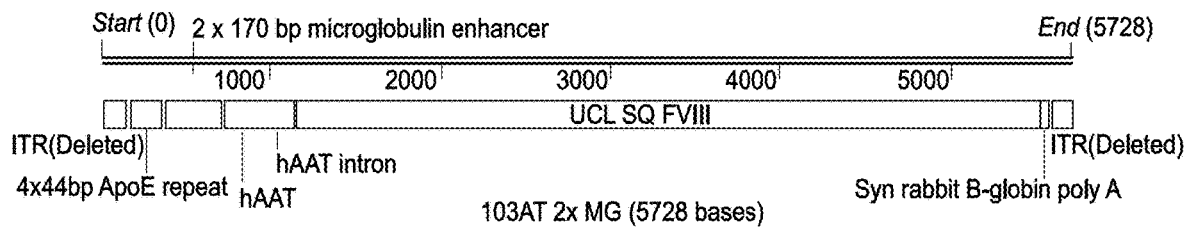
Figure 4E:
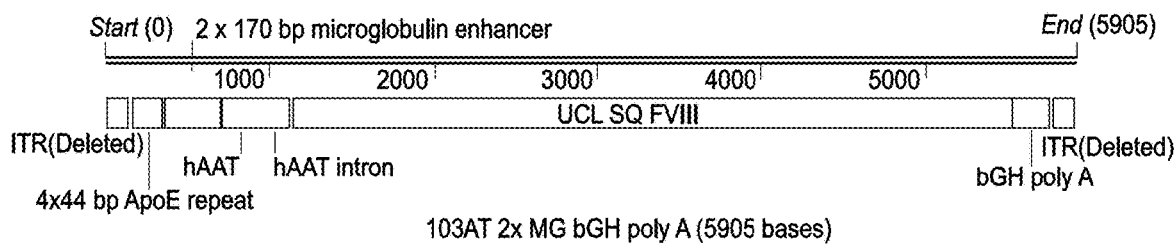
Figure 4F:
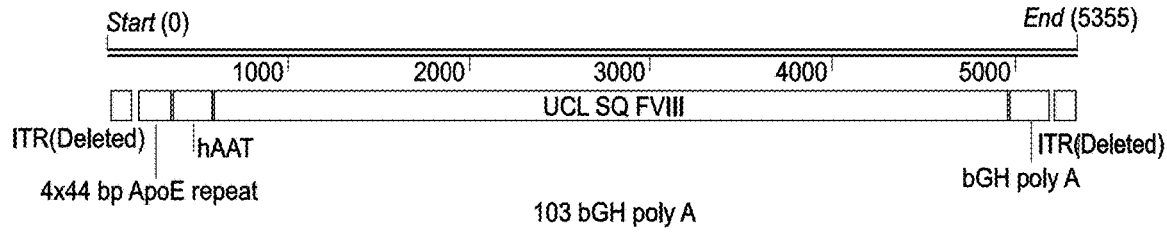
Figure 4G:
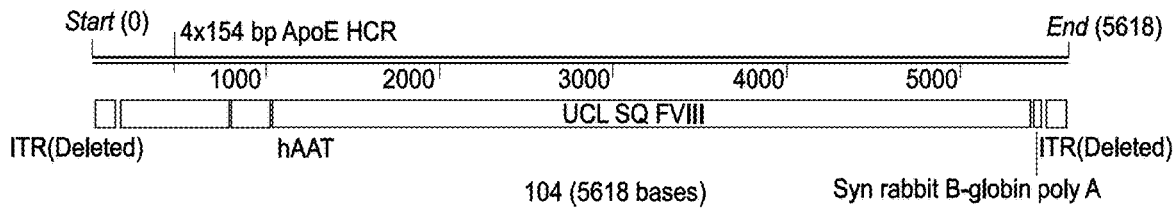
Figure 4H:
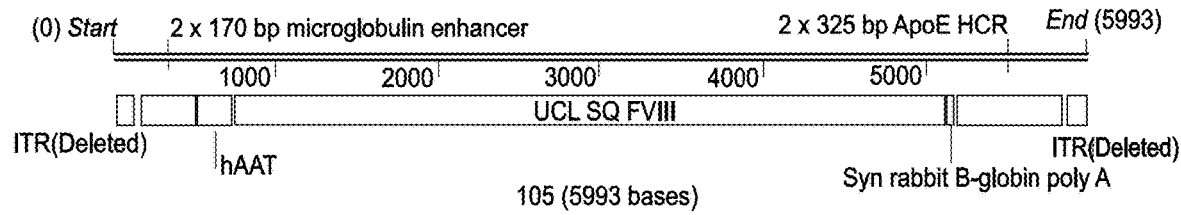
Figure 4I:
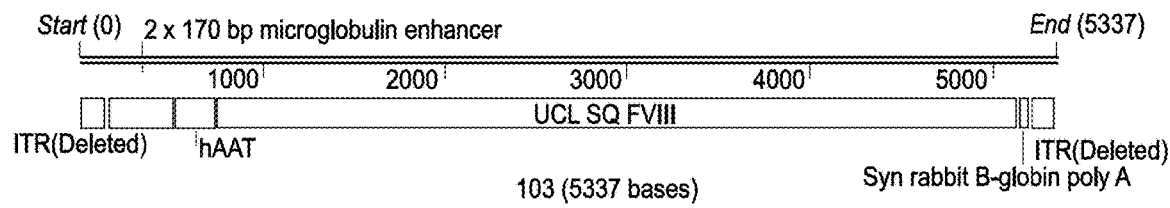
Figure 4J:
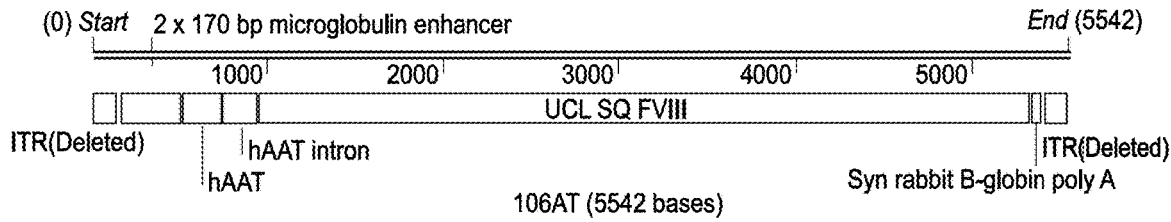
Figure 4K:
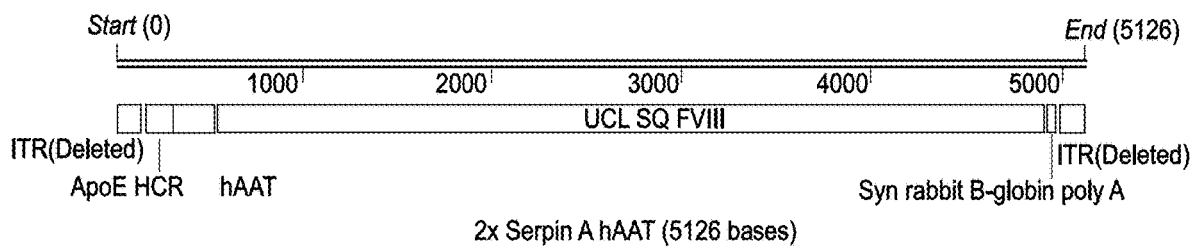

The resultant Proto 7 vector, which is 4934 bases in length and has the intronic ApoE/C1 enhancer in the reverse orientation, is shown in schematic form in FIG. 3D, and the sequence is set forth in SEQ ID NO: 8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays.

A preliminary in vitro assay is performed to compare the FVIII expression and activity from the AAV FVIII vectors of the present invention with that from the UCL SQ vector. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the UCL SQ vector, demonstrating that the Proto 1, Proto 1S and Proto 2S vectors were capable of expressing functional Factor VIII protein.

Production of AAV Virions in 293 Cells and Baculovirus-Infected Insect Cells.

To demonstrate that the AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses Adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5'ITR (sense strand) or 3'ITR (anti-sense strand).

Alternatively, a PCR assay is used to determine whether the AAV FVIII vectors nucleic acids have complete ends, i.e., terminate at the 5' end of the hairpin loop in the AAV2 5'ITR (sense strand) or 3'ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, given intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional AAV vectors with strong promoters that increase expression of functional FVIII, constructs were generated with modified enhancer and/or promoter sequences. In some embodiments, the constructs comprised shortened versions of the ApoE or the μ-globulin enhancers. These constructs were generated using standard DNA cloning techniques and the sequences thereof are shown in SEQ IS NOS: 9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described in Example 1. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1 \times 10^6$ cells/well in a 6-well plate (or $6 \times 10^6$ cells in a 10-cm plate or $1.7 \times 10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30-45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+ antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of baculovirus (P1)

Sf9 cells were grown to approximately 4×10⁶ cells/mL and diluted to approximately 2×10⁶ cells/mL with fresh medium in shaking flasks. An amount of the Sf9 cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV using P1 Recombinant Baculoviruses

Sf9 cells were grown to about 1×10⁷ cells/mL and diluted to about 5×10⁶ cells/mL. An amount of the diluted Sf9 cells were infected with Bac-vector (5Moi) and Bac-helper (15Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV genomes which comprise a codon optimized SQ FVIII-encoding gene sequence were generated using baculovirus and 293 cells using the UCL SQ, Proto 1, Proto S1, Proto S2 and Proto S3 constructs. The packaging limits are 4800 bp for baculovirus and 4950 for 293 cells.

Figure 5:
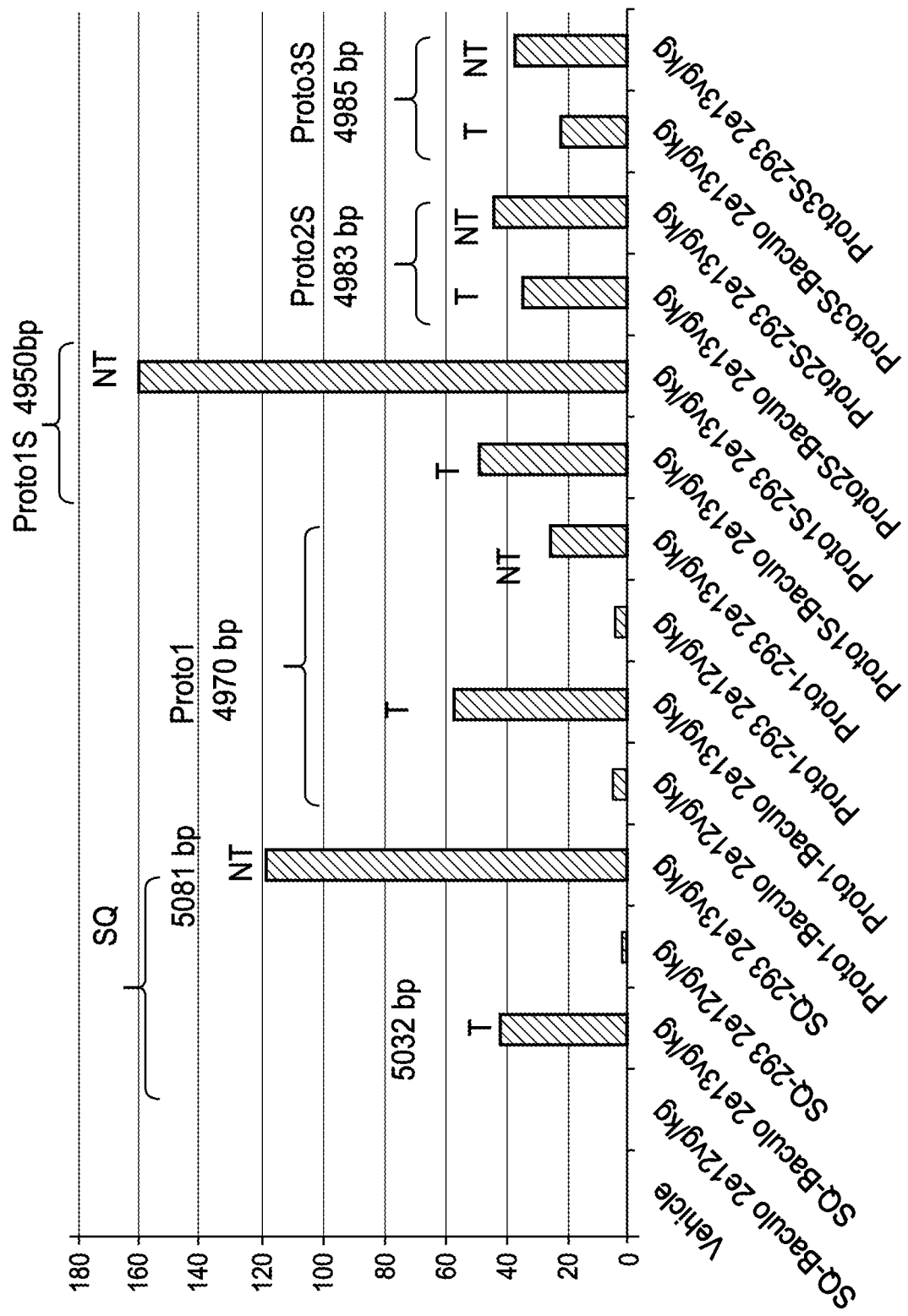
FIG. 5 provides the results of the evaluation of the Proto Constructs in Rag2 mice, and demonstrates Proto 1 transduces FVIII similarly to wild type.
Figure 6:
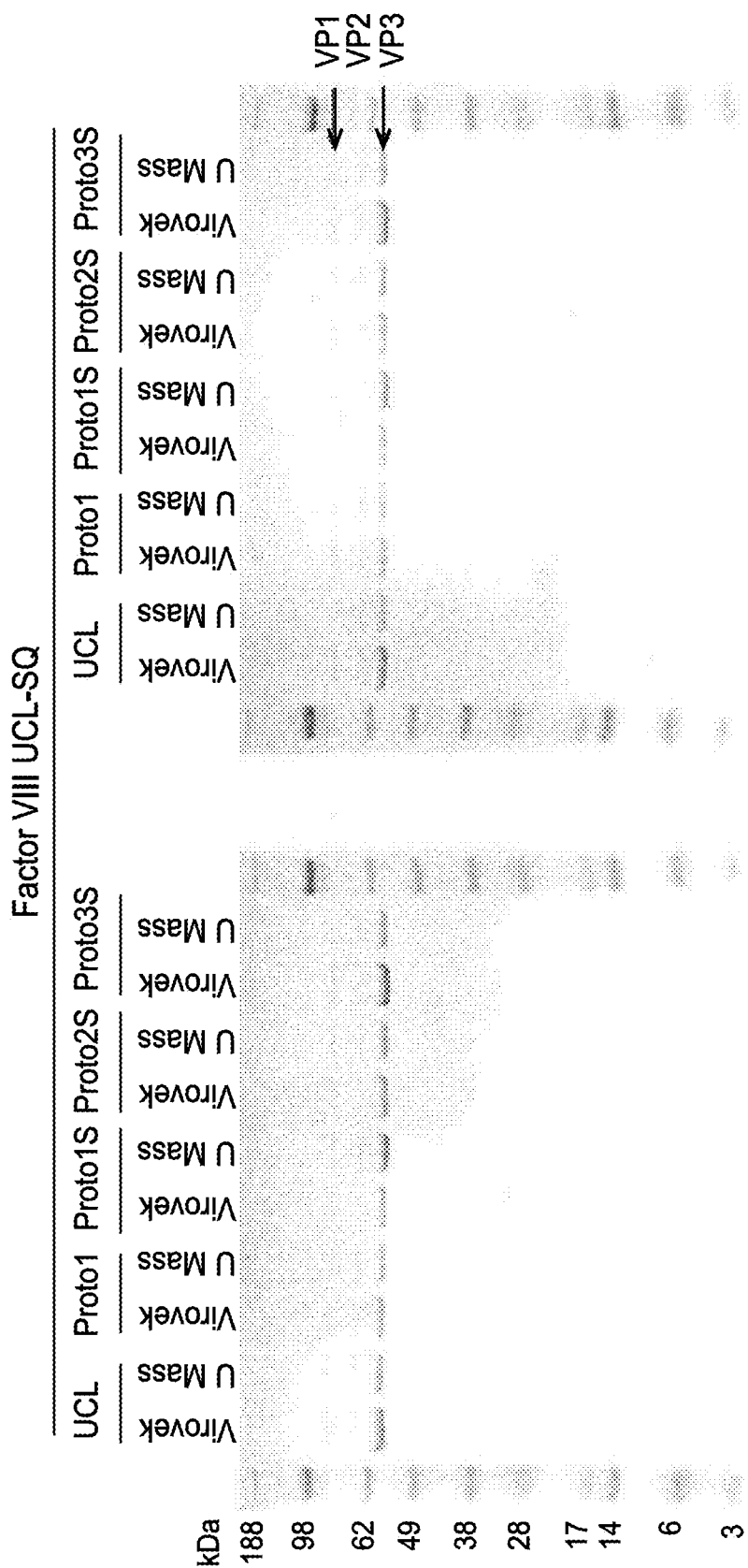
FIGS. 6 and 7 demonstrate that Proto 1, Proto 1S, Proto 2S and Proto 3S express the VP1, VP2 and VP3 protein (FIG. 5) and the VP1, VP2 and VP3 DNA (FIG. 6).
Figure 7:
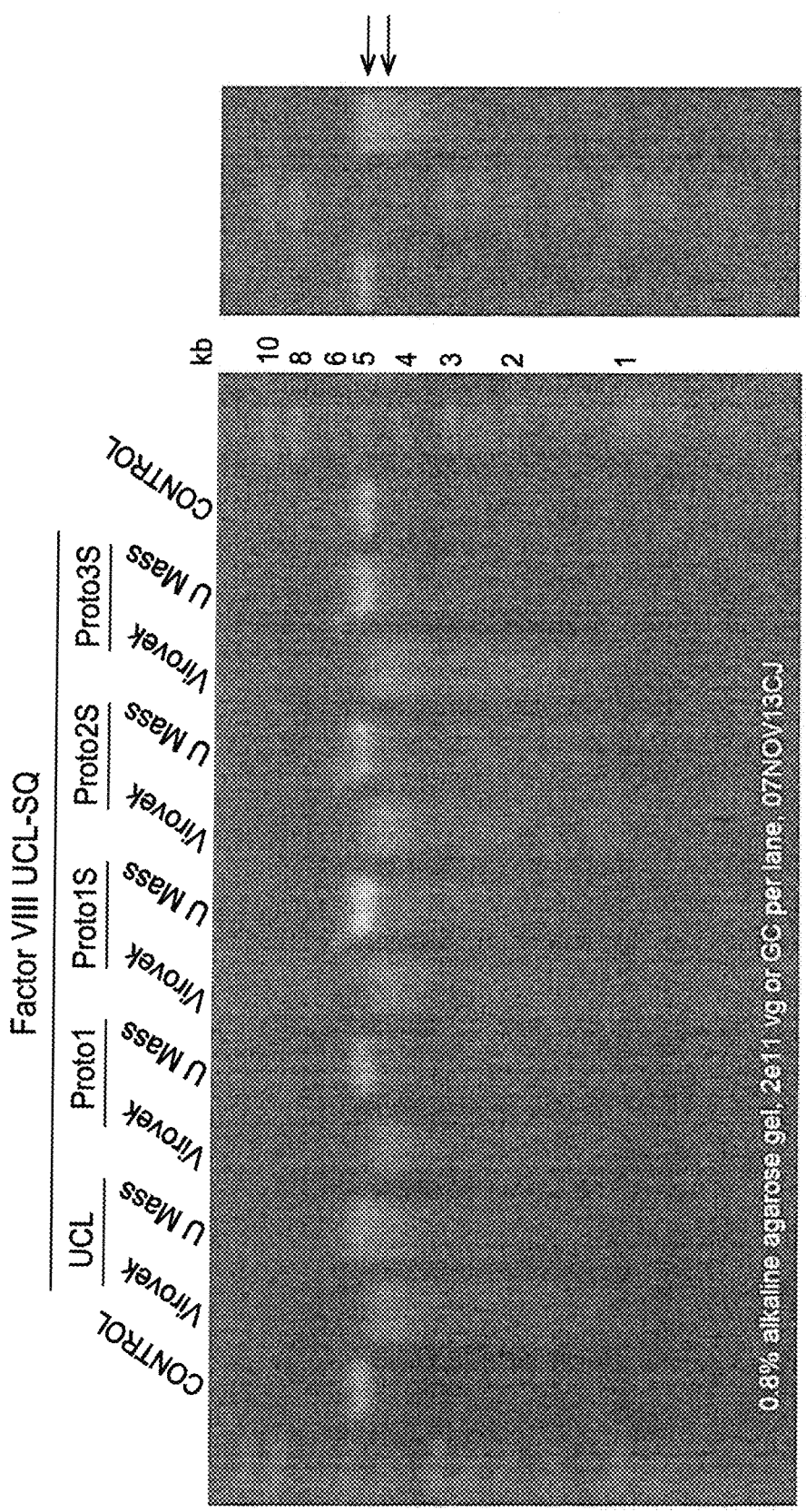

As shown in FIG. 5, Proto 1 with truncated or non-truncated genomes transduce FVIII similar to the UCL SQ construct. The AAV5.2 produced from baculovirus and 293T cell lysates as measured on a on 4-12% Bis-Tris Gel. Each samples expressed VP1, VP2 and VP3 protein, as shown in the FIG. 6. The genomic DNA from the AAV samples was run on 0.8% alkaline agarose gels, as shown in FIG. 7.

Transduction of Proto 1 was similar to the UCL SQ construct when these AAV were made by the baculovirus system. The inclusion of the intron containing Proto2S and 3S did not transduce better than Proto 1. The UCL SQ vector containing the AAV flanking sequences made in 293 cells were more potent than the UCL SQ lacking the AAV sequence made in baculovirus. As a result, additional enhancers were added to Proto 1, e.g. Construct 101, 102, 102 and 104, in an attempt to increase potency.

Example 6

Expression and Activity of AAV FVIII Vectors with Improved Promoters/Enhancer Sequences The expression and activity of AAV vectors comprising Constructs 99 to Construct 106 were tested using the hydrodynamic injection protocol. Hydrodynamic delivery is a rapid method to screen liver promoters in vivo. AAV plasmid DNA was generated using the method described in Example 5 and then diluted in TransIT-QR Hydrodynamic Delivery Solution. The plasmid DNA was injected into the tail vein of 5-6 week old C57Bl/6 mice (18-25 g) at a volume determined by (mouse weight (g)/10)=0.1 ml delivery solution). The injection time was less than 5 seconds. Plasma from each mouse was collected 48 hours after injection and the amount of FVIII antigen expressed was measured using an ELISA assay.

Increasing doses of Proto 1 plasmid (2.5, 5, 12.5 and 50 μg) were injected into the tail vein of mice. The amount of FVIII in the plasma of the injected mouse was measured using an ELISA test and recombinant FVIII (Xyntha SQ equivalents) was used as a standard for comparison.

Figure 8:
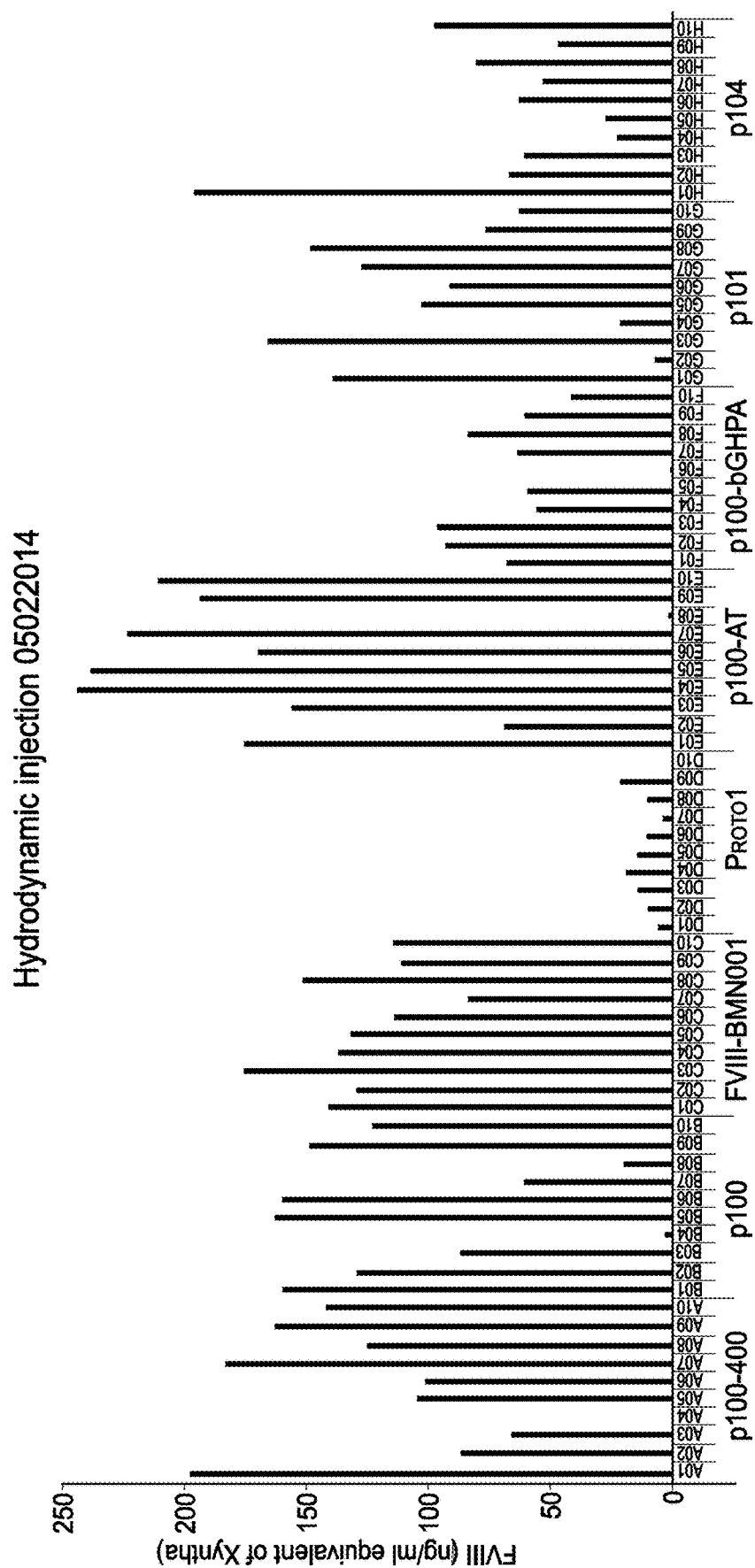
FIGS. 8-10 demonstrate that improved promoter constructs have increased expression of FVIII.

To investigate expression the improved promoter/enhancer elements of construct p100-400, Construct 100 (p100), Construct FVIII-BMN001 (pFVIII-BMN001), Proto1, Construct 100AT (p100-AT), Construct 100 bGH poly A (p100-bGHPA), Construct 101 (p101) and Construct 104 (p104). As shown in FIG. 8, all constructs produced functional FVIII at varying levels of efficiency.

Figure 9:
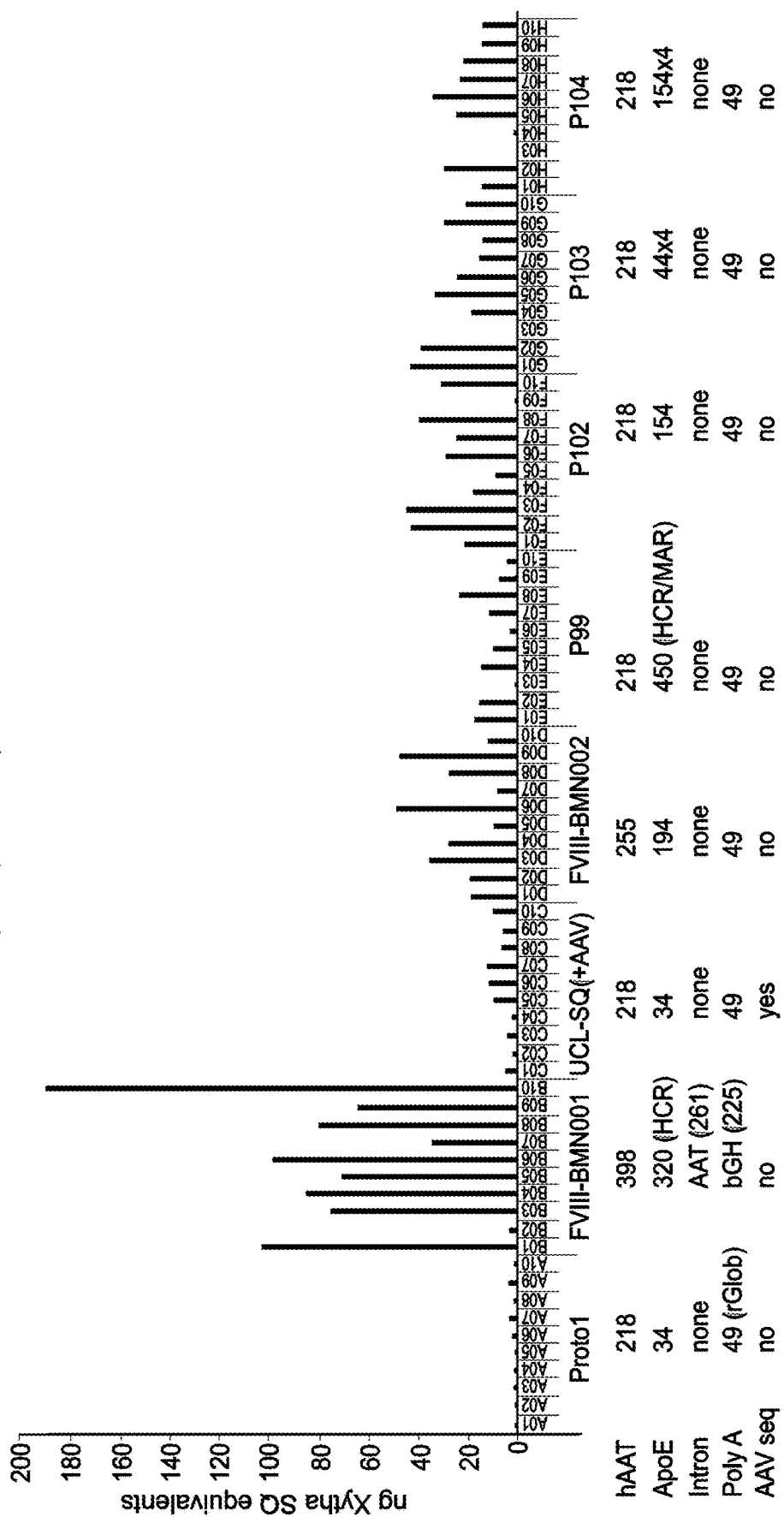
Figure 10:
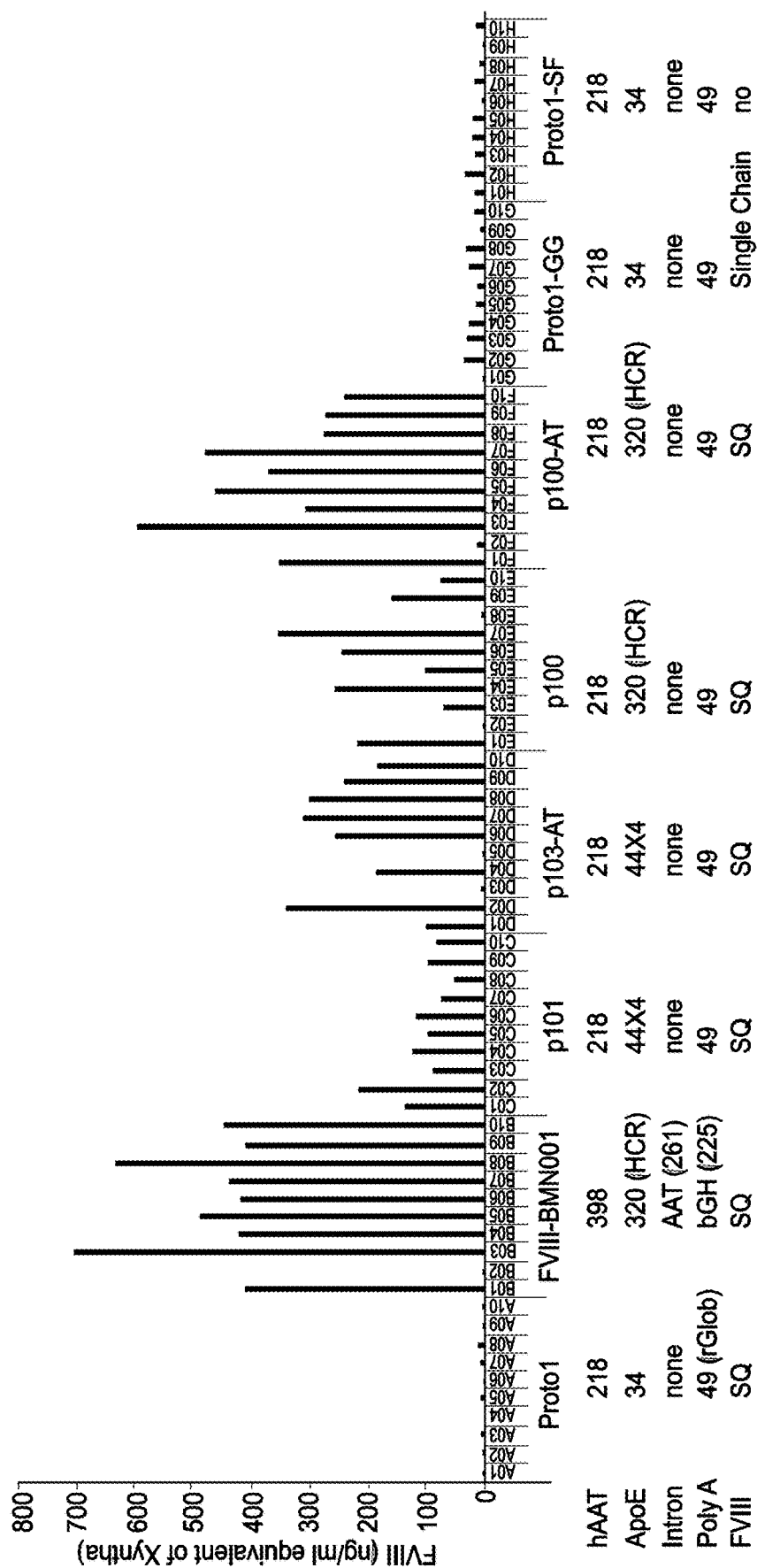

FIGS. 9 and 10 provide data for injection of 1 μg of plasmid of various constructs. As shown in FIG. 8, injection of Construct FVIII-BMN001, Constuct FVIII-BMN002, Construct 102 (p102), Construct 103 (p103) and Construct 104 (p104) resulted in expression of at least 20 ng of FVIII in 5 out of 10 mice. As shown in FIG. 9, injection of Construct FVIII-BMN001, Construct 103 (p103), Construct 103-AT (p103-AT; 398 bp hAAT promoter), Construct 100 (p100), Construct 100AT (p100-AT; 398 bp hAAT promoter) resulted in expression of at least 100 ng/ml of FVIII in 5 out of 10 mice.

What is claimed:

1. An adeno-associated virus (AAV) vector comprising a 5' inverted terminal repeat (ITR), a liver-specific transcription regulatory region operably linked to a codon-optimized nucleic acid sequence encoding a functionally active Factor VIII (FVIII) protein having the A3 and B domain deleted, and a 3' ITR, wherein the nucleic acid sequence comprises nucleotides 646-4611 of SEQ ID NO: 5.

2. A method of producing a recombinant adeno-associated virus (AAV) particle comprising A) culturing a cell that has been transfected with the AAV vector of claim 1 and B) recovering recombinant AAV particle from the supernatant of the transfected cell.

3. A viral particle comprising the AAV vector of claim 1.

4. An isolated host cell comprising the AAV vector of claim 1.

5. The AAV vector of claim 1 wherein the nucleic acid sequence comprises nucleotide sequence of SEQ ID NO: 5, SEQ ID NO: 6, SEQ ID NO: 7, or SEQ ID NO: 8.

\* \* \* \* \*